(12) United States Patent
Erickson et al.

(10) Patent No.: US 8,188,098 B2
(45) Date of Patent: May 29, 2012

(54) GPR119 RECEPTOR AGONISTS

(75) Inventors: Shawn David Erickson, Leonia, NJ (US); Paul Gillespie, Westfield, NJ (US); Kevin Richard Guertin, Verona, NJ (US); Prabha Saba Karnachi, Hillsborough, NJ (US); Kyungjin Kim, Livingston, NJ (US); Chun Ma, Edgewater, NJ (US); Warren William McComas, Denville, NJ (US); Sherrie Lynn Pietranico-Cole, Montclair, NJ (US); Lida Qi, Leonia, NJ (US); Jefferson Wright Tilley, North Caldwell, NJ (US); Qiang Zhang, Parsippany, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 215 days.

(21) Appl. No.: 12/433,921

(22) Filed: May 1, 2009

(65) Prior Publication Data
US 2009/0286812 A1 Nov. 19, 2009

Related U.S. Application Data

(60) Provisional application No. 61/054,227, filed on May 19, 2008.

(51) Int. Cl.
*A01N 43/90* (2006.01)
*A61K 31/519* (2006.01)
*C07D 487/00* (2006.01)

(52) U.S. Cl. ................ 514/262.1; 544/262
(58) Field of Classification Search .......... None
See application file for complete search history.

(56) References Cited

U.S. PATENT DOCUMENTS

| 5,272,151 A | 12/1993 | Marzi et al. |
| 2006/0046965 A1 | 3/2006 | Bailey et al. |
| 2009/0018055 A1* | 1/2009 | Fevig et al. .......... 514/4 |

FOREIGN PATENT DOCUMENTS

| WO | WO 03/099820 | 12/2003 |
| WO | WO2005007658 | 1/2005 |
| WO | WO2005019222 | 3/2005 |
| WO | WO2005047288 | 5/2005 |
| WO | WO 2005054245 | 6/2005 |
| WO | WO 2005117909 | 12/2005 |
| WO | WO 2008/039359 | 4/2008 |
| WO | WO 2008/137435 AI | 11/2008 |
| WO | WO 2008/137436 AI | 11/2008 |

OTHER PUBLICATIONS

Pourcet, B. et al, Expert Opinion Emerging Drugs, (2006), 11, 379-401.
Holman, R.R., Metabolism, 2006, 55, S2-S5.
Fredriksson, R. et al, FEBS Lett., 2003, 554, 381-388.
Chu, Z.-L. et al, Endocrinol, 2007, 148, 2601-2609.
Soga, T. et al, Biochem. Biophys. Res. Commun. 2005, 326, 744-751.
Radinov, R. et al, J. Org. Chem. 1991, 56, 4793-4796.
Carraro, F. et al, J. Med. Chem. 2006, 49, 1549-1561.
Ramesh, R. et al, Tetrahedron, 2007, 63, 9153-9162.
Xu, G. et al, J. Med. Chem. 2001, 44, 4092-4113.
Quiroga, J. et al, *Tetrahedron Letters*, 49(20: 3257-3259 (2008).

* cited by examiner

*Primary Examiner* — Jeffrey Murray
(74) *Attorney, Agent, or Firm* — George W. Johnston; Dennis P. Tramaloni; Samuel H. Megerditchian

(57) ABSTRACT

Provided herein are compounds of the formula (I):

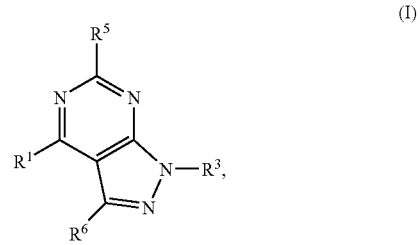

as well as pharmaceutically acceptable salts thereof, wherein the substituents are as those disclosed in the specification. These compounds, and the pharmaceutical compositions containing them, are useful for the treatment of metabolic diseases and disorders such as, for example, type II diabetes mellitus.

2 Claims, No Drawings

GPR119 RECEPTOR AGONISTS

PRIORITY TO RELATED APPLICATION(S)

This application claims the benefit of U.S. Provisional Application No. 61/054,227, filed May 19, 2008, which is hereby incorporated by reference in its entirety.

FIELD OF THE INVENTION

The invention is directed to compounds of the formula (I):

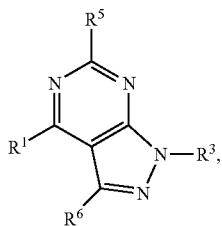

(I)

and to pharmaceutical compositions comprising said compounds. The compounds and compositions disclosed herein are GPR119 agonists useful for the treatment of metabolic diseases and disorders, such as type II diabetes mellitus.

All documents cited or relied upon below are expressly incorporated herein by reference.

BACKGROUND OF THE INVENTION

Diabetes mellitus is a serious illness that affects an increasing number of people across the world. Projections from the International Diabetes Federation suggest that by 2025 there will be a total of 380 million people worldwide suffering from diabetes. The incidence of diabetes in many countries is escalating in parallel with an upward trend in obesity. Serious consequences of diabetes include increased risk of stroke, heart disease, kidney damage, blindness, and amputation. Cardiovascular diseases are the cause of death of more than 70% of patients with Type 2 diabetes mellitus (T2DM) [B. Pourcet et al. *Expert Opin. Emerging Drugs* 2006, 11, 379-401.]

Diabetes is characterized by decreased insulin secretion and/or an impaired ability of peripheral tissues to respond to insulin, resulting in increased plasma glucose levels. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. These factors are especially important in addressing the increased cardiovascular risks associated with diabetes, but they are generally ineffective in controlling the disease itself. There are a number of drug treatments available, including insulin, metformin, sulfonylureas, acarbose, thiazolidinediones, GLP-1 analogues, and DPP IV inhibitors. However, several of these treatments have disadvantages which may include one or more of the following: hypoglycemia, weight gain, intestinal discomfort, and a loss of efficacy over time.

Although drugs have been approved for the treatment of diabetes using a number of different mechanisms, and many other drugs are being evaluated clinically, there remains a need to invent new compounds for the treatment of diabetes. It has recently been disclosed that the results of the United Kingdom Prospective Study indicate that over time, a decline is seen in the beta cell function of diabetic patients irrespective of whether they were being treated with diet, sulfonylureas, metformin, or insulin [R. R. Holman *Metabolism* 2006, 55, S2-S5].

GPR119 is a 335 amino acid protein [R. Fredriksson et al. *FEBS Lett.* 2003, 554, 381-388] which is expressed on the beta-cells of pancreatic islets [Z.-L. Chu et al. *Endocrinol.* 2007, 148, 2601-2609] and also in the GI tract [Z.-L. Chu et al. *Endocrinol.* 2008, 149, 2038-2047]. The protein belongs to the G-protein coupled receptor family, and several candidates have been proposed as the endogenous ligand, including oleoylethanolamide (OEA), N-oleoyldopamine, and olvanil [H. A. Overton et al. *Brit. J. Pharmacol.* 2007, 1-6].

GPR119 plays a role in glucose-dependent secretion of insulin, and the possibility of targeting the GPR119 receptor for the treatment of diabetes is supported by a number of studies in cell lines and in animals. Activation of the GPR119 receptor by lysophosphatidylcholine enhances glucose-dependent insulin secretion in a mouse pancreatic β-cell line, and the insulin secretion can be blocked using GPR119-specific siRNA [T. Soga et al. *Biochem. Biophys. Res. Commun.* 2005, 326, 744-751].

There is a need, therefore, for activators of the GPR119 receptor for the treatment of diseases such as diabetes.

SUMMARY OF THE INVENTION

The present invention is directed to compounds of the formula I:

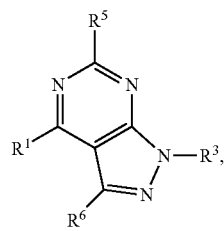

(I)

as well as pharmaceutically acceptable salts thereof, pharmaceutical compositions containing them and to methods of treating diseases and disorders. The compounds and compositions disclosed herein are activators of the GPR119 receptor and are useful for the treatment of metabolic diseases and disorders, preferably diabetes mellitus, more preferably type II diabetes mellitus.

DETAILED DESCRIPTION

In an embodiment of the present invention, provided is a compound of formula (I):

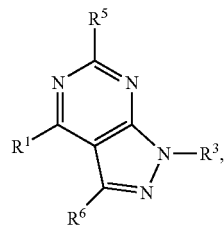

(I)

wherein:
$R^1$ is —$OR^2$, —$NHR^2$, or indolin-1-yl monosubstituted with $SO_2CH_3$;
$R^2$ is -aryl, unsubstituted or mono-, bi- or tri-substituted independently with halogen, lower alkyl, alkoxy, $OCF_3$, alkoxycarbonyl, cyano, $NHC(O)CH_3$, $SO_2CH_3$, SO$_2$CH$_2$CH$_3$, SO$_2$NH$_2$, C(O)CH$_3$, NO$_2$, NHS(O)$_2$CH$_3$, SO$_2$N(CH$_3$)$_2$, S(O)CH$_3$, S(O)CH$_2$CH$_3$, C(O)NH$_2$, acetylpiperazine, unsubstituted monocyclic heteroaryl or monocyclic heteroaryl substituted with lower alkyl,
- -benzo[1,3]dioxolyl,
- -1,1-dioxo-2,3-dihydro-1H-1λ$^6$-benzo[b]thiophenyl,
- -monocyclic heteroaryl, unsubstituted or mono-, bi- or tri-substituted independently with halogen, SO$_2$CH$_3$, SO$_2$CH$_2$CH$_3$, lower alkyl, triazole, oxo, alkoxy, cyano or hydroxy,
- -indole, unsubstituted or mono-, bi- or tri-substituted independently with lower alkyl, oxo, SO$_2$CH$_3$ or SO$_2$CH$_2$CH$_3$,
- -benzo[1,3]dioxole, unsubstituted or mono-, bi- or tri-substituted independently with lower alkyl, oxo, SO$_2$CH$_3$ or SO$_2$CH$_2$CH$_3$,
- -quinoline, unsubstituted or mono-, bi- or tri-substituted independently with lower alkyl, oxo, SO$_2$CH$_3$ or SO$_2$CH$_2$CH$_3$,
- -pyrrolo[2,3-b]pyridine, unsubstituted or mono-, bi- or tri-substituted independently with lower alkyl, oxo, SO$_2$CH$_3$ or SO$_2$CH$_2$CH$_3$,
- -benzothiophene, unsubstituted or mono-, bi- or tri-substituted independently with lower alkyl, oxo, SO$_2$CH$_3$ or SO$_2$CH$_2$CH$_3$, or
- -dioxobenzothiophene, unsubstituted or mono-, bi- or tri-substituted independently with lower alkyl, oxo, SO$_2$CH$_3$ or SO$_2$CH$_2$CH$_3$;

$R^3$ is -cyclohexane substituted with oxadiazole substituted with lower alkyl, or
- -piperidine substituted at nitrogen with $R^4$;

$R^4$ is -benzyl, unsubstituted or substituted with cyano, alkoxy, halogen, hydroxy,
- —OCF$_3$ or —CF$_3$,
- —C(O)—O-lower alkyl,
- —C(O)—O—(CH$_2$)$_n$-cycloalkyl,
- —C(O)—O—(CH$_2$)$_n$-phenyl, said phenyl being unsubstituted or substituted with NO$_2$,
- -heteroaryl, unsubstituted or substituted with halogen or lower alkyl,
- —C(O)-lower alkyl,
- —C(O)(CH$_2$)$_n$-cycloalkyl,
- —C(O)(CH$_2$)$_n$-phenyl, said phenyl being unsubstituted or substituted with halogen or alkoxy,
- —C(O)-heteroaryl, said heteroaryl being unsubstituted or substituted with lower alkyl,
- —CH$_2$-difluorobenzodioxole or
- —SO$_2$-lower alkyl;

$R^5$ is hydrogen, NH$_2$, alkoxy, halogen or lower alkyl;
$R^6$ is hydrogen or lower alkyl; and
n is 0, 1 or 2,
or a pharmaceutically acceptable salt thereof.

In another embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents, with the understanding that said substituents are not, in turn, substituted further unless otherwise specifically indicated. Each substituent can independently be, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexenyl, optionally substituted cycloheptyl, and the like or those which are specifically exemplified herein.

The term "heterocycloalkyl" denotes a mono- or polycyclic alkyl ring, wherein one, two or three of the carbon ring atoms is independently replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless otherwise specifically indicated.

The term "lower alkyl", alone or in combination with other groups, refers to a branched or straight-chain alkyl radical of one to seven carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, napthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless otherwise specifically indicated. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or dialkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, aryl-sulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthyridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms independently selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless otherwise specifically indicated. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthyridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further unless otherwise specifically indicated.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art.

General Synthesis of Compounds of the Invention

Synthesis of Compounds of the Invention According to Scheme 1

Scheme 1

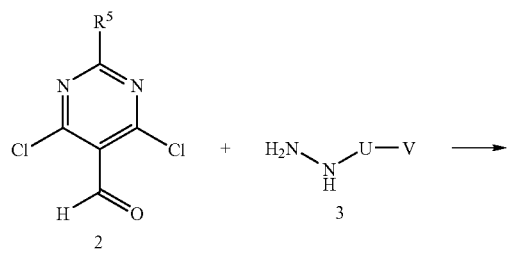

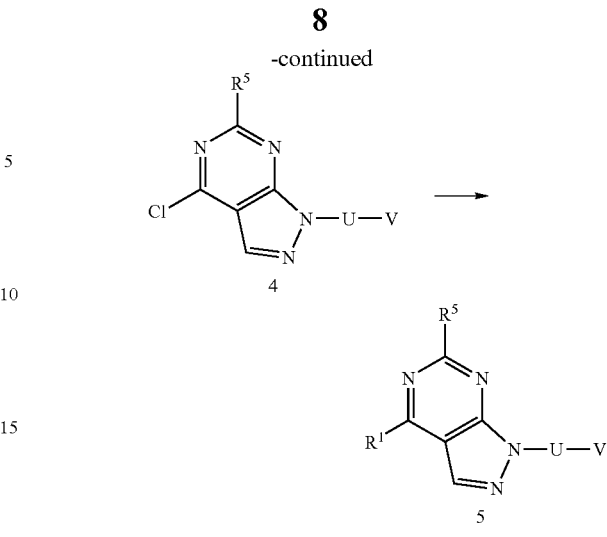

Compounds of the invention may be made by any conventional means. For example, they may be made according to the process outlined in Scheme 1 where U—V may represent $R^3$ in which case the compound of formula 5 represents a compound of the invention, or for example, U represents piperidine and V represents a protective group attached to the piperidine nitrogen, many examples of which are well known in the field of organic chemistry, and many of which are described for example in "Protective Groups in Organic Synthesis" [T. W. Greene and P. G. M. Wuts, 3rd Edition, John Wiley & Sons, N.Y. 1999] in the chapter on protection for the amino group. For example, V may represent a tert-butoxycarbonyl (Boc) group, a benzyloxycarbonyl (Cbz) group, an allyloxycarbonyl (Alloc) group, a 9H-fluoren-9-ylmethoxycarbonyl (Fmoc), a benzyl group or the like. In the case where U represents piperidine and V represents a protective group attached to the piperidine nitrogen, two additional steps are required to give a compound of the invention as outlined below in Scheme V, namely removal of the protective group and functionalization of the piperidine nitrogen with an $R^4$ group.

According to the process shown in scheme 1, the chloro-pyrimidine-carboxaldehyde of formula 2 is treated with a hydrazine of formula 3 to give an intermediate chloro-pyrazolo[3,4-d]pyrimidine of formula 4 which is subsequently reacted with an aminoaromatic or hydroxyaromatic reagent of formula $R^2$—$NH_2$ or $R^2$—OH, respectively, to give the desired product of formula 5. For example, the reaction of the pyrimidine-carboxaldehyde of formula 2 with the hydrazine of formula 3 can be conveniently carried out by combining the reagents in an inert solvent such as toluene or acetonitrile and heating them at elevated temperature such as at about 80-150° C. If a polar solvent such as acetonitrile is used for the reaction, then the reaction may be accelerated by the use of microwave irradiation. Examples of specific conditions that can be used for this kind of reaction can be found in the experimental section below, or in the literature such as for example in S.-C. Kuo et al. WO 2005054245; in M. Marzi et al. U.S. Pat. No. 5,272,151; or in R. Radinov et al. *J. Org. Chem.* 1991, 56, 4793-4796. The reaction of the chloro-pyrazolo[3,4-d]pyrimidine of formula 4 with a reagent of formula $R^1$—H can be carried out according to conditions which are well known to one of average skill in the art of organic synthesis. For example, the reaction may be carried out by treating the compound of formula 4 with the reagent of formula $R^1$—H in an inert solvent such as a polar aprotic solvent (e.g., dimethylformamide, acetonitrile or tetrahydrofuran) in the presence of a base such as sodium hydride, potassium tert-butoxide, triethylamine, or potassium carbonate at a temperature which depends on the reactivity of the reagent R¹—H. In the case of reactive compounds of formula R¹—H, the reaction can be carried out at about room temperature, while unreactive compounds of formula R¹—H such as where the aryl group is substituted by an electron-withdrawing group may require elevated temperatures (for example, approximately 150-180° C.). In the latter cases, the reaction rate may be accelerated by the use of microwave irradiation. Examples of specific conditions that can be used for this kind of reaction can be found in the experimental section below, or in the literature such as for example in N. K. Anand et al. WO 2005117909; in F. Carraro et al. *J. Med. Chem.* 2006, 49, 1549-1561; in R. M. Jones et al. WO 2005007658; in N. Tiberghien et al. WO 2005047288; and in W. Thompson et al. WO 2005019222.

Scheme 1b

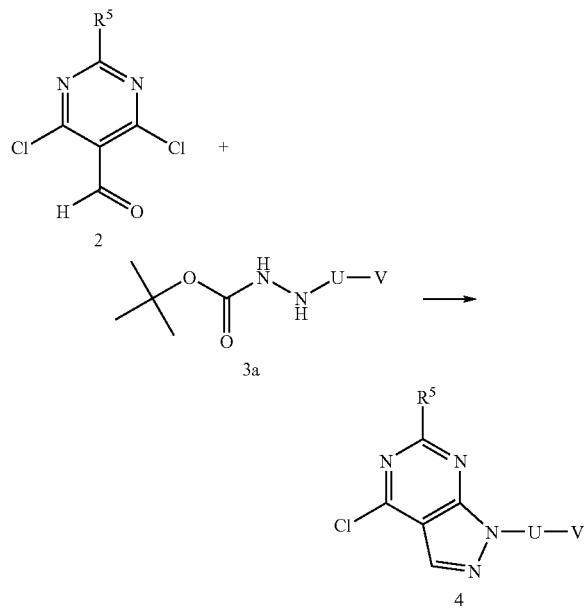

An alternative preparation of the 4-chloro-pyrazolo[3,4-d] pyrimidine of formula 4 is outlined in Scheme 1b. According to this procedure, the chloro-pyrimidine-carboxaldehyde of formula 2 is treated with a Boc-protected hydrazine of formula 3a in tetrahydrofuran at room temperature for several hours, followed by aqueous workup, removal of the solvent, and subsequent heating in toluene at 110° C. for several hours, to give the 4-chloro-pyrazolo[3,4-d]pyrimidine of formula 4. The Boc-protected hydrazine of formula 3a is an example of the intermediate of formula 25, in which PG represents the tert-butoxycarbonyl (Boc) group (see Scheme 5).

Scheme 2

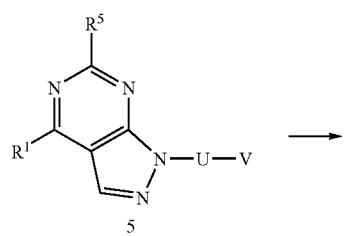

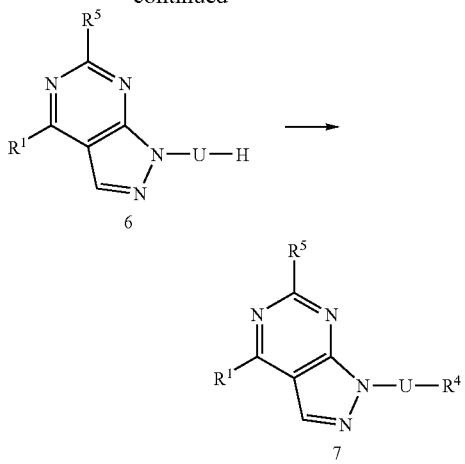

As mentioned above, in the case where U represents piperidine and V represents a protective group attached to the piperidine nitrogen, two additional steps may be required to give a compound of the invention as shown in Scheme 2. Conditions used for the removal of the protective group from the compound of formula 5 are generally well known in the field of organic chemistry and depend on the nature of the protective group. A number of conditions for the removal of common amine protective groups are listed in "Protective Groups in Organic Synthesis" [T. W. Greene and P. G. M. Wuts, 3rd Edition, John Wiley & Sons, N.Y. 1999]. For example, in the case where the protective group in the compound of formula 5 is benzyloxycarbonyl (Cbz), the group can be removed under hydrogenolytic conditions, for example by hydrogenation in the presence of a noble metal catalyst such as palladium-on-carbon, or palladium black, in the presence of an inert solvent (for example, an alcohol such as ethanol) at about room temperature and under atmospheric pressure, or at elevated pressure (such as 50 psi of hydrogen) if required. As a further example, in the case where the protective group is tert-butoxycarbonyl (Boc), the group can be removed by treatment of the compound of formula 5 with acid (either organic or inorganic) in an inert solvent. For example, the Boc group can be removed by treatment of the compound of formula 5 with trifluoroacetic acid in dichloromethane at about room temperature, or it can be removed by treatment of the compound of formula 5 with hydrochloric acid in an alcoholic solvent (e.g., methanol or ethanol) or an ether (e.g., dioxane) or ethyl acetate, also at about room temperature. An alternative and convenient approach for the removal of the Boc group is to use polymer-supported toluenesulfonic acid (MP-TsOH), a reagent commercialized by Argonaut Technologies (which is now part of Biotage AB) and which is available from Aldrich. According to this procedure, the protected derivative of formula 5 is treated with MP-TsOH in an inert solvent such as dichloromethane and the mixture is shaken at room temperature. The compound of formula 6 may then be eluted from the resin using ammonia in methanol.

Conversion of the compound of formula 6 to the compound of the invention of formula 7 can be carried out using conventional reactions that depend on the nature of the R⁴ group. In the case where R⁴ represents an alkoxycarbonyl group, a variety of procedures are known in the field of organic chemistry for the introduction of this group. Several of these are outlined in "Protective Groups in Organic Synthesis" [T. W. Greene and P. G. M. Wuts, 3rd Edition, John Wiley & Sons, N.Y. 1999] in the chapter covering protection for the amino group. For example, in many cases where R⁴ represents an alkoxycarbonyl group of formula C(=O)OR⁷ where R⁷ represents a lower alkyl group or an aralkyl group, the chloroformate of formula ClC(=O)OR$^7$ is commercially available, and this can be reacted with the intermediate of formula 6 in pyridine or in the presence of an inorganic base such as sodium carbonate in water or in a mixture of water and an organic solvent such as dioxane or in the presence of an organic base such as triethylamine in an inert organic solvent such as dichloromethane at about room temperature to give the compound of the invention of formula 7. Examples of commercially available chloroformates include methyl chloroformate, ethyl chloroformate, benzyl chloroformate, vinyl chloroformate, isobutyl chloroformate, n-propyl chloroformate, n-butyl chloroformate, n-hexyl chloroformate, 2,2,2-trichloroethyl chloroformate, 9-fluorenylmethyl chloroformate, 4-nitrobenzyl chloroformate, 2-methoxyethyl chloroformate, n-pentyl chloroformate, isopropyl chloroformate, 3-butenyl chloroformate, propargyl chloroformate, 2-butyn-1-yl chloroformate, 2,2-dimethypropyl chloroformate, 2-chlorobenzyl chloroformate, 3-butyn-1-yl chloroformate, 2-benzyloxyethyl chloroformate. These reagents are available from one or more of the following vendors: Aldrich Chemical Company, Inc., Milwaukee, Wis., USA; Alfa Aesar, Ward Hill, Mass., USA; Acros Organics, Geel, Belgium; TCI America, Portland, Oreg., USA; Oakwood Products, Inc., West Columbia, S.C., USA; and Fluka Chemie, Buchs, Switzerland. Examples of specific conditions that can be used for such a reaction can be found in the literature, for example in M. D. Bailey et al. US 20060046965; in R. M. Jones et al. WO 2005007658; in Y. Qiu et al. US 20040204432; in M. Hedberg et al. WO 2007136323; in R. Ramesh et al. *Tetrahedron* 2007, 63, 9153-9162; and in G. Xu et al. *J. Med. Chem.* 2001, 44, 4092-4113. Chloroformates of formula ClC(=O)OR$^7$ that are not commercially available may be synthesized using reactions that are well known, for example by reacting an alcohol of formula R$^7$OH with phosgene, diphosgene or triphosgene in the optional presence of a base such as pyridine in an inert solvent such as tetrahydrofuran or ether at about 0° C. Examples of precise conditions for carrying out such a reaction can be found in the literature, for example in R. Ramesh et al. *Tetrahedron* 2007, 63, 9153-9162; in X. Gao et al. U.S. Pat. No. 6,965,040; and in R. H. Tang and J. A. Barter U.S. Pat. No. 4,584,142.

As a further example of the preparation of a compound of the invention of formula 7 where U represents piperidine and R$^4$ represents C(=O)OR$^7$, the amine of formula 6 may be treated with a reagent prepared by reacting an alcohol of formula R$^7$OH with either disuccinimidyl carbonate or carbonyl diimidazole in the presence of a catalytic amount of 4-dimethylaminopyridine in an inert solvent such as dimethylformamide or a mixture of acetonitrile, dichloromethane and dimethylformamide. The reaction is conveniently carried out between about room temperature and about 55° C. Examples of specific conditions that can be used for such a reaction can be found in the literature, for example in N. J. Liverton et al. *J. Med. Chem.* 2007, 50, 807-819.

As yet another example of the preparation of a compound of the invention of formula 7 where R$^4$ represents C(=O)OR$^7$, the amine of formula 6 may be treated with 4-nitrophenyl chloroformate to give the 4-nitrophenyl carbamate which reacts with an alcohol of formula R$^7$OH to give the compound of formula 7. For example, the amine of formula 6 may be treated with 4-nitrophenyl chloroformate in the presence of diisopropylethylamine and 4-dimethylaminopyridine in an inert solvent such as dichloromethane at about room temperature to give the corresponding 4-nitrophenyl carbamate intermediate, which is subsequently treated with the alcohol of formula R$^7$OH in the presence of a base such as sodium hydride in a solvent such as tetrahydrofuran at about room temperature to give the compound of the invention of formula 7 where R$^4$ represents C(=O)OR$^7$.

The preparation of a compound of formula 7 according to Scheme 2 where U represents piperidine and R$^4$ represents a group of formula —CH$_2$Ar attached to the piperidine nitrogen where Ar is an aryl group such as benzyl, substituted benzyl, heteroaryl or substituted heteroaryl can be achieved using conventional reactions that are well known to organic chemists such as by nucleophilic substitution or by reductive alkylation. The nucleophilic substitution reaction can be carried out by treating the compound of formula 6 with a compound of formula X—CH$_2$Ar where X represents a leaving group such as a halide (e.g., chloro or bromo) or X represents a sulfonate ester such as mesylate or tosylate in an inert solvent such as acetone, 2-butanone, tetrahydrofuran or dimethylformamide, in the presence of a base such as potassium carbonate or triethylamine in the optional additional presence of potassium iodide which may serve to accelerate the reaction at a temperature about 25-100° C. Examples of specific conditions for reactions of this type can be found in the literature for example in M. Marzabadi et al. WO 2007114902; in S. Galiano et al. *Bioorg. Med. Chem.* 2007, 15, 3896-3911; and in K. Biswas et al. *J. Med. Chem.* 2007, 50, 2200-2212.

The reductive alkylation reaction may be carried out by treating the compound of formula 6, wherein U represents piperidine and the hydrogen shown is attached to the piperidine nitrogen, with an aldehyde of formula ArCHO in the presence of a reducing agent such as sodium cyanoborohydride, sodium triacetoxyborohydride, or the like in a mixture of acetic acid and dichloromethane at about room temperature. Examples of specific conditions for reactions of this type can be found in the literature for example in M. Marzabadi et al. WO 2007114902; in J. A. Lowe and S. McHardy WO 2005037216; and in D. S. Dhanoa et al. US 20050222176.

The preparation of a compound of formula 7 according to Scheme 2 where U represents piperidine and R$^4$ represents a group of formula —C(=O)R$_b$ attached to the piperidine nitrogen can be achieved using conventional reactions that are well known in the field of organic chemistry such as by reaction with a reactive derivative of a carboxylic acid such as the corresponding acid halide (for example, the acid chloride), acid anhydride, mixed anhydride, activated ester etc., or by reaction with a carboxylic acid in the presence of a coupling agent, many of which are well known to one of average skill in the art of organic synthesis and which include for example, dicyclohexylcarbodiimide, N-(3-dimethylaminopropyl)-N-ethylcarbodiimide hydrochloride, (benzotriazole-1-yl-oxy-tris-pyrrolidino-phos-phonium hexa-fluorophosphate), (2-(7-aza-1H-benzotriazol-1-yl)-1,1,3,3-tetramethyluronium hexafluorophosphate), and (O—(N-succinimidyl)-1,1,3,3-tetramethyl uranium tetrafluoroborate). The reaction is conveniently carried out by treating the amine of formula 6 or its acid addition salt with an acid chloride of formula R$_b$C(=O)Cl in the presence of an amine such as diisopropylethylamine or triethylamine in an inert solvent such as dichloromethane at a temperature between about 0° C. and about room temperature, conveniently at about room temperature. Alternatively, the carboxylic acid may be treated with N-hydroxysuccinimide in the presence of a coupling agent such as dicyclohexylcarbodiimide in an inert solvent such as tetrahydrofuran at a temperature between about 0° C. and about room temperature to give the corresponding N-hydroxysuccinimide ester which may then be treated with the amine of formula 6 or its acid addition salt in the presence of an amine such as diisopropylethylamine or triethylamine in an inert solvent such as dimethylformamide at a temperature between about 0° C. and about room temperature. In yet another alternative approach, the amine of formula 6 or its acid addition salt may be treated with the acid of formula $R_bC(=O)OH$ in the presence of an appropriate base, such as diisopropylethylamine, a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methyl-pyrrolidinone, at a temperature between about 0 degrees and about room temperature, preferably at about room temperature to give the compound of formula 7 where $R^4$ represents a group of formula $—C(=O)R_b$.

The preparation of a compound of formula 7 according to Scheme 2 where U represents piperidine and $R^4$ represents an aryl or heteroaryl group attached to the piperidine nitrogen can be achieved using conventional reactions that are well known in the field of organic chemistry such as by a nucleophilic substitution reaction, or by a metal catalyzed arylation of the piperidine derivative of formula 6. It will be readily apparent to one of average skill in the art of organic synthesis that the choice of reaction conditions will depend on the nature of the aryl group of formula $R^4$. For example, the nucleophilic substitution reaction may be the preferred option for the preparation of compounds where $R^4$ represents an electron-deficient aryl group. The nucleophilic substitution reaction may also be preferred for the preparation of compounds where $R^4$ represents a 5-membered heteroaryl system or a 6-membered heteroaryl where the point of attachment of the heteroaryl to the piperidine ring is at the ortho or para position with respect to a ring nitrogen. The reaction may be conveniently carried out by treating the piperidine intermediate of formula 6 with an aryl or heteroaryl derivative of formula $R^4—X$ where X represents a leaving group such as fluoro, chloro, or bromo, in the presence of a base such as potassium carbonate or cesium carbonate or the like in an inert solvent such as a polar aprotic solvent (e.g., dimethylsulfoxide or dimethylacetamide or the like) at elevated temperature such as at about 150° C. It may be possible to accelerate the reaction by using microwave irradiation.

The metal catalyzed reaction may be preferred in the case of aryl rings which are not necessarily electron-deficient, or in the case of 6-membered heteroaryl rings where the point of attachment of the piperidine ring is not ortho or para to a ring nitrogen. However, such reactions are also possible in the case of aryl rings which are electron-deficient, 6-membered heteroaryl rings where the point of attachment of the piperidine ring is ortho or para to a ring nitrogen, and also in the case of 5-membered heteroaryl rings. The reaction is conveniently carried out using palladium or copper catalysis. For example, the reaction may be carried out by reacting the piperidine intermediate of formula 6 with an aryl or a heteroaryl reagent which bears a leaving group (for example, a 4-chloropyrimidine, a 3-bromopyridine, or an iodobenzene derivative) in the presence of a palladium catalyst such as palladium(II) acetate, a ligand such as 1,3-bis(diphenylphosphine)propane, and a base such as sodium tert-butoxide, in an inert solvent such as toluene at a temperature about 65° C. As a further example, the reaction may be carried out by reacting the piperidine intermediate of formula 6 with an aryl or a heteroaryl reagent which bears a leaving group (for example, a 2-bromo-thiophene derivative) in the presence of a copper catalyst such as copper(I) iodide in the absence or presence of an inert solvent such as 2-(dimethylamino)-ethanol at a temperature about 100° C. Further information about such metal-catalyzed amination reactions of heterocycles can be found in the literature, for example in S. Wagaw and S. L. Buchwald *J. Org. Chem.* 1996, 61, 7240-7241; in J. P. Wolfe et al. *Acc. Chem. Res.* 1998, 31, 805-818; in Z. Lu and R. J. Twieg *Tetrahedron* 2005, 61, 903-918.

Synthesis of Compounds of the Invention According to Scheme 3

Scheme 3

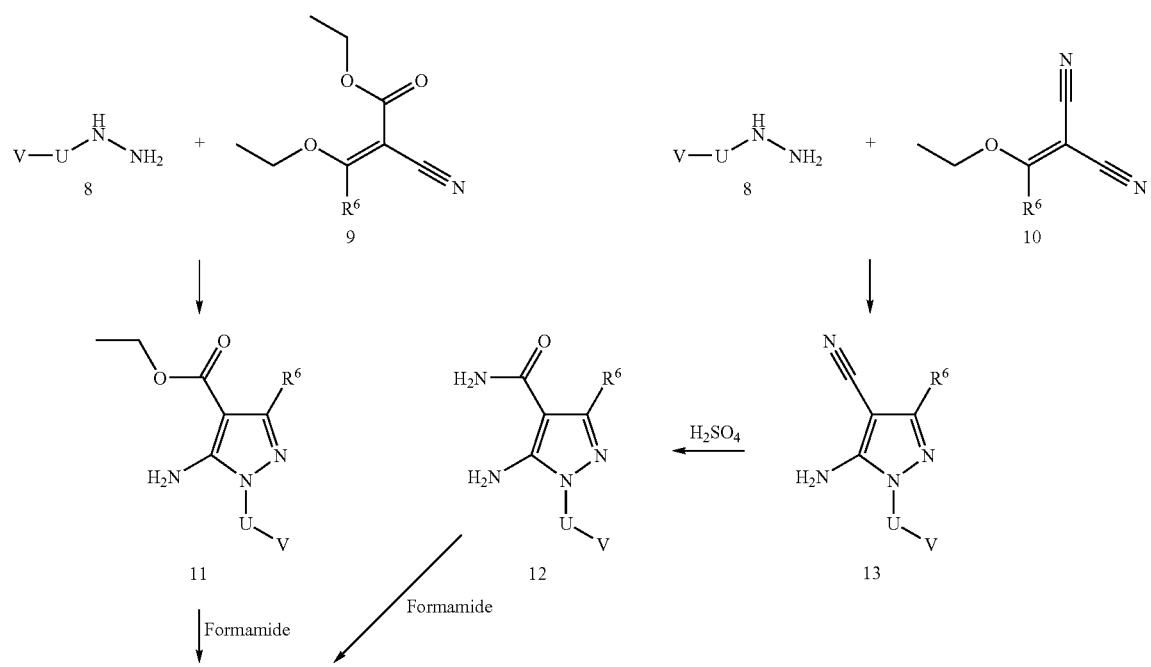

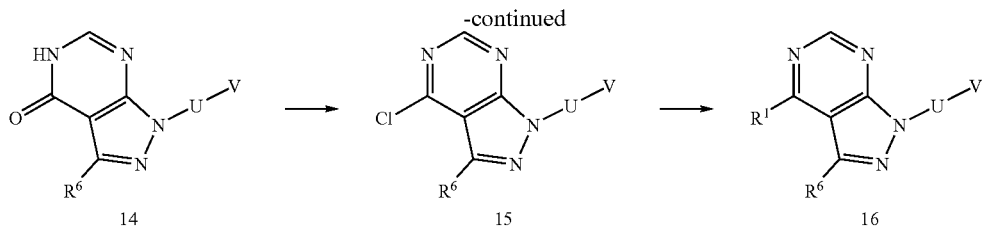

Compounds of the invention may also be made according to the processes outlined in Scheme 3. According to the first of these processes, a hydrazine of formula 8 reacts with an ethyl (ethoxymethylene)cyanoacetate of formula 9 to give the ethyl 3-aminopyrazole-4-carboxylate of formula 11. The reaction is conveniently carried out by treating the hydrazine of formula 8 with the cyanoacetate derivative in an inert solvent such as an alcohol (e.g., ethanol) or toluene at a temperature of about 80° C. Examples of specific conditions that have been used for such reactions can be found in the literature, for example in P. Schmidt et al. *Helv. Chim. Acta* 1958, 41, 1052-1060; in J.-F. Li et al. *J. Heterocyclic Chem.* 2007, 44, 749-755; in F. Bondavalli et al. *J. Med. Chem.* 2002, 45, 4875-4887; and in J. Druey and P. Schmidt U.S. Pat. No. 3,682,918.

The reaction of a pyrazole-4-carboxylate ester of formula 11 to give the pyrazolopyrimidine of formula 14 is conveniently carried out by heating the pyrazole-4-carboxylate ester of formula 11 in formamide at elevated temperature such as at about 180-210° C. Examples of specific conditions that have been used for such reactions can be found in the literature, for example in B. S. Holla et al. *Bioorg. Med. Chem.* 2006, 14, 2040-2047; in P. Schmidt et al. *Helv. Chim. Acta* 1959, 42, 763-772; in F. Carraro et al. *J. Med. Chem.* 2006, 49, 1549-1561; and in N. K. Anand et al. WO 2005117909.

An alternative convenient process for the preparation of compounds of formula 14 is also shown in Scheme 3. According to this process, a hydrazine of formula 8 reacts with an ethoxymethyl-enemalononitrile of formula 10 to give the aminopyrazole of formula 13. This reaction is conveniently carried out in an inert solvent such as an alcohol (e.g., ethanol) at the reflux temperature. Exact conditions for such a reaction can be found in the literature, for example in C. C. Cheng and R. K. Robins *J. Org. Chem.* 1956, 21, 1240-1256; in P. G. Baraldi et al. *J. Med. Chem.* 1996, 39, 1164-1171; in N. Tiberghien et al. WO 2005047288; or in E. Y. Sutcliffe et al. *J. Med. Pharm. Chem.* 1962, 5, 588-607. The pyrazolecarbonitrile of formula 13 is conveniently converted to the carboxamide of formula 12 by hydrolysis. Conditions for the hydrolysis are well known to one of skill in the art of organic synthesis. This reaction can be carried out using either acidic hydrolysis conditions, or using hydrogen peroxide under basic conditions. In the case where acidic conditions are used, the pyrazolecarbonitrile of formula 13 may be added to concentrated sulfuric acid and stirred at a temperature between about 10° C. and about room temperature until the desired hydrolysis reaction is complete. Examples of specific conditions that have been used for such reactions can be found in the literature, for example in C. C. Cheng and R. K. Robins *J. Org. Chem.* 1956, 21, 1240-1256; in L.-D. Cantin et al. WO 2005112923; in H. M. M. Bastiaans et al. WO 2005063020; in N. Tiberghien et al. WO 2005047288; and in J. A. Markwalder et al. *J. Med. Chem.* 2004, 47, 5894-5911. In the case where hydrogen peroxide under basic conditions are used, the reaction is conveniently carried out by treating the pyrazolecarbonitrile of formula 13 with hydrogen peroxide in a base such as aqueous ammonium hydroxide or aqueous potassium carbonate in an inert solvent such as an alcohol (e.g., methanol) or dioxane or dimethylsulfoxide at about 0° C. Examples of specific conditions that have been used for such reactions can be found in the literature, for example in J. Zhou et al. *Tetrahedron* 2006, 62, 7009-7013; in B. K. Bhattacharya et al. *J. Heterocyclic Chem.* 1990, 27, 795-801; in J. G. Buchanan et al. *J. Chem. Soc., Perkin Trans. I* 1989, 925-930; and in G. B. Evans et al. *J. Med. Chem.* 2003, 46, 155-160.

The reaction of a pyrazole-4-carboxamide of formula 12 to give the pyrazolopyrimidine of formula 14 is conveniently carried out by heating the pyrazole-4-carboxylate ester of formula 12 in formamide at elevated temperature such as at about 180-210° C. Examples of specific conditions that have been used for such reactions can be found in the literature, for example in C. C. Cheng and R. K. Robins *J. Org. Chem.* 1956, 21, 1240-1256; in E. C. Taylor and K. S Hartke *J. Am. Chem. Soc.* 1959, 81, 2452-2455; in N. Tiberghien et al. WO 2005047288; in M. El Hedi Jellali et al. *Tetrahedron* 1975, 31, 587-591; and in J. D. Anderson et al. *J. Heterocyclic Chem.* 1986, 23, 1869-1878.

The 1,5-dihydro-pyrazolo[3,4-d]pyrimidin-4-one of formula 14 is conveniently converted to the chloro-1H-pyrazolo[3,4-d]pyrimidine of formula 15 using conditions that are well known in the field of organic synthesis. For example, the compound of formula 14 may be treated with a chlorinating agent such as thionyl chloride or phosphorus oxychloride in the optional presence of dimethylformamide at a temperature around 80° C. in the case of thionyl chloride or around 100° C. in the case of phosphorus oxychloride. Examples of specific conditions that have been used for such reactions can be found in the literature, for example in N. K. Anand et al. WO 2005117909; in F. Gatta et al. *J. Heterocyclic Chem.* 1989, 26, 613-618; in J. B. Press et al. *J. Org. Chem.* 1983, 48, 4605-4611; in F. Carraro et al. *J. Med. Chem.* 2006, 49, 1549-1561; in N. Tiberghien et al. WO 2005047288; and in G. A. Bhat et al. *J. Med. Chem.* 1981, 24, 1165-1172.

The reaction of the intermediate of formula 15 with an aminoaromatic or hydroxyaromatic reagent of formula $R^2$—$NH_2$ or $R^2$—OH, respectively, can be carried out using conventional procedures. For example, the chloro-1H-pyrazolo[3,4-d]pyrimidine of formula 15 may be treated with an aminoaromatic reagent of formula $R^2$—$NH_2$ at reflux in an alcohol such as ethanol or n-butanol, in the optional additional presence of an organic amine, such as diisopropylethylamine to give a compound of formula 16 where $R^1$ represents —$NHR^2$. Examples of specific conditions that have been used for such reactions can be found in the literature, for example in N. Tiberghien et al. WO 2005047288; in D. C. Kim et al. *Eur. J. Med. Chem.* 2003, 38, 525-532; in C. C. Cheng and R. K. Robins *J. Org. Chem.* 1956, 21, 1240-1256. As a second example, the chloro-1H-pyrazolo[3,4-d]pyrimidine of formula 15 may be treated with a hydroxyaromatic reagent of formula R²—OH at about 100° C. in aqueous potassium hydroxide to give a compound of formula 16 where R¹ represents —OR₂. Examples of specific conditions that have been used for such reactions can be found in the literature, for example in C. C. Cheng and R. K. Robins *J. Org. Chem.* 1956, 21, 1240-1256.

Synthesis of Compounds of the Invention According to Scheme 4 perature in tetrahydrofuran and the resulting reagent is treated with an aldehyde of formula R⁶—CHO to give the alcohol intermediate of formula 18.

Oxidation of the alcohol of formula 18 to the ketone of formula 19 can be accomplished using one of a variety of oxidation procedures that are well known in the art of organic synthesis. Two convenient examples are (1) by treatment with chromium(VI) oxide in acetone at room temperature and (2)

Scheme 4

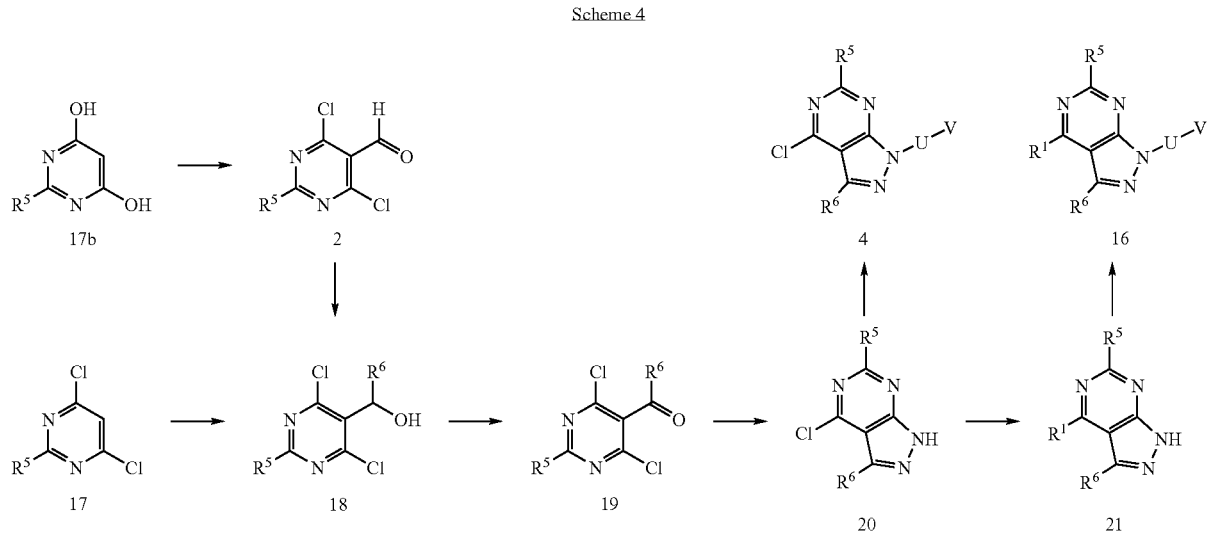

Compounds of the invention may further be made according to the process outlined in Scheme 4. This process begins with 4,6-dihydroxy-pyrimidine (which is available from Aldrich Chemical Company, Inc., Milwaukee, Wis., USA) which has formula 17b where R⁵ represents hydrogen. This starting material reacts under Vilsmeier conditions (treatment with phosphorus oxychloride and dimethylformamide at room temperature) as described in W. Klötzer and M. Herberz *Monatsh.* 1965, 96, 1567-1572, and in G. S. Kauffman et al. WO 2006090261, to give 4,6-dichloro-5-pyrimidinecarboxaldehyde which has formula 2 and which is also commercially available from Key Organics Limited, Camelford, Cornwall, UK and from Apollo Scientific Ltd., Stockport, Cheshire, UK. The compound of formula 2 where R⁵ represents amino (namely 2-amino-4,6-dichloro-pyrimidine-5-carbaldehyde) is commercially available (for example, from Aldrich Chemical Company, Inc., Milwaukee, Wis., USA). Compounds of formula 2 where R⁵ represents lower alkyl can be prepared using Vilsmeier conditions similar to those outlined above starting with 2-alkyl-4,6-dihydroxy-pyrimidine derivatives, which may be prepared using conditions that are well known in the art, such as those outlined in J. H. Clark U.S. Pat. No. 2,513,550.

Reaction of a 4,6-dichloro-5-pyrimidinecarboxaldehyde of formula 2 with an organometallic reagent such as a Grignard reagent in ether at room temperature as described in J. Clark et al. *J. Chem. Soc. Perkin Trans.* 1 1976, 1004-1007 and in G. S. Kauffman et al. WO 2006090261 gives the alcohol of formula 18. In an alternative approach, the alcohol of formula 18 where R⁵ represents hydrogen can be prepared directly from the 4,6-dichloropyrimidine of formula 17 where R⁵ represents hydrogen as reported by I. Mitchell et al. in US 20050130954. According to this process, 4,6-dichloropyrimidine is treated with lithium diisopropylamide at low temby treatment with excess manganese dioxide in dichloromethane at room temperature. Examples of specific conditions for these reactions can be found in J. Clark et al. *J. Chem. Soc. Perkin Trans. 1* 1976, 1004-1007; in G. S. Kauffman et al. WO 2006090261; and in I. Mitchell et al. US 20050130954.

It will be noted by those with average skill in the art of organic synthesis that the compound of formula 2 in Scheme 4 is an example of a compound of formula 19 in which R⁶ represents hydrogen and that the reactions described below through which compounds of formula 19 are converted to compounds of formula 1 also apply to the compound of formula 2 in Scheme 4.

The compound of formula 19 can be conveniently converted to the pyrazolo[3,4-d]pyrimidine of formula 20 by treatment with hydrazine in the presence of a base such as triethylamine in a mixture of water and tetrahydrofuran at room temperature. Examples of precise conditions suitable for such as reaction can be found in the literature, for example in R. O. Dempcy et al. WO 2003022859; and in F. Seela and H. Stecker *Helv. Chim. Acta* 1986, 69, 1602-1613.

The conversion of the compound of formula 20 to the compound of formula 21 may be carried out using conditions similar to those described above for the conversion of the compound of formula 4 to the compound of formula 5 in Scheme 1.

The alkylation of the intermediate of formula 21 can be carried out using procedures that are well known in the field of organic chemistry. For example, the reaction may be carried out by treating the intermediate of formula 21 with an alkylating agent of formula V—U—X where X is a leaving group such as bromo or iodo or a sulfonate ester such as a mesylate or tosylate or triflate, in the presence of a base which may be an organic base such as triethylamine of diisopropylethylamine or an inorganic base such as potassium carbonate or cesium carbonate in an inert solvent such as dimethylformamide at a temperature between about 100° C. and about 150° C. It will be clear to one of skill in the art of organic synthesis that this reaction may lead to a mixture of the desired compound of formula 16 along with its regioisomer where the alkylation takes place at the 2-position of the pyrazole ring. In cases where regioisomeric mixtures result, the desired compound will typically be isolated using a chromatographic purification which may involve flash chromatography on silica gel, or high-performance liquid chromatography, or supercritical fluid chromatography, depending on the difficulty of the separation. Examples of specific conditions used to carry out reactions of this type may be found in the literature, for example, in L. Ballell et al. *Bioorg. Med. Chem. Lett.* 2007, 17, 1736-1740; in T. S. Rao et al. *J. Heterocyclic Chem.* 1997, 34, 257-262; in B. Zacharie et al. *Tetrahedron* 1996, 52, 2271-2278; and in N. Wishart et al. WO 2005074603.

Alternatively, the alkylation of the intermediate of formula 21 can be carried out using the Mitsunobu reaction. This reaction is conveniently carried out by treating the compound of formula 21 with a reagent of formula V—U—OH in the presence of a triaryl phosphine such as triphenylphosphine and a diazodicarboxylate such as diethylazodicarboxylate (DEAD) or diisopropylazodicarboxylate (DIAD) in an inert solvent such as tetrahydrofuran at a temperature between about 0° C. and about room temperature, preferably at about 0° C. Examples of specific conditions used to carry out reactions of this type may be found in the literature, for example, in M. Brændvang and L.-L. Gundersen *Tetrahedron Lett.* 2007, 48, 3057-3059; in S. L. Lindquist et al. WO 2007126841; in N. Wishart et al. WO 2005074603; and in M. Bilodeau et al. WO 2004096131.

As will be clear to one of average skill in the art of organic synthesis, the order of the steps in the conversion of the chloro-pyrazolo[3,4-d]pyrimidine of formula 20 to the compound of formula 16 can be reversed, so that the N1-alkylation is carried out to give the intermediate of formula 4 prior to the displacement of the chloro group. Reaction conditions similar to those described above for the conversion of the intermediate of formula 21 to the compound of formula 16 and for the conversion of the intermediate of formula 20 to the intermediate of formula 21 can be used to effect these transformations.

Synthesis of Compounds of the Invention According to Scheme 4b

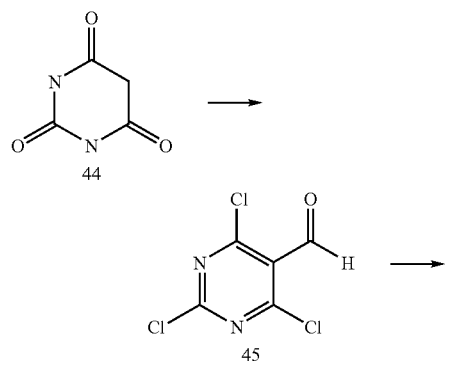

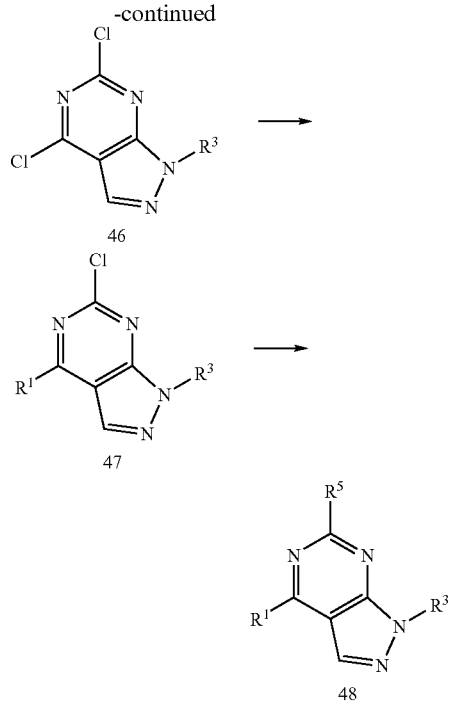

As a further example, certain compounds of the invention may be conveniently prepared using the procedure outlined in Scheme 4b. According to this route, barbituric acid, which has formula 44 and is commercially available, undergoes simultaneous chlorination and Vilsmeier formylation to give the trichloropyrimidine-carboxaldehyde of formula 45. This material may then be condensed with a reagent of formula 3 or a reagent of formula 3b to give the pyrazolo[3,4-d]pyrimidine of formula 46. Displacement of the chlorine at the 4-position by a reagent of formula $R^1$—H gives the intermediate of formula 47. The remaining chlorine may then be displaced in a transition metal-catalyzed reaction with an organometallic reagent to give compounds of formula 48 where $R^5$ represents an alkyl group.

The simultaneous chlorination and Vilemeier formylation of barbituric acid may be carried out by treating barbituric acid with phosphorus oxychloride and dimethylformamide at a temperature of about 85° C. Exact conditions for carrying out this reaction may be found in the literature, for example in J. Dehnert DE 3603797.

The reaction of the intermediate of formula 45 with a reagent of formula 3 to give the pyrazolo[3,4-d]pyrimidine of formula 46 can be conveniently carried out by combining the reagents in an inert solvent such as toluene or acetonitrile and heating them at elevated temperature such as at about 80-150° C. If a polar solvent such as acetonitrile is used for the reaction, then the reaction may be accelerated by the use of microwave irradiation. Examples of specific conditions that can be used for this kind of reaction can be found in the experimental section below, or in the literature such as for example in S.-C. Kuo et al. WO 2005054245; in M. Marzi et al. U.S. Pat. No. 5,272,151; or in R. Radinov et al. *J. Org. Chem.* 1991, 56, 4793-4796. In the case where the reagent of formula 3a is used, the reaction is conveniently carried out by combining the trichloro-pyrimidine-carboxaldehyde of formula 45 is treated with the hydrazine of formula 3a in tetrahydrofuran at room temperature for several hours, followed by aqueous workup, removal of the solvent, and subsequent heating in toluene at 110° C. for several hours, to give the 4,6-dichloro-pyrazolo[3,4-d]pyrimidine of formula 46.

The reaction of the dichloro-pyrazolo[3,4-d]pyrimidine of formula 46 with a reagent of formula R¹—H to give the intermediate of formula 47 can be carried out according to conditions which are well known to one of average skill in the art of organic synthesis. For example, the reaction may be carried out by treating the compound of formula 46 with the reagent of formula R¹—H in an inert solvent such as a polar aprotic solvent (e.g., dimethylformamide, acetonitrile or tetrahydrofuran) in the presence of a base such as sodium hydride, potassium tert-butoxide, triethylamine, or potassium carbonate at a temperature which depends on the reactivity of the reagent R¹—H as discussed above in connection with the preparation of the compound of formula 4.

The conversion of the 6-chloro-pyrazolo[3,4-d]pyrimidine of formula 47 to the compound of formula 48 where $R^5$ represents an alkyl group may be accomplished using one of a number of transition metal-catalyzed reactions which are well known in the field of organic chemistry. For example, the compound of formula 47 may be treated with an organotin reagent, or an organozinc reagent, or an organoaluminum reagent such as trimethylaluminum or tetrabutyltin or the zinc reagent prepared by treating isopropylmagnesium bromide with zinc bromide or the like, in the presence of a noble metal catalyst such as dichloro[1,1'-bis(diphenylphosphine)ferrocene]palladium(II) or tetrakis(triphenylphosphine)palladium(0) or bis(triphenylphosphine)palladium(II) chloride or the like, in an inert solvent such as tetrahydrofuran or dimethylformamide or dioxane or the like at a temperature around 70° C. Examples of specific conditions that can be used for this reaction can be found in the examples below or in the literature, for example in V. Bambuch et al. *Tetrahedron* 2007, 63, 1589-1601; in P. Čapek et al. *Synthesis* 2006, 3515-3526; in P. M. *J. Med. Chem.* 2005, 48, 6887-6896; M Braendvang et al. *Bioorg. Med. Chem.* 2007, 15, 7144-7165; or in L.-L. Gunderson and M. Braendvang US 2007203159.

Synthesis of Compounds of the Invention According to Scheme 4c

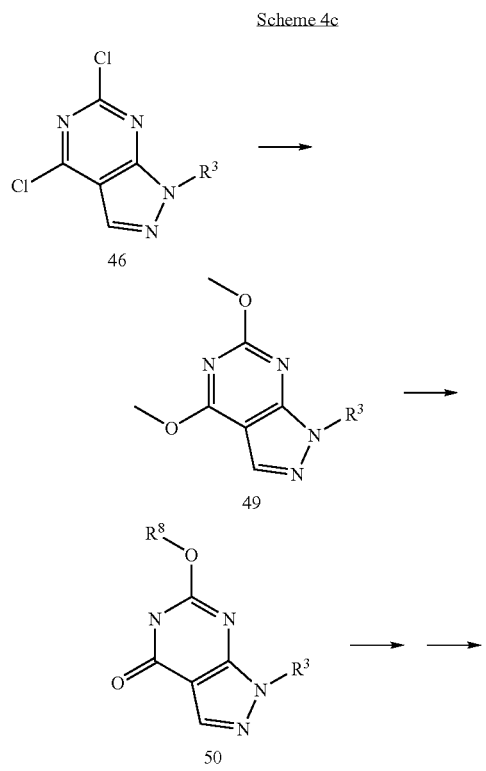

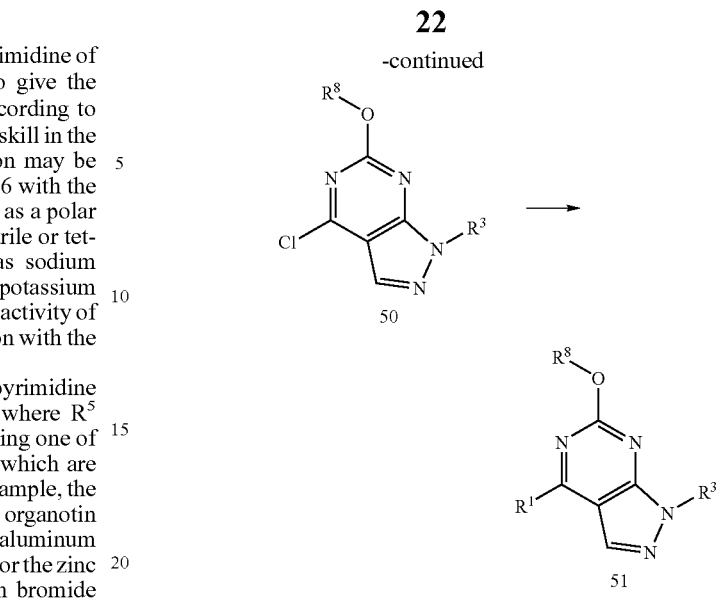

As a further example, certain compounds of the invention may be conveniently prepared using the procedure outlined in Scheme 4c. According to this route, the intermediate 46 from Scheme 4b reacts with methanol under basic conditions to give the dimethoxy derivative of formula 49. Selective hydrolysis of the methyl ether at the 4-position gives the fused pyrimidin-4-one of formula 50 which is then chlorinated and reacted with a reagent of formula R¹—H under basic conditions to give the compound of formula 51, which is a compound of the invention of formula I in which $R^6$ represents hydrogen and $R^5$ represents alkoxy.

The conversion of the compound of formula 46 to the compound of formula 49 may be carried out using conventional reaction conditions. For example, the reaction may be conveniently carried out by treating the dichloro-pyrazolo[3,4-d]pyrimidine of formula 46 with sodium methoxide in methanol at a temperature between about room temperature and about 65° C., preferably at about 65° C. The selective hydrolysis of the dimethoxy compound of formula 49 may be accomplished using the conditions disclosed in a publication by F. Seela and S. Menkhoff (*Liebigs Ann. Chem.* 1986, 1213-1221), namely by reaction with 2M aqueous sodium hydroxide solution at a temperature between about 35° C. and about 50° C. to give the monomethoxy-pyrimidone derivative. The chlorination reaction can be carried out by treating the compound of formula 50 with a chlorinating agent such as thionyl chloride or phosphorus oxychloride in the optional presence of dimethylformamide at a temperature around 80° C. in the case of thionyl chloride or around 100° C. in the case of phosphorus oxychloride. Finally, the reaction of the chloro-pyrazolo[3,4-d]pyrimidine of formula 50 with a reagent of formula R¹—H to give the desired compound of the invention of formula 51 can be carried out according to conditions which are well known to one of average skill in the art of organic synthesis. For example, the reaction may be carried out by treating the compound of formula 50 with the reagent of formula R¹—H in an inert solvent such as a polar aprotic solvent (e.g., dimethylformamide, acetonitrile or tetrahydrofuran) in the presence of a base such as sodium hydride, potassium tert-butoxide, triethylamine, or potassium carbonate at a temperature between about 50° C. and about 150° C., the temperature being selected according to the reactivity of the reagent of formula R¹—H as discussed above.

Availability of Reagents Useful for the Preparation of Compounds of the Invention Availability of Compounds of Formula 3 where U Represents Piperidine and V Represents $C(=O)OR^7$

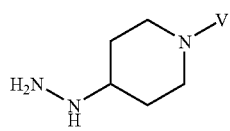

3

The preparation of 4-hydrazino-piperidine-1-carboxylic acid ethyl ester dihydrochloride is described in H. Sakashita et al. US 20040259883. The preparation of 4-hydrazino-piperidine-1-carboxylic acid benzyl ester is described in D. R. Armour et al. U.S. Pat. No. 7,217,714. The preparation of 4-hydrazino-piperidine-1-carboxylic acid 9H-fluoren-9-yl-methyl ester is described in K. Rudolph et al. U.S. Pat. No. 6,344,449.

In addition to the commercially available intermediate and known compounds, additional intermediates of formula 3 can be made using known methods, including methods disclosed in H. Sakashita et al. US 20040259883; in D. R. Armour et al. U.S. Pat. No. 7,217,714; in K. Rudolph et al. U.S. Pat. No. 6,344,449; in R. R. Ranatunge et al. *J. Med. Chem.* 2004, 47, 2180-2193; and in K. Matsushita et al. EP 885890.

Scheme 5

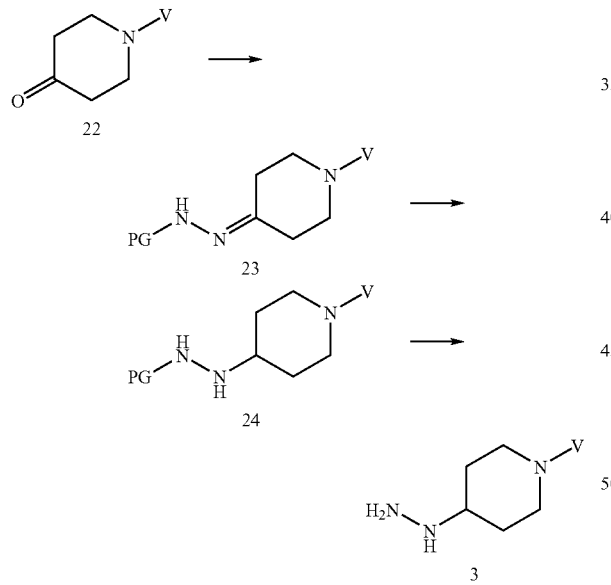

For example, intermediates of formula 3 can be made using the process outlined in Scheme 5 where the protected hydrazone Intermediate 25 may be isolated or where it may alternatively be reduced in situ to the protected hydrazone intermediate of formula 24. According to this process, a protected piperidone of formula 22 is treated with a protected hydrazine of formula PG-NHNH$_2$, where PG represents a protective group for a hydrazine. It will be clear to one of average skill in the art of organic chemistry that it must be possible to remove the PG protective group while the V group remains in place. Many examples of such orthogonal protective groups are known in the field of organic chemistry. For example, in the case where V represents a tert-butoxycarbonyl group (Boc), the PG group may be selected from benzyloxycarbonyl (Cbz), allyloxy-carbonyl (Alloc), 9H-fluoren-9-yl-methoxy-carbonyl (Fmoc), or other protective groups that can be removed by methods other than treatment with acid or heating above about 150° C. Alternatively, in the case where V represents a Cbz group, the PG may be selected from the group of Boc, Alloc, or Fmoc, or other protective groups that can be removed by methods other than hydrogenolysis. These examples of acceptable combinations of V and PG protective groups are given solely for the purposes of illustration and are not intended to constitute a comprehensive list of the possible combinations.

For example, 4-oxo-piperidine-1-carboxylic acid benzyl ester is the compound of formula 22 where V represents the benzyloxycarbonyl group, and it is available from a number of vendors including Aldrich Chemical Company, Inc., Milwaukee, Wis., USA, and Alfa Aesar, Ward Hill, Mass., USA. This material can be combined with hydrazinecarboxylic acid tert-butyl ester in the presence of sodium triacetoxyborohydride in a mixture of acetic acid and dichloromethane at room temperature to give the protected hydrazine of formula 24. This intermediate may then the treated with a strong inorganic acid, for example a hydrohalic acid such as hydrogen chloride, or a strong organic acid, for example a halogenated alkane carboxylic acid such as trifluoroacetic acid and the like. The reaction is conveniently carried out in the presence of an inert organic solvent (such as dioxane or dichloromethane) and at a temperature between about 0 degrees and about room temperature, preferably at about room temperature, to give the desired hydrazine of formula 3.

Scheme 6

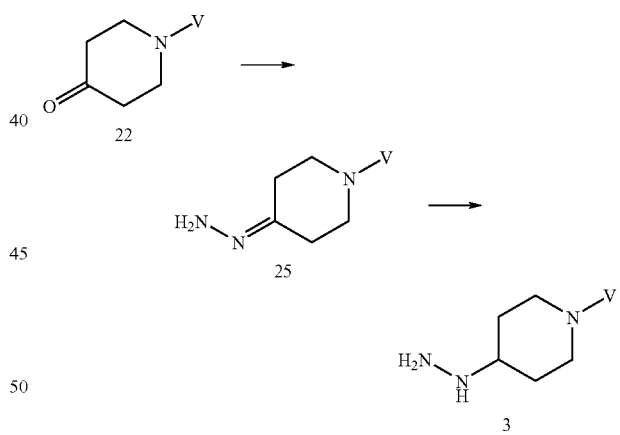

As an additional example, intermediates of formula 3 can be made using the process outlined in Scheme 6. According to this process, the starting material may be 4-oxo-piperidine-1-carboxylic acid tert-butyl ester which is the compound of formula 22 where V represents the tert-butyl carbonyl group, and is available from a number of vendors including Aldrich Chemical Company, Inc., Milwaukee, Wis., USA, and Alfa Aesar, Ward Hill, Mass., USA. This starting material may be combined with hydrazine hydrate in ethanol at about room temperature to give the hydrazone of formula 25, which may or may not be isolated. Reduction of the hydrazone with a reducing agent such as sodium borohydride or the like in ethanol at about room temperature yields the desired hydrazine of formula 3.

A number of intermediates of formula 22 are commercially available from suppliers such as Aldrich Chemical Company, Inc., Milwaukee, Wis., USA; Alfa Aesar, Ward Hill, Mass., USA; Acros Organics, Geel, Belgium; TCI America, Portland, Oreg., USA; Oakwood Products, Inc., West Columbia, S.C., USA; and Fluka Chemie, Buchs, Switzerland. Examples of the commercially available intermediates of formula 22 include: 4-oxo-piperidine-1-carboxylic acid ethyl ester; 1-benzyl-4-piperidone; 4-oxo-piperidine-1-carboxylic acid tert-butyl ester; 4-oxo-piperidine-1-carboxylic acid benzyl ester; 4-oxo-piperidine-1-carboxylic acid 9H-fluoren-9-ylmethyl ester; 4-oxo-piperidine-1-carboxylic acid allyl ester. If additional intermediates of formula 22 are required, they can readily be prepared. For example carbamates of formula 22 where V represents an alkoxycarbonyl group or an aralkoxycarbonyl group may be made by treatment of commercially available 4-hydroxypiperidine with a phenylcarbonate of formula PhO—V in the absence of solvent at about 100° C. followed by oxidation under Swern conditions by treating the resulting alcohol with oxalyl chloride and dimethyl sulfoxide in dichloromethane at low temperature such as at about −70° C., using for example the conditions outline in K. Okano et al. U.S. Pat. No. 5,382,579. Alternatively, commercially available piperidone monohydrate hydrochloride may be treated with a chloroformate of formula Cl—V in tetrahydrofuran at a temperature between about 0° C. and about room temperature to give carbamates of formula 3 where V represents an alkoxycarbonyl group or an aralkoxycarbonyl group, using conditions similar to those described in M. Sunagawa et al. U.S. Pat. No. 4,742,052.

Availability of Compounds of Formula 3 where U Represents Piperidine and V Represents $CH_2Ar$ (1-Benzyl-piperidin-4-yl)-hydrazine is available from Beta Pharma, Inc., New Haven, Conn., USA. Additional compounds of this type can be prepared using reactions similar to those outlined in Schemes 5 and 6, but where V represents $CH_2Ar$. Examples of specific conditions that have been used can be found in K. Matsushita et al. EP 885890 and in C. G. Barber and D. C. Blakemore WO 2006136917.

Availability of Compounds of Formula 22 where V Represents Heteroaryl pounds may be made according to the procedure outlined in Scheme 7. According to this procedure, commercially available 4-piperidinol which has formula 26 reacts with a heteroaromatic reagent which bears a leaving group (for example, a 4-chloropyrimidine, a 2-chloropyridine or a 2-chloropyrazine) in the presence of a base such as triethylamine or diisopropylethylamine in an inert solvent such as acetonitrile at about 80° C. Examples of specific conditions that have been used can be found in J. Yuan et al. US 20070078135; in M. R. Hellberg and A. Rusinko US 20060142307; in B. B. Lohray et al. *J. Med. Chem.* 1999, 42, 2569-2581; and in L.-D. Cantin et al. US 20060084680. An alternative to the nucleophilic substitution is reaction is to carry out the substitution reaction using palladium catalysis, using conditions similar to those described below for the preparation of compounds of formula 29 from compounds of formula 28. As a further alternative, the substitution reaction may be carried out using copper catalysis. For example, commercially available 4-piperidinol which has formula 26 may be treated with a heteroaromatic reagent of formula V—X where X represent a group that can serve as a leaving group under copper catalysis, such as for example bromo or iodo, in the presence of copper iodide in the absence or presence of an inert solvent such as 2-(dimethylamino)-ethanol at a temperature about 100° C. Examples of specific conditions that have been used can be found in B. Cote et al. U.S. Pat. No. 6,200, 993; and in F. Y. Kwong et al. *Org. Lett.* 2002, 4, 581-584. Further information about such metal-catalyzed amination reactions of heterocycles can be found in the literature, for example in S. Wagaw and S. L. Buchwald *J. Org. Chem.* 1996, 61, 7240-7241; in J. P. Wolfe et al. *Acc. Chem. Res.* 1998, 31, 805-818; in Z. Lu and R. J. Twieg *Tetrahedron* 2005, 61, 903-918.

The alcohol intermediate of formula 27 may then be oxidized to the ketone of formula 22 under Swern conditions by treating the alcohol with oxalyl chloride and dimethyl sulfoxide in dichloromethane at low temperature such as at about −70° C., using for example the conditions outlined in K. Okano et al. U.S. Pat. No. 5,382,579.

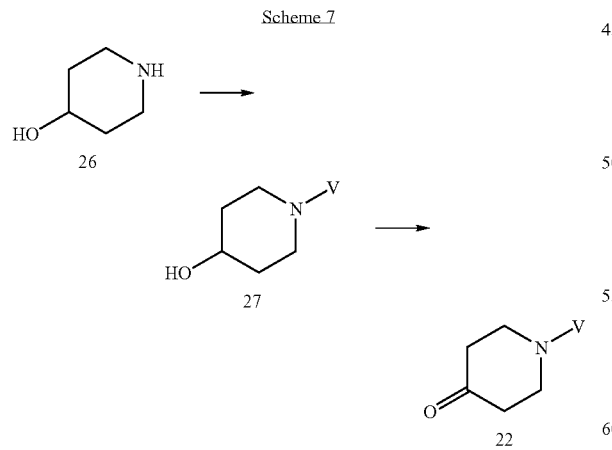

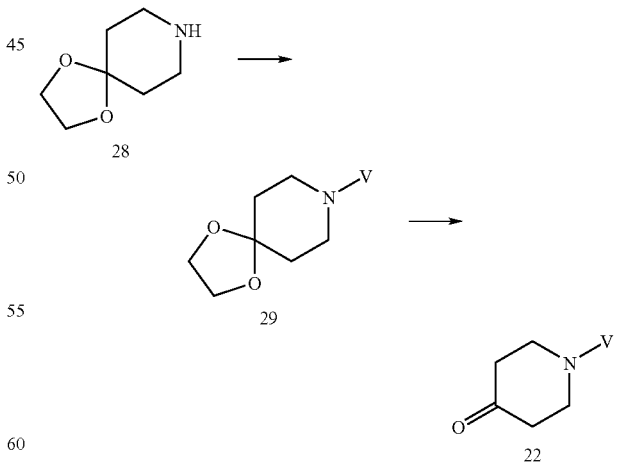

Compounds of Formula 22 where V represents heteroaryl can be prepared according to Scheme 7, using reaction conditions similar to those described above. The compounds of formula 22 where V represents a heteroaryl group can be made using conventional methods. For example, such com- Alternatively, compounds of formula 22 where V represents a heteroaryl group can be made using the procedure outlined in Scheme 8. According to the first step of this process, commercially available 1,4-dioxa-8-azaspiro[4,5] decane which has formula 28 reacts with a heteroaromatic reagent which bears a leaving group (for example, a 4-chloropyrimidine, a 2-chloropyridine or a 2-chloropyrazine) in the presence of a base such as potassium carbonate in an inert solvent such as dimethylformamide or dimethylsulfoxide at about 100° C., or the reaction can be carried out using palladium catalysis by combining the compound of formula 28 with the heteroaromatic reagent bearing a leaving group in the presence of a palladium catalyst such as palladium(II) acetate, a ligand such as 1,3-bis(diphenylphosphine)propane, and a base such as sodium tert-butoxide, in an inert solvent such as toluene at a temperature about 65° C. The conversion of Intermediate 31 to the piperidone 22 may be conveniently carried out by treating the compound of formula 29 with aqueous hydrochloric acid in tetrahydrofuran at a temperature about 60° C. Examples of specific conditions that have been used for these reactions can be found in J. Skotnicki et al. U.S. Pat. No. 4,748,246; in D. J. Kyle et al. US 20070027159; and in U. Schoen et al. *Tetrahedron Lett.* 2007, 48, 2519-2525.

described in R. M. Jones et al. WO 2005007658. The hydroxy group in the intermediate of formula 32 can then be converted to the ketone to give the compound of formula 33 using one of a number of oxidation protocols which are known in the field of organic synthesis. One convenient method is to carry out the oxidation using Swern conditions by treating the alcohol with oxalyl chloride and dimethyl sulfoxide in dichloromethane at low temperature such as at about −70° C. The Swern oxidation and related oxidation reactions have been reviewed in T. T. Tidwell *Synthesis* 1990, 857-870. Another convenient method to effect the oxidation of 32 to 33 is to treat a solution of the alcohol in dichloromethane with a hypervalent iodine reagent such as 2-iodoxybenzoic acid (IBX) or 1,1,1-tris(acetoxy)-1,1-dihydro-1,2-benziodoxol-3-(1H)-one (Dess-Martin periodinane). Oxidation reactions using these reagents have been reviewed in H. Tohma and Y. Kita *Adv. Synth. Catal.* 2004, 346, 111-124.

Availability of Compounds of Formula 3 where U Represents Cyclohexyl and V Represents Substituted 1,2,4-oxadiazol-5-yl

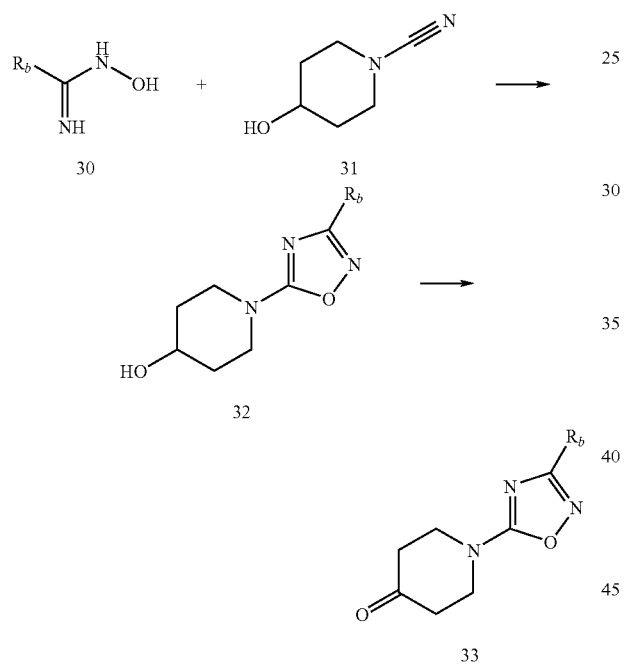

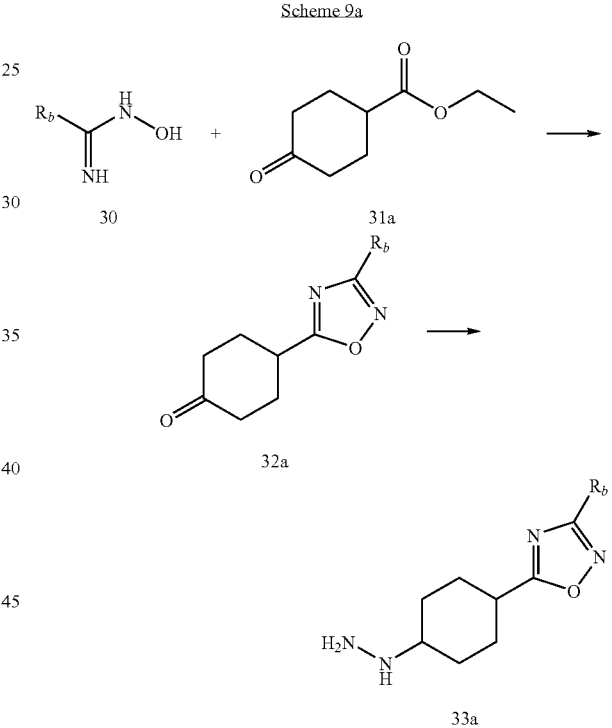

Additional compounds of formula 22 where V represents a heteroaryl group may be made using heteroannulation reactions to generate the heteroaryl ring. An example useful for the preparation of 1-([1,2,4]oxadiazol-5-yl)-piperidin-4-ones is shown in Scheme 9. The preparation of 1-(3-isopropyl-[1,2,4]oxadiazol-5-yl)-piperidin-4-ol according to this route was disclosed in R. M. Jones et al. WO 2005007658; in R. M. Jones et al. WO 2005007647; and in R. M. Jones et al. WO 2005121121. According to this process, the hydroxyamidine of formula 30 (which is conveniently prepared from a nitrile of formula $R_b$—CN by reaction with aqueous hydroxylamine at reflux according to the procedure of A. Hamzé et al. *J. Org. Chem.* 2003, 68, 7316-7321) reacts with the hydroxypiperidine of formula 31 to give the oxadiazole of formula 32. The hydroxypiperidine of formula 31 is conveniently prepared by reaction of commercially available 4-piperidinol with cyanogen bromide in dichloromethane initially at about 0° C. and then at about room temperature according to the conditions Compounds of formula 3 where U represents cyclohexyl and V represents substituted 1,2,4-oxadiazol-5-yl (that is to say, compounds of formula 33a) may be made using heteroannulation reactions to generate the heteroaryl ring. An example of such a process which is useful for the preparation of such compounds is shown in Scheme 9a. According to this process, the hydroxyamidine of formula 30 (which is conveniently prepared as described above) reacts with the ethyl 4-oxocyclohexanecarboxylate (which has formula 31a) to give the oxadiazole of formula 32a. The compound of formula 32a can then be converted into the desired intermediate hydrazine derivative of formula 33a using a reaction which is analogous to that described above in connection with Scheme 6. Thus the compound of formula 32a may be treated with hydrazine hydrate in methanol at the reflux temperature to give an intermediate hydrazone which may or may not be isolated. Reduction of the hydrazone with a reducing agent such as sodium borohydride or the like in an alcoholic solvent such as methanol or ethanol at a temperature between about 0° C. and about room temperature yields the desired hydrazine of formula 33a. In the case where the hydrazone is not isolated, the reaction can be conveniently carried out in a one-pot two step process where the same solvent (for example, methanol) may be used for both steps.

Availability of Reagents of Formula $R^1$—H

Many intermediates of formula $R^1$—H where $R^1$ represents —$OR^2$ or —$NHR^2$ are known or commercially available, including 1-acetyl-4-(4-hydroxyphenyl)piperazine; 3-amino-5-bromo-pyridine; 3-amino-2,6-dimethylpyridine; 5-amino-2-ethoxypyridine; 3-amino-5-fluoro-pyridine; 3-amino-2-methoxy-pyridine; 5-amino-2-methoxypyridine; 3-amino-4-methyl-pyridine; 3-amino-5-methylpyridine; 5-amino-2-methylpyridine; 3-amino-2-picoline; 3-amino-4-(trifluoromethyl)pyridine; 5-amino-2-(trifluoromethyl)-pyridine; 3-bromo-5-hydroxypyridine; 3-chloro-4-fluoro-phenol; 2-chloro-4-hydroxybenzonitrile; 3-chloro-4-hydroxybenzonitrile; 2-chloro-5-hydroxybenzo-trifluoride; 3-chloro-4-hydroxybenzo-trifluoride; 5-chloro-3-pyridinol; 2-cyano-3-hydroxypyridine; 2-cyano-phenol; 4-cyanophenol; 2,6-dichloro-4-(methylsulfonyl)-phenol; 2,3-difluoro-4-hydroxybenzo-nitrile; 2,6-difluoro-4-hydroxybenzonitrile; 2,4-difluorophenol; 3,4-difluorophenol; 2,6-dimethoxy-3-pyridinol; 2,4-dimethyl-3-hydroxypyridine; 2,6-dimethyl-3-hydroxypyridine; 4,6-dimethyl-3-hydroxy-pyridine; 2-fluoro-4-hydroxybenzonitrile; 2-fluoro-4-hydroxybenzonitrile; 3-fluoro-4-hydroxybenzonitrile; 3-fluoro-5-hydroxypyridine; 4-fluoro-3-methylphenol; 2-fluoro-4-(methyl-sulfonyl)aniline; 2-fluorophenol; 3-fluorophenol; 4-fluorophenol; 3-fluoro-5-(trifluoromethyl)-phenol; 4'-hydroxyacetophenone; 4-hydroxybenzenesulfonamide; 4-hydroxy-2,6-dimethyl-benzo-nitrile; 4-hydroxy-3,5-dimethylbenzonitrile; 5-hydroxy-2-methoxypyridine; 4'-hydroxy-2'-methyl-acetophenone; 3-hydroxy-2-methyl-pyridine; 3-hydroxy-2-methylpyridine; 5-hydroxy-2-methyl-pyridine; 3-hydroxy-6-methyl-2-pyridinemethanol; 3-hydroxypyridine; 4-hydroxy-2-(trifluoro-methyl)-benzonitrile; 4-hydroxy-3-(trifluoromethyl)benzonitrile; 4-methoxyphenol; 4-(methyl-sulfonyl)phenol; 2,4,5-trifluoroaniline; 2,4,5-trifluorophenol. These reagents are available from one or more of the following vendors: Acros Organics, Geel, Belgium; Aldrich Chemical Company, Inc., Milwaukee, Wis., USA; Alfa Aesar, Ward Hill, Mass., USA; Apin Chemical Ltd., Abingdon, UK; Apollo Scientific Ltd., Stockport, Cheshire, UK; Combi-Blocks Inc, San Diego, Calif., USA; Fluka Chemie, Buchs, Switzerland; Matrix Scientific, Columbia, S.C., USA; Oakwood Products, Inc., West Columbia, S.C., USA; TCI America, Portland, Oreg., USA; and Tyger Scientific, Ewing, N.J., USA.

Compounds of formula $R^1$—H where $R^1$ represents —$OR^2$ may be commercially available as described above, or they may be known compounds, or they can be synthesized according to a variety of methods which are well known in the field of organic chemistry. A variety of methods for the preparation of phenols is outlined in "Comprehensive Organic Transformations: A Guide to Functional Group Preparations" [R. C. Larock, VCH Publishers, Inc. New York, 1989], for example on pages 483, 490 and 501-504, and also in "Advanced Organic Chemistry" [J. March, 3rd Edition, Wiley Interscience, NY, 1985] on pages 1170-1171. For example, an aryl methyl ether of formula ArOMe, many of which are commercially available or have been reported in the literature, may be treated with a reagent such as boron tribromide in dichloromethane at about room temperature to give the phenol of formula ArOH, using for example conditions reported in S. Bailey et al. U.S. Pat. No. 7,141,586. The same transformation may be achieved by heating the aryl methyl ether as a melt with pyridine hydrochloride at about 190° C., using for example the conditions reported in R. J. Edsall, Jr. et al. *Bioorg. Med. Chem.* 2003, 11, 3457-3474; or by heating the aryl methyl ether with a mixture of 48% aqueous HBr and 33% hydrogen bromide in acetic acid at reflux, using for example the conditions reported in R. Fisher WO 2007054668. As a final but not limiting example, the aryl methyl ether of formula ArOMe may be treated with sodium ethanethiolate in dimethylformamide at about 100° C. to give the phenol of formula ArOH, using for example the conditions described in J. A. Dodge et al. *J. Org. Chem.* 1995, 60, 739-741.

Compounds of formula $R^1$—H where $R^1$ represents —$OR^2$ may be also be synthesized from haloarenes, many examples of which are commercially available, or have been reported in the literature, or can be prepared according to known procedures. According to this process, the haloarene of formula ArBr is treated with potassium hydroxide in the presence of a palladium catalyst such as tris(dibenzylidene-acetone)dipalladium(0) and in the presence of a palladium ligand such as bis(1,1-dimethylethyl)[3,4,5,6-tetramethyl-2',4',6'-tris(1-methylethyl)[1,1'-biphenyl]-2-yl]-phosphine or ditert-butyl (2',4',6'-triisopropylbiphenyl-2-yl)phosphine in a mixture of water and dioxane at about 100° C. Conditions appropriate for this reaction can be found in the literature, for example in K. W. Anderson et al. *J. Am. Chem. Soc.* 2006, 128, 10694-10695.

Compounds of formula $R^1$—H where $R^1$ represents —$NHR^2$ may be commercially available as described above, or they may be known compounds, or they can be synthesized according to a variety of methods which are well known in the field of organic chemistry. A variety of methods for the preparation of anilines is outlined in "Comprehensive Organic Transformations: A Guide to Functional Group Preparations" [R. C. Larock, VCH Publishers, Inc. New York, 1989], for example on pages 399-400, and 412-415. For example, a nitroarene of formula $R^2$—$NO_2$, many of which are commercially available or have been reported in the literature, may be hydrogenated in the presence of a noble metal catalyst such as palladium-on-activated carbon in an inert solvent such as methanol or ethanol at about room temperature to give the aniline of formula $ArNH_2$, for example using the conditions described in S.-R. Choi et al. *J. Med. Chem.* 2007, 50, 3841-3850 or in C. Lazar et al. *J. Med. Chem.* 2004, 47, 6973-6982. The same transformation of nitroarene to aniline can be achieved by treating the nitroarene with tin(II) chloride dihydrate in ethanol at reflux, using for example the conditions described in J. Lau et al. *J. Med. Chem.* 2007, 50, 113-128. Aminoarenes of formula $R^2$—$NH_2$ may also be prepared from haloarenes of formula $R^2$—Br using a palladium-catalyzed amination reaction. According to this process, the haloarene of formula $R^2$—Br is treated with an ammonia equivalent such as benzophenone imine in the presence of a palladium catalyst such as tris(dibenzylideneacetone)dipalladium(0) and in the presence of a palladium ligand such as 2,2'-bis(diphenylphosphino)-1,1'-binaphthyl (BINAP) in the presence of a base such as sodium tert-butoxide in toluene at about 80° C., followed by hydrolysis of the benzophenone imine. Conditions appropriate for this reaction can be found in the literature, for example in J. P. Wolfe et al. *Tetrahedron Lett.* 1997, 38, 6367-6370 and in M. Prashad et al. *J. Org. Chem.* 2000, 65, 2612-2614.

An intermediate of formula $R^1$—H where $R^1$ represents indolin-1-yl monosubstituted with —$SO_2CH_3$ is 5-(methylsulfonyl)-indoline, which is commercially available from Matrix Scientific, Columbia, S.C., USA. A second intermediate of formula $R^1$—H where $R^1$ represents indolin-1-yl mono-substituted with —$SO_2CH_3$ is 6-(methylsulfonyl)-indoline which can be prepared according to reactions that are well known. For example, 6-(methylsulfonyl)-indoline may be prepared using the procedure described in K. D. McCormick et al. US 20080027100.

Scheme 10

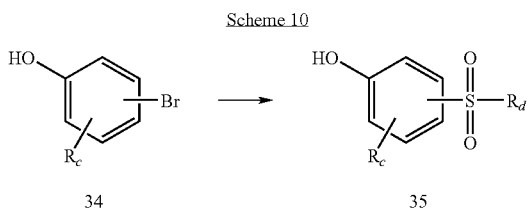

Compounds of formula R¹—H which are hydroxyaryl sulfones can be prepared by copper-catalyzed sulfonylation of a bromophenol of formula 34 with an alkanesulfinic acid of formula $R_dSO_2H$ as shown in Scheme 10. The reaction can be conveniently carried out by reacting the bromophenol of formula 34 with the sodium salt of the alkanesulfinic acid in the presence of copper (I) trifluoromethanesulfonate benzene complex and N,N'-dimethylethylene-diamine in dimethyl sulfoxide at a temperature about 130° C., using the conditions of T. Gharbaoui et al. US 20060155129. Alternatively, the reaction can be carried out by reacting the bromophenol of formula 34 with the sodium salt of the alkanesulfinic acid in the presence of copper iodide and the sodium salt of L-proline in dimethyl sulfoxide at a temperature about 80° C., using the conditions of W. Zhu and D. Ma *J. Org. Chem.* 2005, 70, 2696-2700.

Compounds of formula R¹—H which are hydroxyaryl sulfones may also be made by oxidation of hydroxyaryl sulfides. The oxidation can be conveniently carried out by treating the sulfide with a reagent prepared by mixing periodic acid with chromium trioxide in ethyl acetate. The chromium reaction is carried out at low temperature such as at about −35° C. following the conditions of L. Xu et al. *J. Org. Chem.* 2003, 68, 5388-5391. Alternatively, the oxidation can be carried out using aqueous hydrogen peroxide in acetic acid at a temperature about 100° C., following the conditions of C. Y. Meyers et al. *J. Org. Chem.* 2003, 68, 500-511, or using sodium periodate in aqueous methanol at a temperature of about 4° C. using the conditions of R. T. Walker and A. S. Jones U.S. Pat. No. 5,585,364. The hydroxyaryl sulfide starting material for the oxidation reaction may be commercially available, as is the case for 2-hydroxythioanisole, 2-(ethylthio)phenol, 4-(trifluoromethylthio)phenol, 4-(methylthio)-m-cresol, 2-methyl-4-(trifluoromethylthio)phenol, and 3-(trifluoromethylthio)phenol. Alternatively, the hydroxyaryl sulfide starting material for the oxidation reaction may be prepared from a hydroxybenzenethiol by alkylation with a lower alkyl halide in the presence of a base such as potassium carbonate in an inert solvent such as acetone or 2-butanone at about room temperature, following the conditions of C. Y. Meyers et al. *J. Org. Chem.* 2003, 68, 500-511.

Availability of Compounds of Formula 20

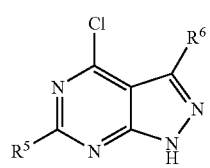

Two intermediates of formula 20 are commercially available. 4-Chloro-1H-pyrazolo[3,4-D]pyrimidine is available from Apollo Scientific Ltd., Stockport, Cheshire, UK and Chontech, Inc., Waterford, Conn. 06385 USA. 3-Bromo-4-chloro-1H-pyrazolo[3,4-D]pyrimidine is available from ChemPacific Corporation, Baltimore, Md. 21224, USA.

Several additional compounds of formula 20 are known in the literature and may be prepared according to known procedures. For example, the synthesis of the following intermediates is described in I. Mitchell et al. US 20050130954 and in N. K. Anand et al. WO 2005117909: 4-chloro-3-cyclopropyl-1H-pyrazolo[3,4-d]pyrimidine; 4-chloro-3-ethyl-1H-pyrazolo[3,4-d]pyrimidine; 4-chloro-3-methyl-1H-pyrazolo[3,4-d]pyrimidine; 4-chloro-3-propyl-1H-pyrazolo[3,4-d]pyrimidine

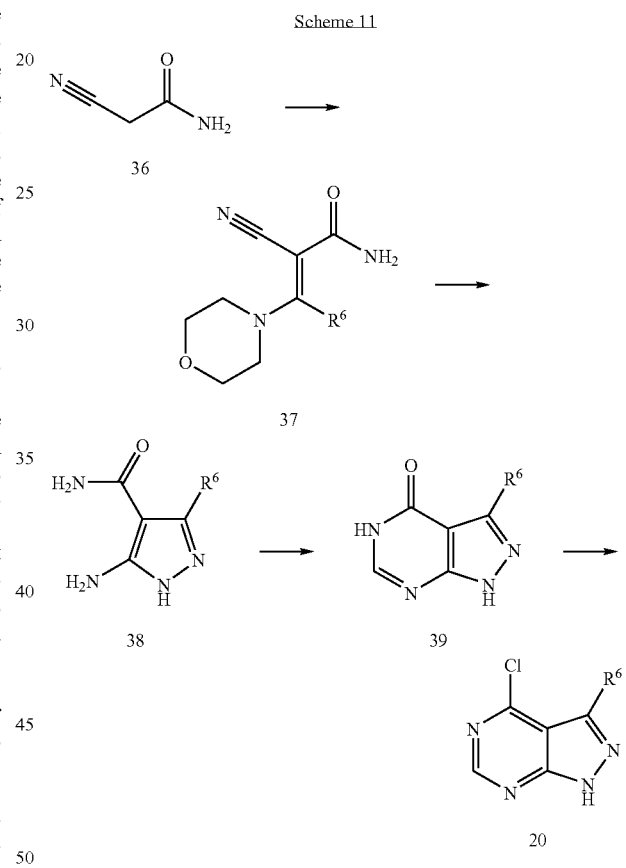

In addition to commercially available reagents, and as an alternative to the procedure outlined in Scheme 3, compounds of formula 20 may be also be made using the procedure outlined in Scheme 11, part of which was reported in GB 1,252,435, and the remaining step in N. K. Anand et al. WO 2005117909. According to this process, cyanoacetamide of formula 36 is treated with an orthoester of formula $R^6C(OEt)_3$ and morpholine in acetonitrile at reflux to give the enamine intermediate 37. This intermediate is then treated with hydrazine hydrate in water at 95° C. to give the aminopyrazole intermediate 38. The aminopyrazole then undergoes a cyclization reaction on treatment with formamide at about 200° C. to give the pyrazolo[3,4-d]pyrimidin-4-one 39, which can be chlorinated as described above for the preparation of intermediate 9 to give the 4-chloro-pyrazolo[3,4-d]pyrimidine of formula 20.

Scheme 12

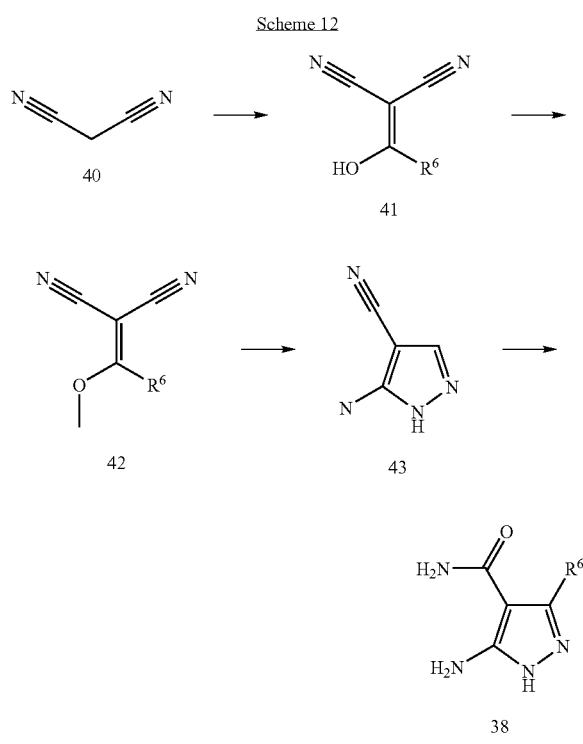

A convenient alternative preparation of an intermediate of formula 39 is shown in Scheme 12, according to a process described in N. K. Anand et al. WO 2005117909. According to this process, malononitrile (which has the formula 40) is treated with sodium hydride in tetrahydrofuran at 0° C. and the resulting anion is acylated using an acid chloride of formula $R^6C(=O)Cl$ to give the intermediate of formula 41. Methylation of 41 by reaction with TMS-diazomethane in a mixture of ether and methanol at 0° C. gives the methyl ether 42, which reacts with hydrazine hydrate in ethanol at 80° C. to give the pyrazole-4-carbonitrile of formula 43. The nitrile is hydrolyzed to the carboxamide by treatment with formic acid at about 110° C. to give the desired intermediate of formula 38.

Several additional compounds of formula 20 are known in the literature and may be prepared according to known procedures. For example, the synthesis of the following intermediates is described in I. Mitchell et al. US 20050130954 and in N. K. Anand et al. WO 2005117909: 4-chloro-3-cyclopropyl-1H-pyrazolo[3,4-d]pyrimidine; 4-chloro-3-ethyl-1H-pyrazolo[3,4-d]pyrimidine; 4-chloro-3-methyl-1H-pyrazolo[3,4-d]pyrimidine; 4-chloro-3-propyl-1H-pyrazolo[3,4-d]pyrimidine. The synthesis of 4-chloro-1H-pyrazolo[3,4-d]pyrimidine has been described a number of times, including in C. Podesva et al. U.S. Pat. No. 3,772,294; in J.-H. Chern et al. *Bioorg. Med. Chem. Lett.* 2004, 14, 2519-2525; and in M. A. Seefeld et al. WO 2007076423.

The invention will now be further described in the Examples below, which are intended as an illustration only and do not limit the scope of the invention.

EXAMPLES

I. Preparation of Preferred Intermediates

Intermediate 1: 2-Fluoro-4-methanesulfonyl-phenol

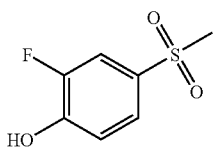

Step 1: 1,2-Difluoro-4-methanesulfonyl-benzene

A mixture of thionyl chloride (12.73 mL, 0.175 mol) and methanesulfonic acid (28.4 mL, 0.438 mol) was heated at reflux overnight and then cooled to 80° C. 1,2-Difluorobenzene (8.64 mL, 88 mmol) was and trifluoromethanesulfonic acid (0.675 mL, 8.8 mmol) were added dropwise. The reaction mixture was then heated at 120° C. for 3 h, cooled to room temperature and poured into ice-water (200 mL). The mixture was extracted three times with ethyl acetate and the combined organic extracts were dried (sodium sulfate), filtered, evaporated, and purified by flash chromatography, eluting with 15% ethyl acetate/hexanes, to give 1,2-difluoro-4-methanesulfonyl-benzene (9.98 g, 59%) as a white solid. $^1$H NMR (300 MHz, CDCl$_3$) δ 3.27 (s, 3H), 7.70-7.84 (m, 2H), 8.02-8.09 (m, 1H).

Step 2: 2-Fluoro-4-methanesulfonyl-1-methoxy-benzene

A solution of potassium hydroxide (85%; 824 mg, 12.5 mmol) in methanol (5 mL) was added to a refluxing solution of 1,2-difluoro-4-methanesulfonyl-benzene (2.00 g, 10.4 mmol) in methanol (10 mL) over 20 min. The resulting mixture was heated at reflux for 1 h and then cooled to room temperature. The solvent was evaporated, water was added, and the resulting precipitate was filtered off, washed with water, and dried in vacuo to give 2-fluoro-4-methanesulfonyl-1-methoxy-benzene (1.8 g, 85%) as a white solid which was used directly in the next step without purification.

Step 3: 2-Fluoro-4-methanesulfonyl-phenol

A solution of 2-fluoro-4-methanesulfonyl-1-methoxy-benzene (1.00 g, 4.9 mmol) in a mixture of 48% aqueous HBr (3 mL) and 33% HBr in acetic acid (1.5 mL) was heated at reflux for 20 h. The reaction mixture was cooled to room temperature and extracted with ethyl acetate. The organic layer was dried (sodium sulfate), filtered, evaporated and chromatographed, eluting with 30% ethyl acetate/hexanes, to give 2-fluoro-4-methanesulfonyl-phenol (800 mg, 86%) as a white solid. Mass spectrum (APCI) m/z M−H=189.

Intermediate 2: 3-Fluoro-4-methanesulfonyl-phenol

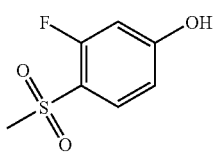

Step 1: 2-Fluoro-1-methylsulfanyl-4-nitro-benzene

A mixture of 3,4-difluoro-nitrobenzene (25 g, 0.157 mol) and sodium methanethiolate (10.5 g, 0.15 mol) was stirred at room temperature overnight. The reaction mixture was poured into water and extracted twice with ether. The extracts were combined, washed with water (twice) and brine, dried (sodium sulfate), filtered, evaporated, and purified by column chromatography, eluting with 17% dichloromethane/hexanes to give 2-fluoro-1-methylsulfanyl-4-nitro-benzene (18.6 g, 63%).

Step 2: 3-Fluoro-4-methylsulfanyl-phenylamine

Iron (33 g, 0.59 mol) was added to 2-fluoro-1-methylsulfanyl-4-nitro-benzene (18.5 g, 99 mmol) in a mixture of acetic acid (350 mL) and water (70 mL). The mixture was stirred for 2 h with periodic swirling, and then the solvents were evaporated. Ethyl acetate and aqueous sodium bicarbonate solution were added and the mixture was filtered through Celite. The aqueous layer was extracted three times with ethyl acetate. The combined organic layers were washed with brine, dried (sodium sulfate), filtered, evaporated, and purified by column chromatography, eluting with 20% ethyl acetate/hexanes to give 3-fluoro-4-methylsulfanyl-phenylamine (15.1 g, 97%).

Step 3: 3-Fluoro-4-methylsulfanyl-phenol

Concentrated sulfuric acid (40 mL) was added to a rapidly stirred mixture of 3-fluoro-4-methylsulfanyl-phenylamine (15.5 g, 99 mmol), water (750 mL) and tetrahydrofuran (23 mL). The mixture was cooled to 0° C. and a solution of sodium nitrite (7.5 g, 163 mmol) in water (15 mL) was added. The resulting mixture was stirred for 2 h at 0° C. and it was then added dropwise over 10 min to a stirring solution of copper(II) nitrate (230 g, 1.2 mol) and copper(I) oxide (12.8 g, 89 mmol) in water (1 L). The reaction mixture was stirred for 15 min and then extracted twice with ethyl acetate. The combined organic layers were washed with brine, dried (sodium sulfate), filtered, evaporated, and purified by column chromatography, eluting with 20% ethyl acetate/hexanes to give 3-fluoro-4-methylsulfanyl-phenol (3.73 g, 24%) as a brown oil.

Step 4: 3-Fluoro-4-methanesulfonyl-phenol

A solution of oxone (19.6 g, 32 mmol) in water (50 mL) was added to a rapidly stirred solution of 3-fluoro-4-methylsulfanyl-phenol (2.47 g, 15.6 mmol) in tetrahydrofuran (100 mL). The mixture was stirred for 1 h at room temperature and then it was poured into aqueous sodium bicarbonate solution. The mixture was extracted three times with ethyl acetate, and the combined extracts were washed with brine, dried (magnesium sulfate), filtered, evaporated, and eluted through a short silica plug with 50% ethyl acetate/hexanes to give 3-fluoro-4-methanesulfonyl-phenol (2.31 g, 78%) as a light brown oil that solidified on standing.

Intermediate 3: 6-Chloro-2-methyl-pyridin-3-ol

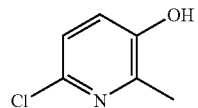

Step 1: Acetic acid 6-chloro-2-methyl-pyridin-3-yl ester

A mixture of boron trifluoride etherate (667 µL, 5.3 mmol) and 1,2-dimethoxyethane (2 mL) was cooled to −15° C. in an ice/acetonitrile bath and stirred at this temperature for 15 min under nitrogen. A solution of 3-amino-6-chloro-2-picoline (Oakwood Products, Inc., West Columbia, S.C., USA; 500 mg, 3.5 mmol) in 1,2-dimethoxyethane (16 mL) was added dropwise at −15° C. and the mixture was stirred at this temperature for 15 min. tert-Butyl nitrite (Aldrich Chemical Company, Inc., Milwaukee, Wis., USA 1.15 mL, 4.2 mmol) was added dropwise and the mixture was stirred at −15° C. for 15 min and then at 0° C. (ice/water bath) for 1 h. Hexane (20 mL) was added and the precipitate was filtered off and washed with hexane. This solid was added to acetic anhydride (5.00 g, 49 mmol) and the mixture was heated at 100° C. for 2 h. The acetic anhydride was evaporated under high vacuum and then 1 M aqueous sodium carbonate was added to pH 9. The mixture was stirred, and then extracted three times with dichloromethane. The solvent was evaporated and the residue purified using a silica gel column, eluting with 0-10% ethyl acetate) to give acetic acid 6-chloro-2-methyl-pyridin-3-yl ester (316 mg, 49%) as an oil.

Step 2: 6-Chloro-2-methyl-pyridin-3-ol

A mixture of acetic acid 6-chloro-2-methyl-pyridin-3-yl ester (316 mg, 1.7 mmol) and 15% aqueous sodium hydroxide (2.5 mL) was stirred at 0° C. for 15 min and then at room temperature for 1 h. 1 M HCl (12 mL) was added and the mixture was extracted 4 times with ethyl acetate. The ethyl acetate was evaporated to give 6-chloro-2-methyl-pyridin-3-ol (235 mg, 96%) as a white powder. $^1$H NMR (300 MHz, DMSO-$d_6$) δ 2.26 (s, 3H), 7.09 (d, 1H, J=8.4 Hz), 7.14 (d, 1H, J=8.4 Hz), 10.08 (br s, 1H).

Intermediate 4: 6-Methanesulfonyl-2-methyl-pyridin-3-ylamine

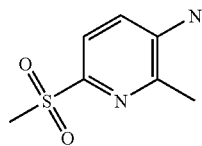

A mixture of 3-amino-6-bromo-2-methylpyridine (ECA International Corporation, Palatine, Ill., USA; 2.0 g, 10.7 mmol), sodium methanesulfinate (Aldrich Chemical Company, Inc., Milwaukee, Wis., USA 5.13 g, 42.8 mmol), copper trifluoromethanesulfonate benzene complex (598 mg, 1.07 mmol), and N,N'-dimethylethylenediamine (115 µL, 1.07 mmol) in dimethylsulfoxide (15 mL) was heated at 150° C. for 4 h. The mixture was cooled and water and ethyl acetate were added. The aqueous layer was extracted three times with ethyl acetate. The combined organic layers were washed twice with water, and then concentrated to approximately 5 mL. This gave a precipitate which was filtered off, washed with a small amount of ethyl acetate and air dried to give 6-Methanesulfonyl-2-methyl-pyridin-3-ylamine (1 g, 50%) as a brown powder. $^1$H NMR (300 MHz, DMSO-$d_6$) δ 2.30 (s, 3H), 3.05 (s, 3H), 6.04 (br s, 2H), 6.98 (d, 1H, J=8.4 Hz), 7.55 (d, 1H, J=8.2 Hz).

Intermediate 5: 4-Ethoxy-2-fluoro-phenol

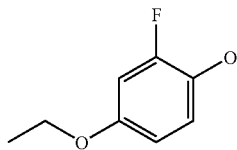

Step 1: 1-Benzyloxy-4-ethoxy-2-fluoro-benzene

Sodium hydride (60% dispersion; 55 mg, 1.38 mmol) was added to a mixture of 4-benzyloxy-3-fluoro-phenol (Bionet Research, Camelford, Cornwall, UK; 250 mg, 1.15 mmol) in dimethylformamide (4 mL). After stirring for 15 min, iodoethane (Aldrich Chemical Company, Inc., Milwaukee, Wis., USA 215 mg, 1.38 mmol) was added and the reaction mixture was stirred overnight. Saturated sodium chloride was added to quench the reaction and the aqueous layer was extracted three times with ethyl acetate. The combined organic extracts were washed with saturated ammonium chloride and saturated sodium carbonate, and then dried over sodium sulfate. The mixture was filtered, concentrated and purified by flash chromatography on silica gel, eluting with 5% ethyl acetate/hexane to give 1-benzyloxy-4-ethoxy-2-fluoro-benzene (270 mg, 96%) as a white solid. $^1$H NMR (300 MHz, DMSO-d$_6$) δ 1.26 (t, 3H, J=7.0 Hz), 3.93 (q, 2H, J=7.0 Hz), 5.07 (s, 2H), 6.62-6.67 (m, 1H), 6.82-6.87 (m, 1H), 7.11 (t, 1H, J=9.0 Hz), 7.31-7.42 (m, 5H).

Step 2: 4-Ethoxy-2-fluoro-phenol

10% Palladium-on-carbon (26 mg, 0.11 mmol) was added to a solution of 1-benzyloxy-4-ethoxy-2-fluoro-benzene (260 mg, 1.06 mmol) in ethyl acetate (20 mL). The reaction mixture was shaken under hydrogen (30 psi) overnight. The reaction mixture was filtered through celite and a pad of silica gel, which was washed with 40% ethyl acetate/hexane. The solvent was removed to give 4-ethoxy-2-fluoro-phenol (155 mg, 94%) as a white solid which was used directly in the next step without further purification. $^1$H NMR (300 MHz, DMSO-d$_6$) δ 1.25 (t, 3H, J=6.9 Hz), 3.89 (q, 2H, J=6.9 Hz), 6.52-6.56 (m, 1H), 6.71-6.85 (m, 2H), 9.21 (s, 1H).

Intermediate 6: 6-Methanesulfonyl-2-methyl-pyridin-3-ol

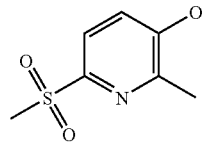

Step 1: Acetic acid 6-methanesulfonyl-2-methyl-pyridin-3-yl ester

A solution of boron trifluoride etherate (670 μL, 5.3 mmol) in dimethylformamide (2 mL) was cooled to −15° C. using an ice-acetonitrile bath, and then stirred for 15 min at this temperature. A solution of 6-methanesulfonyl-2-methyl-pyridin-3-ylamine (Intermediate 4; 653 mg, 3.5 mmol) in 1,2-dimethoxyethane (16 mL) was added dropwise to the solution at −15° C. and the stirring was continued for a further 15 min. tert-Butyl nitrite (Aldrich Chemical Company, Inc., Milwaukee, Wis., USA 90%; 483 mg, 4.2 mmol) was added dropwise, and the reaction mixture was stirred at −15° C. for 15 min and then at 0° C. for 1 h. Hexane (20 mL) was added and the solid was filtered off and washed with hexane. The solid was added to acetic anhydride (5 g, 49 mmol) and the mixture was heated at 100° C. for 1 h. The acetic anhydride was evaporated under high vacuum and then 1 M aqueous sodium carbonate solution was added. The mixture was extracted three times with dichloromethane. The dichloromethane was evaporated and the residue was purified by silica gel column chromatography, eluting with 0-40% ethyl acetate/hexane to give acetic acid 6-methanesulfonyl-2-methyl-pyridin-3-yl ester (331 mg, 41%) as a solid. $^1$H NMR (CDCl$_3$) δ 2.39 (s, 3H), 2.52 (s, 3H), 3.22 (s, 3H), 7.62 (d, 1H, J=8.2 Hz), 7.98 (d, 1H, J=8.4 Hz).

Step 2: 6-Methanesulfonyl-2-methyl-pyridin-3-ol

Acetic acid 6-methanesulfonyl-2-methyl-pyridin-3-yl ester (331 mg, 1.44 mmol) was added to 4 M aqueous sodium hydroxide solution (2 mL) at 0° C. to give a suspension, and the mixture was stirred at 0° C. for 15 min and then at room temperature for 1 h. 2 M Aqueous hydrochloric acid was added to bring the pH to 6, and the mixture was extracted four times with ethyl acetate. The organic layers were combined and the solvent was evaporated under vacuum to give 6-methanesulfonyl-2-methyl-pyridin-3-ol (261 mg, 97%) as a solid. $^1$H NMR (300 MHz, DMSO-d$_6$) δ 2.38 (s, 3H), 3.13 (s, 3H), 7.29 (d, 1H, J=8.4 Hz), 7.72 (d, 1H, J=8.2 Hz), 11.01 (br s, 1H).

Intermediate 7: 2-Methyl-6-[1,2,4]triazol-1-yl-pyridin-3-ol

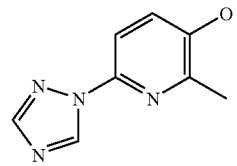

Step 1: 2-Methyl-3-nitro-6-[1,2,4]triazol-1-yl-pyridine

A mixture of 2-bromo-6-methyl-5-nitropyridine (ECA International Corporation, Palatine, Ill., USA; 2 g, 9.2 mmol), 1,2,4-triazole (Aldrich Chemical Company, Inc., Milwaukee, Wis., USA 0.64 g, 9.2 mmol) and potassium carbonate (1.27 g, 9.2 mmol) in dimethylsulfoxide (4 mL) was stirred at room temperature for 1.5 days and then poured into a mixture of ice and water (400 mL). The resulting mixture was stirred until all of the ice melted to give a dark purple slurry. The solid was filtered off to give 2-methyl-3-nitro-6-[1,2,4]triazol-1-yl-pyridine (1.34 g, 71%) as a purple solid with a purity estimated at 93% by LC-MS. This was used directly in the next step without further purification.

Step 2: 2-Methyl-6-[1,2,4]triazol-1-yl-pyridin-3-ylamine

A mixture of zinc (Aldrich, <10 micron; 798 mg, 12.2 mmol) in aqueous ammonium chloride (2 M; 6.1 mL, 12.2 mmol) was cooled to 0° C. using an ice-water bath, and stirred at this temperature for 15 min. A solution of 2-methyl-3-nitro- 6-[1,2,4]triazol-1-yl-pyridine (500 mg, 2.44 mmol) in ethyl acetate (8 mL) was added and the mixture was stirred at 0° C. for 1 h and then at room temperature overnight. The mixture was then filtered through Celite™ to remove zinc dust, and the Celite™ was washed with ethyl acetate and methanol. Water and ethyl acetate were added to the filtrate and the mixture was shaken and then filtered to remove some solid material between the two layers. The aqueous layer was extracted twice with ethyl acetate and the combined organic layers were evaporated to dryness under high vacuum to give 2-methyl-6-[1,2,4]triazol-1-yl-pyridin-3-ylamine (322 mg, 75%) as a yellow solid. $^1$H NMR (300 MHz, DMSO-d$_6$) δ 2.30 (s, 3H), 5.37 (s, 2H), 7.11 (d, 1H, J=8.4 Hz), 7.38 (d, 1H, J=8.4 Hz), 8.13 (s, 1H), 9.03 (s, 1H).

Step 3: Acetic acid 2-methyl-6-[1,2,4]triazol-1-yl-pyridin-3-yl ester

A solution of boron trifluoride etherate (217 µL, 1.7 mmol) in dimethylformamide (1 mL) was cooled to −15° C. using an ice-acetonitrile bath, and then stirred for 15 min at this temperature. A solution of 2-methyl-6-[1,2,4]triazol-1-yl-pyridin-3-ylamine (from Step 2; 200 mg, 1.14 mmol) in 1,2-dimethoxyethane (7 mL) was added dropwise to the solution at −15° C. and the stirring was continued for a further 15 min. tert-Butyl nitrite (Aldrich Chemical Company, Inc., Milwaukee, Wis., USA 90%; 157 mg, 1.4 mmol) was added dropwise, and the reaction mixture was stirred at −15° C. for 15 min and then at 0° C. for 1 h. Hexane (10 mL) was added and the solid was filtered off, washed with hexane, and air-dried. The solid was added to acetic anhydride (5 g, 49 mmol) and the mixture was heated at 100° C. for 1.5 h. The acetic anhydride was evaporated under high vacuum and then 1 M aqueous sodium carbonate solution was added. The mixture was extracted three times with dichloromethane. The dichloromethane was evaporated and the residue was purified by silica gel column chromatography, eluting with 0-40% ethyl acetate/hexane to give acetic acid 2-methyl-6-[1,2,4]triazol-1-yl-pyridin-3-yl ester (125 mg, 50%). $^1$H NMR (CDCl$_3$) δ 2.38 (s, 3H), 2.46 (s, 3H), 7.56 (d, 1H, J=8.8 Hz), 7.77 (d, 1H, J=8.6 Hz), 8.10 (s, 1H), 9.16 (s, 1H).

Step 4: 2-Methyl-6-[1,2,4]triazol-1-yl-pyridin-3-ol

Acetic acid 2-methyl-6-[1,2,4]triazol-1-yl-pyridin-3-yl ester (125 mg, 0.57 mmol) was added to 2 M aqueous sodium hydroxide solution (1.6 mL) at 0° C. to give a slurry, and the mixture was stirred at 0° C. for 20 min and then at room temperature for 3 h. 2 M Aqueous hydrochloric acid was added to bring the pH to 6, and the mixture was extracted four times with ethyl acetate. The organic layers were combined and the solvent was evaporated to dryness to give 2-methyl-6-[1,2,4]triazol-1-yl-pyridin-3-ol (96 mg, 95%) as a white powder. $^1$H NMR (300 MHz, DMSO-d$_6$) δ 2.36 (s, 3H), 7.33 (d, 1H, J=8.7 Hz), 7.51 (d, 1H, J=8.5 Hz), 8.18 (s, 1H), 9.12 (s, 1H), 10.19 (br s, 1H).

Intermediate 8: N-Hydroxy-isobutyramidine

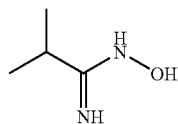

Loosely following the procedure of A. Hamzé et al. (*J. Org. Chem.* 2003, 68, 7316-7321), a mixture of isobutyronitrile (15 g, 217 mmol) and 50% aqueous hydroxylamine (60 mL, 908 mmol) was heated at reflux for 5 h. The solvent was evaporated and the residue was co-evaporated with toluene to remove water. Dichloromethane (100 mL) was added and the solution was dried (sodium sulfate), filtered, evaporated, and dried under high vacuum to give N-hydroxy-isobutyramidine (17.5 g, 93%) as a white solid which was used directly in the subsequent step without further purification.

Intermediate 9: 4-Hydrazino-piperidine-1-carboxylic acid tert-butyl ester

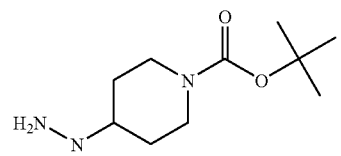

Hydrazine hydrate (100 mL, ~2 mol) was added to a solution of 1-Boc-4-piperidone (available from Aldrich Chemical Company, Inc., Milwaukee, Wis., USA 20.0 g, 100 mmol) in ethanol (180 mL) under nitrogen at room temperature and the reaction mixture was stirred at room temperature overnight. Methanol (180 mL) was added and the reaction mixture was cooled to 0-5° C. Sodium borohydride (14.2 g, 375 mmol) was added in portions and the reaction mixture was allowed to warm to room temperature and stir for 2 h. The solvents were evaporated under reduced pressure, dichloromethane was added and the mixture was washed with water, dried (sodium sulfate), filtered, and evaporated to give 4-hydrazino-piperidine-1-carboxylic acid tert-butyl ester (18.9 g, 88%) as a viscous oil, which was used for the next step without further purification.

Intermediate 10: 4-Hydrazino-piperidine-1-carboxylic acid isopropyl ester hydrochloride

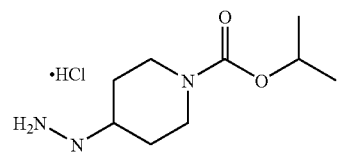

Triethylamine (8.35 g, 60 mmol) was added to a mixture of 4-oxopiperidine hydrate hydrochloride (4.61 g, 30 mmol) and tetrahydrofuran (200 mL) and the resulting poorly soluble mixture was stirred for 1 h. Isopropyl chloroformate (3.3 mL, 34.7 mmol) was added and the mixture was stirred overnight and then filtered. The solvent was evaporated to give a crude intermediate which was dissolved in methanol (80 mL). tert-Butyl carbazate (26 mmol) was added and the mixture was stirred for 2 h. Volatiles were evaporated to give an oil which was dissolved in 50% aqueous acetic acid (80 mL). Sodium cyanoborohydride (35 mmol) was added and the mixture was stirred for 3 h. The reaction mixture was neutralized with 3 M aqueous sodium hydroxide and then extracted three times with dichloromethane. The combined organic extracts were dried, filtered, and evaporated. HCl in dioxane (4 M; 25 mL) and methanol (20 mL) were added and the mixture was stirred for 1 h. Volatiles were evaporated to give 4-hydrazino-piperidine-1-carboxylic acid isopropyl ester hydrochloride (4.02 g, 56%) as a white solid.

Intermediate 11: 4-(3-Isopropyl-[1,2,4]oxadiazol-5-yl)-cyclohexanone

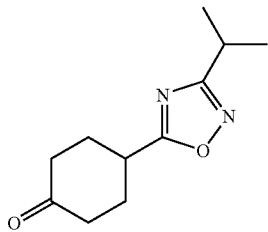

A mixture of N-hydroxy-isobutyramidine (Intermediate 8; 500 mg, 4.9 mmol) and 4 Å molecular sieves in tetrahydrofuran (15 mL) was stirred for 30 min at room temperature. Sodium hydride (60% dispersion; 204 mg, 5.1 mmol) was added and the mixture was heated to 60° C. for 20 min, and then cooled to room temperature. A solution of 4-oxo-cyclohexanecarboxylic acid ethyl ester (TCI America, Portland, Oreg., USA; 1.67 g, 9.8 mmol) in tetrahydrofuran (5 mL) was added. The reaction mixture was heated at reflux for 1 h and then cooled to room temperature and filtered. The solvent was evaporated and the residue was purified by flash chromatography, eluting with 1% methanol/dichloromethane to give 4-(3-isopropyl-[1,2,4]oxadiazol-5-yl)-cyclohexanone (630 mg, 62%) as a white solid.

Intermediate 12: [4-(3-Isopropyl-[1,2,4]oxadiazol-5-yl)-cyclohexyl]-hydrazine

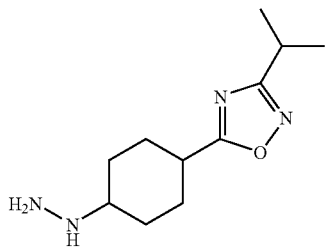

A mixture of 4-(3-isopropyl-[1,2,4]oxadiazol-5-yl)-cyclohexanone (Intermediate 11; 600 mg, 2.9 mmol) and hydrazine hydrate (160 mg, 3.2 mmol) in methanol (2 mL) was heated at reflux for 3 h. The reaction mixture was cooled to 0° C. and sodium borohydride (220 mg, 5.8 mmol) was added portionwise. The reaction mixture was stirred at 0° C. for 4 h and then at room temperature overnight. Water was added and the aqueous layer was extracted three times with ethyl acetate. The combined organic layers were dried (sodium sulfate), filtered, and evaporated to give [4-(3-isopropyl-[1,2,4]oxadiazol-5-yl)-cyclohexyl]-hydrazine (280 mg, 43%) which was used directly in the next step without further purification. Mass spectrum M+=224.

Intermediate 13: N'-[4-(3-Isopropyl-[1,2,4]oxadiazol-5-yl)-cis-cyclohexyl]-hydrazinecarboxylic acid tert-butyl ester and Intermediate 14: N'-[4-(3-Isopropyl-[1,2,4]oxadiazol-5-yl)-trans-cyclohexyl]-hydrazinecarboxylic acid tert-butyl ester

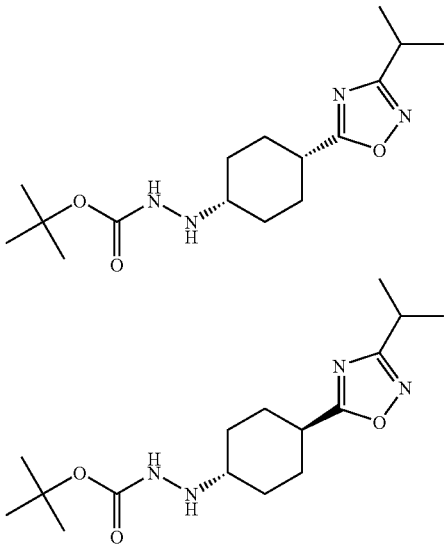

Step 1: N'-[4-(3-Isopropyl-[1,2,4]oxadiazol-5-yl)-cyclohexylidene]-hydrazinecarboxylic acid tert-butyl ester A mixture of 4-(3-isopropyl-[1,2,4]oxadiazol-5-yl)-cyclohexanone (Intermediate 11; 1.6 g, 7.7 mmol) and tert-butyl carbazate (1.12 g, 8.5 mmol) in hexanes (3 mL) was heated at reflux for 3 h, then allowed to cool to room temperature and stand overnight. The white solid was filtered off, washed with hexanes and held under high vacuum to give N'-[4-(3-isopropyl-[1,2,4]oxadiazol-5-yl)cyclohexylidene]-hydrazinecarboxylic acid tert-butyl ester (1.9 g, 77%) as a white solid. $^1$H NMR (300 MHz, DMSO-$d_6$) δ 1.22 (d, 6H, J=6.9 Hz), 1.41 (s, 9H), 1.60-1.76 (m, 2H), 1.98-2.20 (m, 2H), 2.25-2.36 (m, 2H), 2.75-2.84 (m, 1H), 2.96-3.06 (m, 1H), 3.24-3.35 (m, 2H), 9.62 (br s, 1H).

Step 2: N'-[4-(3-Isopropyl-[1,2,4]oxadiazol-5-yl)-cis-cyclohexyl]-hydrazinecarboxylic acid tert-butyl ester and N'-[4-(3-Isopropyl-[1,2,4]oxadiazol-5-yl)-trans-cyclohexyl]-hydrazinecarboxylic acid tert-butyl ester Sodium cyanoborohydride (389 mg, 6.2 mmol) was added in 8 portions to a solution of N'-[4-(3-isopropyl-[1,2,4]oxadiazol-5-yl)-cyclohexylidene]-hydrazinecarboxylic acid tert-butyl ester (from Step 1; 1.9 g, 5.9 mmol) in 50% aqueous acetic acid, and the mixture was stirred at room temperature for 2.5 h. The mixture was cooled slightly using cold water, and then 2 M aqueous sodium hydroxide solution was added to bring the pH to approximately 7. The mixture was extracted four times with dichloromethane, and the combined extracts were washed with water and brine, then dried (sodium sulfate), filtered, evaporated, and held under high vacuum to give a gum. This was purified on a Supelco 100 g column, eluting with 0-3% methanol/dichloromethane, to give N'-[4-(3-isopropyl-[1,2,4]oxadiazol-5-yl)-cis-cyclohexyl]-hydrazinecarboxylic acid tert-butyl ester (309 mg), N'-[4-(3-isopropyl-[1,2,4]oxadiazol-5-yl)-trans-cyclohexyl]-hydrazinecarboxylic acid tert-butyl ester (680 mg, 36%), and some mixed fractions. $^1$H NMR (300 MHz, DMSO-d$_6$) δ 1.22 (d, 6H, J=7.0 Hz), 1.36 (s, 9H), 1.45-1.53 (m, 4H), 1.60-1.68 (m, 2H), 1.94-2.04 (m, 2H), 2.90-3.05 (m, 3H), 4.20-4.25 (m, 1H), 8.16 (br s, 1H).

Intermediate 15: 4-(tert-Butoxycarbonyl-hydrazino)-piperidine-1-carboxylic acid tert-butyl ester

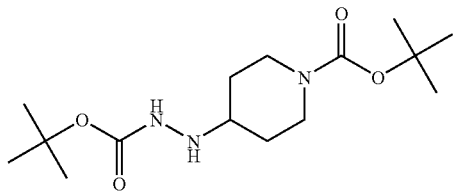

Step 1: 4-(tert-Butoxycarbonyl-hydrazono)-piperidine-1-carboxylic acid tert-butyl ester To a three-neck flask equipped with a mechanical stirrer and a condenser was loaded 1-Boc-4-piperidone (10.0 g, 50.2 mmol), tert-butyl carbazate (7.30 g, 55.2 mmol) and hexanes (20 mL). The mixture was heated to reflux for 3 h, then cooled to room temperature and filtered. The solid was washed with hexanes and dried at room temperature to give 4-(tert-butoxycarbonyl-hydrazono)piperidine-1-carboxylic acid tert-butyl ester (14.84 g, 94%) as a white powder. $^1$H NMR (CDCl$_3$) δ 1.46 (s, 9H), 1.50 (s, 9H), 2.32 (m, 2H), 2.52 (m, 2H), 3.55 (m, 4H), 7.48 (br, 1H).

Step 2: 4-(tert-Butoxycarbonyl-hydrazino)-piperidine-1-carboxylic acid tert-butyl ester A solution of 4-(tert-butoxycarbonyl-hydrazono)-piperidine-1-carboxylic acid tert-butyl ester (from Step 1; 12.0 g, 38.3 mmol) in methanol (60 mL) and tetrahydrofuran (120 mL) was cooled to 0° C. Sodium borohydride (9.0 g, 238 mmol) was added slowly in three portions in 15-30 min intervals. The reaction mixture was heated to 60° C. for 2 h and then cooled to room temperature. A solution of 20% brine (90.0 mL) and 10% sodium bicarbonate (200 mL) were slowly added to the stirred reaction mixture. The organic layer was separated and the aqueous layer was extracted with methyl tert-butyl ether (2×50 mL). The combined organic layers were washed with brine (3×50 mL) and concentrated. To the residue was added acetonitrile (15 mL). The mixture was concentrated again to remove trace amounts of water, to give 4-(tert-butoxycarbonyl-hydrazino)-piperidine-1-carboxylic acid tert-butyl ester (12.0 g, 99%) as a white solid. $^1$H NMR (CDCl$_3$) δ 1.27 (m, 2H), 1.44 (s, 18H), 1.76 (m, 2H), 2.84 (t, 2H, J=11.7 Hz), 3.00 (m, 1H), 3.95 (m, 3H), 6.03 (br, 1H).

Intermediate 16: 4,6-Dichloro-pyrimidine-5-carbaldehyde

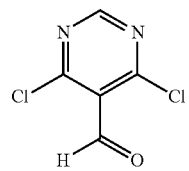

Phosphorous oxychloride (249 mL, 671 mmol) was added slowly to dimethylformamide (75 mL) with continuous stirring at 0° C. under nitrogen. After the addition was complete, was added 4,6-dihydroxypyrimidine (available from Aldrich Chemical Company, Inc., Milwaukee, Wis., USA 50.0 g, 446 mmol) and stirred at room temperature for 2 hours followed by refluxing (135° C.) for 3 hours. The reaction mixture was cooled to room temperature, poured into chilled water with stirring and extracted with diethyl ether (3×200 mL). The combined organic extracts were dried over anhydrous sodium sulfate and concentrated in vacuo to give 4,6-dichloro-pyrimidine-5-carbaldehyde (54.0 g, 68%) as a white solid, which was used for the next step without further purification. $^1$H NMR (400 MHz, CDCl$_3$) δ 8.88 (s, 1H), 10.45 (s, 1H).

Intermediate 17: 1-(4,6-Dichloro-pyrimidin-5-yl)-ethanone

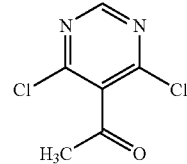

Step 1. 1-(4,6-Dichloro-pyrimidin-5-yl)-ethanol

Methylmagnesium bromide solution (1.4 M in toluene/tetrahydrofuran (75:25); 2.4 mL, 3.4 mmol) was added to a solution of 4,6-dichloro-pyrimidine-5-carbaldehyde (Intermediate 16; 500 mg, 2.8 mmol) in tetrahydrofuran at 0° C. under nitrogen. The reaction mixture was stirred at 0° C. for 10 min and then at room temperature for 30 min. Water was added and the mixture was extracted with ethyl acetate (3×25 mL). The organic layers were washed with water and brine, dried (sodium sulfate), filtered, and evaporated to give 1-(4,6-dichloro-pyrimidin-5-yl)-ethanol (540 mg, 100%) which was used directly in the next step without further purification. $^1$H NMR (300 MHz, CDCl$_3$) δ 1.19 (d, 3H, J=6.3 Hz), 2.62 (br s, 1H), 5.48-5.54 (m, 1H), 8.68 (s, 1H).

Step 2. 1-(4,6-Dichloro-pyrimidin-5-yl)-ethanone 1,1,1-Tris(acetyloxy)-1,1-dihydro-1,2-benziodoxol-3-(1H)-one (Dess-Martin periodinane; 1.3 g, 3.1 mmol) was added to a solution of 1-(4,6-dichloro-pyrimidin-5-yl)-ethanol (from Step 1; 540 mg, 2.8 mmol) in dichloromethane at 0° C. under nitrogen. The reaction mixture was stirred at 0° C. for 5 min and then at room temperature for 90 min. Saturated aqueous sodium bicarbonate solution was added and the mixture was extracted with dichloromethane (3×50 mL). The organic layers were washed with water and brine, dried (sodium sulfate), filtered, and evaporated. The residue was triturated twice with ether/petroleum ether (2:1), the solvent was decanted and the solvent was evaporated to give 1-(4,6-dichloro-pyrimidin-5-yl)-ethanone (500 mg, 93%) which was used directly in the next step without further purification. $^1$H NMR (300 MHz, CDCl$_3$) δ 2.64 (s, 3H), 8.83 (s, 1H).

Intermediate 18: 4-Chloro-6-(2-methyl-pyridin-3-yloxy)-pyrimidine-5-carbaldehyde

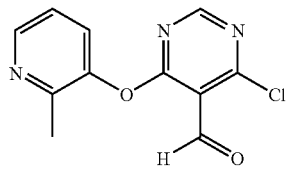

Potassium carbonate (10.22 g, 74 mmol) was added to a mixture of 4,6-dichloro-pyrimidine-5-carbaldehyde (Intermediate 16; 5.0 g, 28.3 mmol) and 3-hydroxy-2-methylpyridine (Aldrich Chemical Company, Inc., Milwaukee, Wis., USA 3.66 g, 33.5 mmol) in anhydrous dimethylformamide (100 mL). The mixture was stirred at room temperature. The mixture was cooled to 0° C. and water (100 mL) was slowly added. The temperature rose to 18° C. during the addition. The mixture was recooled to 0° C. and stored in the freezer overnight. The precipitate was filtered off. LC-MS indicated that this was the result of the addition of two 3-hydroxy-2-methylpyridine moieties to the pyrimidine. The mother liquor was extracted with ethyl acetate and the extract was concentrated and purified using a Supelco 100 g column, eluting with 0-5% methanol/dichloromethane. Fractions containing the desired product were pooled, concentrated, and held under vacuum to give 4-chloro-6-(2-methyl-pyridin-3-yloxy)-pyrimidine-5-carbaldehyde (521 mg, 7%) as a solid. $^1$H NMR (300 MHz, DMSO-$d_6$) δ 2.32 (s, 3H), 7.36 (dd, 1H, J=4.8, 8.2 Hz), 7.66 (dd, 1H, J=1.2, 8.2 Hz), 7.8.41 (dd, 1H, J=1.5, 4.8 Hz), 8.72 (s, 1H).

Intermediate 19: 4-(4-Chloro-pyrazolo[3,4-d]pyrimidin-1-yl)-piperidine-1-carboxylic acid tert-butyl ester

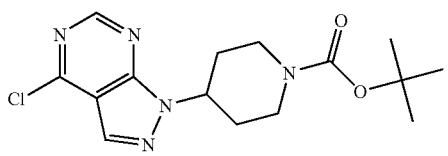

Method A

Triethylamine (19.5 mL, 140 mmol) was added to a stirred solution of 4-hydrazino-piperidine-1-carboxylic acid tert-butyl ester (Intermediate 9; 15.0 g, 69.7 mmol) and 4,6-dichloro-pyrimidine-5-carbaldehyde (Intermediate 16; 12.34 g, 69.7 mmol) in toluene (100 mL) at room temperature under nitrogen and the resulting mixture was heated to reflux for 6 hours. The solvent was removed in vacuo and the crude reaction mixture was purified by column chromatography (silica gel, 100-200 mesh; 5% ethyl acetate/hexanes) to give 4-(4-chloro-pyrazolo[3,4-d]pyrimidin-1-yl)-piperidine-1-carboxylic acid tert-butyl ester (8.0 g, 34%) as a white solid. $^1$H NMR (400 MHz, CDCl$_3$) δ 1.43 (s, 9H), 1.97-2.00 (m, 2H), 2.19-2.29 (m, 2H), 2.90-3.00 (br s, 2H), 4.25-4.35 (m, 2H), 4.92-5.00 (m, 1H), 8.15 (s, 1H), 8.74 (s, 1H); $^{13}$C NMR (100 MHz, CDCl$_3$) δ 28.3, 31.1, 42.8, 55.3, 79.8, 113.8, 131.8, 152.4, 154.1, 154.4, 154.7. HRMS Calcd. for C$_{15}$H$_{21}$ClN$_5$O$_2$ (MH+): 338.1379. Found: 338.1377.

Method B

A solution of triphenylphosphine (30.5 g, 116.3 mmol) in anhydrous tetrahydrofuran (450 mL) was cooled to 0° C. under nitrogen. Diisopropylazodicarboxylate (22.9 mL, 116.3 mmol) was added dropwise over 10 min. The mixture was stirred at 0° C. for 15 min and then 1-Boc-4-hydroxypiperidine (Aldrich, 20.3 g, 100 mmol) was added. The mixture was stirred at 0° C. for 10 min and then solid 4-chloro-1H-pyrazolo[3,4-d]pyrimidine (Intermediate 30; 13.0 g, 84 mmol) was added in portions. The flask containing Intermediate 30 was rinsed with THF and the washings were added to the reaction mixture. The reaction mixture was stirred in the ice-bath for 3 h, and then stored in the refrigerator overnight. The reaction mixture was evaporated to dryness and the residue was taken up in a mixture of ether and hexanes (2:1; 1 L). The mixture was stirred at room temperature for 20 min, and then the white solid was filtered off and washed with a mixture of ether and hexanes (2:1). The filtrate was evaporated to dryness to give a yellow solid. This was taken up in toluene with warming, applied to a column of flash silica gel (90 mm×6") and eluted with 20-25% ethyl acetate/hexanes to give 4-(4-chloro-pyrazolo[3,4-d]pyrimidin-1-yl)-piperidine-1-carboxylic acid tert-butyl ester (11.0 g, 39%) along with mixed fractions which were repurified by flash chromatography.

Method C

A solution of 4-(tert-butoxycarbonyl-hydrazino)-piperidine-1-carboxylic acid tert-butyl ester (Intermediate 15; 1.80 g, 5.71 mmol), diisopropylethylamine (2.0 mL, 11.3 mmol), and 4,6-dichloropyrimidine-5-carbaldehyde (Intermediate 16; 1.00 g, 5.65 mmol) in tetrahydrofuran (10 mL) was stirred at 0° C. for 30 min, then it was warmed up to rt and stirred for 4 h. The solid was filtered. The filtrate was washed with brine (10 mL) and the aqueous layer was extracted with methyl tert-butyl ether (1×10 mL). The combined organic layers were washed with brine (1×10 mL) and concentrated to give an orange-red semi-solid. Toluene (10 mL) was added and the solution was heated to 110° C. for 6 h. The reaction mixture was cooled to room temperature and concentrated to give a semi-solid. This crude solid was dissolved in the minimum amount of dichloromethane and passed through a pad of silica gel, eluting with 9% ethyl acetate/hexanes. Concentration of fractions homogeneous for the product gave 4-(4-chloropyrazolo[3,4-d]pyrimidin-1-yl)-piperidine-1-carboxylic acid tert-butyl ester (1.33 g, 70%) as a cream white solid. $^1$H NMR (CDCl$_3$) δ 1.49 (s, 9H), 1.9-2.1 (m, 2H), 2.25 (qd, 2H, J=12.6, 4.5 Hz), 2.97 (t, 2H, J=12.0 Hz), 4.30 (br, 2H), 4.96 (tt, 1H, J=11.4, 4.2 Hz), 8.15 (s, 1H), 8.75 (s, 1H).

Intermediate 20: 4-(4-Chloro-pyrazolo[3,4-d]pyrimidin-1-yl)-piperidine-1-carboxylic acid isopropyl ester

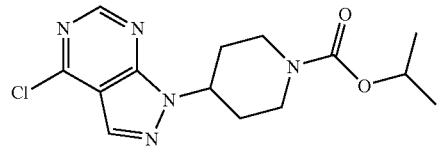

4-(4-Chloro-pyrazolo[3,4-d]pyrimidin-1-yl)-piperidine-1-carboxylic acid isopropyl ester was prepared from the reaction of 4-hydrazino-piperidine-1-carboxylic acid isopropyl ester (Intermediate 10) and 4,6-dichloro-pyrimidine-5-carbaldehyde (Intermediate 16) using the procedure described for 4-chloro-1-[4-(3-isopropyl-[1,2,4]oxadiazol-5-yl)-cyclohexyl]-1H-pyrazolo[3,4-d]pyrimidine (Intermediate 23). The product was purified by flash chromatography eluting with 40% ethyl acetate/hexanes to give 4-(4-chloro-pyrazolo[3,4-d]pyrimidin-1-yl)-piperidine-1-carboxylic acid isopropyl ester as a white solid. Mass spectrum M+=323.0.

Intermediate 21: 4-(4-Chloro-3-methyl-pyrazolo[3,4-d]pyrimidin-1-yl)-piperidine-1-carboxylic acid isopropyl ester

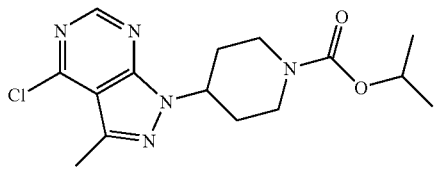

Triethylamine (0.33 mL, 2.4 mmol) was added to a stirred mixture of 4-hydrazino-piperidine-1-carboxylic acid isopropyl ester hydrochloride (Intermediate 10; 188 mg, 0.8 mmol) and 1-(4,6-dichloro-pyrimidin-5-yl)-ethanone (Intermediate 17; 150 mg, 0.8 mmol) in toluene (5 mL) at room temperature under nitrogen and the resulting mixture was heated to reflux for 8 hours. The solvent was removed in vacuo and the crude reaction mixture was purified on a flash silica column (30 mm×4") eluting with 10-33% ethyl acetate/hexanes to give 4-(4-chloro-3-methyl-pyrazolo[3,4-d]pyrimidin-1-yl)-piperidine-1-carboxylic acid isopropyl ester (90 mg, 33%). $^1$H NMR (300 MHz, DMSO-d$_6$) δ 1.19 (d, 6H, J=6.3 Hz), 1.86-1.99 (m, 4H), 2.63 (s, 3H), 2.94-3.10 (m, 2H), 4.04-4.15 (m, 1H), 4.74-4.82 (m, 1H), 4.91-4.98 (m, 1H), 8.77 (s, 1H).

Intermediate 22: 4-Chloro-1-[1-(3-isopropyl-[1,2,4]oxadiazol-5-yl)-piperidin-4-yl]-1H-pyrazolo[3,4-d]pyrimidine

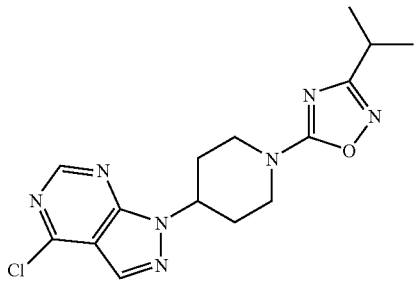

Step 1: 4-Hydroxy-piperidine-1-carbonitrile

A slurry of sodium bicarbonate (24.9 g, 296 mmol) in water (15 mL) was cooled in an ice-bath and a solution of 4-hydroxypiperidine (15 g, 148 mmol) in dichloromethane (25 mL) was added. With rapid stirring, a solution of cyanogen bromide (18.8 g, 177 mmol) in dichloromethane (25 mL) was added dropwise over 15 min. The reaction was stirred for 30 min at ~4° C., then the cooling bath was removed and the reaction mixture was stirred overnight at room temperature. Sodium carbonate (3 g) and magnesium sulfate (15 g) were added and the mixture was stirred for 30 min, and then filtered. The solids were washed with dichloromethane (50 mL) and the solvents were evaporated from the combined filtrate and washings to give 4-hydroxy-piperidine-1-carbonitrile (15.6 g, 84%) which was used directly in the subsequent step without further purification.

Step 2: 1-(3-Isopropyl-[1,2,4]oxadiazol-5-yl)-piperidin-4-ol

A solution of zinc chloride (1 M in ether; 9.5 mL, 9.5 mmol) was added dropwise over 10 min to a solution of N-hydroxy-isobutyramidine (Intermediate 8; 8.28 g, 81 mmol) and 4-hydroxy-piperidine-1-carbonitrile (from Step 1; 10.0 g, 79 mmol) in ethyl acetate (400 mL). The mixture was stirred at room temperature for 20 min, then the precipitate was filtered off and washed with ether (2×50 mL). A mixture of concentrated HCl (50 mL) and ethanol (100 mL) was added to the precipitate, and the resulting mixture was heated at reflux for 1 h, cooled to room temperature and filtered. The volume of the filtrate was reduced to approximately 50 mL. Water (80 mL) was added and the mixture was made slightly basic by the addition of solid sodium carbonate. Dichloromethane (150 mL) was added. The mixture was filtered and the solids were washed with dichloromethane. The combined organic solutions were dried (magnesium sulfate), filtered, evaporated, and dried under high vacuum to give crude 1-(3-isopropyl-[1,2,4]oxadiazol-5-yl)-piperidin-4-ol (6.7 g, 40%). $^1$H NMR (CDCl$_3$, 300 MHz) showed that the isolated material contained about 10 mol % of unreacted 4-hydroxy-piperidine-1-carbonitrile and minor solvent related impurities. This material was used directly in the next step without further purification.

Step 3: 1-(3-Isopropyl-[1,2,4]oxadiazol-5-yl)-piperidin-4-one

A solution of dimethylsulfoxide (1.07 g, 13.7 mmol) in anhydrous dichloromethane (30 mL) was added dropwise over 10 min to oxalyl chloride (2M in dichloromethane; 5.44 mL, 10.9 mmol) which had been cooled to −60° C. The reaction mixture was stirred at −60° C. for 20 min, and then a solution of crude 1-(3-isopropyl-[1,2,4]oxadiazol-5-yl)-piperidin-4-ol (from Step 2; 2.00 g, ~9.5 mmol) in anhydrous dichloromethane (100 mL) was added dropwise over 20 min. The reaction mixture was stirred at −60° C. for 1 h, and then triethylamine (2.68 g, 26.5 mmol) was added. The reaction mixture was stirred at −60° C. for 30 min, then allowed to warm to room temperature and stir for 1 h. Dichloromethane (200 mL) was added, and then the mixture was washed with water (3×150 mL) and brine (150 mL). The organic layer was dried (sodium sulfate), filtered, evaporated, and dried under high vacuum to give 1-(3-isopropyl-[1,2,4]oxadiazol-5-yl)-piperidin-4-one (1.75 g, 88%) as a light tan solid. Mass spectrum (ES) MH+=209.9.

Step 4: [1-(3-Isopropyl-[1,2,4]oxadiazol-5-yl)-piperidin-4-yl]-hydrazine trifluoroacetic acid salt A mixture of 1-(3-isopropyl-[1,2,4]oxadiazol-5-yl)-piperidin-4-one (from Step 3; 441 mg, 2.1 mmol) and tert-butyl-carbazate (278 mg, 2.1 mmol) in anhydrous methanol (8 mL) was stirred overnight at room temperature. The solvent was evaporated and the residue was held under high vacuum for 1 h to give a light tan foam (663 mg). 50% Acetic acid (6 mL) was added. Sodium cyanoborohydride (138 mg, 2.2 mmol) was added in three portions and the reaction mixture was stirred at room temperature for 3 h. The pH was adjusted to 7 by the addition of 2N NaOH, and then the mixture was extracted with dichloromethane (3×20 mL). The combined organic layers were washed with water (50 mL) and brine (50 mL), dried (sodium sulfate), filtered, evaporated and held under high vacuum for 1 h to give a white solid (420 mg). A 50% solution of trifluoroacetic acid in dichloromethane (1 mL) was added and the mixture was stirred for 1 h. The solvents were evaporated. Tetrahydrofuran (3 mL) was added, followed by Silia Bond Carbonate (Silicycle, Quebec City, Canada; 0.7 mmol/g loading; 1.5 g, 1.1 mmol). The mixture was stirred slowly at room temperature for 90 min, then the resin was filtered off and washed with tetrahydrofuran (2 mL). The solvent was evaporated and the residue was purified on a silica column (ISCO 12 g) eluting with 0-5% methanol/dichloromethane to give [1-(3-isopropyl-[1,2,4]oxadiazol-5-yl)-piperidin-4-yl]-hydrazine trifluoro-acetic acid salt (378 mg, 53%).

Step 5: 4-Chloro-1-[1-(3-isopropyl-[1,2,4]oxadiazol-5-yl)-piperidin-4-yl]-1H-pyrazolo[3,4-d]pyrimidine SiliaBond Carbonate (Silicycle, Quebec City, Canada; 0.69 mmol/g loading; 395 mg, 0.27 mmol) was added to a mixture of [1-(3-isopropyl-[1,2,4]oxadiazol-5-yl)-piperidin-4-yl]-hydrazine trifluoroacetic acid salt (from Step 4; 185 mg, 0.55 mmol) and 4,6-dichloro-pyrimidine-5-carbaldehyde (Intermediate 16; 81 mg, 0.45 mmol) in anhydrous acetonitrile (3 mL). The reaction mixture was heated in a Biotage Optimizer microwave at 140° C. for 5 min. The resin was filtered off and washed with acetonitrile. The solvent was evaporated and the residue was purified on a silica column (ISCO 12 g) eluting with 0-3% methanol/dichloromethane to give 4-chloro-1-[1-(3-isopropyl-[1,2,4]oxadiazol-5-yl)-piperidin-4-yl]-1H-pyrazolo[3,4-d]pyrimidine (31 mg, 20%). Mass spectrum (ES) MH+=348.

Intermediate 23: 4-Chloro-1-[4-(3-isopropyl-[1,2,4]oxadiazol-5-yl)-cyclohexyl]-1H-pyrazolo[3,4-d]pyrimidine

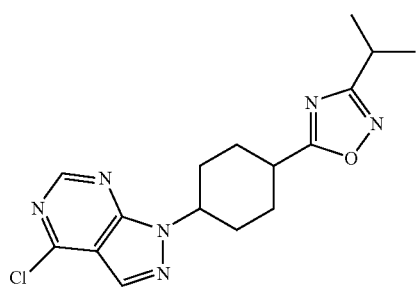

A mixture of [4-(3-isopropyl-[1,2,4]oxadiazol-5-yl)-cyclohexyl]-hydrazine (Intermediate 12; 230 mg, 1.0 mmol), 4,6-dichloro-pyrimidine-5-carbaldehyde (Intermediate 16; 182 mg, 1.0 mmol) and sodium carbonate (218 mg, 2.1 mmol) in acetonitrile was heated in the microwave at 140° C. for 10 min. Saturated aqueous sodium carbonate was added and the reaction mixture was filtered. The filtrate was extracted with ethyl acetate, and the combined organic layers were dried (sodium sulfate), filtered, evaporated, and purified by flash chromatography, eluting with 10% ethyl acetate/hexanes to give 4-chloro-1-[4-(3-isopropyl-[1,2,4]oxadiazol-5-yl)-cyclohexyl]-1H-pyrazolo[3,4-d]pyrimidine (125 mg, 35%) as a white solid. Mass spectrum M+=346.

Intermediate 24: 4-(4,6-Dichloro-pyrazolo[3,4-d]pyrimidin-1-yl)-piperidine-1-carboxylic acid tert-butyl ester

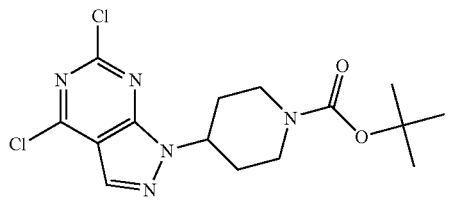

4-(4,6-Dichloro-pyrazolo[3,4-d]pyrimidin-1-yl)-piperidine-1-carboxylic acid tert-butyl ester was prepared using Method C described for the preparation of Intermediate 19, by the reaction of 4-(tert-butoxycarbonyl-hydrazino)-piperidine-1-carboxylic acid tert-butyl ester (Intermediate 15) with 2,4,6-trichloro-pyrimidine-5-carbaldehyde (which can be prepared from barbituric acid using the procedure of J. Dehnert DE 3603797).

Intermediate 25: 4-Chloro-1-[4-(3-isopropyl-[1,2,4]oxadiazol-5-yl)-cis-cyclohexyl]-1H-pyrazolo[3,4-d]pyrimidine

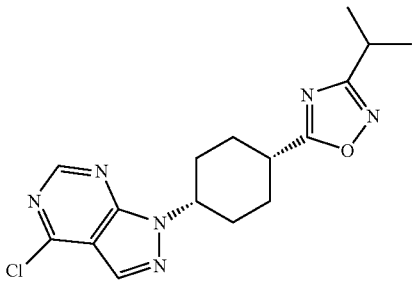

A solution of N'-[4-(3-isopropyl-[1,2,4]oxadiazol-5-yl)-cis-cyclohexyl]-hydrazinecarboxylic acid tert-butyl ester (Intermediate 13; 309 mg, 2.03 mmol) in tetrahydrofuran (3 mL) was added to a cooled (0° C.) solution of 4,6-dichloro-pyrimidine-5-carbaldehyde (Intermediate 16; 169 mg, 0.95 mmol) and diisopropylethylamine (337 µL, 1.9 mmol) in tetrahydrofuran (2 mL), and the mixture was stirred at 0° C. for 30 min and then at room temperature for 5 h. The mixture was filtered, and the filtrate was washed with brine. The aqueous layer was extracted with methyl tert-butyl ether and the organic extracts were combined, washed with brine, dried (sodium sulfate), filtered, evaporated, and held under high vacuum. Toluene (10 mL) was added and the mixture was held at 110° C. overnight. The solvent was evaporated and the residue was purified on a Supelco 23 g column, eluting with 0-3% methanol/dichloromethane to give 4-chloro-1-[4-(3-isopropyl-[1,2,4]oxadiazol-5-yl)-cis-cyclohexyl]-1H-pyrazolo[3,4-d]pyrimidine (211 mg, 64%).

Intermediate 26: 4-Chloro-1-[4-(3-isopropyl-[1,2,4]oxadiazol-5-yl)-trans-cyclohexyl]-1H-pyrazolo[3,4-d]pyrimidine

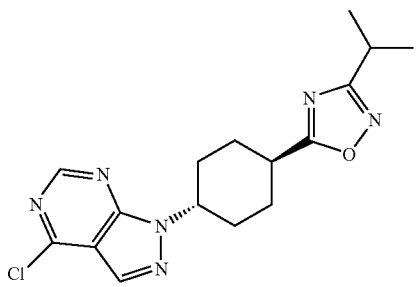

A solution of N'-[4-(3-isopropyl-[1,2,4]oxadiazol-5-yl)-trans-cyclohexyl]-hydrazinecarboxylic acid tert-butyl ester (Intermediate 13; 691 mg, 2.03 mmol) in tetrahydrofuran (3 mL) was added to a cooled (0° C.) solution of 4,6-dichloro-pyrimidine-5-carbaldehyde (Intermediate 16; 361 mg, 2.03 mmol) and diisopropylethylamine (718 µL, 4.06 mmol) in anhydrous tetrahydrofuran (6 mL), and the mixture was stirred at 0° C. for 30 min and then at room temperature for 5 h. The mixture was filtered, and the filtrate was washed with brine. The aqueous layer was extracted with methyl tert-butyl ether and the organic extracts were combined, washed with brine, dried (sodium sulfate), filtered, evaporated, and held under high vacuum. Toluene (15 mL) was added and the mixture was held at 110° C. overnight. The solvent was evaporated and the residue was purified on a Supelco 50 g column, eluting with 0-3% methanol/dichloromethane to give 4-chloro-1-[4-(3-isopropyl-[1,2,4]oxadiazol-5-yl)-trans-cyclo-hexyl]-1H-pyrazolo[3,4-d]pyrimidine (489 mg, 69%). $^1$H NMR (300 MHz, DMSO-$d_6$) δ 1.24 (d, 6H, J=6.9 Hz), 1.74-1.88 (m, 2H), 2.04-2.28 (m, 6H), 2.98-3.08 (m, 1H), 3.11-3.22 (m, 1H), 4.91-4.97 (m, 1H), 8.49 (s, 1H), 8.86 (s, 1H).

Intermediate 27: 4-(4-Methanesulfonyl-phenoxy)-1-piperidin-4-yl-1H-pyrazolo[3,4-d]pyrimidine trifluoroacetate salt

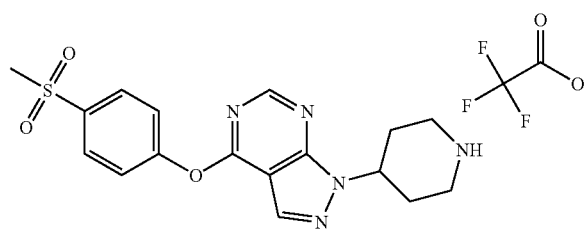

Trifluoroacetic acid (38.0 mL, 512 mmol) was added to a cooled solution of 4-[4-(4-methanesulfonyl-phenoxy)-pyrazolo[3,4-d]pyrimidin-1-yl]-piperidine-1-carboxylic acid tert-butyl ester (Example 59; 12.0 g, 25.4 mmol) in dichloromethane (70 mL) at about 0° C. The reaction mixture was stirred for 3 h. The solvent was evaporated under reduced pressure, and the residue was coevaporated three times with toluene to give 4-(4-methanesulfonyl-phenoxy)-1-piperidin-4-yl-1H-pyrazolo[3,4-d]pyrimidine trifluoroacetate salt (12.0 g, 97%) as an off-white solid which was used in the next step without further purification. $^1$H NMR (300 MHz, DMSO-$d_6$) δ 2.14-2.17 (m, 2H), 2.32-2.41 (m, 2H), 3.22-3.30 (m, 2H), 3.30 (methyl sulfonyl peak and water peak), 3.45-3.50 (m, 2H), 5.15-5.21 (m, 1H), 7.62-7.64 (m, 2H), 8.06-8.08 (m, 2H), 8.44 (s, 1H), 8.50-8.58 (br s, 1H), 8.59 (s, 1H), 8.76-8.83 (br s, 1H). Mass spectrum (ES) MH+=374.

Intermediate 28: 4-(2-Methyl-pyridin-3-yloxy)-1-piperidin-4-yl-1H-pyrazolo[3,4-d]pyrimidine

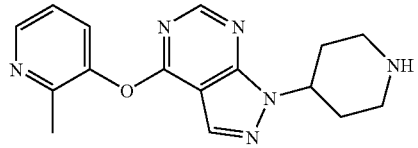

A solution of 4-[4-(2-methyl-pyridin-3-yloxy)-pyrazolo[3,4-d]pyrimidin-1-yl]-piperidine-1-carboxylic acid tert-butyl ester (Example 92; 710 mg, 1.7 mmol) in 20% trifluoroacetic acid/dichloromethane (15 mL) was stirred at room temperature for 40 min, then the solvents were evaporated and the residue held under high vacuum to give a pale yellow thick oil. SiliaBond Carbonate (Silicycle, Quebec City, Canada; 4 equivalents) was added and the mixture was stirred slowly for 2.5 h, then filtered. The filtrate was evaporated and held under high vacuum to give 4-(2-methyl-pyridin-3-yloxy)-1-piperidin-4-yl-1H-pyrazolo[3,4-d]pyrimidine (363 mg, 68%) as a white solid.

Intermediate 29: 4-(4-Ethoxy-2-fluoro-phenoxy)-1-piperidin-4-yl-1H-pyrazolo[3,4-d]pyrimidine trifluoroacetate salt

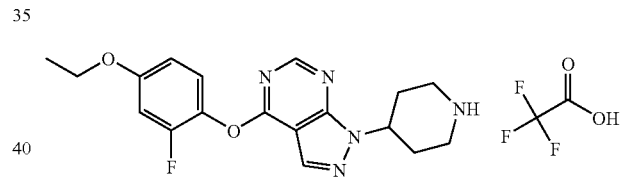

A solution of 4-[4-(4-ethoxy-2-fluoro-phenoxy)-pyrazolo[3,4-d]pyrimidin-1-yl]-piperidine-1-carboxylic acid tert-butyl ester (Example 43; 110 mg) in 20% trifluoroacetic acid/dichloromethane (5 mL) was stirred at room temperature for 3 hours. The solvent was removed to afford 4-(4-ethoxy-2-fluoro-phenoxy)-1-piperidin-4-yl-1H-pyrazolo[3,4-d]pyrimidine trifluoroacetate salt (112 mg, 99%) which was used directly in the next step without further purification.

Intermediate 30: 4-Chloro-1H-pyrazolo[3,4-d]pyrimidine

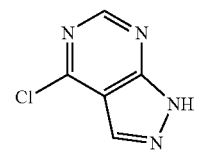

Phosphorus oxychloride (300 mL, 3.2 mol) was added to allopurinol (Aldrich Chemical Company, Inc., Milwaukee, Wis., USA 20 g, 0.15 mol) and then N,N-dimethylaniline (30 mL, 0.24 mol) was added at room temperature. The resulting mixture was heated at reflux for 90 min and then cooled. The solvent was removed under vacuum. The residue was co-evaporated twice with toluene, and the resulting dark colored syrup was poured into a mixture of ice and water (500 mL). The mixture was stirred for 15 min, then transferred to a separatory funnel and extracted with ether (4×500 mL) and ethyl acetate (2×500 mL). The combined organic layers were washed twice with ice-water, dried (sodium sulfate), and concentrated to approximately 1.5 L. Charcoal was added to the slightly purple solution and the mixture was filtered through Celite. The Celite was washed with ethyl acetate and the combined filtrates were evaporated to dryness to give 4-chloro-1H-pyrazolo[3,4-d]pyrimidine (13 g, 56%) as a pale green solid. $^1$H NMR (300 MHz, DMSO-$d_6$) δ 8.44 (s, 1H), 8.81 (s, 1H), 14.50 (br s, 1H).

Intermediate 31: 4-(4-Methanesulfonyl-phenoxy)-1H-pyrazolo[3,4-d]pyrimidine

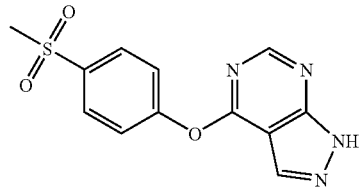

Step 1: 4-Chloro-1-(tetrahydro-pyran-2-yl)-1H-pyrazolo[3,4-d]pyrimidine 3,4-Dihydro-2H-pyran (10 mL) and 10-camphorsulfonic acid (200 mg, 0.86 mmol) were added to a solution of 4-chloro-1H-pyrazolo[3,4-d]pyrimidine (Intermediate 30; 2.1 g, 13.6 mmol) in ethyl acetate (80 mL). The mixture was stirred at room temperature for 70 h, poured into saturated aqueous sodium bicarbonate, and extracted three times with ethyl acetate. The combined organic extracts were washed with brine, dried (magnesium sulfate), filtered, evaporated, and purified by column chromatography eluting with 20% ethyl acetate/hexanes to give 4-chloro-1-(tetrahydro-pyran-2-yl)-1H-pyrazolo[3,4-d]pyrimidine (2.61 g, 80%) as a lavender-colored crystalline solid.

Step 2: 4-(4-Methanesulfonyl-phenoxy)-1-(tetrahydro-pyran-2-yl)-1H-pyrazolo[3,4-d]pyrimidine 4-(Methylsulfonyl)-phenol (Oakwood Products, Inc., West Columbia, S.C., USA; 516 mg, 3 mmol) and cesium carbonate (1.63 g, 5 mmol) were added to a solution of 4-chloro-1-(tetrahydro-pyran-2-yl)-1H-pyrazolo[3,4-d]pyrimidine (from Step 1; 610 mg, 2.56 mmol) in dimethylformamide (15 mL). The mixture was heated at 90° C. for 1 h, then cooled, poured into saturated aqueous sodium bicarbonate solution, and extracted three times with ethyl acetate. The combined organic extracts were washed with twice with water and once with brine, dried (magnesium sulfate), filtered, and evaporated to give 4-(4-methanesulfonyl-phenoxy)-1-(tetrahydro-pyran-2-yl)-1H-pyrazolo[3,4-d]pyrimidine (780 mg, 58%).

Step 3. 4-(4-Methanesulfonyl-phenoxy)-1H-pyrazolo[3,4-d]pyrimidine

Triethylsilane (150 μL, 0.94 mmol) was added to a solution of 4-(4-methanesulfonyl-phenoxy)-1-(tetrahydro-pyran-2-yl)-1H-pyrazolo[3,4-d]pyrimidine (150 mg, 0.4 mmol) in dichloromethane (3 mL). A solution of trifluoroacetic acid (1 mL) in dichloromethane (3 mL) was added dropwise and then the reaction mixture was stirred for 1 h. Toluene (2 mL) was added and the volatiles were evaporated. The residue was purified by column chromatography, eluting with 0-5% methanol/ethyl acetate to give 4-(4-methanesulfonyl-phenoxy)-1H-pyrazolo[3,4-d]pyrimidine (71 mg, 61%) as a white solid.

Intermediate 32: 3-(4-Chloro-pyrazolo[3,4-d]pyrimidin-1-yl)-piperidine-1-carboxylic acid tert-butyl ester

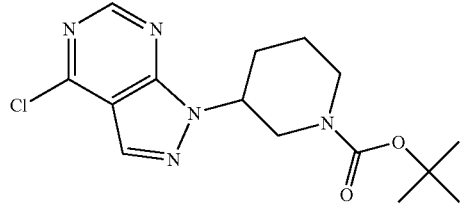

A solution of triphenylphosphine (1.41 g, 5.4 mmol) in tetrahydrofuran (50 mL) under argon was cooled to 0° C. Diisopropylcarbodiimide (1.06 mL, 5.4 mmol) was added dropwise, followed by 1-Boc-3-hydroxypiperidine (Alfa Aesar, Ward Hill, Mass., USA; 0.92 g, 4.6 mmol) and then 4-chloro-1H-pyrazolo[3,4-d]pyrimidine (Intermediate 30; 0.55 g, 3.6 mmol). The mixture was stirred at room 0° C. for 4 h and the volatiles were then evaporated. The crude product was purified by silica gel chromatography, eluting with 16-20% ethyl acetate/hexanes to give 3-(4-chloro-pyrazolo[3,4-d]pyrimidin-1-yl)-piperidine-1-carboxylic acid tert-butyl ester (135 mg, 11%).

Intermediate 33: 4-(6-Amino-4-chloro-pyrazolo[3,4-d]pyrimidin-1-yl)-piperidine-1-carboxylic acid tert-butyl ester

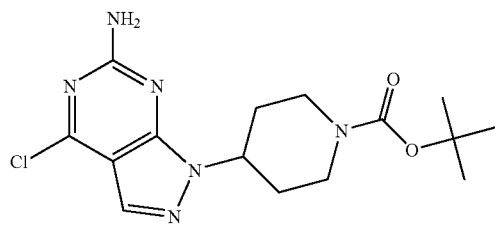

4-(tert-Butoxycarbonyl-hydrazino)-piperidine-1-carboxylic acid tert-butyl ester (Intermediate 15; 315 mg, 1 mmol) and diisopropylethylamine (2 mmol) were added to a solution of 2-amino-4,6-dichloro-pyrimidine-5-carbaldehyde (Aldrich Chemical Company, Inc., Milwaukee, Wis., USA; 200 mg, 1 mmol) in tetrahydrofuran (3 mL). The mixture was warmed to room temperature, heated to reflux for 3 h, and then stirred overnight. The mixture was heated to reflux for a further 2 h and then cooled. Brine was added and the mixture was extracted three times with ethyl acetate. The combined organic extracts were dried (magnesium sulfate), filtered and evaporated to give a yellow foam. Toluene was added and the mixture was heated at 110° C. for 2 h. The mixture was cooled and purified by column chromatography (50% ethyl acetate/hexanes) to give 4-(6-amino-4-chloro-pyrazolo[3,4-d]pyrimidin-1-yl)-piperidine-1-carboxylic acid tert-butyl ester (315 mg, 69%) as a white powder.

II. Preparation of Preferred Compounds of the Invention

General Procedure A

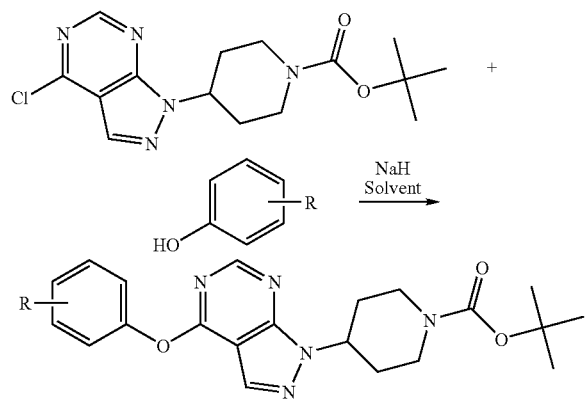

A 0.2 M solution of the phenol in dimethylformamide or tetrahydrofuran or acetonitrile was cooled to 0° C. and sodium hydride (60% dispersion in paraffin oil; 1.5 equivalents) was added. The mixture was stirred for 30 min at about 0° C. and 4-(4-chloro-pyrazolo[3,4-d]pyrimidin-1-yl)-piperidine-1-carboxylic acid tert-butyl ester (Intermediate 19; 1 equivalent) was added. The mixture was stirred at room temperature for 12 h. Saturated aqueous ammonium chloride was added and the mixture was extracted three times with ethyl acetate. The combined organic layers were dried (sodium sulfate), filtered, evaporated, and purified on neutral alumina, eluting with ethyl acetate/hexanes.

General Procedure B

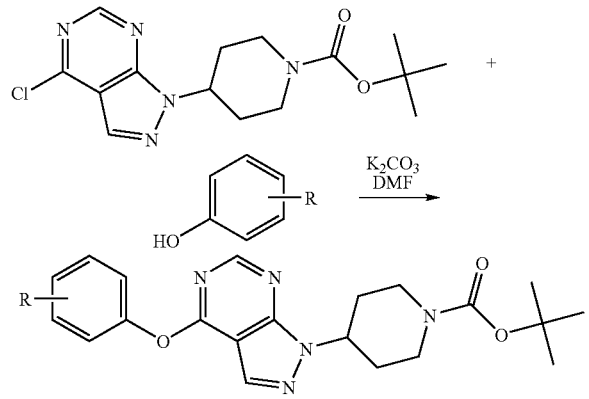

Potassium carbonate (1.5 equivalents) was added to a solution of the phenol (1 equivalent) in dimethylformamide at room temperature under nitrogen. The mixture was stirred for 5 min at room temperature and 4-(4-chloro-pyrazolo[3,4-d]pyrimidin-1-yl)-piperidine-1-carboxylic acid tert-butyl ester (Intermediate 19; 1 equivalent) was added. The mixture was stirred at 80-100° C. for 2 h, then cooled to room temperature and diluted with ice water. The mixture was extracted three times with ethyl acetate and the combined organic extracts were washed with water, dried (sodium sulfate), filtered, evaporated, and purified on neutral alumina, eluting with ethyl acetate/hexanes.

General Procedure C

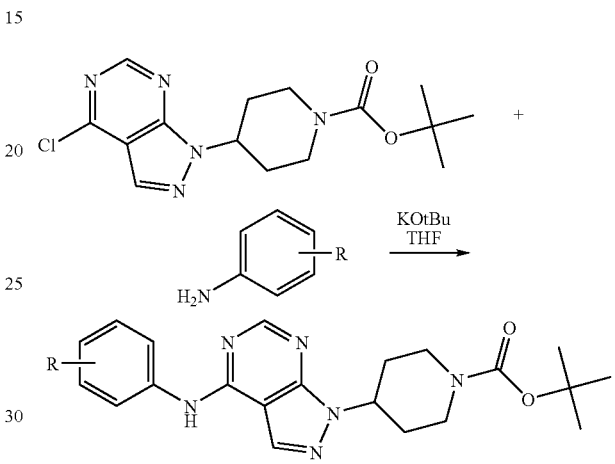

Potassium tert-butoxide (2 equivalents) was added in portions to a solution of 4-(4-chloro-pyrazolo[3,4-d]pyrimidin-1-yl)-piperidine-1-carboxylic acid tert-butyl ester (Intermediate 19; 1 equivalent) and the aniline (1 equivalent) in tetrahydrofuran (25 mL per gram of 4-(4-chloro-pyrazolo[3,4-d]pyrimidin-1-yl)-piperidine-1-carboxylic acid tert-butyl ester) which had been cooled to about −20° C. under nitrogen. The mixture was stirred at this temperature for 2 h and then at room temperature for 12 h. Saturated aqueous ammonium chloride was added and the mixture was extracted three times with ethyl acetate. The combined organic layers were dried (sodium sulfate), filtered, evaporated, and purified on neutral alumina, eluting with ethyl acetate/hexanes.

General Procedure D

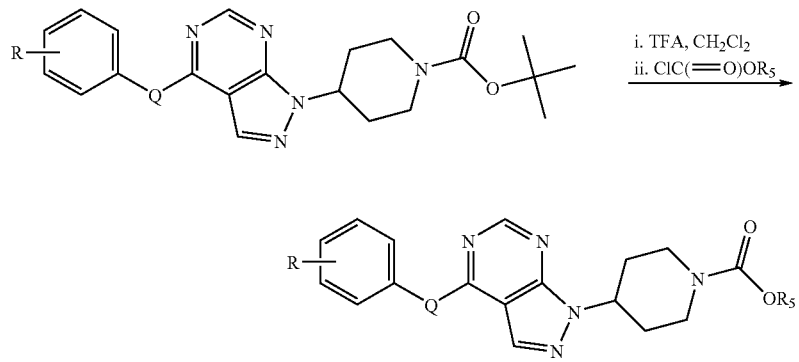

Trifluoroacetic acid (20 parts) was added to a stirred 0.1 M solution of the tert-butyl carbamate (1 part) in dichloromethane at 0° C. under nitrogen. The reaction mixture was stirred at room temperature for 4 h and the solvent was evaporated under reduced pressure. The crude residue was washed with diethyl ether to give the piperidine trifluoroacetate salt. The alkyl chloroformate (1 equivalent) was added to a mixture of the piperidine trifluoroacetate salt (1 equivalent) and triethylamine (2 equivalents) in dichloromethane (0.05 M) at 0° C. under an inert atmosphere, and the mixture was stirred overnight. The mixture was diluted with dichloromethane and washed with aqueous sodium bicarbonate solution. The layers were separated and the aqueous layer was extracted twice with dichloromethane. The combined organic extracts were dried (sodium sulfate), filtered, evaporated, and purified by column chromatography on neutral alumina, eluting with ethyl acetate/hexanes.

General Procedure E romethane at 0° C. under nitrogen. The reaction mixture was stirred at room temperature for 4 h and the solvent was evaporated under reduced pressure. The crude residue was washed with diethyl ether to give the piperidine trifluoroacetate salt. The halomethyl arene (1 equivalent) was added to a mixture of the piperidine trifluoroacetate salt (1 equivalent) and potassium carbonate (2 equivalents) in tetrahydrofuran (0.05 M) at 0° C. under an inert atmosphere, and the mixture was stirred for 8 h. The mixture was diluted with ethyl acetate and washed with aqueous sodium bicarbonate solution. The layers were separated and the aqueous layer was extracted twice with ethyl acetate. The combined organic extracts were dried (sodium sulfate), filtered, evaporated, and purified by column chromatography on neutral alumina, eluting with methanol/dichloromethane.

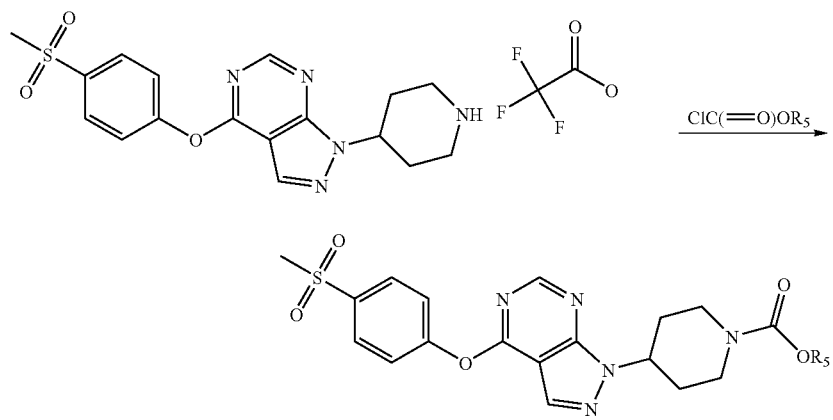

Diisopropylethylamine (5 equivalents) was added to a cooled and stirred solution of 4-(4-methanesulfonyl-phenoxy)-1-piperidin-4-yl-1H-pyrazolo[3,4-d]pyrimidine trifluoroacetate salt (Intermediate 27; 1 equivalent) in dichloromethane (0.07 M) at about 0° C., and the mixture was stirred for 30 min. The chloroformate (1.5 equivalents) was added and the mixture was stirred for 3 h. Dichloromethane was added, and the solution was washed with water, dried (sodium sulfate), filtered, evaporated, and purified by column chromatography on neutral alumina, eluting with ethyl acetate/hexanes.

General Procedure F

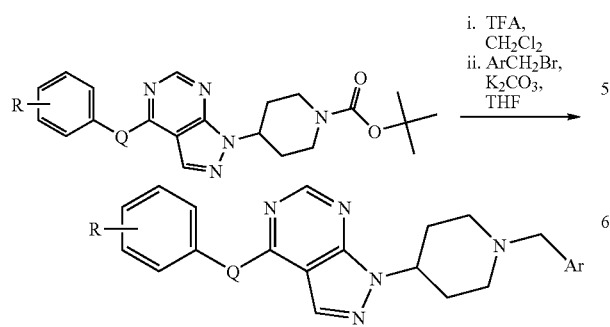

General Procedure G

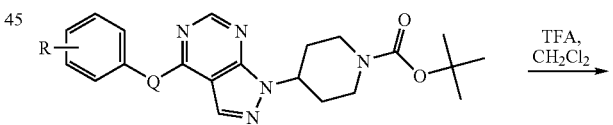
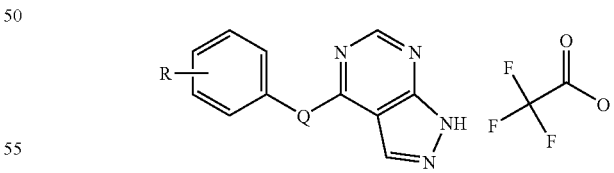

Trifluoroacetic acid (20 parts) was added to a stirred 0.1 M solution of the tert-butyl carbamate (1 part) in dichloromethane at 0° C. under nitrogen. The reaction mixture was stirred at room temperature for 4 h and the solvent was evaporated under reduced pressure. The crude residue was washed with diethyl ether to give the piperidine trifluoroacetate salt.

General Procedure H

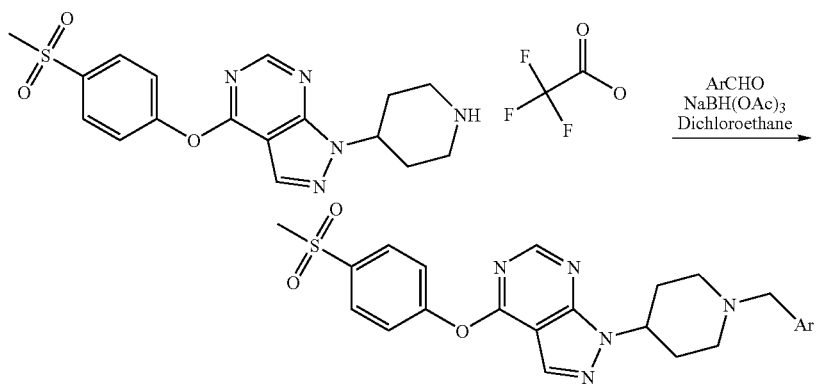

Triethylamine (5 equivalents) was added to a cooled solution of 4-(4-methanesulfonyl-phenoxy)-1-piperidin-4-yl-1H-pyrazolo[3,4-d]pyrimidine trifluoroacetate salt (Intermediate 27; 1 equivalent) in 1,2-dichloroethane (0.1 M) at about 0° C., and the mixture was stirred for 15 min. Sodium triacetoxyborohydride (1.2 equivalents) was added, followed by the aldehyde of formula ArCHO. The reaction mixture was heated at reflux for 4-5 h, then cooled to room temperature. Saturated aqueous sodium bicarbonate solution was added until the effervescence stopped, and the mixture was then extracted with dichloromethane. The organic extracts were washed with water, dried (sodium sulfate), filtered, evaporated, and purified by column chromatography on neutral alumina, eluting with methanol/dichloromethane.

General Procedure I

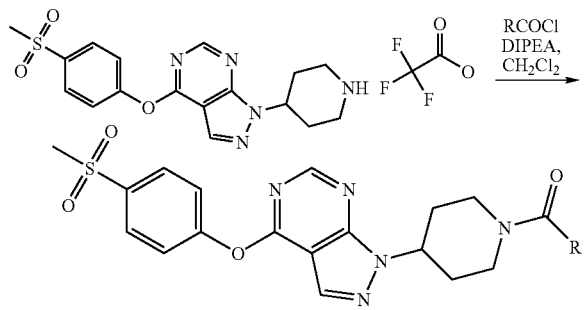

Diisopropylethylamine (5 equivalents) was added to a cooled and stirred solution of 4-(4-methanesulfonyl-phenoxy)-1-piperidin-4-yl-1H-pyrazolo[3,4-d]pyrimidine trifluoroacetate salt (Intermediate 27; 1 equivalent) in dichloromethane (0.07 M) at about 0° C., and the mixture was stirred for 30 min. The acid chloride of formula RCOCl (1.5 equivalents) was added and the mixture was stirred for 3 h. Dichloromethane was added, and the solution was washed with water, dried (sodium sulfate), filtered, evaporated, and purified by column chromatography on neutral alumina or silica gel, eluting with ethyl acetate/hexanes.

General Procedure J

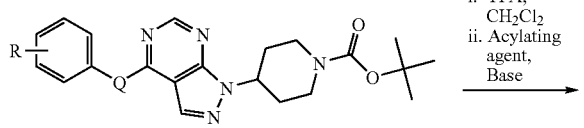

Trifluoroacetic acid (20 parts) was added to a stirred 0.1 M solution of the tert-butyl carbamate (1 part) in dichloromethane at 0° C. under nitrogen. The reaction mixture was stirred at room temperature for 4 h and the solvent was evaporated under reduced pressure. The crude residue was washed with diethyl ether to give the piperidine trifluoroacetate salt. The acylating agent (trifluoroacetic anhydride, acetyl chloride or trimethylacetyl chloride) (1 equivalent) was added to a suspension of the piperidine trifluoroacetate salt (1 equivalent) and triethylamine (2 equivalents) in dichloromethane (0.05 M) at 0° C. under an inert atmosphere. The mixture was stirred for 16 h and then it was diluted with dichloromethane and washed with saturated aqueous sodium bicarbonate. The layers were separated and the aqueous phase was extracted twice with dichloromethane. The combined organic extracts were dried (sodium sulfate), filtered, evaporated, and purified by column chromatography on neutral alumina, eluting with ethyl acetate/hexanes.

Example 1

4-[4-(2-Fluoro-4-methanesulfonyl-phenylamino)-pyrazolo[3,4-d]pyrimidin-1-yl]-piperidine-1-carboxylic acid tert-butyl ester 4-[4-(2-Fluoro-4-methanesulfonyl-phenylamino)-pyrazolo[3,4-d]pyrimidin-1-yl]-piperidine-1-carboxylic acid tert-butyl ester was prepared according to General Procedure C by the reaction of 4-(4-chloro-pyrazolo[3,4-d]pyrimidin-1-yl)-piperidine-1-carboxylic acid tert-butyl ester (Intermediate 19) with 2-fluoro-4-(methylsulfonyl)aniline (available from Aldrich Chemical Company, Inc., Milwaukee, Wis., USA). $^1$H NMR (400 MHz, DMSO-$d_6$) δ 1.43 (s, 9H), 1.90-2.00 (m, 4H), 2.95-3.05 (m, 2H), 3.30 (methyl sulfonyl and water peak), 4.03-4.09 (m, 2H), 4.90-4.93 (m, 1H), 7.79-7.81 (m, 1H), 7.88-7.91 (m, 1H), 8.21-8.24 (m, 1H), 8.40-8.42 (m, 2H), 10.36 (s, 1H). Mass spectrum MH+=491.

Example 2

4-[4-(2,4,5-Trifluoro-phenylamino)-pyrazolo[3,4-d]pyrimidin-1-yl]-piperidine-1-carboxylic acid isopropyl ester

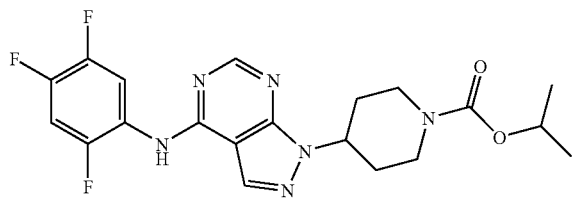

4-[4-(2,4,5-Trifluoro-phenylamino)-pyrazolo[3,4-d]pyrimidin-1-yl]-piperidine-1-carboxylic acid isopropyl ester was prepared according to General Procedure D by the reaction of 4-[4-(2,4,5-trifluoro-phenylamino)-pyrazolo[3,4-d]pyrimidin-1-yl]-piperidine-1-carboxylic acid tert-butyl ester (Example 4) with trifluoroacetic acid, followed by reaction of the resulting amine with isopropyl chloroformate (available from Aldrich Chemical Company, Inc., Milwaukee, Wis., USA). $^1$H NMR (400 MHz, DMSO-$d_6$) δ 1.20 (d, 6H, J=6.2 Hz), 1.90-1.99 (m, 4H), 3.04-3.15 (m, 3H), 4.08-4.17 (m, 2H), 4.77-4.83 (m, 1H), 4.89-4.94 (m, 1H), 7.69-7.76 (m, 1H), 7.96-7.99 (m, 1H), 8.25 (m, 1H), 8.36 (s, 1H), 10.13 (s, 1H). Mass spectrum MH+=435.

Example 3

4-[4-(4-Methanesulfonyl-phenylamino)-pyrazolo[3,4-d]pyrimidin-1-yl]-piperidine-1-carboxylic acid isopropyl ester

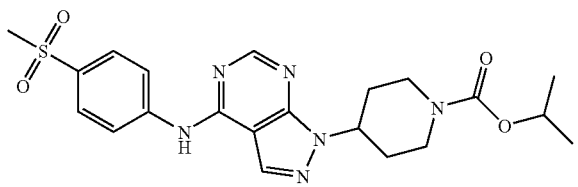

4-[4-(4-Methanesulfonyl-phenylamino)-pyrazolo[3,4-d]pyrimidin-1-yl]-piperidine-1-carboxylic acid isopropyl ester was prepared according to General Procedure D by the reaction of 4-[4-(4-methanesulfonyl-phenylamino)-pyrazolo[3,4-d]pyrimidin-1-yl]-piperidine-1-carboxylic acid tert-butyl ester (Example 5) with trifluoroacetic acid, followed by reaction of the resulting amine with isopropyl chloroformate (available from Aldrich Chemical Company, Inc., Milwaukee, Wis., USA). $^1$H NMR (400 MHz, DMSO-$d_6$) δ 1.20 (d, 6H, J=6.2 Hz), 1.95-2.01 (m, 4H), 2.98-3.09 (m, 2H), 3.19 (s, 3H), 4.07-4.12 (m, 2H), 4.78-4.82 (m, 1H), 4.93-4.97 (m, 1H), 7.92-7.94 (m, 2H), 8.17-8.19 (m, 2H), 8.41 (s, 1H), 8.54 (s, 1H), 10.49 (s, 1H). Mass spectrum MH+=459.

Example 4

4-[4-(2,4,5-Trifluoro-phenylamino)-pyrazolo[3,4-d]pyrimidin-1-yl]-piperidine-1-carboxylic acid tert-butyl ester

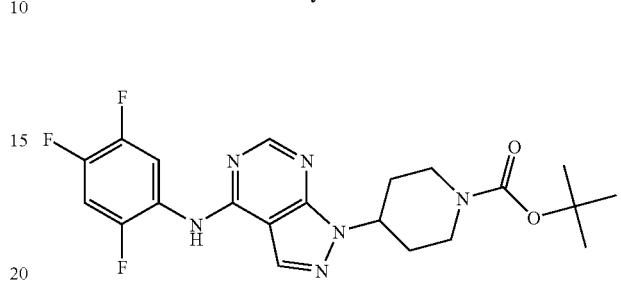

4-[4-(2,4,5-Trifluoro-phenylamino)-pyrazolo[3,4-d]pyrimidin-1-yl]-piperidine-1-carboxylic acid tert-butyl ester was prepared according to General Procedure C by the reaction of 4-(4-chloro-pyrazolo[3,4-d]pyrimidin-1-yl)-piperidine-1-carboxylic acid tert-butyl ester (Intermediate 19) with 2,4,5-trifluoroaniline (available from Oakwood Products, Inc., West Columbia, S.C., USA). $^1$H NMR (400 MHz, DMSO-$d_6$) δ 1.43 (s, 9H), 1.91-1.99 (m, 4H), 2.95-3.05 (m, 2H), 4.00-4.10 (m, 2H), 4.88-4.93 (m, 1H), 7.71-7.74 (m, 1H), 7.96-7.99 (m, 1H), 8.24 (br s, 1H), 8.36 (s, 1H), 10.17 (s, 1H). Mass spectrum MH+=449.

Example 5

4-[4-(4-Methanesulfonyl-phenylamino)-pyrazolo[3,4-d]pyrimidin-1-yl]-piperidine-1-carboxylic acid tert-butyl ester

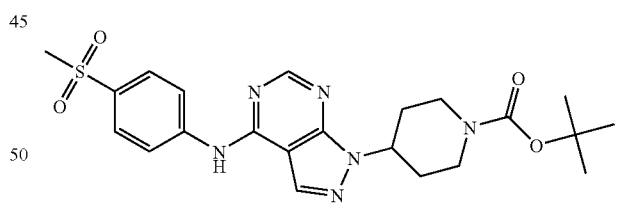

4-[4-(4-Methanesulfonyl-phenylamino)-pyrazolo[3,4-d]pyrimidin-1-yl]-piperidine-1-carboxylic acid tert-butyl ester was prepared according to General Procedure C by the reaction of 4-(4-chloro-pyrazolo[3,4-d]pyrimidin-1-yl)-piperidine-1-carboxylic acid tert-butyl ester (Intermediate E1) with 4-(methylsulfonyl)aniline (available from Oakwood Products, Inc., West Columbia, S.C., USA). $^1$H NMR (400 MHz, DMSO-$d_6$) δ 1.43 (s, 9H), 1.90-2.00 (m, 4H), 2.92-3.05 (m, 2H), 3.30 (methyl sulfonyl and water peak), 4.03-4.10 (m, 2H), 4.91-4.95 (m, 1H), 7.92-7.94 (m, 2H), 8.17-8.19 (m, 2H), 8.32 (s, 1H), 8.54 (s, 1H), 10.50 (s, 1H). Mass spectrum MH+=473.

Example 6

4-[4-(2-Fluoro-4-methanesulfonyl-phenylamino)-pyrazolo[3,4-d]pyrimidin-1-yl]-piperidine-1-carboxylic acid isopropyl ester

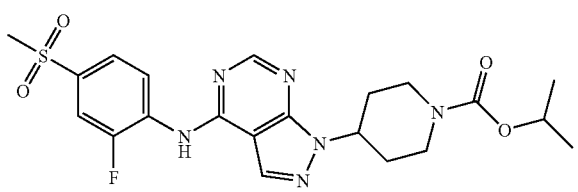

4-[4-(2-Fluoro-4-methanesulfonyl-phenylamino)-pyrazolo[3,4-d]pyrimidin-1-yl]-piperidine-1-carboxylic acid isopropyl ester was prepared according to General Procedure D by the reaction of 4-[4-(2-fluoro-4-methanesulfonyl-phenylamino)-pyrazolo[3,4-d]pyrimidin-1-yl]-piperidine-1-carboxylic acid tert-butyl ester (Example 1) with trifluoroacetic acid, followed by reaction of the resulting amine with isopropyl chloroformate (available from Aldrich Chemical Company, Inc., Milwaukee, Wis., USA). $^1$H NMR (400 MHz, DMSO-$d_6$) δ 1.20 (d, 6H, J=6.2 Hz), 1.94-2.03 (m, 4H), 3.00-3.10 (m, 2H), 3.30 (methyl sulfonyl and water peak), 4.05-4.15 (m, 2H), 4.77-4.84 (m, 1H), 4.92-4.96 (m, 1H), 7.79-7.81 (m, 1H), 7.89-7.92 (m, 1H), 8.20-8.23 (m, 1H), 8.40-8.43 (m, 2H), 10.38 (s, 1H). Mass spectrum MH+=477.

Example 7

4-[4-(2-Methyl-pyridin-3-ylamino)-pyrazolo[3,4-d]pyrimidin-1-yl]-piperidine-1-carboxylic acid tert-butyl ester

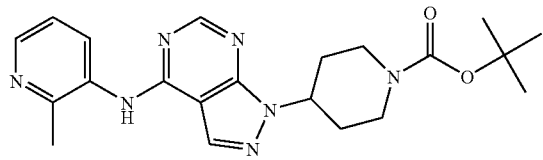

A mixture of 4-(4-chloro-pyrazolo[3,4-d]pyrimidin-1-yl)-piperidine-1-carboxylic acid tert-butyl ester (Intermediate 19; 50 mg, 0.15 mmol), 3-amino-2-methylpyridine (Aldrich Chemical Company, Inc., Milwaukee, Wis., USA 21 mg, 0.19 mmol), and potassium tert-butoxide (22 mg, 0.19 mmol) in dimethylformamide (2 mL) was heated in the microwave oven at 160° C. for 10 min. Ethyl acetate and water were added, and the aqueous layer was extracted twice with ethyl acetate. The ethyl acetate layers were combined, evaporated, and purified by preparative C18 HPLC, eluting with 10-100% acetonitrile/water. Samples containing the product were extracted twice with dichloromethane and the solvent was evaporated under high vacuum to give 4-[4-(2-methyl-pyridin-3-ylamino)pyrazolo[3,4-d]pyrimidin-1-yl]-piperidine-1-carboxylic acid tert-butyl ester (15 mg, 24%) as a white powder. Mass spectrum (ES) MH+=410. HRMS Calcd. for $C_{21}H_{28}N_7O_2$ (MH+): 410.2299. Found: 410.2299.

Example 8

4-[4-(6-Methanesulfonyl-2-methyl-pyridin-3-ylamino)-pyrazolo[3,4-d]pyrimidin-1-yl]-piperidine-1-carboxylic acid tert-butyl ester

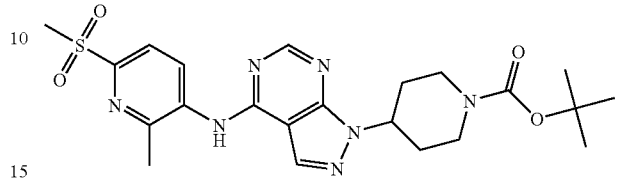

A mixture of 4-(4-chloro-pyrazolo[3,4-d]pyrimidin-1-yl)-piperidine-1-carboxylic acid tert-butyl ester (Intermediate 19; 50 mg, 0.15 mmol), 6-methanesulfonyl-2-methyl-pyridin-3-ylamine (Intermediate 4; 28 mg, 0.15 mmol), palladium acetate (0.33 mg, 0.01 equivalent), sodium tert-butoxide (34 mg, 0.36 mmol), and 2,8,9-triisobutyl-2,5,8,9-tetraaza-1-phosphabicyclo[3.3.3]undecane (Aldrich, 1 mg, 0.02 equivalents) in dimethylformamide (2 mL) was heated in the microwave oven at 160° C. for 10 min. Ethyl acetate and water were added, and the aqueous layer was extracted three times with ethyl acetate. The ethyl acetate layers were combined, evaporated, and purified by preparative C18 HPLC, eluting with 10-100% acetonitrile/water. Samples containing the product were extracted twice with dichloromethane and the solvent was evaporated under high vacuum to give 4-[4-(6-methanesulfonyl-2-methyl-pyridin-3-ylamino)-pyrazolo[3,4-d]pyrimidin-1-yl]-piperidine-1-carboxylic acid tert-butyl ester (34 mg, 46%) as a white powder. $^1$H NMR (300 MHz, DMSO-$d_6$) δ 1.41 (s, 9H), 1.92-2.00 (m, 4H), 2.55 (s, 3H), 2.90-3.04 (m, 2H), 3.30 (water peak and $SO_2CH_3$ peak), 4.00-4.12 (m, 2H), 4.84-4.96 (m, 1H), 7.92 (d, 1H, J=8.5 Hz), 8.22-8.36 (m, 3H), 10.06 (br s, 1H). HRMS Calcd. for $C_{22}H_{30}N_7O_4S$ (MH+): 488.2075. Found: 488.2073.

Example 9

4-[4-(2-Methyl-6-[1,2,4]triazol-1-yl-pyridin-3-ylamino)-pyrazolo[3,4-d]pyrimidin-1-yl]-piperidine-1-carboxylic acid tert-butyl ester

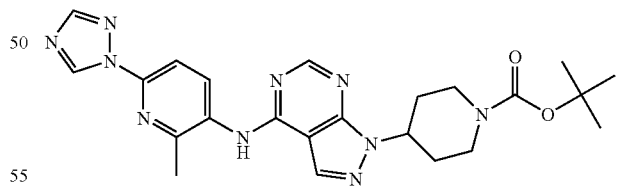

A mixture of 4-(4-chloro-pyrazolo[3,4-d]pyrimidin-1-yl)-piperidine-1-carboxylic acid tert-butyl ester (Intermediate 19; 50 mg, 0.15 mmol), 2-methyl-6-[1,2,4]triazol-1-yl-pyridin-3-ylamine (Intermediate 7, Step 2; 26 mg, 0.15 mmol), palladium(II) acetate (0.3 mg, 0.01 eq), triisobutylphosphatrane (1 mg, 0.02 eq) and sodium tert-butoxide (34 mg, 0.36 mmol) in dimethylformamide (2 mL) was heated in the microwave oven at 160° C. for 10 min. The mixture was filtered through a PTFE filter with a 0.45 μM pore size to remove the catalyst, and the solid was rinsed with ethyl acetate. Ethyl acetate and water were added to the combined filtrate and washings, and the aqueous layer was extracted twice with ethyl acetate. The ethyl acetate layers were combined, evaporated, and purified by preparative C18 HPLC, eluting with 10-100% acetonitrile/water. Samples containing the product were extracted twice with dichloromethane and the solvent was evaporated to give 4-[4-(2-methyl-6-[1,2,4] triazol-1-yl-pyridin-3-ylamino)-pyrazolo[3,4-d]pyrimidin-1-yl]-piperidine-1-carboxylic acid tert-butyl ester (18 mg, 26%) as a light yellow powder. $^1$H NMR (300 MHz, DMSO-d$_6$) δ 1.43 (s, 9H), 1.75-2.07 (m, 4H), 2.99 (br s, 2H), 3.98-4.15 (m, 2H), 4.77-5.00 (m, 1H), 7.77 (d, 1H, J=8.5 Hz), 8.04-8.15 (m, 2H), 8.30 (s, 2H), 9.33 (s, 1H), 10.00 (br s, 1H). Mass spectrum (ES) MH+=477. HRMS Calcd. for C$_{23}$H$_{29}$N$_{10}$O$_2$ (MH+): 477.2470. Found: 477.2468.

Example 10

4-[4-(5-Methanesulfonyl-2,3-dihydro-indol-1-yl)-pyrazolo[3,4-d]pyrimidin-1-yl]-piperidine-1-carboxylic acid tert-butyl ester

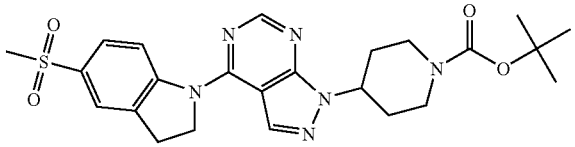

5-(Methylsulfonyl)-indoline (Matrix Scientific, Columbia, S.C., USA; 30 mg, 0.15 mmol) and triethylamine (70 μL, 0.5 mmol) were added to a solution of 4-(4-chloro-pyrazolo[3,4-d]pyrimidin-1-yl)-piperidine-1-carboxylic acid tert-butyl ester (Intermediate 19; 45 mg, 0.133 mmol) in tetrahydrofuran (1 mL). The mixture was heated to reflux. No reaction had occurred after 2 h. The volatiles were evaporated. Dimethylformamide (1 mL) and cesium carbonate (250 mg, 0.77 mmol) were added. The mixture was heated at 70° C. overnight, then poured into saturated aqueous sodium bicarbonate, and extracted three times with ethyl acetate. The combined organic extracts were washed twice with water and once with brine, dried (magnesium sulfate), filtered, evaporated, and purified by column chromatography eluting with ethyl acetate to give 4-[4-(5-methanesulfonyl-2,3-dihydroindol-1-yl)pyrazolo[3,4-d]pyrimidin-1-yl]-piperidine-1-carboxylic acid tert-butyl ester (14 mg, 21%) as an off-white solid.

Example 11

[1-(1-Benzyl-piperidin-4-yl)-1H-pyrazolo[3,4-d]pyrimidin-4-yl]-(2-fluoro-4-methanesulfonylphenyl)-amine

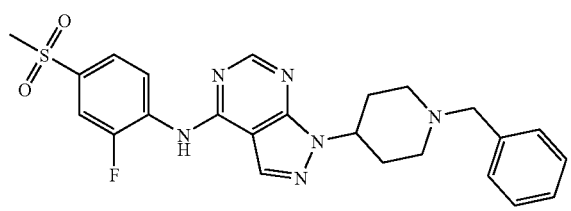

[1-(1-Benzyl-piperidin-4-yl)-1H-pyrazolo[3,4-d]pyrimidin-4-yl]-(2-fluoro-4-methanesulfonylphenyl)-amine was prepared according to General Procedure F by the reaction of 4-[4-(2-fluoro-4-methanesulfonyl-phenylamino)-pyrazolo[3,4-d]pyrimidin-1-yl]-piperidine-1-carboxylic acid tert-butyl ester (Example 1) with trifluoroacetic acid in dichloromethane followed by reaction with benzyl bromide (available from Aldrich Chemical Company, Inc., Milwaukee, Wis., USA). $^1$H NMR (400 MHz, DMSO-d$_6$) δ 1.87-1.90 (m, 2H), 2.13-2.24 (m, 4H), 2.93-2.97 (m, 2H), 3.54 (s, 2H), 4.67-4.72 (m, 1H), 7.25-7.35 (m, 5H), 7.78-7.81 (m, 1H), 7.88-7.91 (m, 1H), 8.20-8.24 (m, 1H), 8.38-8.41 (m, 2H), 11.71 (s, 1H). Mass spectrum MH+=481.

Example 12

4-[4-(4-Methanesulfonyl-phenoxy)-pyrazolo[3,4-d]pyrimidin-1-yl]-piperidine-1-carboxylic acid methyl ester

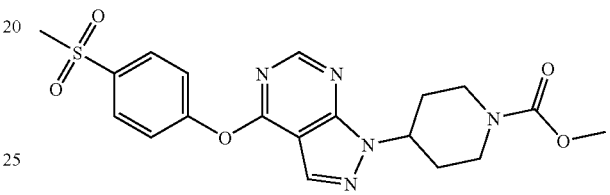

4-[4-(4-Methanesulfonyl-phenoxy)-pyrazolo[3,4-d]pyrimidin-1-yl]-piperidine-1-carboxylic acid methyl ester was prepared according to General Procedure E by the reaction of 4-(4-methanesulfonyl-phenoxy)-1-piperidin-4-yl-1H-pyrazolo[3,4-d]pyrimidine trifluoroacetate salt (Intermediate 27) with methyl chloroformate (available from Aldrich Chemical Company, Inc., Milwaukee, Wis., USA). $^1$H NMR (400 MHz, DMSO-d$_6$) δ 1.94-2.06 (m, 4H), 3.09-3.14 (m, 2H), 3.30 (methyl sulfonyl and water peak), 3.61 (s, 3H), 4.02-4.10 (m, 2H), 4.98-5.04 (m, 1H), 7.59-7.61 (m, 2H), 8.02-8.04 (m, 2H), 8.35 (s, 1H), 8.54 (s, 1H). Mass spectrum MH+=432.

Example 13

4-[4-(4-Methanesulfonyl-phenoxy)-pyrazolo[3,4-d]pyrimidin-1-yl]-piperidine-1-carboxylic acid ethyl ester

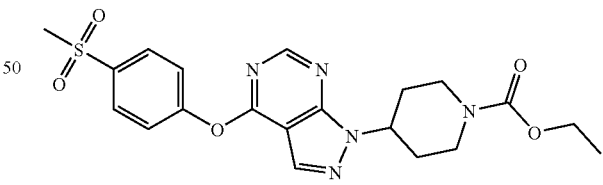

4-[4-(4-Methanesulfonyl-phenoxy)-pyrazolo[3,4-d]pyrimidin-1-yl]-piperidine-1-carboxylic acid ethyl ester was prepared according to General Procedure E by the reaction of 4-(4-methanesulfonyl-phenoxy)-1-piperidin-4-yl-1H-pyrazolo[3,4-d]pyrimidine trifluoroacetate salt (Intermediate 27) with ethyl chloroformate (available from Aldrich Chemical Company, Inc., Milwaukee, Wis., USA). $^1$H NMR (400 MHz, DMSO-d$_6$) δ 1.21 (t, 3H, J=7.1 Hz), 1.98-2.06 (m, 6H), 3.04-3.16 (m, 2H), 3.30 (methyl sulfonyl and water peak), 4.05-4.14 (m, 4H), 5.02-5.08 (m, 1H), 7.63-7.65 (m, 2H), 8.05-8.07 (m, 2H), 8.40 (s, 1H), 8.57 (s, 1H). Mass spectrum MH+=446.

Example 14

4-[4-(2-Fluoro-4-methanesulfonyl-phenoxy)-pyrazolo[3,4-d]pyrimidin-1-yl]-piperidine-1-carboxylic acid ethyl ester

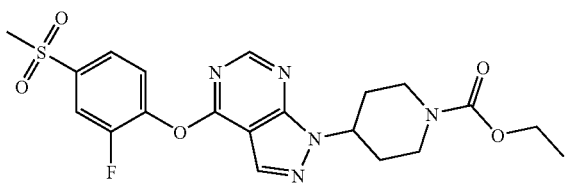

A 20% solution of trifluoroacetic acid in dichloromethane (12 mL) was added to a solution of 4-[4-(2-fluoro-4-methanesulfonyl-phenoxy)-pyrazolo[3,4-d]pyrimidin-1-yl]-piperidine-1-carboxylic acid tert-butyl ester (Example 60; 520 mg, 1.06 mmol) in dichloromethane (2 mL). The mixture was stirred at room temperature until TLC (6% methanol/dichloromethane) showed that all of the starting material had reacted. Volatiles were evaporated. Ether (5 mL) was added, and the solvents were evaporated again. The resulting white semi-solid was held under vacuum, then triturated with ether and held under vacuum again to give 4-[4-(2-fluoro-4-methanesulfonyl-phenoxy)-pyrazolo[3,4-d]pyrimidin-1-yl]-piperidine trifluoroacetate salt (479 mg, 90%) as a white powder. A portion of this material (200 mg, 0.4 mmol) was taken up in anhydrous dichloromethane (5 mL) with diisopropylethylamine (210 µL, 1.2 mmol) and the resulting suspension was cooled to about 0° C. Ethyl chloroformate (57 µL, 0.6 mmol) was added, and the reaction mixture was stirred at 0° C. for 2 min and then at room temperature for 30 min. Water (5 mL) was added, and the layers were separated. The organic layer was washed with brine, dried (sodium sulfate), filtered, evaporated, and purified on a 4 g Isco column, eluting with 0-10% methanol/dichloromethane, to give 4-[4-(2-fluoro-4-methanesulfonyl-phenoxy)-pyrazolo[3,4-d]pyrimidin-1-yl]-piperidine-1-carboxylic acid ethyl ester (140 mg, 77%). $^1$H NMR (300 MHz, DMSO-$d_6$) δ 1.19 (t, 3H, J=7.1 Hz), 1.95-2.06 (m, 4H), 3.05-3.14 (m, 2H), 4.02-4.16 (m, 4H), 4.98-5.07 (m, 1H), 7.82 (dd, 1H, J=7.1, 8.5 Hz), 7.89 (dd, 1H, J=1.8, 8.8 Hz), 8.06 (dd, 1H, J=2.0, 9.5 Hz), 8.50 (s, 1H), 8.56 (s, 1H).

Example 15

4-(4-Phenoxy-pyrazolo[3,4-d]pyrimidin-1-yl)-piperidine-1-carboxylic acid isopropyl ester

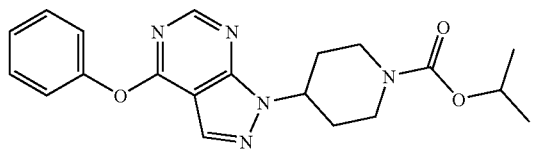

Step 1: 4-(4-Phenoxy-pyrazolo[3,4-d]pyrimidin-1-yl)-piperidine-1-carboxylic acid tert-butyl ester Sodium hydride [60% dispersion in paraffin; 1.5 equivalents] in DMF was added to a solution of phenol (1 equivalent) in dimethylformamide (0.2 M) at 0° C. under nitrogen. After 30 minutes, 4-(4-chloro-pyrazolo[3,4-d]pyrimidin-1-yl)-piperidine-1-carboxylic acid tert-butyl ester (Intermediate 19; 1 equivalent) was added and the mixture was stirred for 12 h at room temperature. Saturated aqueous ammonium chloride was added and the solution was extracted with ethyl acetate. The combined organic extracts were dried (sodium sulfate), filtered, evaporated, and purified by chromatography on neutral alumina, eluting with ethyl acetate/hexane, to give 4-(4-phenoxy-pyrazolo[3,4-d]pyrimidin-1-yl)-piperidine-1-carboxylic acid tert-butyl ester.

Step 2: 4-(4-Phenoxy-pyrazolo[3,4-d]pyrimidin-1-yl)-piperidine-1-carboxylic acid isopropyl ester 4-(4-Phenoxy-pyrazolo[3,4-d]pyrimidin-1-yl)-piperidine-1-carboxylic acid isopropyl ester was prepared according to General Procedure D by the reaction of 4-(4-phenoxy-pyrazolo[3,4-d]pyrimidin-1-yl)-piperidine-1-carboxylic acid tert-butyl ester (from Step 1) with trifluoroacetic acid, followed by reaction of the resulting amine with isopropyl chloroformate (available from Aldrich Chemical Company, Inc., Milwaukee, Wis., USA). $^1$H NMR (400 MHz, DMSO-$d_6$) δ 1.20 (d, 6H, J=6.2 Hz), 1.94-2.03 (m, 4H), 3.00-3.12 (m, 2H), 4.08-4.15 (m, 2H), 4.78-4.82 (m, 1H), 5.00-5.02 (m, 1H), 7.32-7.38 (m, 3H), 7.49-7.53 (m, 2H), 8.11 (s, 1H), 8.54 (s, 1H). Mass spectrum MH+=382.

Example 16

4-[4-(2,4,5-Trifluoro-phenoxy)-pyrazolo[3,4-d]pyrimidin-1-yl]-piperidine-1-carboxylic acid isopropyl ester

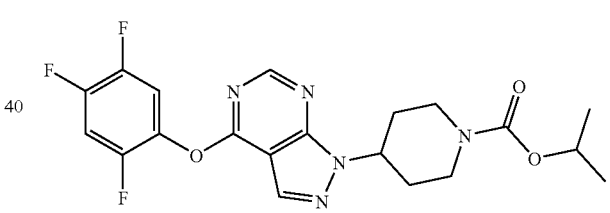

A mixture of 4-[4-(2,4,5-trifluoro-phenoxy)-pyrazolo[3,4-d]pyrimidin-1-yl]-piperidine-1-carboxylic acid tert-butyl ester (Example 35; 66 mg, 0.15 mmol) and 4M HCl in 1,4-dioxane (10 mL) was stirred at 40° C. for 1 h. The solvent was evaporated under vacuum to provide 1-piperidin-4-yl-4-(2,4,5-trifluoro-phenoxy)-1H-pyrazolo[3,4-d]pyrimidine hydrochloride as a solid which was used directly in the next step without purification. Dichloromethane (5 mL) was added, and the mixture was cooled to about 0° C. using an ice-water bath. Isopropyl chloroformate (available from Aldrich Chemical Company, Inc., Milwaukee, Wis., USA; 0.22 mL, 1.0 M in toluene, 0.22 mmol) was added, followed by triethylamine (0.13 mL, 0.96 mmol). The mixture was stirred at 0° C. for 30 min and then at room temperature for 2 h. Water and dichloromethane were added and the aqueous phase was extracted twice with each of the following solvents: dichloromethane, ether and hexane. The combined organic phases were evaporated and the resulting residue was purified by C18 reversed phase HPLC using a gradient of 20-100% acetonitrile/water to give 4-[4-(2,4,5-trifluoro-phenoxy)-pyrazolo[3,4-d]pyrimidin-1-yl]-piperidine-1-carboxylic acid isopropyl ester (47 mg, 73%) as a white powder. $^1$H NMR (400 MHz, DMSO-$d_6$) δ 1.28 (d, 6H, J=6.2 Hz), 1.98-2.05 (m, 4H), 2.18-2.25 (m, 2H), 3.00-3.10 (m, 2H), 4.08-4.15 (m, 2H), 4.80-4.82 (m, 1H), 5.00-5.05 (m, 1H), 7.88-7.94 (m, 2H), 8.47 (s, 1H), 8.59 (s, 1H). Mass spectrum MH+=436. HRMS Calcd. For $C_{20}H_{21}F_3N_5O_3$ (MH+): 436.1591. Found: 436.1589.

Example 17

4-[3-Methyl-4-(2,4,5-trifluoro-phenoxy)-pyrazolo[3,4-d]pyrimidin-1-yl]-piperidine-1-carboxylic acid isopropyl ester

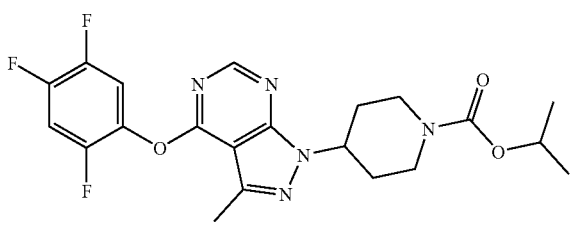

Sodium hydride (60% dispersion in mineral oil; 7 mg, 0.18 mmol) was added to a solution of 2,4,5-trifluorophenol (18 mg, 0.12 mmol) in dimethylformamide (1 mL) and the mixture was stirred at room temperature for 15 min. A solution of 4-(4-chloro-3-methyl-pyrazolo[3,4-d]pyrimidin-1-yl)piperidine-1-carboxylic acid isopropyl ester (Intermediate 21; 40 mg, 0.12 mmol) in dimethylformamide (1 mL) was added, and the reaction mixture was heated at 100° C. for 2 h. Saturated aqueous ammonium chloride solution was added and the mixture was extracted with ethyl acetate (3×25 mL). The organic layer was washed with water (3 times) and brine, dried (sodium sulfate), filtered, evaporated and purified on a flash silica column (20 mm×3") eluting with 25-33% ethyl acetate/hexanes to give 4-[3-methyl-4-(2,4,5-trifluoro-phenoxy)-pyrazolo[3,4-d]pyrimidin-1-yl]-piperidine-1-carboxylic acid isopropyl ester (37 mg, 70%) as a white foam. $^1$H NMR (300 MHz, DMSO-$d_6$) δ 1.20 (d, 6H, J=6.3 Hz), 1.93-2.02 (m, 4H), 2.62 (s, 3H), 2.96-3.09 (m, 2H), 3.32 (s, 3H), 4.04-4.12 (m, 2H), 4.74-4.83 (m, 1H), 4.89-4.96 (m, 1H), 7.81-7.90 (m, 2H), 8.48 (s, 1H). Mass spectrum (ES) MH+=450.

Example 18

4-[4-(4-Ethoxy-2-fluoro-phenoxy)-pyrazolo[3,4-d]pyrimidin-1-yl]-piperidine-1-carboxylic acid isopropyl ester

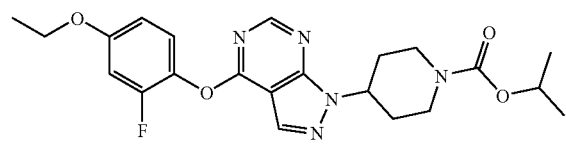

Isopropyl chloroformate (Aldrich Chemical Company, Inc., Milwaukee, Wis., USA; 1 M in toluene; 0.079 ml, 0.079 mol) was added to a mixture of 4-(4-ethoxy-2-fluoro-phenoxy)-1-piperidin-4-yl-1H-pyrazolo[3,4-d]pyrimidine trifluoroacetate salt (Intermediate 29; 28 mg, 0.078 mmol), and diisopropylethylamine (30 mg, 0.235 mmol) in dichloromethane (2 mL). The reaction mixture was stirred at room temperature overnight. Water was added to quench the reaction and the aqueous layer was extracted three times with dichloromethane. The combined organic layers were dried (sodium sulfate), filtered, evaporated and purified by flash chromatography on silica gel, eluting with 4% methanol/dichloromethane to give 4-[4-(4-ethoxy-2-fluoro-phenoxy)pyrazolo[3,4-d]pyrimidin-1-yl]-piperidine-1-carboxylic acid isopropyl ester (27 mg, 80%) as a white solid. Mass spectrum MH+=444.

Example 19

4-[4-(2-Cyano-phenoxy)-pyrazolo[3,4-d]pyrimidin-1-yl]-piperidine-1-carboxylic acid isopropyl ester

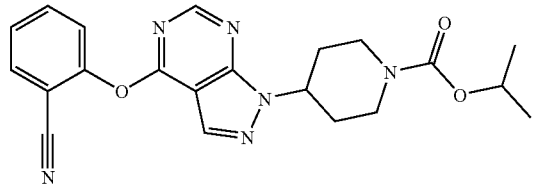

Isopropyl chloroformate (Aldrich Chemical Company, Inc., Milwaukee, Wis., USA 1M in toluene; 0.34 mL, 0.34 mmol) was added to a mixture of 2-(1-piperidin-4-yl-1H-pyrazolo[3,4-d]pyrimidine-4-yloxy)-benzonitrile trifluoroacetate salt (which was prepared from 4-[4-(2-cyano-phenoxy)-pyrazolo[3,4-d]pyrimidin-1-yl]-piperidine-1-carboxylic acid tert-butyl ester [Example 45] following the procedure described for the preparation of Intermediate 29; 150 mg, 0.344 mmol), diisopropylethylamine (133 mg, 1.03 mmol) in dichloromethane (6 mL). The reaction was stirred at room temperature overnight. Water was added to quench the reaction and the aqueous layer was extracted three times with dichloromethane. The combined organic layers were dried (sodium sulfate), filtered, evaporated and purified by flash chromatography on silica gel, eluting with 4% methanol/dichloromethane to give 4-[4-(2-cyano-phenoxy)-pyrazolo[3,4-d]pyrimidin-1-yl]-piperidine-1-carboxylic acid isopropyl ester (98 mg, 70%) as a white solid. Mass spectrum MH+=407.

Example 20

4-[4-(6-Cyano-2,3-difluoro-phenoxy)-pyrazolo[3,4-d]pyrimidin-1-yl]-piperidine-1-carboxylic acid isopropyl ester

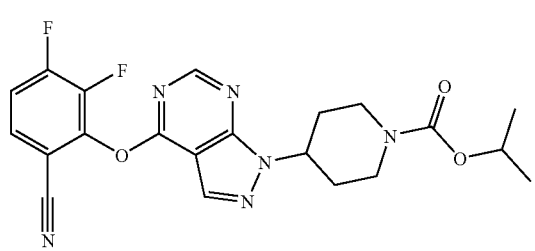

Isopropyl chloroformate (Aldrich Chemical Company, Inc., Milwaukee, Wis., USA 1M in toluene; 0.35 mL, 0.35 mmol) was added to a mixture of 3,4-difluoro-2-(1-piperidin-4-yl-1H-pyrazolo[3,4-d]pyrimidine-4-yloxy)-benzonitrile trifluoroacetate salt (which was prepared from 4-[4-(6-cyano-2,3-difluoro-phenoxy)-pyrazolo[3,4-d]pyrimidin-1-yl]-piperidine-1-carboxylic acid tert-butyl ester [Example 49] following the procedure described for the preparation of Intermediate 29; 180 mg, 0.35 mmol), diisopropylethylamine (136 mg, 1.06 mmol) in dichloromethane (6 mL). The reaction was stirred at room temperature overnight. Water was added to quench the reaction and the aqueous layer was extracted three times with dichloromethane. The combined organic layers were dried (sodium sulfate), filtered, evaporated and purified by flash chromatography on silica gel, eluting with 4% methanol/dichloromethane to give 4-[4-(6-cyano-2,3-difluoro-phenoxy)-pyrazolo-[3,4-d]pyrimidin-1-yl]-piperidine-1-carboxylic acid isopropyl ester (147 mg, 85%) as a white solid. Mass spectrum MH+=443.

Example 21

4-[4-(4-Methanesulfonyl-phenoxy)-pyrazolo[3,4-d]pyrimidin-1-yl]-piperidine-1-carboxylic acid isopropyl ester

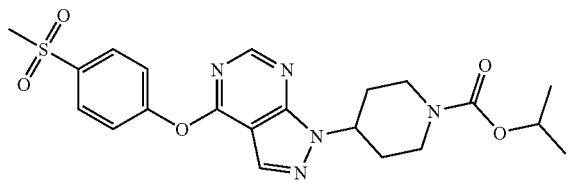

A solution of 4-[4-(4-methanesulfonyl-phenoxy)-pyrazolo[3,4-d]pyrimidin-1-yl]-piperidine-1-carboxylic acid tert-butyl ester (Example 59; 400 mg, 0.84 mmol) in a mixture of trifluoroacetic acid (3 mL) and dichloromethane (7 mL) was stirred at room temperature for 45 min. The solvents were evaporated and the residue was co-evaporated three times with dichloromethane, dried under high vacuum, and then diluted with 1M aqueous sodium carbonate solution. The mixture was extracted twice with dichloromethane and twice with 10% methanol/chloroform. The combined organic layers were dried (sodium sulfate) and evaporated. A solution of the residue in tetrahydrofuran (6 mL) and triethylamine (0.23 mL, 1.65 mmol) was cooled to −20° C. under nitrogen and a solution of isopropyl chloroformate in toluene (1 M; 0.8 mL, 0.8 mmol) was added. The mixture was stirred at −10° C. to −20° C. for 45 min, then allowed to reach room temperature, and then filtered through a Millipore filter. The filter was washed with tetrahydrofuran and ethyl acetate and the combined filtrate and washings were evaporated. The crude material was purified on a flash silica column (30 mm×4") eluting with 75-83% ethyl acetate/hexanes to give 4-[4-(4-methanesulfonyl-phenoxy)-pyrazolo[3,4-d]pyrimidin-1-yl]-piperidine-1-carboxylic acid isopropyl ester (235 mg, 61%) as a white solid. $^1$H NMR (300 MHz, DMSO-d$_6$) δ 1.20 (d, 6H, J=6.3 Hz), 1.92-2.04 (m, 4H), 2.98-3.12 (m, 2H), 3.28-3.30 (m, methyl sulfone and water peak), 4.07-4.15 (m, 2H), 4.75-4.84 (m, 1H), 4.96-5.05 (m, 1H), 7.60-7.63 (m, 2H), 8.02-8.05 (m, 2H), 8.37 (s, 1H), 8.55 (s, 1H). Mass spectrum (ES) MH+=460.

Example 22

4-[4-(4-Methanesulfonyl-phenoxy)-3-methyl-pyrazolo[3,4-d]pyrimidin-1-yl]-piperidine-1-carboxylic acid isopropyl ester

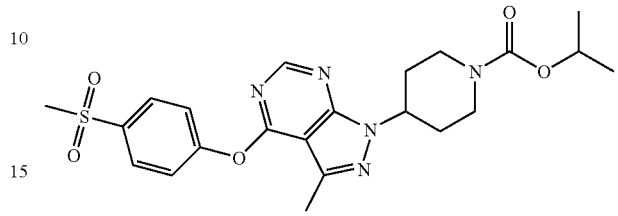

Sodium hydride (60% dispersion in mineral oil; 7 mg, 0.18 mmol) was added to a solution of 4-(methylsulfonyl)phenol (20 mg, 0.12 mmol) in dimethylformamide (1 mL) and the mixture was stirred at room temperature for 15 min. A solution of 4-(4-chloro-3-methyl-pyrazolo[3,4-d]pyrimidin-1-yl)-piperidine-1-carboxylic acid isopropyl ester (Intermediate 21; 40 mg, 0.12 mmol) in dimethylformamide (1 mL) was added, and the reaction mixture was allowed to stir at room temperature overnight. Saturated aqueous ammonium chloride solution was added and the mixture was extracted with ethyl acetate (3×25 mL). The organic layer was washed with water (3 times) and brine, dried (sodium sulfate), filtered, evaporated and purified on a flash silica column (20 mm×3") eluting with 75-80% ethyl acetate/hexanes to give 4-[4-(4-methanesulfonyl-phenoxy)-3-methyl-pyrazolo[3,4-d]pyrimidin-1-yl]-piperidine-1-carboxylic acid isopropyl ester (38 mg, 68%) as a white solid. $^1$H NMR (300 MHz, DMSO-d$_6$) δ 1.20 (d, 6H, J=6.3 Hz), 1.93-2.02 (m, 4H), 2.62 (s, 3H), 3.03-3.09 (m, 2H), 3.32 (s, 3H), 4.08-4.12 (m, 2H), 4.77-4.81 (m, 1H), 4.85-4.95 (m, 1H), 7.59-7.62 (m, 2H), 8.01-8.04 (m, 2H), 8.46 (s, 1H). Mass spectrum (ES) MH+=474.

Example 23

4-[4-(2-Fluoro-4-methanesulfonyl-phenoxy)-pyrazolo[3,4-d]pyrimidin-1-yl]-piperidine-1-carboxylic acid isopropyl ester

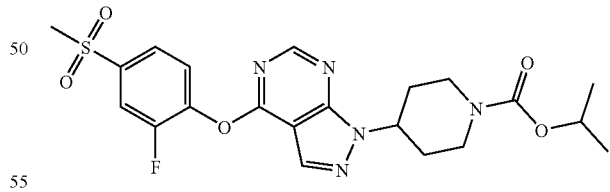

A mixture of 4-[4-(2-fluoro-4-methanesulfonyl-phenoxy)-pyrazolo[3,4-d]pyrimidin-1-yl]-piperidine-1-carboxylic acid tert-butyl ester (Example 60; 90 mg, 0.18 mmol) and 4 M HCl in dioxane (2 mL) was stirred at room temperature for 5 h. The solvent was evaporated and the residue was dried in vacuo to give a solid. To the solid were added ethyl acetate (3 mL) and triethylamine (74 mg, 0.73 mmol). The mixture was cooled to 10° C. and isopropyl chloroformate (1 M in toluene; 0.22 mL, 0.22 mmol) was added dropwise. The reaction mixture was allowed to warm to room temperature and stirred overnight. Water was added and the mixture was extracted with ethyl acetate. The combined organic layers were dried (sodium sulfate), filtered, evaporated, and purified by flash chromatography, eluting with 30% ethyl acetate/hexanes, to give 4-[4-(2-fluoro-4-methanesulfonyl-phenoxy)pyrazolo[3,4-d]pyrimidin-1-yl]-piperidine-1-carboxylic acid isopropyl ester (30 mg, 35%) as an off-white solid. Mass spectrum (ES) MH+=478.

Example 24

4-[4-(3-Fluoro-4-methanesulfonyl-phenoxy)-pyrazolo[3,4-d]pyrimidin-1-yl]-piperidine-1-carboxylic acid isopropyl ester

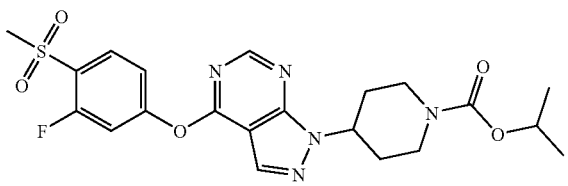

4-[4-(3-Fluoro-4-methanesulfonyl-phenoxy)-pyrazolo[3,4-d]pyrimidin-1-yl]-piperidine-1-carboxylic acid isopropyl ester was prepared using the procedure described above for the preparation of 4-(2-fluoro-4-methanesulfonyl-phenoxy)-1-[4-(3-isopropyl-[1,2,4]oxadiazol-5-yl)-cyclohexyl]-1H-pyrazolo[3,4-d]pyrimidine (Example 129) by the reaction of 4-(4-chloro-pyrazolo[3,4-d]pyrimidin-1-yl)-piperidine-1-carboxylic acid isopropyl ester (Intermediate 20) with 3-fluoro-4-methanesulfonyl-phenol (Intermediate 2) in dimethylformamide. The product was purified by flash chromatography, eluting with 5% methanol/dichloromethane to give 4-[4-(3-fluoro-4-methanesulfonyl-phenoxy)pyrazolo[3,4-d]pyrimidin-1-yl]-piperidine-1-carboxylic acid isopropyl ester (70 mg, 40%) as a white solid. Mass spectrum (ES) MH+=478.

Example 25

4-[4-(4-Acetylamino-phenoxy)-pyrazolo[3,4-d]pyrimidin-1-yl]-piperidine-1-carboxylic acid isopropyl ester

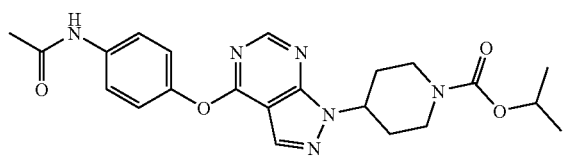

4-[4-(4-Acetylamino-phenoxy)-pyrazolo[3,4-d]pyrimidin-1-yl]-piperidine-1-carboxylic acid isopropyl ester was prepared was prepared according to General Procedure D by the reaction of 4-[4-(4-acetylamino-phenoxy)-pyrazolo[3,4-d]pyrimidin-1-yl]-piperidine-1-carboxylic acid tert-butyl ester (Example 70) with trifluoroacetic acid, followed by reaction of the resulting amine with isopropyl chloroformate (available from Aldrich Chemical Company, Inc., Milwaukee, Wis., USA).

Example 26

4-{4-[4-(5-Methyl-tetrazol-1-yl)-phenoxy]-pyrazolo[3,4-d]pyrimidin-1-yl}-piperidine-1-carboxylic acid isopropyl ester

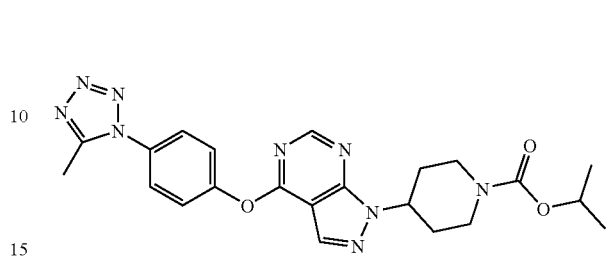

A solution of 20% trifluoroacetic acid/dichloromethane (12 mL) was added to a solution of 4-{4-[4-(5-methyl-tetrazol-1-yl)-phenoxy]-pyrazolo[3,4-d]pyrimidin-1-yl}-piperidine-1-carboxylic acid tert-butyl ester (Example 84; 486 mg, 1.02 mmol) in dichloromethane (2 mL) and the mixture was stirred at room temperature for 25 min. The volatiles were evaporated and the residue held at high vacuum and then triturated with ether to give 4-{4-[4-(5-methyl-tetrazol-1-yl)-phenoxy]-pyrazolo[3,4-d]pyrimidin-1-yl}-piperidine-1-carboxylic acid trifluoro-acetate salt (493 mg, 98%) as a white solid. This was taken up in dichloromethane (3 mL) and diisopropylethylamine (243 µL, 1.37 mmol) was added. The mixture was cooled to 0° C., and isopropyl chloroformate (Aldrich Chemical Company, Inc., Milwaukee, Wis., USA; 1 M in toluene; 458 µL, 0.46 mol) was added dropwise. The mixture was stirred at room temperature for 1.5 h. Water (5 mL) was added and the layers were separated. The organic layers was washed with brine, dried (sodium sulfate), filtered, and evaporated. The residue was purified on a Supelco 11 g column, eluting with 6% methanol/dichloromethane to give 4-{4-[4-(5-methyl-tetrazol-1-yl)-phenoxy]-pyrazolo[3,4-d]pyrimidin-1-yl}-piperidine-1-carboxylic acid isopropyl ester (136 mg, 64%) as a white powder. $^1$H NMR (DMSO-$d_6$) δ 1.20 (d, 6H, J=6.4 Hz), 1.93-2.05 (m, 4H), 2.59 (s, 3H), 2.96-3.14 (m, 2H), 4.04-4.18 (m, 2H), 4.79 (pentet, 1H, J=6.3 Hz), 4.96-5.08 (m, 1H), 7.61-7.64 (m, 2H), 7.79-7.82 (m, 2H), 8.36 (s, 1H), 8.57 (s, 1H).

Example 27

4-[4-(2-Methyl-pyridin-3-yloxy)-pyrazolo[3,4-d]pyrimidin-1-yl]-piperidine-1-carboxylic acid isopropyl ester

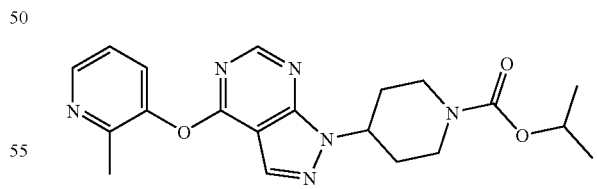

Trifluoroacetic acid (3 mL) was added to a solution of 4-[4-(2-methyl-pyridin-3-yloxy)-pyrazolo[3,4-d]pyrimidin-1-yl]-piperidine-1-carboxylic acid tert-butyl ester (Example 92; 300 mg, 0.7 mmol) in dichloromethane (12 mL). The solution was stirred at room temperature for 30 min and then the solvents were evaporated, first using house vacuum and then high vacuum. Dichloromethane (10 mL) was added to the residue, and then a solution of isopropyl chloroformate in toluene (Aldrich Chemical Company, Inc., Milwaukee, Wis., USA 1 M; 1.1 mL, 1.1 mmol) was added at room temperature, followed by triethylamine (480 mg, 4.7 mmol). The mixture was stirred for 2 h at room temperature and then water was added. The layers were separated and the aqueous layer was extracted twice with dichloromethane. The combined organic layers were evaporated, and purified by silica gel column chromatography, eluting with 0-80% ethyl acetate/hexanes) to give 4-[4-(2-methyl-pyridin-3-yloxy)-pyrazolo[3,4-d]pyrimidin-1-yl]-piperidine-1-carboxylic acid isopropyl ester (291 mg, 100%) as a viscous oil. $^1$H NMR (300 MHz, CDCl$_3$) δ 1.28 (d, 6H, J=6.4 Hz), 2.00-2.03 (m, 1H), 2.24-2.30 (m, 2H), 2.46 (s, 3H), 2.95-3.04 (m, 2H), 4.27-4.39 (m, 2H), 4.93-5.00 (m, 2H), 7.28-7.32 (m, 1H), 7.52-7.55 (m, 1H), 8.07 (s, 1H), 8.48-8.52 (m, 2H). Mass spectrum MH+=397. HRMS Calcd. For C$_{20}$H$_{25}$N$_6$O$_3$ (MH+): 397.1983. Found: 397.1982.

Example 28

4-[4-(2-Methyl-pyridin-3-yloxy)-pyrazolo[3,4-d]pyrimidin-1-yl]-piperidine-1-carboxylic acid isopropyl ester hydrochloride salt

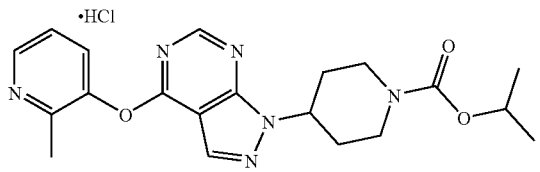

HCl (Sigma Aldrich Chemical Company, Inc., Milwaukee, Wis., USA 2M in ether; 0.43 mL, 0.86 mmol) was added to a solution of 4-[4-(2-Methyl-pyridin-3-yloxy)-pyrazolo[3,4-d]pyrimidin-1-yl]-piperidine-1-carboxylic acid isopropyl ester (170 mg, 0.43 mmol) in anhydrous ether (2 mL). The resulting mixture was shaken at room temperature for 10 min. The solvent was evaporated under high vacuum to give a white powder which still contained some ether by NMR. The solid was ground to a fine powder using a spatula and then it was held overnight in a vacuum oven overnight at 80° C. to give 4-[4-(2-methyl-pyridin-3-yloxy)-pyrazolo[3,4-d]pyrimidin-1-yl]-piperidine-1-carboxylic acid isopropyl ester hydrochloride salt (147 mg, 79%) as a white powder. $^1$H NMR (300 MHz, CDCl$_3$) δ 1.28 (d, 6H, J=6.0 Hz), 2.01-2.04 (m, 2H), 2.22-2.31 (m, 2H), 2.87 (s, 3H), 2.98-3.06 (m, 2H), 4.30-4.42 (m, 2H), 4.95-5.05 (m, 2H), 7.79-7.84 (m, 1H), 8.19-8.24 (m, 2H), 8.44 (s, 1H), 8.61-8.63 (m, 1H).

Example 29

4-[4-(6-Methanesulfonyl-2-methyl-pyridin-3-yloxy)-pyrazolo[3,4-d]pyrimidin-1-yl]-piperidine-1-carboxylic acid isopropyl ester

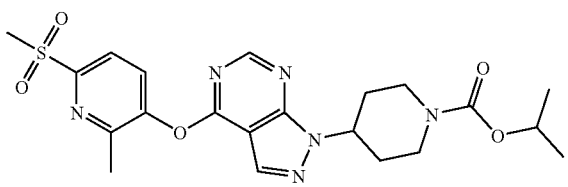

Trifluoroacetic acid (0.4 mL) was added to a solution of 4-[4-(6-methanesulfonyl-2-methyl-pyridin-3-ylamino)-pyrazolo[3,4-d]pyrimidin-1-yl]-piperidine-1-carboxylic acid tert-butyl ester (Example 98; 50 mg, 0.10 mmol) in dichloromethane (2 mL). The solution was stirred at room temperature for 30 min and then the solvents were evaporated under vacuum. Dichloromethane (3 mL) was added to the residue, and then isopropyl chloroformate (1 M in toluene; 0.15 mL, 0.15 mmol) was added, followed by triethylamine (92 µL, 0.66 mmol). The mixture was stirred overnight at room temperature and then water and dichloromethane were added. The layers were separated and the aqueous layer was extracted twice with dichloromethane. The combined organic layers were evaporated, and purified by preparative C18 HPLC, eluting with 10-100% acetonitrile/water. Samples containing the product were extracted three times with dichloromethane and the solvent was evaporated to give the desired product along with a protonated triethylammonium cation. This material was purified by chromatography on silica gel, and the material from this column was dissolved in dichloromethane. The solution was washed with 1 M sodium carbonate solution and the aqueous layer was extracted twice with dichloromethane. The combined organic layers were evaporated to give 4-[4-(6-methanesulfonyl-2-methyl-pyridin-3-yloxy)-pyrazolo[3,4-d]pyrimidin-1-yl]-piperidine-1-carboxylic acid isopropyl ester (25 mg, 52%) as a white solid. $^1$H NMR (300 MHz, DMSO-d$_6$) δ 1.20 (d, 6H, J=6.3 Hz), 1.93-2.06 (m, 4H), 2.43 (s, 3H), 3.00-3.13 (m, 2H), 3.30 (water peak and SO$_2$CH$_3$ peak), 4.07-4.14 (m, 2H), 4.75-4.84 (m, 1H), 4.98-5.08 (m, 1H), 8.02 (d, 1H, J=8.2 Hz), 8.10 (d, 1H, J=8.2 Hz), 8.48 (s, 1H), 8.54 (s, 1H). Mass spectrum MH+=475, M+Na=497. HRMS Calcd. for C$_{21}$H$_{27}$N$_6$O$_5$S (MH+): 475.1758. Found: 475.1757.

Example 30

4-[4-(2-Methyl-6-[1,2,4]triazol-1-yl-pyridin-3-yloxy)-pyrazolo[3,4-d]pyrimidin-1-yl]-piperidine-1-carboxylic acid isopropyl ester

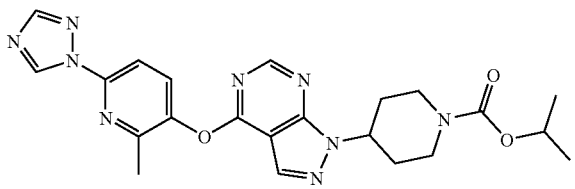

A mixture of 4-[4-(2-methyl-6-[1,2,4]triazol-1-yl-pyridin-3-yloxy)-pyrazolo[3,4-d]pyrimidin-1-yl]-piperidine-1-carboxylic acid tert-butyl ester (Example 101; 50 mg, 0.105 mmol), trifluoroacetic acid (428 µL) and dichloromethane (2 mL) was stirred at room temperature for 30 min. The volatiles were evaporated under high vacuum and the residue was dissolved in dichloromethane (3 mL). Isopropyl chloroformate (1 M in toluene; 158 µL, 0.16 mmol) and triethylamine (95 µL, 0.68 mmol) were added and the mixture was stirred overnight at room temperature. 1 M aqueous sodium carbonate (6 mL) and dichloromethane (3 mL) were added, and the aqueous layer was extracted twice with dichloromethane. The combined organic extracts were evaporated and the residue was purified by preparative C18 HPLC, eluting with 10-100% acetonitrile/water. Samples containing the product were extracted three times with dichloromethane and the solvent was evaporated to give 4-[4-(2-methyl-6-[1,2,4]triazol-1-yl-pyridin-3-yloxy)-pyrazolo[3,4-d]pyrimidin-1-yl]- piperidine-1-carboxylic acid isopropyl ester (35 mg, 72%) as a white powder. ¹H NMR (300 MHz, CDCl₃) δ 1.28 (d, 6H, J=6.0 Hz), 1.97-2.10 (m, 2H, J=10.9 Hz), 2.20-2.35 (m, 2H), 2.46 (s, 3H), 2.89-3.14 (m, 2H), 4.32-4.48 (m, 2H), 4.84-5.08 (m, 2H), 7.68 (d, 1H, J=8.8 Hz), 7.86 (d, 1H, J=8.8 Hz), 8.11 (s, 1H), 8.17 (s, 1H), 8.48 (s, 1H), 9.19 (s, 1H). Mass spectrum (ES) MH+=464. HRMS Calcd. for $C_{22}H_{26}N_9O_3$ (MH+): 464.2153. Found: 464.2151.

Example 31

4-[4-(1-Methyl-6-oxo-1,6-dihydro-pyridazin-3-yloxy)-pyrazolo[3,4-d]pyrimidin-1-yl]-piperidine-1-carboxylic acid isopropyl ester

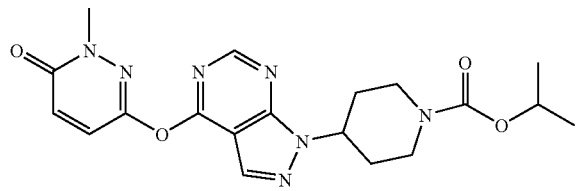

A mixture of 4-[4-(1-methyl-6-oxo-1,6-dihydro-pyridazin-3-yloxy)-pyrazolo[3,4-d]pyrimidin-1-yl]-piperidine-1-carboxylic acid tert-butyl ester (Example 102; 120 mg, 0.28 mmol), trifluoroacetic acid (1.1 mL) and dichloromethane (5.5 mL) was stirred at room temperature for 30 min. The volatiles were evaporated under high vacuum and the residue was dissolved in dichloromethane (6 mL). Isopropyl chloroformate (1 M in toluene; 0.42 mL, 0.42 mmol) and triethylamine (254 μL, 1.8 mmol) were added and the mixture was stirred overnight at room temperature. 1 M aqueous sodium carbonate and dichloromethane were added, and the aqueous layer was extracted three times with dichloromethane. The combined organic extracts were evaporated and the residue was purified by column chromatography on silica gel, eluting with 0-4% methanol/dichloromethane, to give 4-[4-(1-methyl-6-oxo-1,6-dihydro-pyridazin-3-yloxy)-pyrazolo[3,4-d]pyrimidin-1-yl]-piperidine-1-carboxylic acid isopropyl ester (79 mg, 68%) as a white powder. ¹H NMR (300 MHz, CDCl₃) δ 1.27 (d, 6H, J=6.0 Hz), 2.01 (d, 2H, J=10.9 Hz), 2.11-2.39 (m, 2H), 3.01 (t, 2H, J=12.8 Hz), 3.76 (s, 3H), 4.35 (br s, 2H), 4.85-5.06 (m, 2H), 7.07 (d, 1H, J=10.0 Hz), 7.23 (d, 1H, J=10.0 Hz), 8.17 (s, 1H), 8.51 (s, 1H). Mass spectrum (ES) MH+=414. HRMS Calcd. for $C_{19}H_{24}N_7O_4$ (MH+): 414.1885. Found: 414.1884.

Example 32

4-[4-(2-Fluoro-phenoxy)-pyrazolo[3,4-d]pyrimidin-1-yl]-piperidine-1-carboxylic acid tert-butyl ester

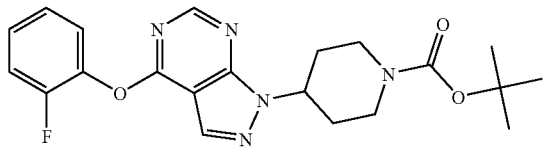

4-[4-(2-Fluoro-phenoxy)-pyrazolo[3,4-d]pyrimidin-1-yl]-piperidine-1-carboxylic acid tert-butyl ester was prepared according to General Procedure A by the reaction of 4-(4-chloro-pyrazolo[3,4-d]pyrimidin-1-yl)-piperidine-1-carboxylic acid tert-butyl ester (Intermediate 19) with 2-fluorophenol (available from Aldrich Chemical Company, Inc., Milwaukee, Wis., USA) in acetonitrile. ¹H NMR (400 MHz, DMSO-d₆) δ 1.43 (s, 9H), 1.97-2.07 (m, 4H), 2.97-3.07 (m, 2H), 4.05-4.12 (m, 2H), 4.98-5.05 (m, 1H), 7.31-7.50 (m, 4H), 8.38 (s, 1H), 8.55 (s, 1H). Mass spectrum MH+=414.

Example 33

4-[4-(3-Fluoro-phenoxy)-pyrazolo[3,4-d]pyrimidin-1-yl]-piperidine-1-carboxylic acid tert-butyl ester

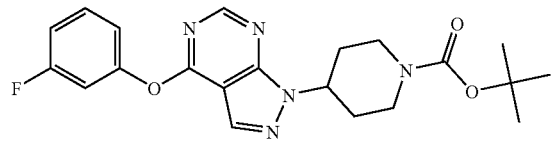

4-[4-(3-Fluoro-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 3-fluorophenol (available from Aldrich Chemical Company, Inc., Milwaukee, Wis., USA) in dimethylformamide. ¹H NMR (400 MHz, DMSO-d₆) δ 1.43 (s, 9H), 1.93-2.08 (m, 4H), 2.97-3.07 (m, 2H), 4.05-4.15 (m, 2H), 4.98-5.03 (m, 1H), 7.20-7.24 (m, 2H), 7.33-7.38 (m, 1H), 7.52-7.56 (m, 1H), 8.28 (s, 1H), 8.58 (s, 1H). Mass spectrum MH+=414.

Example 34

4-[4-(4-Fluoro-phenoxy)-pyrazolo[3,4-d]pyrimidin-1-yl]-piperidine-1-carboxylic acid tert-butyl ester

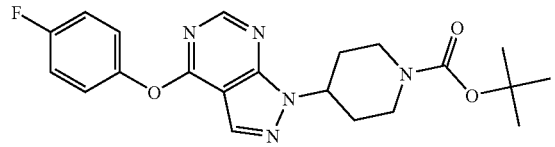

4-[4-(4-Fluoro-phenoxy)-pyrazolo[3,4-d]pyrimidin-1-yl]-piperidine-1-carboxylic acid tert-butyl ester was prepared according to General Procedure A by the reaction of 4-(4-chloro-pyrazolo[3,4-d]pyrimidin-1-yl)-piperidine-1-carboxylic acid tert-butyl ester (Intermediate 19) with 4-fluorophenol (available from Aldrich Chemical Company, Inc., Milwaukee, Wis., USA) in tetrahydrofuran. ¹H NMR (400 MHz, DMSO-d₆) δ 1.43 (s, 9H), 1.93-2.05 (m, 4H), 2.97-3.07 (m, 2H), 4.05-4.15 (m, 2H), 4.99-5.02 (m, 1H), 7.23-7.41 (m, 4H), 8.22 (s, 1H), 8.54 (s, 1H). Mass spectrum MH+=414.

Example 35

4-[4-(2,4,5-Trifluoro-phenoxy)-pyrazolo[3,4-d]pyrimidin-1-yl]-piperidine-1-carboxylic acid tert-butyl ester

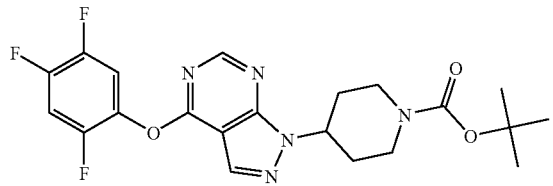

Potassium carbonate (53 mg, 0.39 mmol) was added to a solution of 4-(4-chloro-pyrazolo[3,4-d]pyrimidin-1-yl)-piperidine-1-carboxylic acid tert-butyl ester (Intermediate 19; 100 mg, 0.3 mmol) and 2,4,5-trifluoro-phenol (available from Alfa Aesar, Ward Hill, Mass., USA; 57 mg, 0.39 mmol) in dimethylformamide (5 mL). The reaction mixture was heated at 100° C. in an oil bath overnight, then it was cooled to room temperature, and water and diethyl ether were added. The aqueous phase was extracted twice with diethyl ether and three times with hexane. The combined organic phases were evaporated and the resulting residue was purified by C18 reversed phase HPLC using a gradient of 20-100% acetonitrile/water to give 4-[4-(2,4,5-trifluoro-phenoxy)-pyrazolo[3,4-d]pyrimidin-1-yl]-piperidine-1-carboxylic acid tert-butyl ester (66 mg, 50%) as a white powder. $^1$H NMR (300 MHz, CDCl$_3$) δ 1.49 (s, 9H), 1.95-2.06 (m, 2H), 2.18-2.34 (m, 2H), 2.90-3.06 (m, 2H), 4.26-4.38 (m, 2H), 4.90-5.02 (m, 1H), 7.09-7.21 (m, 2H), 8.16 (s, 1H), 8.49 (s, 1H). HRMS Calcd. for C$_{21}$H$_{23}$F$_3$N$_5$O$_3$ (MH+): 450.1748. Found: 450.1745.

Example 36

4-[4-(2,4,6-Trifluoro-phenoxy)-pyrazolo[3,4-d]pyrimidin-1-yl]-piperidine-1-carboxylic acid tert-butyl ester

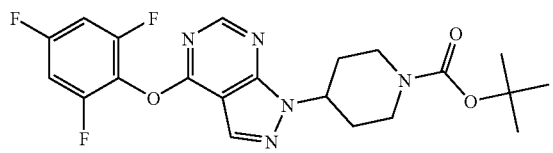

4-[4-(2,4,6-Trifluoro-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 2,4,6-trifluorophenol (available from Aldrich Chemical Company, Inc., Milwaukee, Wis., USA) in dimethylformamide. $^1$H NMR (400 MHz, DMSO-d$_6$) δ 1.43 (s, 9H), 1.99-2.05 (m, 4H), 2.97-3.05 (m, 2H), 4.07-4.11 (m, 2H), 5.00-5.05 (m, 1H), 7.51-7.55 (m, 2H), 8.53 (s, 1H), 8.60 (s, 1H). Mass spectrum MH+=450.

Example 37

4-[4-(2,3,5-Trifluoro-phenoxy)-pyrazolo[3,4-d]pyrimidin-1-yl]-piperidine-1-carboxylic acid tert-butyl ester

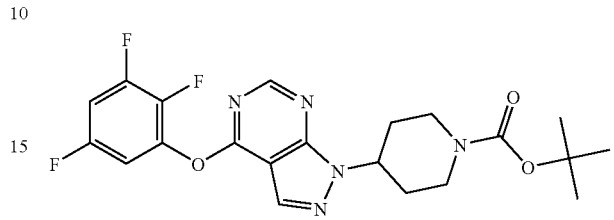

4-[4-(2,3,5-Trifluoro-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 2,4,6-trifluorophenol (available from Acros Organics, Geel, Belgium) in dimethylformamide. $^1$H NMR (400 MHz, CDCl$_3$) δ 1.42 (s, 9H), 1.99-2.03 (m, 2H), 2.21-2.30 (m, 2H), 2.94-3.00 (m, 2H), 4.26-4.35 (m, 2H), 4.93-4.99 (m, 1H), 6.88-6.95 (m, 2H), 8.15 (s, 1H), 8.49 (s, 1H). Mass spectrum MH+=450.

Example 38

4-[4-(2,4-Dichloro-phenoxy)-pyrazolo[3,4-d]pyrimidin-1-yl]-piperidine-1-carboxylic acid tert-butyl ester

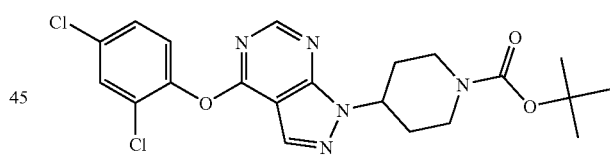

A mixture of 4-(4-chloro-pyrazolo[3,4-d]pyrimidin-1-yl)-piperidine-1-carboxylic acid tert-butyl ester (Intermediate 19; 42 mg, 0.12 mmol), anhydrous potassium carbonate (22 mg, 0.16 mmol) and 2,4-dichlorophenol (26 mg, 0.16 mmol) in N-methylpyrrolidinone (0.5 mL) was heated to 100° C. in a sealed scintillation vial. After 18 hr, the mixture was allowed to cool to room temperature and the reaction mixture purified by reverse phase HPLC to give 4-[4-(2,4-dichloro-phenoxy)-pyrazolo[3,4-d]pyrimidin-1-yl]-piperidine-1-carboxylic acid tert-butyl ester (8 mg, 14%) as a white powder. $^1$H NMR (300 MHz, CDCl$_3$) δ 1.49 (s, 9H), 1.97-2.05 (m, 2H), 2.18-2.33 (m, 2H), 2.90-3.04 (m, 2H), 4.24-4.40 (m, 2H), 4.90-5.02 (m, 1H), 7.23-7.25 (m, 1H), 7.36 (dd, 1H, J=8.6, 2.6 Hz), 7.64 (d, 1H, J=2.1 Hz), 8.12 (s, 1H), 8.49 (s, 1H). Mass spectrum MH+=464.

Example 39

4-[4-(4-Methoxy-phenoxy)-pyrazolo[3,4-d]pyrimidin-1-yl]-piperidine-1-carboxylic acid tert-butyl ester

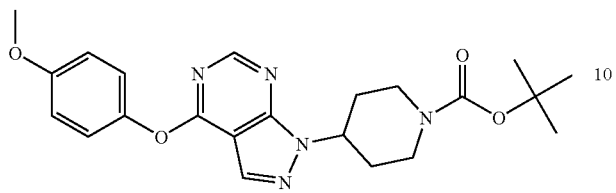

A mixture of 4-(4-chloro-pyrazolo[3,4-d]pyrimidin-1-yl)-piperidine-1-carboxylic acid tert-butyl ester (Intermediate 19; 50 mg, 0.15 mmol), 4-methoxy-phenol (Aldrich Chemical Company, Inc., Milwaukee, Wis., USA 24 mg, 0.19 mmol), and potassium carbonate (27 mg, 0.2 mmol) in dimethylformamide (2 mL) was heated in the microwave oven at 160° C. for 10 min. Dichloromethane and water were added, and the dichloromethane layer was washed twice with water. The dichloromethane layer was evaporated, and purified by preparative C18 HPLC, eluting with 25-100% acetonitrile/water to give 4-[4-(4-methoxy-phenoxy)-pyrazolo[3,4-d]pyrimidin-1-yl]-piperidine-1-carboxylic acid tert-butyl ester (19 mg, 28%) as an off-white powder. $^1$H NMR (300 MHz, CDCl$_3$) δ 1.49 (s, 9H), 1.95-2.02 (m, 2H), 2.16-2.30 (m, 2H), 2.90-3.04 (m, 2H), 3.85 (s, 3H), 4.22-4.37 (m, 2H), 4.88-4.99 (m, 1H), 6.98 (d, 1H, J=8.7 Hz), 7.16 (d, 1H, J=8.9 Hz), 7.77 (s, 1H), 8.54 (s, 1H). Mass spectrum MH+=426. HRMS Calcd. For C$_{22}$H$_{28}$N$_5$O$_4$ (MH+): 426.2136. Found: 426.2134.

Example 40

4-[4-(4-Ethoxy-phenoxy)-pyrazolo[3,4-d]pyrimidin-1-yl]-piperidine-1-carboxylic acid tert-butyl ester

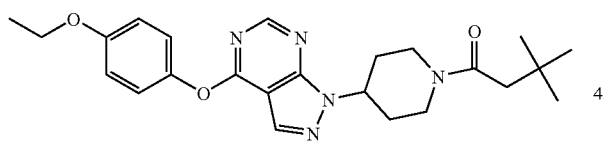

A mixture of 4-(4-chloro-pyrazolo[3,4-d]pyrimidin-1-yl)-piperidine-1-carboxylic acid tert-butyl ester (Intermediate 19; 50 mg, 0.15 mmol), 4-ethoxyphenol (Aldrich Chemical Company, Inc., Milwaukee, Wis., USA 27 mg, 0.19 mmol), and potassium carbonate (27 mg, 0.2 mmol) in dimethylformamide (2 mL) was heated in the microwave oven at 160° C. for 10 min. Ethyl acetate and water were added, and the aqueous layer was extracted twice with ethyl acetate. The ethyl acetate layers were combined, evaporated, and purified by preparative C18 HPLC, eluting with 10-100% acetonitrile/water. Samples containing the product were extracted twice with dichloromethane and the solvent was evaporated under high vacuum to give 4-[4-(4-ethoxy-phenoxy)-pyrazolo[3,4-d]pyrimidin-1-yl]-piperidine-1-carboxylic acid tert-butyl ester (34 mg, 52%) as a white powder. $^1$H NMR (300 MHz, CDCl$_3$) δ 1.44 (t, 3H, J=7.0 Hz), 1.49 (s, 9H), 1.96-2.05 (m, 2H), 2.17-2.30 (m, 1H), 2.86-3.04 (m, 2H), 4.06 (q, 2H, J=6.9 Hz), 4.23-4.36 (m, 2H), 4.90-5.00 (m, 1H), 6.97 (d, 2H, J=8.8 Hz), 7.15 (d, 2H, J=9.0 Hz), 8.54 (s, 1H), 8.54 (s, 1H). Mass spectrum (ES) MH+=440. HRMS Calcd. for C$_{23}$H$_{30}$N$_5$O$_4$ (MH+): 440.2293. Found: 440.2292.

Example 41

4-[4-(Benzo[1,3]dioxol-5-yloxy)-pyrazolo[3,4-d]pyrimidin-1-yl]-piperidine-1-carboxylic acid tert-butyl ester

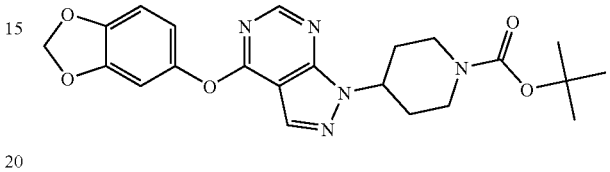

A mixture of Benzo[1,3]dioxol-5-ol (Aldrich Chemical Company, Inc., Milwaukee, Wis., USA; 11 mg, 0.074 mmol), 4-(4-chloro-pyrazolo[3,4-d]pyrimidin-1-yl)-piperidine-1-carboxylic acid tert-butyl ester (Intermediate 19; 25 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(Benzo[1,3]dioxol-5-yloxy)-pyrazolo[3,4-d]pyrimidin-1-yl]-piperidine-1-carboxylic acid tert-butyl ester (3 mg, 10%) as a white solid. Mass spectrum MH+=440.

Example 42

4-[4-(4-Trifluoromethoxy-phenoxy)-pyrazolo[3,4-d]pyrimidin-1-yl]-piperidine-1-carboxylic acid tert-butyl ester

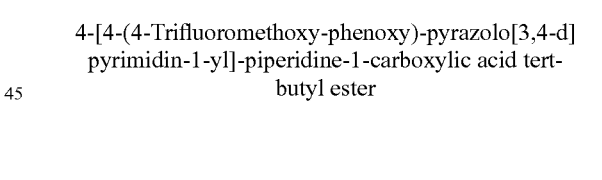

4-[4-(4-Trifluoromethoxy-phenoxy)-pyrazolo[3,4-d]pyrimidin-1-yl]-piperidine-1-carboxylic acid tert-butyl ester (12.8 mg, 30%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 30 mg, 0.09 mmol) with 4-(trifluoromethoxy)-phenol (Avocado Research Chemicals; 16 mg, 0.09 mmol) in the presence of potassium carbonate (27 mg, 0.195 mmol). Mass spectrum MH+=480.

Example 43

4-[4-(4-Ethoxy-2-fluoro-phenoxy)-pyrazolo[3,4-d]pyrimidin-1-yl]-piperidine-1-carboxylic acid tert-butyl ester

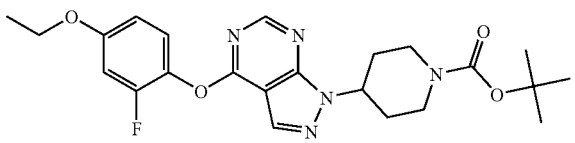

A mixture of 4-ethoxy-2-fluoro-phenol (Intermediate 5; 125 mg, 0.801 mmol), 4-(4-chloro-pyrazolo[3,4-d]pyrimidin-1-yl)-piperidine-1-carboxylic acid tert-butyl ester (Intermediate 19; 270 mg, 0.801 mmol), and potassium carbonate (244 mg, 1.761 mmol) in 4 mL of dimethylformamide was heated in a microwave oven at 160° C. for 10 min. Saturated sodium carbonate solution was added to the reaction mixture, the precipitate was filtered and the filtrate was extracted with ethyl acetate three times and the combined organic extracts were washed with saturated brine, and dried over sodium sulfate. The mixture was filtered, concentrated and purified by flash silica gel chromatography (4% methanol in dichloromethane) to afford 4-[4-(4-ethoxy-2-fluoro-phenoxy)-pyrazolo[3,4-d]pyrimidin-1-yl]-piperidine-1-carboxylic acid tert-butyl ester (141 mg, 39%) as a white solid. Mass spectrum M+H-Boc=358.

Example 44

4-[4-(2-Chloro-4-methoxy-phenoxy)-pyrazolo[3,4-d]pyrimidin-1-yl]-piperidine-1-carboxylic acid tert-butyl ester

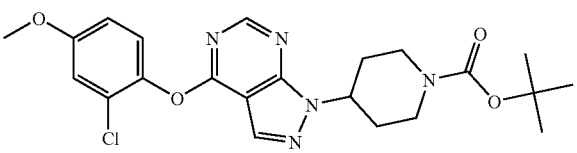

A mixture of 2-chloro-4-methoxy-phenol (Aldrich Chemical Company, Inc., Milwaukee, Wis., USA 29 mg, 0.178 mmol), 4-(4-chloro-pyrazolo[3,4-d]pyrimidin-1-yl)-piperidine-1-carboxylic acid tert-butyl ester (Intermediate 19; 60 mg, 0.178 mmol), and potassium carbonate (54 mg, 0.391 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to afford 4-[4-(2-chloro-4-methoxy-phenoxy)-pyrazolo[3,4-d]pyrimidin-1-yl]-piperidine-1-carboxylic acid tert-butyl ester (28 mg, 34%) as a white solid. Mass spectrum MH+=460.

Example 45

4-[4-(2-Cyano-phenoxy)-pyrazolo[3,4-d]pyrimidin-1-yl]-piperidine-1-carboxylic acid tert-butyl ester

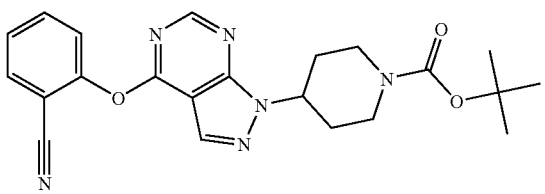

4-[4-(2-Cyano-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 2-hydroxybenzonitrile (available from Alfa Aesar, Ward Hill, Mass., USA) in dimethylformamide. $^1$H NMR (400 MHz, DMSO-$d_6$) δ 1.43 (s, 9H), 1.98-2.08 (m, 4H), 2.98-3.08 (m, 2H), 4.08-4.11 (m, 2H), 5.01-5.06 (m, 1H), 7.55-7.59 (m, 1H), 7.63-7.65 (m, 1H), 7.85-7.90 (m, 1H), 8.02-8.04 (m, 1H), 8.47 (s, 1H), 8.58 (s, 1H). Mass spectrum MH+=421.

Example 46

4-[4-(4-Cyano-phenoxy)-pyrazolo[3,4-d]pyrimidin-1-yl]-piperidine-1-carboxylic acid tert-butyl ester

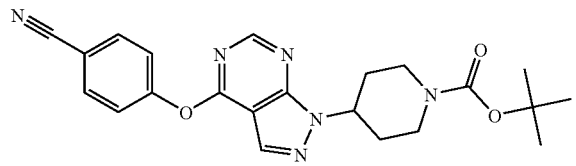

4-[4-(4-Cyano-phenoxy)-pyrazolo[3,4-d]pyrimidin-1-yl]-piperidine-1-carboxylic acid tert-butyl ester was prepared according to General Procedure A by the reaction of 4-(4-chloro-pyrazolo[3,4-d]pyrimidin-1-yl)-piperidine-1-carboxylic acid tert-butyl ester (Intermediate 19) with 4-cyanophenol (available from Aldrich Chemical Company, Inc., Milwaukee, Wis., USA) in acetonitrile. $^1$H NMR (400 MHz, DMSO-$d_6$) δ 1.43 (s, 9H), 1.94-2.04 (m, 4H), 2.95-3.05 (m, 2H), 4.08-4.11 (m, 2H), 4.98-5.04 (m, 1H), 7.58-7.60 (m, 2H), 7.99-8.01 (m, 2H), 8.37 (s, 1H), 8.56 (s, 1H). Mass spectrum MH+=421.

Example 47

4-[4-(4-Cyano-2-fluoro-phenoxy)-pyrazolo[3,4-d]pyrimidin-1-yl]-piperidine-1-carboxylic acid tert-butyl ester

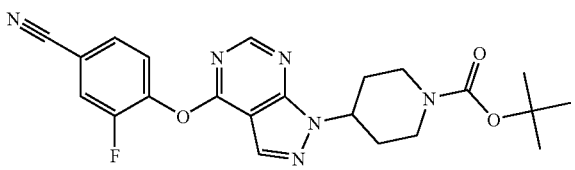

4-[4-(4-Cyano-2-fluoro-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 3-fluoro-4-hydroxybenzonitrile (available from Alfa Aesar, Ward Hill, Mass., USA) in dimethylformamide. $^1$H NMR (400 MHz, DMSO-$d_6$) δ 1.43 (s, 9H), 1.98-2.07 (m, 4H), 2.99-3.07 (m, 2H), 4.07-4.12 (m, 2H), 5.00-5.05 (m, 1H), 7.76-7.80 (m, 1H), 7.88-7.90 (m, 1H), 8.16-8.19 (m, 1H), 8.50 (s, 1H), 8.57 (s, 1H). Mass spectrum MH+=439.

Example 48

4-[4-(4-Cyano-3-fluoro-phenoxy)-pyrazolo[3,4-d]pyrimidin-1-yl]-piperidine-1-carboxylic acid tert-butyl ester

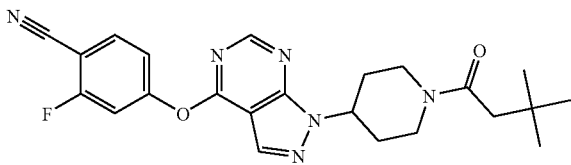

4-[4-(4-Cyano-3-fluoro-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 2-fluoro-4-hydroxybenzonitrile (available from Aldrich Chemical Company, Inc., Milwaukee, Wis., USA) in dimethylformamide. $^1$H NMR (400 MHz, DMSO-$d_6$) δ 1.43 (s, 9H), 1.94-2.04 (m, 4H), 2.99-3.07 (m, 2H), 4.08-4.11 (m, 2H), 5.01-5.05 (m, 1H), 7.47-7.50 (m, 1H), 7.75-7.79 (m, 1H), 8.08-8.12 (m, 1H), 8.42 (s, 1H), 8.60 (s, 1H). Mass spectrum MH+=439.

Example 49

4-[4-(6-Cyano-2,3-difluoro-phenoxy)-pyrazolo[3,4-d]pyrimidin-1-yl]-piperidine-1-carboxylic acid tert-butyl ester

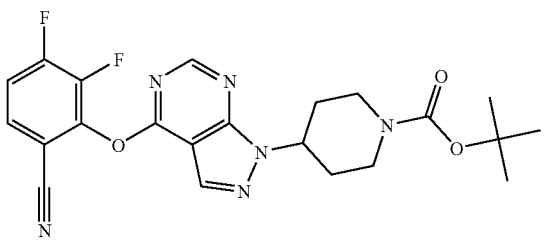

A mixture of 3,4-difluoro-2-hydroxy-benzonitrile (Oakwood Products, Inc., West Columbia, S.C., USA; 14 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(6-cyano-2,3-difluoro-phenoxy)-pyrazolo[3,4-d]pyrimidin-1-yl]-piperidine-1-carboxylic acid tert-butyl ester (7 mg, 17%) as a white solid. Mass spectrum MH+=457.

Example 50

4-[4-(2-Cyano-4,5-difluoro-phenoxy)-pyrazolo[3,4-d]pyrimidin-1-yl]-piperidine-1-carboxylic acid tert-butyl ester

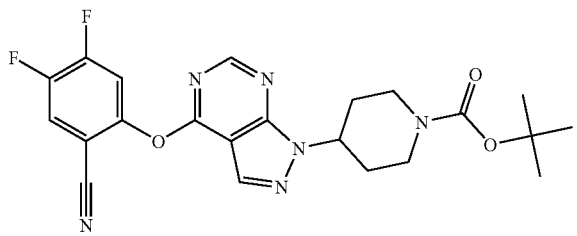

A mixture of 4,5-difluoro-2-hydroxy-benzonitrile (Lancaster Synthesis Ltd. (Lancashire, UK; 14 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(2-cyano-4,5-difluorophenoxy)-pyrazolo[3,4-d]pyrimidin-1-yl]-piperidine-1-carboxylic acid tert-butyl ester (5 mg, 13%) as a white solid.

Example 51

4-[4-(4-Chloro-2-cyano-phenoxy)-pyrazolo[3,4-d]pyrimidin-1-yl]-piperidine-1-carboxylic acid tert-butyl ester

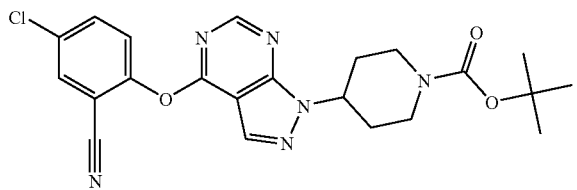

A mixture of 4-(4-chloro-pyrazolo[3,4-d]pyrimidin-1-yl)-piperidine-1-carboxylic acid tert-butyl ester (Intermediate 19; 60 mg, 0.178 mmol), 5-chloro-2-hydroxybenzonitrile (Maybridge, Tintagel, Cornwall, UK; 28 mg, 0.178 mmol), and potassium carbonate (54 mg, 0.392 mmol) in dimethylformamide (1 mL) was heated in the microwave oven at 160° C. for 10 min. Saturated sodium carbonate solution was added to the reaction mixture and the resulting precipitate was filtered through a silica gel plug, eluting with methanol. The solvent was removed and the residue was purified by HPLC to give 4-[4-(4-chloro-2-cyano-phenoxy)-pyrazolo[3,4-d]pyrimidin-1-yl]-piperidine-1-carboxylic acid tert-butyl ester (19 mg, 24%) as a white solid. Mass spectrum MH+=455. $^1$H NMR (300 MHz, DMSO-$d_6$) δ 1.41 (s, 9H), 1.96-2.04 (m, 4H), 2.96-3.08 (m, 2H), 4.02-4.12 (m, 2H), 4.96-5.06 (m, 1H), 7.69 (d, 1H, J=8.7 Hz), 7.94 (dd, 1H, J=2.6, 8.9 Hz), 8.25 (d, 1H, J=2.4 Hz), 8.50 (s, 1H), 8.57 (s, 1H).

Example 52

4-[4-(4-Bromo-2-cyano-phenoxy)-pyrazolo[3,4-d]pyrimidin-1-yl]-piperidine-1-carboxylic acid tert-butyl ester

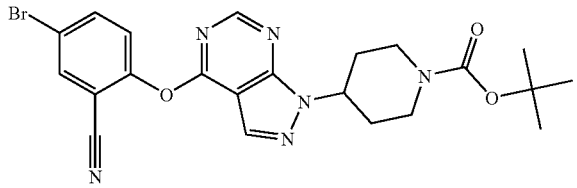

A mixture of 5-bromo-2-hydroxy-benzonitrile (Oakwood Products, Inc., West Columbia, S.C., USA; 18 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(4-bromo-2-cyano-phenoxy)-pyrazolo[3,4-d]pyrimidin-1-yl]-piperidine-1-carboxylic acid tert-butyl ester (4 mg, 30%) as a white solid. Mass spectrum MH+=499.

Example 53

4-[4-(3-Fluoro-5-trifluoromethyl-phenoxy)-pyrazolo[3,4-d]pyrimidin-1-yl]-piperidine-1-carboxylic acid tert-butyl ester

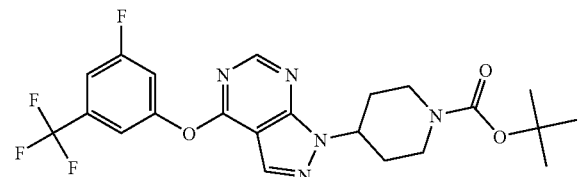

4-[4-(3-Fluoro-5-trifluoromethyl-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 3-fluoro-5-(trifluoromethyl)phenol (available from Aldrich Chemical Company, Inc., Milwaukee, Wis., USA) in dimethylformamide. $^1$H NMR (400 MHz, DMSO-$d_6$) δ 1.43 (s, 9H), 1.94-2.06 (m, 4H), 2.99-3.07 (m, 2H), 4.08-4.11 (m, 2H), 4.99-5.05 (m, 1H), 7.71-7.78 (m, 3H), 8.40 (s, 1H), 8.59 (s, 1H). Mass spectrum MH+=482.

Example 54

4-[4-(2-Chloro-4-trifluoromethyl-phenoxy)-pyrazolo[3,4-d]pyrimidin-1-yl]-piperidine-1-carboxylic acid tert-butyl ester

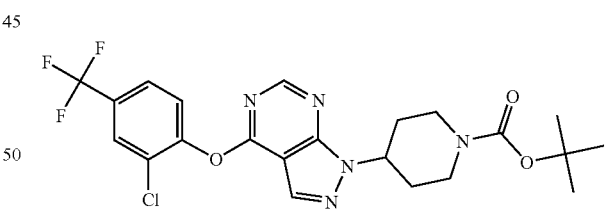

4-[4-(2-Chloro-4-trifluoromethyl-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 3-chloro-4-hydroxybenzotrifluoride (available from Oakwood Products, Inc., West Columbia, S.C., USA) in dimethylformamide. $^1$H NMR (400 MHz, DMSO-$d_6$) δ 1.43 (s, 9H), 1.99-2.08 (m, 4H), 2.98-3.07 (m, 2H), 4.08-4.11 (m, 2H), 5.00-5.05 (m, 1H), 7.78-7.80 (m, 1H), 7.89-7.91 (m, 1H), 8.15 (s, 1H), 8.49 (s, 1H), 8.55 (s, 1H). Mass spectrum MH+=498.

Example 55

4-[4-(4-Chloro-3-trifluoromethyl-phenoxy)-pyrazolo[3,4-d]pyrimidin-1-yl]-piperidine-1-carboxylic acid tert-butyl ester

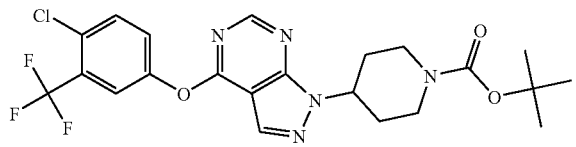

4-[4-(4-Chloro-3-trifluoromethyl-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 2-chloro-5-hydroxybenzotrifluoride (available from Alfa Aesar, Ward Hill, Mass., USA) in dimethylformamide. $^1$H NMR (400 MHz, DMSO-$d_6$) δ 1.43 (s, 9H), 1.96-2.05 (m, 4H), 2.96-3.04 (m, 2H), 4.08-4.11 (m, 2H), 4.99-5.04 (m, 1H), 7.73-7.76 (m, 1H), 7.86-7.89 (m, 1H), 7.96-7.98 (m, 1H), 8.41 (s, 1H), 8.58 (s, 1H). Mass spectrum MH+=498.

Example 56

4-[4-(4-Sulfamoyl-phenoxy)-pyrazolo[3,4-d]pyrimidin-1-yl]-piperidine-1-carboxylic acid tert-butyl ester

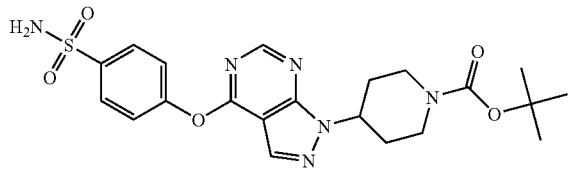

4-[4-(4-Sulfamoyl-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 4-hydroxybenzenesulfonamide (available from TCI America, Portland, Oreg., USA) in dimethylformamide. $^1$H NMR (400 MHz, DMSO-$d_6$) δ 1.43 (s, 9H), 1.94-2.06 (m, 4H), 2.94-3.04 (m, 2H), 4.02-4.10 (m, 2H), 4.98-5.04 (m, 1H), 7.45 (s, 2H), 7.53-7.55 (m, 2H), 7.93-7.95 (m, 2H), 8.34 (s, 1H), 8.55 (s, 1H). Mass spectrum MH+=475.

Example 57

4-[4-(4-Dimethylsulfamoyl-phenoxy)-pyrazolo[3,4-d]pyrimidin-1-yl]-piperidine-1-carboxylic acid tert-butyl ester

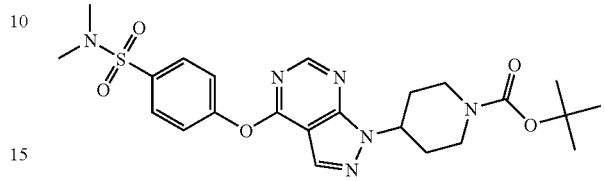

A mixture of 4-hydroxy-N,N-dimethyl-benzenesulfonamide (ChemService Inc., West Chester, Pa., USA; 18 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(4-dimethylsulfamoyl-phenoxy)-pyrazolo[3,4-d]pyrimidin-1-yl]-piperidine-1-carboxylic acid tert-butyl ester (13 mg, 28%) as a white solid. Mass spectrum MH+=503.

Example 58

4-[4-(4-Methanesulfinyl-phenoxy)-pyrazolo[3,4-d]pyrimidin-1-yl]-piperidine-1-carboxylic acid tert-butyl ester

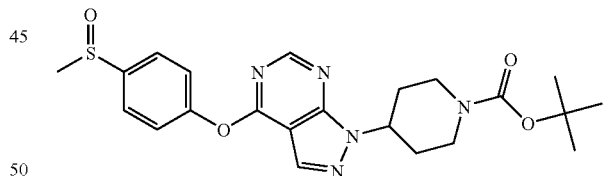

A mixture of 4-methanesulfinyl-phenol (Combi-Blocks Inc, San Diego, Calif., USA; 14 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(4-methanesulfinyl-phenoxy)-pyrazolo[3,4-d]pyrimidin-1-yl]-piperidine-1-carboxylic acid tert-butyl ester (15 mg, 36%) as a white solid. Mass spectrum MH+=458.

Example 59

4-[4-(4-Methanesulfonyl-phenoxy)-pyrazolo[3,4-d]pyrimidin-1-yl]-piperidine-1-carboxylic acid tert-butyl ester

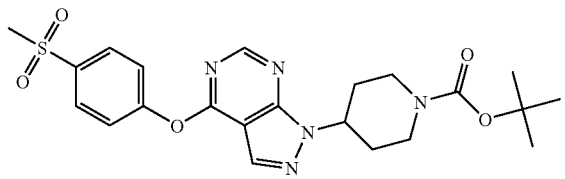

Sodium hydride (60% dispersion in mineral oil; 82 mg, 2.1 mmol) was added to a solution of 4-(methylsulfonyl)phenol (281 mg, 1.6 mmol) in dimethylformamide (9 mL) and the mixture was stirred at room temperature for 20 min. A solution of 4-(4-chloro-pyrazolo[3,4-d]pyrimidin-1-yl)piperidine-1-carboxylic acid tert-butyl ester (Intermediate 19; 551 mg, 1.6 mmol) in dimethylformamide (5 mL) was added, and the reaction mixture was stirred at room temperature for 3.5 h. Saturated aqueous ammonium chloride solution was added and the mixture was extracted with ethyl acetate (3×90 mL). The organic layer was washed with water (3 times) and brine, dried (sodium sulfate), filtered, evaporated and purified on a flash silica column (40 mm×4") eluting with 66-75% ethyl acetate/hexanes to give 4-[4-(4-methanesulfonyl-phenoxy)-pyrazolo[3,4-d]pyrimidin-1-yl]-piperidine-1-carboxylic acid tert-butyl ester (400 mg, 52%) as a white solid. $^1$H NMR (300 MHz, DMSO-$d_6$) δ 1.41 (s, 9H), 1.92-2.02 (m, 4H), 2.94-3.05 (m, 2H), 3.28-3.30 (m, methyl sulfone and water peak), 4.04-4.12 (m, 2H), 4.94-5.06 (m, 1H), 7.59-7.64 (m, 2H), 8.01-8.06 (m, 2H), 8.37 (s, 1H), 8.54 (s, 1H). Mass spectrum (ES) MH+=474.

Example 60

4-[4-(2-Fluoro-4-methanesulfonyl-phenoxy)-pyrazolo[3,4-d]pyrimidin-1-yl]-piperidine-1-carboxylic acid tert-butyl ester

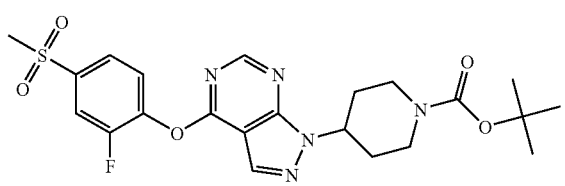

A mixture of 2-fluoro-4-methanesulfonyl-phenol (Intermediate 1; 112 mg, 0.6 mmol), 4-(4-chloro-pyrazolo[3,4-d]pyrimidin-1-yl)-piperidine-1-carboxylic acid tert-butyl ester (200 mg, 0.6 mmol) and potassium carbonate (180 mg, 1.3 mmol) in DMF (2 mL) was heated in a microwave oven at 160° C. for 10 min. Saturated sodium carbonate solution was added to the reaction mixture to give a precipitate which was filtered off and dissolved in ethyl acetate. The organic solution was dried (sodium sulfate), filtered, evaporated, and purified by flash chromatography, eluting with 20% ethyl acetate/hexanes, to give 4-[4-(2-fluoro-4-methane-sulfonyl-phenoxy)-pyrazolo[3,4-d]pyrimidin-1-yl]-piperidine-1-carboxylic acid tert-butyl ester (140 mg, 47%) as a white solid.

Example 61

4-[4-(3-Fluoro-4-methanesulfonyl-phenoxy)-pyrazolo[3,4-d]pyrimidin-1-yl]-piperidine-1-carboxylic acid tert-butyl ester

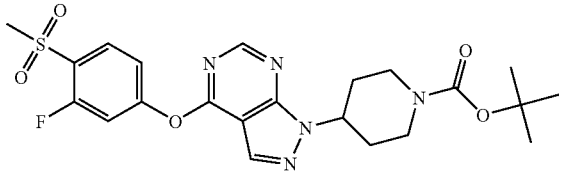

4-[4-(3-Fluoro-4-methanesulfonyl-phenoxy)-pyrazolo[3,4-d]pyrimidin-1-yl]-piperidine-1-carboxylic acid tert-butyl ester was prepared using the procedure described for the preparation of 4-(2-fluoro-4-methanesulfonyl-phenoxy)-1-[4-(3-isopropyl-[1,2,4]oxadiazol-5-yl)-cyclo-hexyl]-1H-pyrazolo[3,4-d]pyrimidine (Example 129) by the reaction of 4-(4-chloro-pyrazolo[3,4-d]pyrimidin-1-yl)-piperidine-1-carboxylic acid tert-butyl ester (Intermediate 19) with 3-fluoro-4-methanesulfonyl-phenol (Intermediate 2) in dimethylformamide. The product was purified by flash chromatography, eluting with 40% ethyl acetate/hexanes to give 4-[4-(3-fluoro-4-methanesulfonyl-phenoxy)pyrazolo[3,4-d]pyrimidin-1-yl]-piperidine-1-carboxylic acid tert-butyl ester (75 mg, 43%) as a white solid. Mass spectrum: Observed 491.9.

Example 62

4-[4-(4-Carbamoyl-phenoxy)-pyrazolo[3,4-d]pyrimidin-1-yl]-piperidine-1-carboxylic acid tert-butyl ester

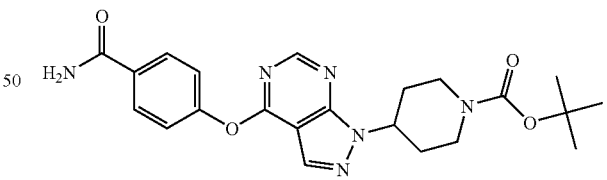

A mixture of 4-hydroxy-benzamide (Aldrich Chemical Company, Inc., Milwaukee, Wis., USA; 13 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(4-carbamoyl-phenoxy)-

Example 63

4-[4-(2-Fluoro-4-methoxycarbonyl-phenoxy)-pyrazolo[3,4-d]pyrimidin-1-yl]-piperidine-1-carboxylic acid tert-butyl ester

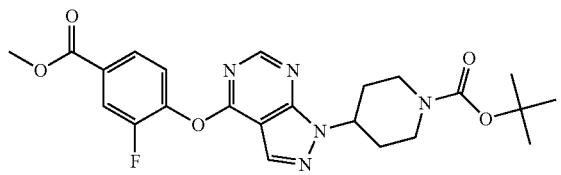

A mixture of 3-fluoro-4-hydroxy-benzoic acid methyl ester (Combi-Blocks Inc, San Diego, Calif., USA; 31 mg, 0.178 mmol), 4-(4-chloro-pyrazolo[3,4-d]pyrimidin-1-yl)-piperidine-1-carboxylic acid tert-butyl ester (Intermediate 19; 60 mg, 0.178 mmol), and potassium carbonate (54 mg, 0.391 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to afford 4-[4-(2-fluoro-4-methoxycarbonyl-phenoxy)-pyrazolo[3,4-d]pyrimidin-1-yl]-piperidine-1-carboxylic acid tert-butyl ester (31 mg, 37%) as a white solid. Mass spectrum MH+=472.

Example 64

4-[4-(4-Acetyl-phenoxy)-pyrazolo[3,4-d]pyrimidin-1-yl]-piperidine-1-carboxylic acid tert-butyl ester

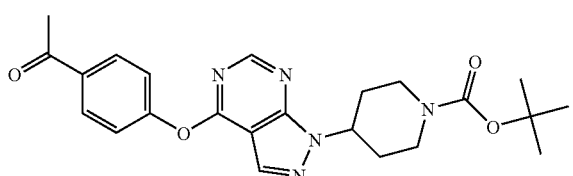

4-[4-(4-Acetyl-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 4'-hydroxyacetophenone (available from Aldrich Chemical Company, Inc., Milwaukee, Wis., USA) in dimethylformamide. $^1$H NMR (400 MHz, DMSO-$d_6$) δ 1.43 (s, 9H), 1.94-2.06 (m, 4H), 2.67 (s, 3H), 2.94-3.04 (m, 2H), 4.02-4.10 (m, 2H), 5.00-5.04 (m, 1H), 7.48-7.50 (m, 2H), 8.08-8.10 (m, 1H), 8.32 (s, 1H), 8.55 (s, 1H). Mass spectrum MH+=438.

Example 65

4-[4-(4-Acetyl-3-methyl-phenoxy)-pyrazolo[3,4-d]pyrimidin-1-yl]-piperidine-1-carboxylic acid tert-butyl ester

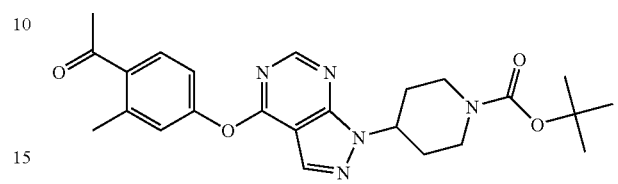

4-[4-(4-Acetyl-3-methyl-phenoxy)-pyrazolo[3,4-d]pyrimidin-1-yl]-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 4'-hydroxy-2'-methylacetophenone (available from Aldrich Chemical Company, Inc., Milwaukee, Wis., USA) in dimethylformamide. $^1$H NMR (400 MHz, DMSO-$d_6$) δ 1.43 (s, 9H), 1.97-2.06 (m, 4H), 2.33 (s, 3H), 2.67 (s, 3H), 2.94-3.04 (m, 2H), 4.04-4.10 (m, 2H), 4.98-5.04 (m, 1H), 7.29-7.31 (m, 2H), 7.96-7.98 (m, 1H), 8.29 (s, 1H), 8.55 (s, 1H). Mass spectrum MH+=452.

Example 66

4-[4-(2-Fluoro-4-nitro-phenoxy)-pyrazolo[3,4-d]pyrimidin-1-yl]-piperidine-1-carboxylic acid tert-butyl ester

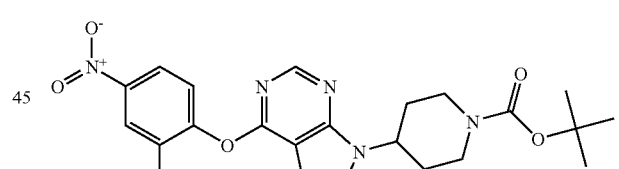

A mixture of 2-fluoro-4-nitro-phenol (Aldrich Chemical Company, Inc., Milwaukee, Wis., USA 32 mg, 0.074 mmol), 4-(4-chloro-pyrazolo[3,4-d]pyrimidin-1-yl)-piperidine-1-carboxylic acid tert-butyl ester (Intermediate 19; 25 mg, 0.074 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to afford 4-[4-(2-fluoro-4-nitro-phenoxy)-pyrazolo[3,4-d]pyrimidin-1-yl]-piperidine-1-carboxylic acid tert-butyl ester (5 mg, 15%) as a white solid. Mass spectrum MH+=459.

(pyrazolo[3,4-d]pyrimidin-1-yl]-piperidine-1-carboxylic acid tert-butyl ester (7 mg, 18%) as a white solid. Mass spectrum MH+=439.)

Example 67

4-{4-[4-(4-Acetyl-piperazin-1-yl)-phenoxy]-pyrazolo[3,4-d]pyrimidin-1-yl}-piperidine-1-carboxylic acid tert-butyl ester

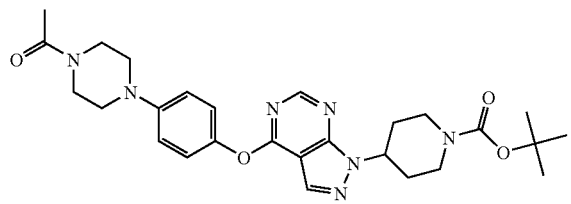

4-{4-[4-(4-Acetyl-piperazin-1-yl)-phenoxy]-pyrazolo[3,4-d]pyrimidin-1-yl}-piperidine-1-carboxylic acid tert-butyl ester was prepared according to General Procedure B by the reaction of 4-(4-chloro-pyrazolo[3,4-d]pyrimidin-1-yl)-piperidine-1-carboxylic acid tert-butyl ester (Intermediate 19) with 1-acetyl-4-(4-hydroxyphenyl)piperazine (available from Aldrich Chemical Company, Inc., Milwaukee, Wis., USA) in dimethylformamide. $^1$H NMR (400 MHz, DMSO-$d_6$) δ 1.43 (s, 9H), 1.94-2.01 (m, 4H), 2.05 (s, 3H), 2.93-3.02 (m, 2H), 3.10-3.20 (m, 4H), 3.55-3.65 (m, 4H), 4.08-4.11 (m, 2H), 4.96-5.01 (m, 1H), 7.04-7.08 (m, 2H), 7.17-7.20 (m, 2H), 7.95 (s, 1H), 8.53 (s, 1H). Mass spectrum M+Na=544, MH+=522.

Example 68

4-[4-(4-Methanesulfonylamino-3-methyl-phenoxy)-pyrazolo[3,4-d]pyrimidin-1-yl]-piperidine-1-carboxylic acid tert-butyl ester

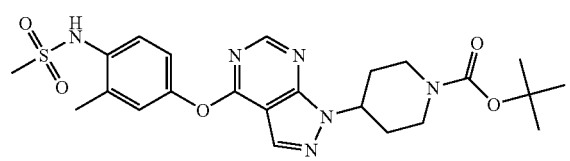

A mixture of 4-(4-chloro-pyrazolo[3,4-d]pyrimidin-1-yl)-piperidine-1-carboxylic acid tert-butyl ester (Intermediate 19; 25 mg, 0.075 mmol), N-(4-hydroxy-2-methyl-phenyl)methanesulfonamide (ChemBridge Corporation, San Diego, Calif., USA; 15 mg, 0.075 mmol), and potassium carbonate (27 mg, 0.2 mmol) in dimethylformamide was heated in the microwave oven at 160° C. for 10 min. Saturated sodium carbonate solution was added to the reaction mixture and the precipitate was filtered through a silica plug, washing with methanol. The solvent was removed and the residue was purified by HPLC to afford 4-[4-(4-methanesulfonylamino-3-methyl-phenoxy)pyrazolo[3,4-d]pyrimidin-1-yl]-piperidine-1-carboxylic acid tert-butyl ester (12 mg, 33%) as an off white solid. Mass Spec MH+=503.

Example 69

4-[4-(3-Acetylamino-phenoxy)-pyrazolo[3,4-d]pyrimidin-1-yl]-piperidine-1-carboxylic acid tert-butyl ester

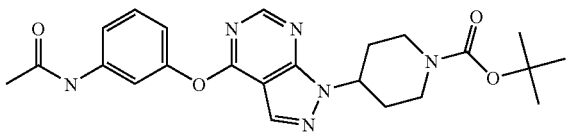

A mixture of N-(3-hydroxy-phenyl)-acetamide (Aldrich Chemical Company, Inc., Milwaukee, Wis., USA; 14 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(3-acetylamino-phenoxy)-pyrazolo[3,4-d]pyrimidin-1-yl]-piperidine-1-carboxylic acid tert-butyl ester (10 mg, 26%) as a white solid.

Example 70

4-[4-(4-Acetylamino-phenoxy)-pyrazolo[3,4-d]pyrimidin-1-yl]-piperidine-1-carboxylic acid tert-butyl ester

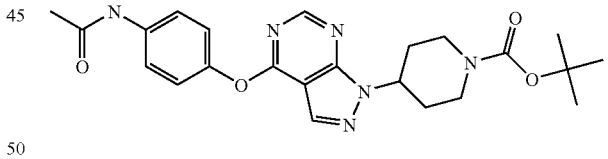

A mixture of N-(4-hydroxy-phenyl)-acetamide (Aldrich Chemical Company, Inc., Milwaukee, Wis., USA; 14 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(4-acetylamino-phenoxy)-pyrazolo[3,4-d]pyrimidin-1-yl]-piperidine-1-carboxylic acid tert-butyl ester (15 mg, 35%) as a white solid. Mass spectrum MH+=453.

Example 71

4-[4-(Quinolin-5-yloxy)-pyrazolo[3,4-d]pyrimidin-1-yl]-piperidine-1-carboxylic acid tert-butyl ester

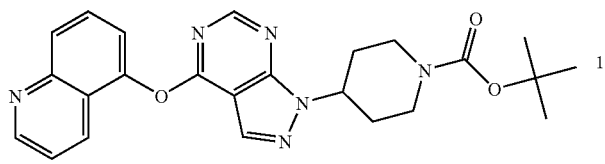

A mixture of quinolin-5-ol (Aldrich Chemical Company, Inc., Milwaukee, Wis., USA 26 mg, 0.178 mmol), 4-(4-chloro-pyrazolo[3,4-d]pyrimidin-1-yl)-piperidine-1-carboxylic acid tertbutyl ester (Intermediate 19; 60 mg, 0.178 mmol), and potassium carbonate (54 mg, 0.391 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to afford 4-[4-(quinolin-5-yloxy)-pyrazolo[3,4-d]pyrimidin-1-yl]-piperidine-1-carboxylic acid tert-butyl ester (37 mg, 47%) as a white solid. Mass spectrum MH+=447.

Example 72

4-[4-(1H-Pyrrolo[2,3-b]pyridin-5-yloxy)-pyrazolo[3,4-d]pyrimidin-1-yl]-piperidine-1-carboxylic acid tert-butyl ester

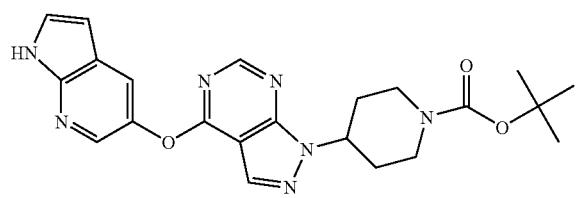

A mixture of 4-(4-chloro-pyrazolo[3,4-d]pyrimidin-1-yl)-piperidine-1-carboxylic acid tert-butyl ester (Intermediate 19; 50 mg, 0.15 mmol), 1H-pyrrolo[2,3-B]pyridin-5-ol (Matrix Scientific, Columbia, S.C., USA; 26 mg, 0.19 mmol), and potassium carbonate (27 mg, 0.19 mmol) in dimethylformamide (2 mL) was heated in the microwave oven at 160° C. for 10 min. Ethyl acetate and water were added, and the aqueous layer was extracted twice with ethyl acetate. The ethyl acetate layers were combined, evaporated, and purified by preparative C18 HPLC, eluting with 10-100% acetonitrile/water. Samples containing the product were extracted twice with dichloromethane and the solvent was evaporated under high vacuum to give 4-[4-(1H-pyrrolo[2,3-b]pyridin-5-yloxy)pyrazolo[3,4-d]pyrimidin-1-yl]-piperidine-1-carboxylic acid tert-butyl ester (21 mg, 33%) as a white powder. $^1$H NMR (300 MHz, DMSO-d$_6$) δ 1.43 (s, 9H), 1.80-2.15 (m, 4H), 3.02 (br s, 2H), 4.08 (d, 2H, J=12.4 Hz), 4.85-5.10 (m, 1H), 6.45-6.52 (m, 1H), 7.58 (d, 1H, J=2.9 Hz), 7.94 (d, 1H, J=2.5 Hz), 8.20 (d, 1H, J=2.5 Hz), 8.22 (s, 1H), 8.50 (s, 1H), 11.85 (br s, 1H). Mass spectrum (ES) MH+=436. HRMS Calcd. for $C_{22}H_{26}N_7O_3$ (MH+): 436.2092. Found: 436.2090.

Example 73

4-[4-(1H-Indol-4-yloxy)-pyrazolo[3,4-d]pyrimidin-1-yl]-piperidine-1-carboxylic acid tert-butyl ester

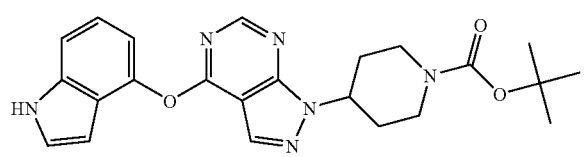

4-[4-(1H-Indol-4-yloxy)-pyrazolo[3,4-d]pyrimidin-1-yl]-piperidine-1-carboxylic acid tert-butyl ester (25 mg, 32%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 60 mg, 0.18 mmol) with 4-hydroxyindole (TCI America, Portland, Oreg., USA; 24 mg, 0.18 mmol) in the presence of potassium carbonate (54 mg, 0.39 mmol). Mass spectrum MH+=435.

Example 74

4-[4-(1H-Indol-5-yloxy)-pyrazolo[3,4-d]pyrimidin-1-yl]-piperidine-1-carboxylic acid tert-butyl ester

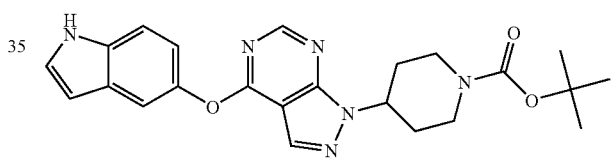

4-[4-(1H-Indol-5-yloxy)-pyrazolo[3,4-d]pyrimidin-1-yl]-piperidine-1-carboxylic acid tert-butyl ester (29 mg, 38%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 60 mg, 0.18 mmol) with 5-hydroxyindole (Aldrich Chemical Company, Inc., Milwaukee, Wis., USA; 24 mg, 0.18 mmol) in the presence of potassium carbonate (54 mg, 0.39 mmol). Mass spectrum MH+=435.

Example 75

4-[4-(2-Oxo-2H-chromen-7-yloxy)-pyrazolo[3,4-d]pyrimidin-1-yl]-piperidine-1-carboxylic acid tert-butyl ester

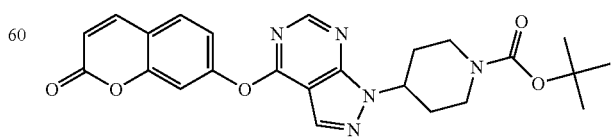

4-[4-(2-Oxo-2H-chromen-7-yloxy)-pyrazolo[3,4-d]pyrimidin-1-yl]-piperidine-1-carboxylic acid tert-butyl ester (6.4 mg, 16%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 30 mg, 0.09 mmol) with 7-hydroxy-coumarin (Aldrich Chemical Company, Inc., Milwaukee, Wis., USA; 15 mg, 0.09 mmol) in the presence of potassium carbonate (27 mg, 0.195 mmol). Mass spectrum MH+=464.

Example 76

4-[4-(4-Methyl-2-oxo-2H-chromen-7-yloxy)-pyrazolo[3,4-d]pyrimidin-1-yl]-piperidine-1-carboxylic acid tert-butyl ester

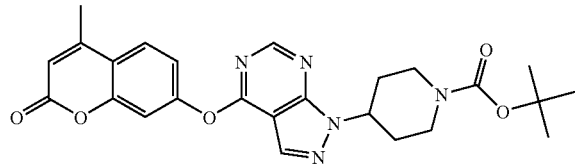

4-[4-(4-Methyl-2-oxo-2H-chromen-7-yloxy)-pyrazolo[3,4-d]pyrimidin-1-yl]-piperidine-1-carboxylic acid tert-butyl ester (6 mg, 14%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 30 mg, 0.09 mmol) with 7-hydroxy-4-methylcoumarin (Aldrich Chemical Company, Inc., Milwaukee, Wis., USA; 15 mg, 0.09 mmol) in the presence of potassium carbonate (27 mg, 0.195 mmol). Mass spectrum MH+=478.

Example 77

4-[4-(1,1-Dioxo-1H-1$\lambda^6$-benzo[b]thiophen-5-yloxy)-pyrazolo[3,4-d]pyrimidin-1-yl]-piperidine-1-carboxylic acid tert-butyl ester

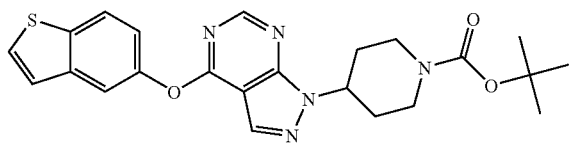

A mixture of benzo[b]thiophen-5-ol (MCAT GmbH, Konstanz, Germany; 300 mg, 2 mmol), 4-(4-chloro-pyrazolo[3,4-d]pyrimidin-1-yl)-piperidine-1-carboxylic acid tert-butyl ester (Intermediate 19; 607 mg, 1.8 mmol), and potassium carbonate (414 mg, 3 mmol) in dimethylformamide (20 mL) was heated at 80° C. for 3 h. The mixture was cooled and then poured into saturated aqueous ammonium chloride solution, and the resulting mixture was extracted three times with ethyl acetate. The combined organic layers were washed twice with water and once with brine, dried (magnesium sulfate), filtered, evaporated and chromatographed, eluting with 50% ethyl acetate/hexanes to give 4-[4-(benzo[b]thio-phen-5-yloxy)-pyrazolo[3,4-d]pyrimidin-1-yl]-piperidine-1-carboxylic acid tert-butyl ester as a pale yellow foam.

Example 78

4-[4-(1,1-Dioxo-1H-1$\lambda^6$-benzo[b]thiophen-5-yloxy)-pyrazolo[3,4-d]pyrimidin-1-yl]-piperidine-1-carboxylic acid tert-butyl ester

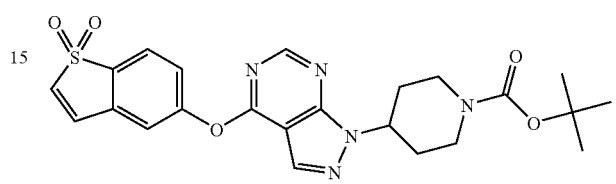

4-[4-(Benzo[b]thio-phen-5-yloxy)-pyrazolo[3,4-d]pyrimidin-1-yl]-piperidine-1-carboxylic acid tert-butyl ester (Example 77; approximately 1.8 mmol) was dissolved in dichloromethane (50 mL) and metachloroperoxybenzoic acid (60-70%, 5 mmol) was added. The mixture was stirred at room temperature overnight and then poured into saturated aqueous sodium hydrogen carbonate solution. The resulting mixture was extracted twice with dichloromethane and the combined organic layers were washed twice with saturated aqueous sodium hydrogen carbonate solution, dried (magnesium sulfate), filtered, evaporated and chromatographed, eluting with 50% ethyl acetate/hexanes to give 4-[4-(1,1-dioxo-1H-1$\lambda^6$-benzo[b]thiophen-5-yloxy)-pyrazolo[3,4-d]pyrimidin-1-yl]-piperidine-1-carboxylic acid tert-butyl ester (535 mg, 61% over two steps) as a white solid.

Example 79

4-[4-(1,1-Dioxo-2,3-dihydro-1H-1$\lambda^6$-benzo[b]thiophen-5-yloxy)-pyrazolo[3,4-d]pyrimidin-1-yl]-piperidine-1-carboxylic acid tert-butyl ester

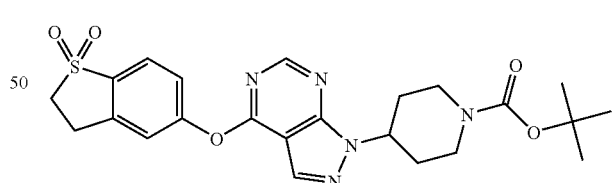

A mixture of 4-[4-(1,1-dioxo-1H-1$\lambda^6$-benzo[b]thiophen-5-yloxy)-pyrazolo[3,4-d]pyrimidin-1-yl]-piperidine-1-carboxylic acid tert-butyl ester (Example 78; 531 mg, 1.1 mmol) and 10% palladium on carbon (50 mg) in ethyl acetate (40 mL) was stirred under an atmosphere of hydrogen for 3 h. The mixture was then filtered through Celite™ and the filtrate was evaporated and chromatographed, eluting with 50% ethyl acetate/hexanes to give 4-[4-(1,1-dioxo-2,3-dihydro-1H-1$\lambda^6$-benzo[b]thiophen-5-yloxy)-pyrazolo[3,4-d]pyrimidin-1-yl]-piperidine-1-carboxylic acid tert-butyl ester (497 mg, 93%) as a white solid.

Example 80

4-[4-(4-[1,2,4]Triazol-1-yl-phenoxy)-pyrazolo[3,4-d]pyrimidin-1-yl]-piperidine-1-carboxylic acid tert-butyl ester

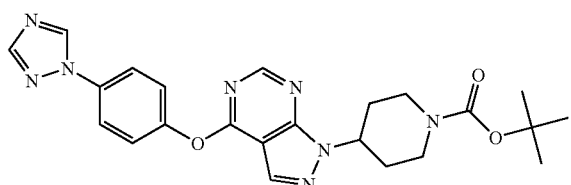

A mixture of 4-(1,2,4)-triazol-1-yl-phenol (Lancaster; 14 mg, 0.09 mmol), 4-(4-chloro-pyrazolo[3,4-d]pyrimidin-1-yl)-piperidine-1-carboxylic acid tert-butyl ester (Intermediate 19; 29.5 mg, 0.09 mmol) and potassium carbonate (14.4 mg, 0.10 mmol) in anhydrous DMF (1 mL) was heated in a microwave at 180° C. for 10 min. The mixture was cooled and filtered. The solid was washed with dichloromethane. The filtrate was concentrated and purified using a 4 g silica gel column, eluting with 0-5% methanol/dichloromethane to give 4-[4-(4-[1,2,4]triazol-1-yl-phenoxy)-pyrazolo[3,4-d]pyrimidin-1-yl]-piperidine-1-carboxylic acid tert-butyl ester (17 mg, 42%).

Example 81

4-{4-[4-(1H-Tetrazol-5-yl)-phenoxy]-pyrazolo[3,4-d]pyrimidin-1-yl}-piperidine-1-carboxylic acid tert-butyl ester

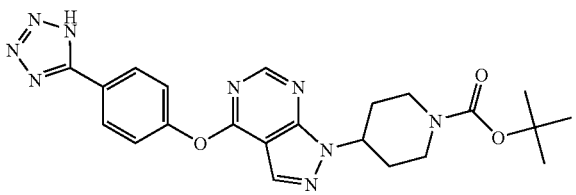

4-{4-[4-(1H-Tetrazol-5-yl)-phenoxy]-pyrazolo[3,4-d]pyrimidin-1-yl}-piperidine-1-carboxylic acid tert-butyl ester (5.3 mg, 13%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 30 mg, 0.09 mmol) with 5-(4-hydroxyphenyl)tetrazole (Biofine International Inc., Blaine, Wash., USA; 15 mg, 0.09 mmol) in the presence of potassium carbonate (27 mg, 0.195 mmol).

Example 82

4-[4-(4-Tetrazol-2-yl-phenoxy)-pyrazolo[3,4-d]pyrimidin-1-yl]-piperidine-1-carboxylic acid tert-butyl ester

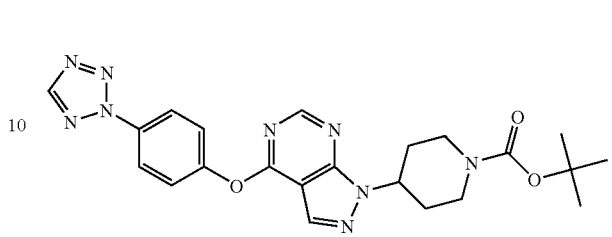

4-[4-(4-Tetrazol-2-yl-phenoxy)-pyrazolo[3,4-d]pyrimidin-1-yl]-piperidine-1-carboxylic acid tert-butyl ester (16 mg, 19%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 60 mg, 0.18 mmol) with 4-(2H-tetrazol-2-yl)phenol (ChemBridge Corporation, San Diego, Calif., USA; 29 mg, 0.18 mmol) in the presence of potassium carbonate (54 mg, 0.39 mmol).

Example 83

4-[4-(4-Tetrazol-1-yl-phenoxy)-pyrazolo[3,4-d]pyrimidin-1-yl]-piperidine-1-carboxylic acid tert-butyl ester

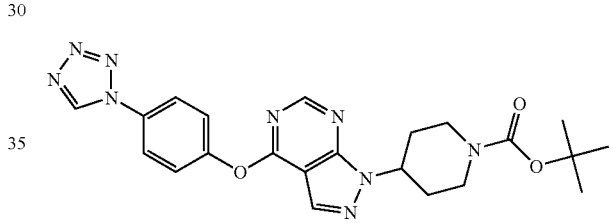

4-[4-(4-Tetrazol-1-yl-phenoxy)-pyrazolo[3,4-d]pyrimidin-1-yl]-piperidine-1-carboxylic acid tert-butyl ester (6 mg, 7%) was prepared using the procedure described for the preparation of Example 41 by the reaction of 4-(4-chloro-pyrazolo[3,4-d]pyrimidin-1-yl)-piperidine-1-carboxylic acid tertbutyl ester (Intermediate 19; 60 mg, 0.18 mmol) with 4-tetrazol-1-yl-phenol (Enamine Ltd., Kiev, Ukraine; 29 mg, 0.18 mmol) in the presence of potassium carbonate (54 mg, 0.39 mmol).

Example 84

4-{4-[4-(5-Methyl-tetrazol-1-yl)-phenoxy]-pyrazolo[3,4-d]pyrimidin-1-yl}-piperidine-1-carboxylic acid tert-butyl ester

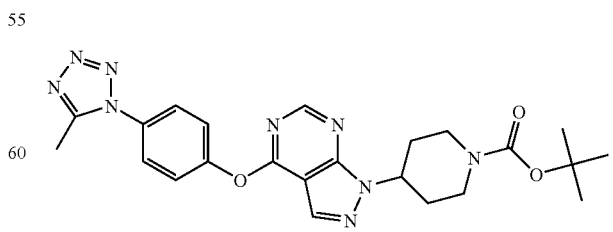

A mixture of 4-(5-methyl-tetrazol-1-yl)-phenol (Chembridge Corporation, San Diego, Calif., USA; 32 mg, 0.178 mmol), 4-(4-chloro-pyrazolo[3,4-d]pyrimidin-1-yl)-piperidine-1-carboxylic acid tert-butyl ester (Intermediate 19; 60 mg, 0.178 mmol), and potassium carbonate (54 mg, 0.391 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to afford 4-{4-[4-(5-methyl-tetrazol-1-yl)-phenoxy]-pyrazolo[3,4-d]pyrimidin-1-yl}-piperidine-1-carboxylic acid tert-butyl ester (10 mg, 12%) as a white solid. Mass spectrum MH+=478.

Example 85

4-{4-[4-(5-Methyl-[1,2,4]oxadiazol-3-yl)-phenoxy]-pyrazolo[3,4-d]pyrimidin-1-yl}-piperidine-1-carboxylic acid tert-butyl ester

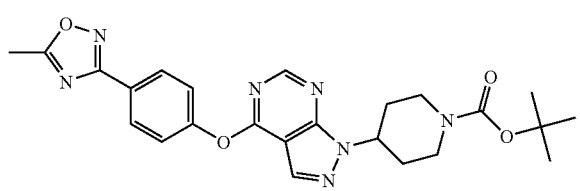

A mixture of 4-(5-methyl-[1,2,4]oxadiazol-3-yl)-phenol (Enamine Ltd., Kiev, Ukraine; 32 mg, 0.178 mmol), 4-(4-chloro-pyrazolo[3,4-d]pyrimidin-1-yl)-piperidine-1-carboxylic acid tert-butyl ester (Intermediate 19; 60 mg, 0.178 mmol), and potassium carbonate (54 mg, 0.391 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to afford 4-{4-[4-(5-methyl-[1,2,4]oxadiazol-3-yl)-phenoxy]-pyrazolo[3,4-d]pyrimidin-1-yl}-piperidine-1-carboxylic acid tert-butyl ester (17 mg, 20%) as an off white solid. Mass spectrum M+H-Boc=378.

Example 86

4-[4-(4-Thiophen-3-yl-phenoxy)-pyrazolo[3,4-d]pyrimidin-1-yl]-piperidine-1-carboxylic acid tert-butyl ester

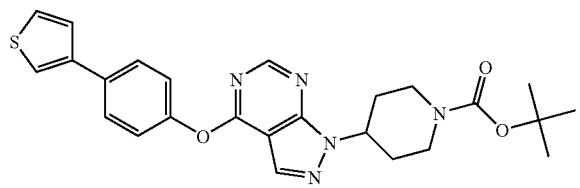

A mixture of 4-thiophen-3-yl-phenol (Aldrich Chemical Company, Inc., Milwaukee, Wis., USA; 16 mg, 0.089 mmol), 4-(4-chloro-pyrazolo[3,4-d]pyrimidin-1-yl)-piperidine-1-carboxylic acid tert-butyl ester (Intermediate 19; 30 mg, 0.089 mmol), and potassium carbonate (27 mg, 0.196 mmol) in dimethylformamide (1 mL) was heated in a microwave oven at 160° C. for 10 min. Saturated sodium carbonate solution was added to the reaction mixture, and the mixture was then filtered through a pad of silica gel to remove the precipitate. The silica gel pad was washed with methanol and the solvents were evaporated from the filtrate. The residue was purified by HPLC to give 4-[4-(4-thiophen-3-yl-phenoxy)-pyrazolo[3,4-d]pyrimidin-1-yl]-piperidine-1-carboxylic acid tert-butyl ester (10 mg, 22%) as a white solid. Mass spectrum MH+=478.

Example 87

3-[4-(4-Methanesulfonyl-phenoxy)-pyrazolo[3,4-d]pyrimidin-1-yl]-piperidine-1-carboxylic acid tert-butyl ester

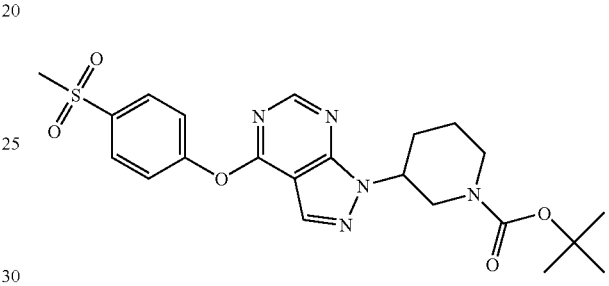

Boc-3-hydroxypiperidine (Alfa Aesar, Ward Hill, Mass., USA; 80 mg, 0.4 mmol) and triphenylphosphine (136 mg, 0.52 mmol) were added to a solution of 4-(4-methanesulfonyl-phenoxy)-1H-pyrazolo[3,4-d]pyrimidine (Intermediate 31; 100 mg, 0.34 mmol) in tetrahydrofuran (1 mL). The mixture was cooled to 0° C., and then diisopropylazodicarboxylate (102 µL, 0.52 mmol) was added. The mixture was stirred overnight, then silica gel (~500 mg) was added, the solvents were evaporated and the product was eluted from a silica gel column with 50% ethyl acetate/hexanes to give 3-[4-(4-methanesulfonyl-phenoxy)-pyrazolo[3,4-d]pyrimidin-1-yl]-piperidine-1-carboxylic acid tert-butyl ester (10.5 mg, 6.5%) as a solid.

Example 88 and Example 89

(R)-3-[4-(4-Methanesulfonyl-phenoxy)-pyrazolo[3,4-d]pyrimidin-1-yl]-piperidine-1-carboxylic acid tert-butyl ester and (S)-3-[4-(4-Methanesulfonyl-phenoxy)-pyrazolo[3,4-d]pyrimidin-1-yl]-piperidine-1-carboxylic acid tert-butyl ester

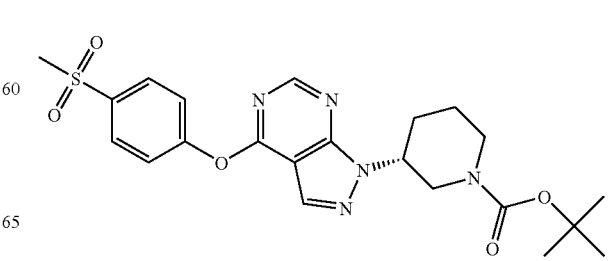

-continued

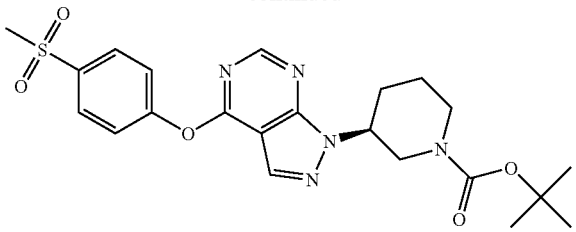

Chiral separation of racemic 3-[4-(4-methanesulfonyl-phenoxy)-pyrazolo[3,4-d]pyrimidin-1-yl]-piperidine-1-carboxylic acid tert-butyl ester (Example 87; 90 mg) was performed by supercritical fluid chromatography using a Thar technologies Multigram 2 instrument and a Daicel OJ 3×25 cm column at 100 bar and 35° C., eluting with 30% methanol in supercritical fluid carbon dioxide. This separation afforded (R)-3-[4-(4-Methanesulfonyl-phenoxy)-pyrazolo[3,4-d]pyrimidin-1-yl]-piperidine-1-carboxylic acid tert-butyl ester and (S)-3-[4-(4-Methanesulfonyl-phenoxy)-pyrazolo[3,4-d]pyrimidin-1-yl]-piperidine-1-carboxylic acid tert-butyl ester (44 mg of one isomer and 41 mg of the other).

Example 90

3-[4-(2-Cyano-phenoxy)-pyrazolo[3,4-d]pyrimidin-1-yl]-piperidine-1-carboxylic acid tert-butyl ester

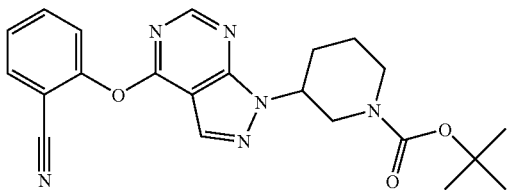

A mixture of 3-(4-Chloro-pyrazolo[3,4-d]pyrimidin-1-yl)-piperidine-1-carboxylic acid tert-butyl ester (Intermediate 32; 40 mg, 0.12 mmol), 2-hydroxybenzonitrile (available from Aldrich Chemical Company, Inc., Milwaukee, Wis., USA 15.5 mg, 0.13 mmol) and potassium carbonate (15 mg, 0.25 mmol) in dimethylformamide (0.6 mL) was heated in a microwave oven at 160° C. for 10 min. The reaction mixed was cooled and filtered. Volatiles were evaporated and the residue purified twice by chromatography on silica gel, eluting first with 25% ethyl acetate/hexanes and then with 20% ethyl acetate/hexanes to give 3-[4-(2-cyano-phenoxy)-pyrazolo[3,4-d]pyrimidin-1-yl]-piperidine-1-carboxylic acid tert-butyl ester (22 mg, 47%) as a viscous oil Example 91

4-[4-(Pyridin-3-yloxy)-pyrazolo[3,4-d]pyrimidin-1-yl]-piperidine-1-carboxylic acid tert-butyl ester

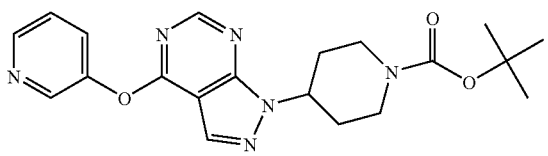

A mixture of 4-(4-chloro-pyrazolo[3,4-d]pyrimidin-1-yl)-piperidine-1-carboxylic acid tert-butyl ester (Intermediate 19; 50 mg, 0.15 mmol), 3-hydroxypyridine (Aldrich Chemical Company, Inc., Milwaukee, Wis., USA 18 mg, 0.19 mmol), and potassium carbonate (27 mg, 0.19 mmol) in dimethylformamide (2 mL) was heated in the microwave oven at 160° C. for 10 min. Dichloromethane and water were added, and the aqueous layer was extracted twice with dichloromethane. The dichloromethane layers were combined, evaporated, and purified by preparative C18 HPLC, eluting with 10-100% acetonitrile/water. Samples containing the product were extracted twice with dichloromethane and the solvent was evaporated under high vacuum to give 4-[4-(pyridin-3-yloxy)-pyrazolo[3,4-d]pyrimidin-1-yl]-piperidine-1-carboxylic acid tert-butyl ester (20 mg, 34%) as a white powder. Mass spectrum (ES) MH+=397. HRMS Calcd. for $C_{20}H_{25}N_6O_3$ (MH+): 397.1983. Found: 397.1983.

Example 92

4-[4-(2-Methyl-pyridin-3-yloxy)-pyrazolo[3,4-d]pyrimidin-1-yl]-piperidine-1-carboxylic acid tert-butyl ester

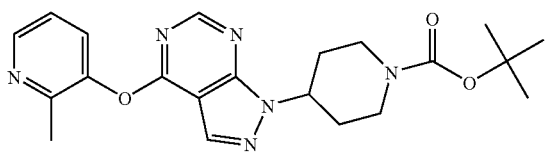

Method A

A mixture of 4-(4-chloro-pyrazolo[3,4-d]pyrimidin-1-yl)-piperidine-1-carboxylic acid tert-butyl ester (Intermediate 19; 3.00 g, 8.9 mmol), 3-hydroxy-2-methylpyridine (Aldrich Chemical Company, Inc., Milwaukee, Wis., USA 1.26 g, 12 mmol), and potassium carbonate (1.59 g, 11.5 mmol) in dimethylformamide (30 mL) was heated at 100° C. overnight. The solvent was evaporated under high vacuum. Water (50 mL) and dichloromethane (50 mL) were added. The layers were separated and the organic layer was washed twice with water and then evaporated to dryness to give 4-[4-(2-methyl-pyridin-3-yloxy)-pyrazolo[3,4-d]pyrimidin-1-yl]-piperidine-1-carboxylic acid tert-butyl ester (3.24 g, 89%). A sample of this material (500 mg) was purified by silica gel column chromatography, eluting with 0-75% ethyl acetate/hexanes, to give 4-[4-(2-methyl-pyridin-3-yloxy)-pyrazolo[3,4-d]pyrimidin-1-yl]-piperidine-1-carboxylic acid tert-butyl ester (381 mg, 10%) as a white powder. $^1$H NMR (300 MHz, CDCl$_3$) δ 1.49 (s, 9H), 1.97-2.06 (m, 2H), 2.20-2.34 (m, 2H), 2.47 (s, 3H), 2.91-3.05 (m, 2H), 4.26-4.39 (m, 2H), 4.91-5.03 (m, 1H), 7.27-7.29 (m, 1H), 7.50-7.55 (m, 1H), 8.07 (s, 1H), 8.48-8.51 (m, 2H). Mass spectrum MH+=411. HRMS Calcd. For $C_{21}H_{27}N_6O_3$ (MH+): 411.2139. Found: 411.2137.

Method B

A mixture of 4-chloro-6-(2-methyl-pyridin-3-yloxy)-pyrimidine-5-carbaldehyde (Intermediate 18; 515 mg, 2.1 mmol) and 4-hydrazino-piperidine-1-carboxylic acid tert-butyl ester (Intermediate 9; 688 mg, 3.2 mmol) in toluene (5 mL) was heated at reflux overnight. Aqueous sodium bicarbonate solution was added and the mixture was extracted with ethyl acetate. The organic phases were evaporated and purified on an Isco 40 g column, eluting with 0-3% methanol/dichloromethane to give 4-[4-(2-methyl-pyridin-3-yloxy)-pyrazolo[3,4-d]pyrimidin-1-yl]-piperidine-1-carboxylic acid tert-butyl ester (330 mg, 38%).

Example 93

4-[4-(2,6-Dimethyl-pyridin-3-yloxy)-pyrazolo[3,4-d]pyrimidin-1-yl]-piperidine-1-carboxylic acid tert-butyl ester

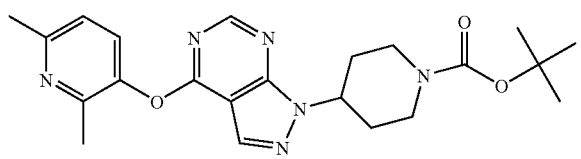

4-[4-(2,6-Dimethyl-pyridin-3-yloxy)-pyrazolo[3,4-d]pyrimidin-1-yl]-piperidine-1-carboxylic acid tert-butyl ester (41 mg, 65%) was prepared using the procedure described for the preparation of Example 96, by the reaction of 4-(4-chloro-pyrazolo[3,4-d]pyrimidin-1-yl)-piperidine-1-carboxylic acid tert-butyl ester (Intermediate 19; 50 mg, 0.15 mmol) with 2,6-dimethyl-3-hydroxypyridine (Apollo Scientific Ltd., Stockport, Cheshire, UK; 16 mg) in the presence of potassium carbonate (27 mg, 0.19 mmol) in dimethylformamide (2 mL). Mass spectrum (ES) MH+=425. HRMS Calcd. for $C_{22}H_{29}N_6O_3$ (MH+): 425.2296. Found: 425.2294.

Example 94

4-[4-(6-Trifluoromethyl-pyridin-3-yloxy)-pyrazolo[3,4-d]pyrimidin-1-yl]-piperidine-1-carboxylic acid tert-butyl ester

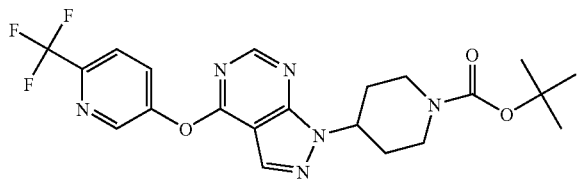

4-[4-(6-Trifluoromethyl-pyridin-3-yloxy)-pyrazolo[3,4-d]pyrimidin-1-yl]-piperidine-1-carboxylic acid tert-butyl ester (15 mg, 22%) was prepared using the procedure described for the preparation of Example 96, by the reaction of 4-(4-chloro-pyrazolo[3,4-d]pyrimidin-1-yl)-piperidine-1-carboxylic acid tert-butyl ester (Intermediate 19; 50 mg, 0.15 mmol) with 6-trifluoromethyl-pyridin-3-ol (Matrix Scientific, Columbia, S.C., USA; 31 mg, 0.19 mmol) in the presence of potassium carbonate (27 mg, 0.19 mmol) in dimethylformamide (2 mL). Mass spectrum (ES) MH+=465. HRMS Calcd. for $C_{21}H_{24}F_3N_6O_3$ (MH+): 465.1857. Found: 465.1857.

Example 95

4-[4-(2,6-Dimethoxy-pyridin-3-yloxy)-pyrazolo[3,4-d]pyrimidin-1-yl]-piperidine-1-carboxylic acid tert-butyl ester

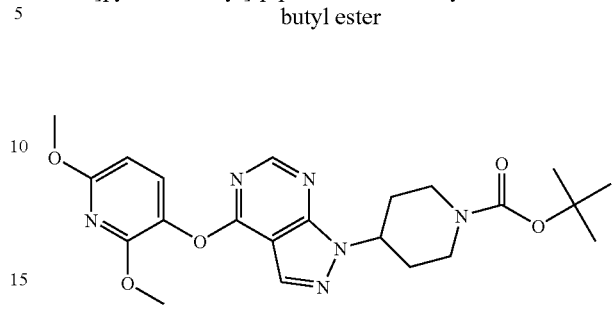

A mixture of 4-(4-chloro-pyrazolo[3,4-d]pyrimidin-1-yl)-piperidine-1-carboxylic acid tert-butyl ester (Intermediate 19; 50 mg, 0.15 mmol), 2,6-dimethoxy-pyridin-3-ol (Aagile Labs Division of Tyger Scientific, Ewing, N.J., USA; 30 mg, 0.19 mmol), and potassium carbonate (27 mg, 0.2 mmol) in dimethylformamide (2 mL) was heated in the microwave oven at 160° C. for 10 min. Dichloromethane and water were added, and the aqueous layer was extracted twice with dichloromethane. The dichloromethane layers were combined, evaporated, and purified by preparative C18 HPLC, eluting with 10-100% acetonitrile/water to give 4-[4-(2,6-dimethoxy-pyridin-3-yloxy)pyrazolo[3,4-d]pyrimidin-1-yl]-piperidine-1-carboxylic acid tert-butyl ester (20 mg, 29%) as an off-white powder. $^1$H NMR (300 MHz, CDCl$_3$) δ 1.49 (s, 9H), 1.96-2.04 (m, 2H), 2.18-2.30 (m, 2H), 2.90-3.05 (m, 2H), 3.90 (s, 3H), 3.95 (s, 3H), 4.25-4.38 (m, 2H), 4.90-5.00 (m, 1H), 6.37 (d, 1H, J=8.2 Hz), 7.41 (d, 1H, J=8.2 Hz), 8.03 (s, 1H), 8.50 (s, 1H). Mass spectrum MH+=457. HRMS Calcd. For $C_{22}H_{29}N_6O_5$ (MH+): 457.2194. Found: 457.2193.

Example 96

4-[4-(6-Methoxy-pyridin-3-yloxy)-pyrazolo[3,4-d]pyrimidin-1-yl]-piperidine-1-carboxylic acid tert-butyl ester

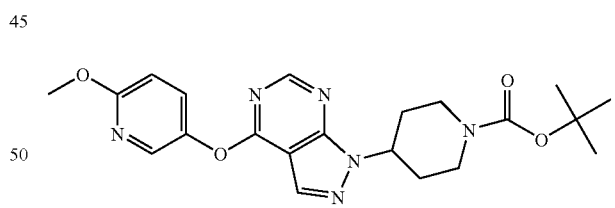

A mixture of 4-(4-chloro-pyrazolo[3,4-d]pyrimidin-1-yl)-piperidine-1-carboxylic acid tert-butyl ester (Intermediate 19; 50 mg, 0.15 mmol), 5-hydroxy-2-methoxypyridine (Tyger Scientific, Ewing, N.J., USA; 24 mg, 0.19 mmol), and potassium carbonate (27 mg, 0.19 mmol) in dimethylformamide (2 mL) was heated in the microwave oven at 160° C. for 10 min. Ethyl acetate and water were added, and the aqueous layer was extracted twice with ethyl acetate. The ethyl acetate layers were combined, evaporated, and purified by preparative C18 HPLC, eluting with 10-100% acetonitrile/water. Samples containing the product were extracted twice with dichloromethane and the solvent was evaporated to give 4-[4-(6-methoxy-pyridin-3-yloxy)-pyrazolo[3,4-d]pyrimidin-1-yl]-piperidine-1-carboxylic acid tert-butyl ester (34 mg, 54%) as a white powder. Mass spectrum (ES) MH+=427. HRMS Calcd. for $C_{21}H_{27}N_6O_4$ (MH+): 427.2089. Found: 427.2088.

Example 97

4-[4-(6-Chloro-2-methyl-pyridin-3-yloxy)-pyrazolo[3,4-d]pyrimidin-1-yl]-piperidine-1-carboxylic acid tert-butyl ester

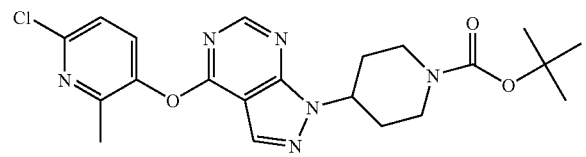

4-[4-(6-Chloro-2-methyl-pyridin-3-yloxy)-pyrazolo[3,4-d]pyrimidin-1-yl]-piperidine-1-carboxylic acid tert-butyl ester was prepared in 19% yield as a white powder using Method A described for the preparation of Example 92 by the reaction of 4-(4-chloro-pyrazolo[3,4-d]pyrimidin-1-yl)-piperidine-1-carboxylic acid tert-butyl ester (Intermediate 19; 50 mg, 0.15 mmol) with 6-chloro-2-methyl-pyridin-3-ol (Intermediate 3; 28 mg, 0.19 mmol). $^1$H NMR (300 MHz, CDCl$_3$) δ 1.50 (s, 9H), 1.96-2.06 (m, 2H), 2.20-2.35 (m, 2H), 2.42 (s, 3H), 2.92-3.05 (m, 2H), 4.26-4.38 (m, 2H), 4.90-5.02 (m, 1H), 7.27-7.30 (m, 1H), 7.48 (d, 1H, J=8.4 Hz), 8.15 (s, 1H), 8.47 (s, 1H). Mass spectrum (ES) MH+=445. HRMS Calcd. for $C_{21}H_{26}ClN_6O_3$ (MH+): 445.1750. Found: 445.1750.

Example 98

4-[4-(6-Methanesulfonyl-2-methyl-pyridin-3-yloxy)-pyrazolo[3,4-d]pyrimidin-1-yl]-piperidine-1-carboxylic acid tert-butyl ester

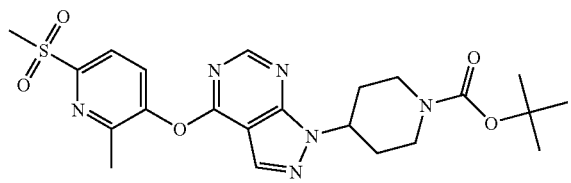

A mixture of 4-(4-chloro-pyrazolo[3,4-d]pyrimidin-1-yl)-piperidine-1-carboxylic acid tert-butyl ester (Intermediate 19; 50 mg, 0.15 mmol), 6-methanesulfonyl-2-methyl-pyridin-3-ol (Intermediate 6; 36 mg, 0.19 mmol), and potassium carbonate (27 mg, 0.2 mmol) in dimethylformamide (2 mL) was heated in the microwave oven at 160° C. for 10 min. Ethyl acetate and water were added, and the aqueous layer was extracted three times with ethyl acetate. The ethyl acetate layers were combined, evaporated, and purified by preparative C18 HPLC, eluting with 10-100% acetonitrile/water. Samples containing the product were extracted with dichloromethane and the solvent was evaporated to give 4-[4-(6-methanesulfonyl-2-methyl-pyridin-3-yloxy)-pyrazolo[3,4-d]pyrimidin-1-yl]-piperidine-1-carboxylic acid tert-butyl ester (30 mg, 42%) as a white powder. $^1$H NMR (300 MHz, CDCl$_3$) δ 1.50 (s, 9H), 1.96-2.06 (m, 2H), 2.20-2.34 (m, 2H), 2.92-3.05 (m, 2H), 4.26-4.39 (m, 2H), 4.92-5.04 (m, 1H), 7.76 (d, 1H, J=8.4 Hz), 8.06 (d, 1H, J=8.4 Hz), 8.21 (s, 1H), 8.46 (s, 1H). Mass spectrum (ES) MH+=489. HRMS Calcd. for $C_{22}H_{29}N_6O_5S$ (MH+): 489.1915. Found: 489.1915.

Example 99

4-[4-(2-Cyano-pyridin-3-yloxy)-pyrazolo[3,4-d]pyrimidin-1-yl]-piperidine-1-carboxylic acid tert-butyl ester

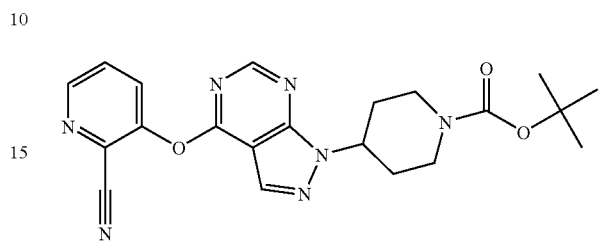

A mixture of 4-(4-chloro-pyrazolo[3,4-d]pyrimidin-1-yl)-piperidine-1-carboxylic acid tert-butyl ester (Intermediate 19; 50 mg, 0.15 mmol), 2-cyano-3-hydroxypyridine (Matrix Scientific, Columbia, S.C., USA; 26 mg, 0.19 mmol), and potassium carbonate (27 mg, 0.19 mmol) in dimethylformamide (2 mL) was heated in the microwave oven at 160° C. for 10 min. Ethyl acetate and water were added, and the aqueous layer was extracted twice with ethyl acetate. The ethyl acetate layers were combined, evaporated, and purified by preparative C18 HPLC, eluting with 10-100% acetonitrile/water. Samples containing the product were extracted three times with dichloromethane and the solvent was evaporated to give 4-[4-(2-cyano-pyridin-3-yloxy)-pyrazolo[3,4-d]pyrimidin-1-yl]-piperidine-1-carboxylic acid tert-butyl ester (37 mg, 59%) as a white powder. $^1$H NMR (300 MHz, CDCl$_3$) δ 1.51 (s, 9H), 1.85-2.11 (m, 2H), 2.15-2.43 (m, 2H), 2.85-3.15 (m, 2H), 4.34 (br s, 2H), 4.88-5.09 (m, 1H), 7.68 (dd, 1H, J=8.4, 4.7 Hz), 7.88 (d, 1H, J=8.4 Hz), 8.27 (s, 1H), 8.49 (s, 1H), 8.69 (d, 1H, J=4.7 Hz). Mass spectrum (ES) MH+=422. HRMS Calcd. for $C_{21}H_{24}N_7O_3$ (MH+): 422.1935. Found: 422.1934.

Example 100

4-[4-(5-Chloro-pyridin-3-yloxy)-pyrazolo[3,4-d]pyrimidin-1-yl]-piperidine-1-carboxylic acid tert-butyl ester

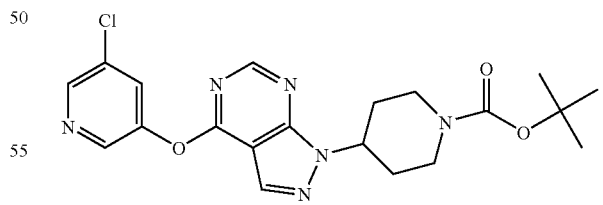

4-[4-(5-Chloro-pyridin-3-yloxy)-pyrazolo[3,4-d]pyrimidin-1-yl]-piperidine-1-carboxylic acid tert-butyl ester (10 mg, 16%) was prepared using the procedure described for the preparation of Example 96, by the reaction of 4-(4-chloro-pyrazolo[3,4-d]pyrimidin-1-yl)-piperidine-1-carboxylic acid tert-butyl ester (Intermediate 19; 50 mg, 0.15 mmol) with 5-chloro-3-pyridinol (Aldrich Chemical Company, Inc., Milwaukee, Wis., USA 25 mg, 0.19 mmol) in the presence of potassium carbonate (27 mg, 0.19 mmol) in dimethylforma-

Example 101

4-[4-(2-Methyl-6-[1,2,4]triazol-1-yl-pyridin-3-yloxy)-pyrazolo[3,4-d]pyrimidin-1-yl]-piperidine-1-carboxylic acid tert-butyl ester

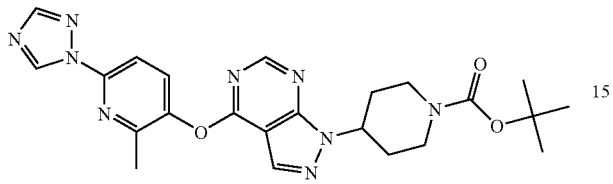

A mixture of 4-(4-chloro-pyrazolo[3,4-d]pyrimidin-1-yl)-piperidine-1-carboxylic acid tert-butyl ester (Intermediate 19; 100 mg, 0.30 mmol), 2-methyl-6-[1,2,4]triazol-1-yl-pyridin-3-ol (Intermediate 7; 68 mg, 0.385 mmol), and potassium carbonate (53 mg, 0.385 mmol) in dimethylformamide (3 mL) was heated in the microwave oven at 160° C. for 10 min. Dichloromethane and water were added, and the aqueous layer was extracted three times with dichloromethane. The dichloromethane layers were combined, evaporated, and purified by preparative C18 HPLC, eluting with 10-100% acetonitrile/water. Samples containing the product were extracted three times with dichloromethane and the solvent was evaporated to give 4-[4-(2-methyl-6-[1,2,4]triazol-1-yl-pyridin-3-yloxy)pyrazolo[3,4-d]pyrimidin-1-yl]-piperidine-1-carboxylic acid tert-butyl ester (96 mg, 68%) as a white powder. $^1$H NMR (300 MHz, CDCl$_3$) δ 1.49 (s, 9H), 1.95-2.04 (m, 2H), 2.20-2.35 (m, 2H), 2.90-3.05 (m, 2H), 4.25-4.40 (m, 2H), 4.90-5.02 (m, 1H), 7.69 (d, 1H, J=8.5 Hz), 7.86 (d, 1H, J=8.8 Hz), 8.12 (s, 1H), 8.17 (s, 1H), 8.47 (s, 1H), 9.20 (s, 1H). Mass spectrum (ES) MH+=478. HRMS Calcd. for C$_{23}$H$_{28}$N$_9$O$_3$ (MH+): 478.2310. Found: 478.2307.

Example 102

4-[4-(1-Methyl-6-oxo-1,6-dihydro-pyridazin-3-yloxy)-pyrazolo[3,4-d]pyrimidin-1-yl]-piperidine-1-carboxylic acid tert-butyl ester

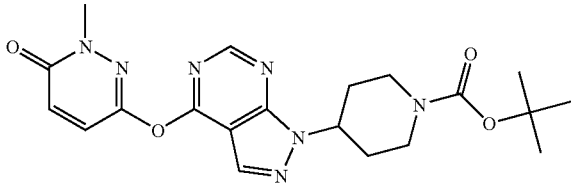

A mixture of 4-(4-chloro-pyrazolo[3,4-d]pyrimidin-1-yl)-piperidine-1-carboxylic acid tert-butyl ester (Intermediate 19; 50 mg, 0.15 mmol), 3-hydroxy-1-methylpyridazin-6(1H)-one (Oakwood Products, Inc., West Columbia, S.C., USA; 24 mg, 0.19 mmol), and potassium carbonate (27 mg, 0.2 mmol) in dimethylformamide (2 mL) was heated in the microwave oven at 160° C. for 10 min. Ethyl acetate and water were added, and the aqueous layer was extracted three times with ethyl acetate. The ethyl acetate layers were combined, evaporated, and purified by preparative C18 HPLC, eluting with 10-100% acetonitrile/water. Samples containing the product were extracted twice with dichloromethane and the solvent was evaporated under high vacuum to give 4-[4-(1-methyl-6-oxo-1,6-dihydro-pyridazin-3-yloxy)-pyrazolo[3,4-d]pyrimidin-1-yl]-piperidine-1-carboxylic acid tert-butyl ester (25 mg, 39%) as a white powder. $^1$H NMR (300 MHz, CDCl$_3$) δ 1.49 (s, 9H), 1.95-2.04 (m, 2H), 2.20-2.36 (m, 2H), 2.92-3.05 (m, 2H), 3.76 (s, 3H), 4.26-4.40 (m, 2H), 4.90-5.02 (m, 1H), 7.07 (d, 1H, J=9.7 Hz), 7.24 (d, 1H, J=9.7 Hz), 8.17 (s, 1H), 8.51 (s, 1H). Mass spectrum (ES) MH+=428. HRMS Calcd. for C$_{20}$H$_{26}$N$_7$O$_4$ (MH+): 428.2041. Found: 428.2040.

Example 103

4-[4-(6-Ethyl-2-methyl-pyrimidin-4-yloxy)-pyrazolo[3,4-d]pyrimidin-1-yl]-piperidine-1-carboxylic acid tert-butyl ester

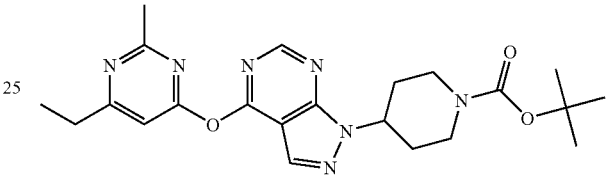

4-[4-(6-Ethyl-2-methyl-pyrimidin-4-yloxy)-pyrazolo[3,4-d]pyrimidin-1-yl]-piperidine-1-carboxylic acid tert-butyl ester (10 mg, 13%) was prepared using the procedure described for the preparation of Example 41 by the reaction of 4-(4-chloro-pyrazolo[3,4-d]pyrimidin-1-yl)-piperidine-1-carboxylic acid tert-butyl ester (Intermediate 19; 60 mg, 0.18 mmol) with 4-ethyl-6-hydroxy-2-methylpyrimidine (Synchem Inc., Des Plaines, Ill., USA; 25 mg, 0.18 mmol) in the presence of potassium carbonate (54 mg, 0.39 mmol). Mass spectrum MH+=440.

Example 104

4-[4-(2-Methyl-pyridin-3-yloxy)-pyrazolo[3,4-d]pyrimidin-1-yl]-piperidine-1-carboxylic acid butyl ester

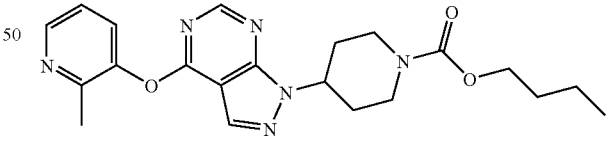

A solution of 4-[4-(2-methyl-pyridin-3-yloxy)-pyrazolo[3,4-d]pyrimidin-1-yl]-piperidine-1-carboxylic acid tert-butyl ester (Example 92; 50 mg, 0.12 mmol) in a mixture of trifluoroacetic acid (0.5 mL) and dichloromethane (2 mL) was stirred at room temperature for 30 min, then the solvents were evaporated under vacuum. Dichloromethane (4 mL) was added, followed successively by n-butyl chloroformate (24 µL, 0.18 mmol) and triethylamine (110 µL, 0.8 mmol). The mixture was stirred overnight at room temperature. Water was added and the mixture was extracted with three times with dichloromethane. The combined dichloromethane layers were evaporated and the residue was purified by C18

Example 105

4-[4-(4-Methanesulfonyl-phenoxy)-pyrazolo[3,4-d]pyrimidin-1-yl]-piperidine-1-carboxylic acid (R)-sec-butyl ester

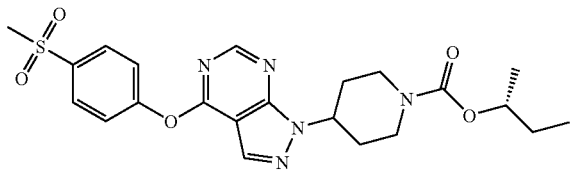

Triphosgene (217 mg, 0.73 mmol) was added to a solution of (R)-(−)-2-butanol (Aldrich Chemical Company, Inc., Milwaukee, Wis., USA 148 mg, 2 mmol) in a mixture of pyridine (190 μL, 2.3 mmol) and 1,2-dichloroethane (10 mL). The solution was stirred at 40° C. for 3 h and then cooled to room temperature. 1 M aqueous hydrochloric acid (2.5 mL) and water (3 mL) were added. The layers were separated and the organic phase was dried (magnesium sulfate), filtered, and evaporated. 4-(4-Methanesulfonyl-phenoxy)-1-piperidin-4-yl-1H-pyrazolo[3,4-d]pyrimidine trifluoroacetate salt (Intermediate 27; 220 mg, 0.45 mmol) and diisopropylethylamine (250 μL) were added and the mixture was stirred for 30 min and then chromatographed, eluting with 50-75% ethyl acetate/hexanes, to give 4-[4-(4-methanesulfonyl-phenoxy)-pyrazolo[3,4-d]pyrimidin-1-yl]-piperidine-1-carboxylic acid (R)-sec-butyl ester (78 mg, 36%) as an off-white foam/solid.

Example 106

4-[4-(4-Methanesulfonyl-phenoxy)-pyrazolo[3,4-d]pyrimidin-1-yl]-piperidine-1-carboxylic acid isobutyl ester

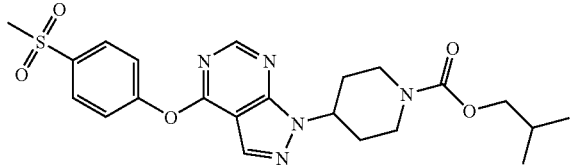

4-[4-(4-Methanesulfonyl-phenoxy)-pyrazolo[3,4-d]pyrimidin-1-yl]-piperidine-1-carboxylic acid isobutyl ester was prepared according to General Procedure E by the reaction of 4-(4-methanesulfonyl-phenoxy)-1-piperidin-4-yl-1H-pyrazolo[3,4-d]pyrimidine trifluoroacetate salt (Intermediate 27) with isobutyl chloroformate (available from Aldrich Chemical Company, Inc., Milwaukee, Wis., USA). $^1$H NMR (400 MHz, DMSO-d$_6$) δ 0.91 (d, 6H, J=6.7 Hz), 1.86-2.09 (m, 6H), 3.04-3.16 (m, 2H), 3.30 (methyl sulfonyl and water peak), 3.82-3.84 (m, 2H), 4.12-4.16 (m, 2H), 5.02-5.08 (m, 1H), 7.62-7.64 (m, 2H), 8.05-8.07 (m, 2H), 8.38 (s, 1H), 8.57 (s, 1H). Mass spectrum MH+=474.

Example 107

4-[4-(2-Methyl-pyridin-3-yloxy)-pyrazolo[3,4-d]pyrimidin-1-yl]-piperidine-1-carboxylic acid isobutyl ester

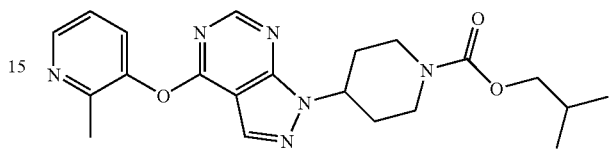

Trifluoroacetic acid (0.5 mL) was added to a solution of 4-[4-(2-methyl-pyridin-3-yloxy)pyrazolo[3,4-d]pyrimidin-1-yl]-piperidine-1-carboxylic acid tert-butyl ester (Example 92; 50 mg, 0.12 mmol) in dichloromethane (2 mL). The solution was stirred at room temperature for 30 min and then the solvents were evaporated using high vacuum. Dichloromethane (4 mL) was added to the residue, and then isobutyl chloroformate (available from Aldrich Chemical Company, Inc., Milwaukee, Wis., USA 25 mg, 0.18 mmol) was added at room temperature, followed by triethylamine (80 mg, 0.79 mmol). The mixture was stirred overnight at room temperature and then water was added. The layers were separated and the aqueous layer was extracted twice with dichloromethane. The combined organic layers were evaporated, and purified by preparative C18 HPLC, eluting with 10-100% acetonitrile/water to give 4-[4-(2-methyl-pyridin-3-yloxy)-pyrazolo[3,4-d]pyrimidin-1-yl]-piperidine-1-carboxylic acid isobutyl ester (31 mg, 63%) as a powder. $^1$H NMR (300 MHz, CDCl$_3$) δ 0.97 (d, 6H, J=6.5 Hz), 1.90-2.06 (m, 3H), 2.20-2.35 (m, 2H), 2.45 (s, 3H), 2.95-3.10 (m, 2H), 3.90 (d, 2H, J=6.3 Hz), 4.32-4.48 (m, 2H), 4.95-5.10 (m, 1H), 7.26-7.72 (m, 1H), 7.50-7.54 (m, 1H), 8.07 (s, 1H), 8.45-8.60 (m, 2H). Mass spectrum MH+=411. HRMS Calcd. For C$_{21}$H$_{27}$N$_6$O$_3$ (MH+): 411.2139. Found: 411.2138.

Example 108

4-[4-(4-Methanesulfonyl-phenoxy)-pyrazolo[3,4-d]pyrimidin-1-yl]-piperidine-1-carboxylic acid 2,2-dimethyl-propyl ester

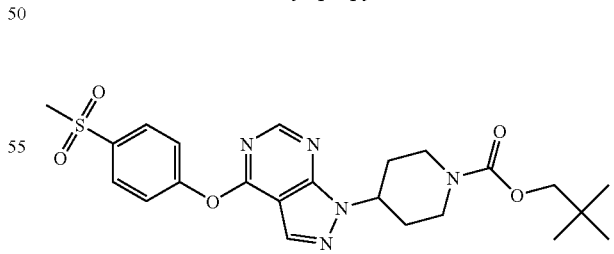

4-[4-(4-Methanesulfonyl-phenoxy)-pyrazolo[3,4-d]pyrimidin-1-yl]-piperidine-1-carboxylic acid 2,2-dimethyl-propyl ester was prepared according to General Procedure E by the reaction of 4-(4-methanesulfonyl-phenoxy)-1-piperidin-4-yl-1H-pyrazolo[3,4-d]pyrimidine trifluoro-acetate salt (Intermediate 27) with 2,2-dimethylpropyl chloroformate (available from Aldrich Chemical Company, Inc., Milwaukee, Wis., USA). $^1$H NMR (400 MHz, DMSO-$d_6$) δ 0.93 (s, 9H), 1.98-2.01 (m, 4H), 3.00-3.10 (m, 2H), 3.30 (methyl sulfonyl and water peak), 3.70-3.80 (m, 2H), 4.14-4.17 (m, 2H), 5.03-5.09 (m, 1H), 7.63-7.65 (m, 2H), 8.05-8.07 (m, 2H), 8.37 (s, 1H), 8.57 (s, 1H). Mass spectrum MH+=488.

Example 109

4-[4-(4-Methanesulfonyl-phenoxy)-pyrazolo[3,4-d]pyrimidin-1-yl]-piperidine-1-carboxylic acid 2-fluoro-1-fluoromethyl-ethyl ester

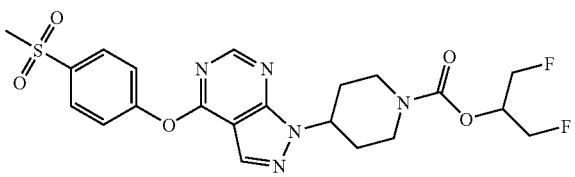

Triphosgene (208 mg, 0.7 mmol) was added to a solution of 1,3-difluoro-2-propanol (Aldrich Chemical Company, Inc., Milwaukee, Wis., USA 192 mg, 2 mmol) in a mixture of pyridine (2.2 mmol) and 1,2-dichloroethane (10 mL). The solution was stirred at 40° C. for 3 h and then cooled to room temperature. 1 M aqueous hydrochloric acid (2.5 mL) and water (5 mL) were added. The aqueous layer was extracted with dichloromethane and the combined organic layers were dried (magnesium sulfate), filtered, and evaporated. 4-(4-Methanesulfonyl-phenoxy)-1-piperidin-4-yl-1H-pyrazolo[3,4-d]pyrimidine trifluoroacetate salt (Intermediate 27; 200 mg, 0.41 mmol) and diisopropylethylamine (350 µL) were added and the mixture was stirred for 15 min and then chromatographed, eluting with 50-75% ethyl acetate/hexanes, to give 4-[4-(4-methanesulfonyl-phenoxy)-pyrazolo[3,4-d]pyrimidin-1-yl]-piperidine-1-carboxylic acid 2-fluoro-1-fluoromethyl-ethyl ester (64 mg, 32%) as a foamy solid.

Example 110

4-[4-(4-Methanesulfonyl-phenoxy)-pyrazolo[3,4-d]pyrimidin-1-yl]-piperidine-1-carboxylic acid 2,2,2-trifluoro-1-methyl-ethyl ester

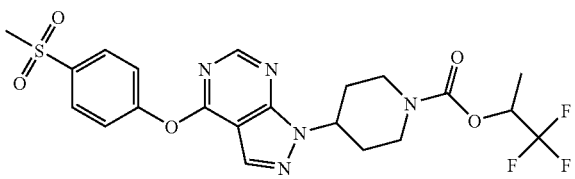

Triphosgene (1.6 g, 5.5 mmol) was added in portions to a solution of 1,1,1-trifluoro-2-propanol (Aldrich Chemical Company, Inc., Milwaukee, Wis., USA 0.45 mL, 5 mmol) in a mixture of pyridine (0.48 mL, 6 mmol) and carbon tetrachloride (25 mL) under nitrogen. The solution was stirred at 60° C. for 5.5 h and then cooled using an ice bath. 1 M aqueous hydrochloric acid (4 mL) was added and then the mixture was diluted with water and the layers were separated. The organic layer was dried (sodium sulfate), and filtered to give approximately 20 mL of solution, of which 6 mL were used directly in the next reaction without further purification. The solution (6 mL) as added to a mixture of 4-(4-methanesulfonyl-phenoxy)-1-piperidin-4-yl-1H-pyrazolo[3,4-d]pyrimidine trifluoroacetate salt (Intermediate 27; 250 mg, 0.5 mmol) in tetrahydrofuran (1 mL). Diisopropylethylamine (0.5 mL, 2.8 mL) was added slowly and the mixture was stirred for 10 min and then evaporated to dryness and chromatographed using a 30 mm×3" column of silica gel, eluting with 66-75% ethyl acetate/hexanes, to give 4-[4-(4-methanesulfonyl-phenoxy)-pyrazolo[3,4-d]pyrimidin-1-yl]-piperidine-1-carboxylic acid 2,2,2-trifluoro-1-methyl-ethyl ester (72 mg, 28%) as a white solid.

Example 111

4-[4-(4-Methanesulfonyl-phenoxy)-pyrazolo[3,4-d]pyrimidin-1-yl]-piperidine-1-carboxylic acid 2,2,2-trifluoro-1,1-dimethyl-ethyl ester

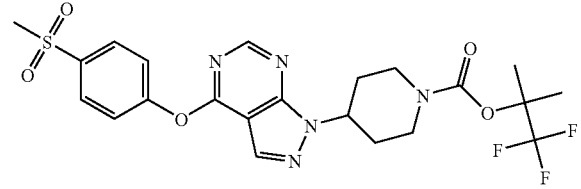

A solution of 2-trifluoromethyl-2-propanol (Aldrich Chemical Company, Inc., Milwaukee, Wis., USA; 500 mg, 3.91 mmol) in pyridine (347 µL) was added to a cooled (0° C.) solution of triphosgene (386 mg, 1.3 mmol) in diethyl ether (35 mL). The mixture was stirred overnight and then 1 M aqueous hydrochloric acid (4 mL) was added. The organic layer was separated and washed with brine, dried (magnesium sulfate), filtered, and evaporated. The resulting material was dissolved in tetrahydrofuran (5 mL) and the solution was cooled to 0° C. 4-(4-Methanesulfonyl-phenoxy)-1-piperidin-4-yl-1H-pyrazolo[3,4-d]pyrimidine trifluoroacetate salt (Intermediate 27; 210 mg, 0.43 mmol) and triethylamine (560 µL, 4 mmol) were added. The mixture was stirred for 30 min and then poured into saturated aqueous ammonium chloride solution and extracted three times with ethyl acetate. The combined organic extracts were washed with brine, dried (magnesium sulfate), filtered, evaporated, and purified by column chromatography, eluting with 50% ethyl acetate/hexanes, to give 4-[4-(4-methanesulfonyl-phenoxy)-pyrazolo[3,4-d]pyrimidin-1-yl]-piperidine-1-carboxylic acid 2,2,2-trifluoro-1,1-dimethyl-ethyl ester (20.5 mg, 10%).

Example 112

4-[4-(4-Methanesulfonyl-phenoxy)-pyrazolo[3,4-d]pyrimidin-1-yl]-piperidine-1-carboxylic acid 2,2,2-trifluoro-1-trifluoromethyl-ethyl ester

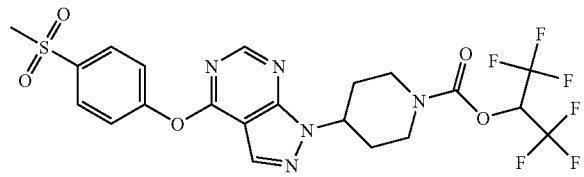

Triphosgene (1.6 g, 5.5 mmol) was added in portions to a solution of 1,1,1,3,3,3-hexafluoro-2-propanol (Aldrich Chemical Company, Inc., Milwaukee, Wis., USA 790 mg, 5 mmol) in a mixture of pyridine (0.48 mL, 6 mmol) and carbon tetrachloride (25 mL) under nitrogen. The solution was stirred at 60° C. for 5.5 h and then cooled using an ice bath. 1 M aqueous hydrochloric acid (4 mL) was added and then the mixture was diluted with water and the layers were separated. The organic layer was dried (sodium sulfate), and filtered to give approximately 20 mL of solution, of which 6 mL were used directly in the next reaction without further purification. The solution (7 mL) as added to a mixture of 4-(4-methanesulfonyl-phenoxy)-1-piperidin-4-yl-1H-pyrazolo[3,4-d]pyrimidine trifluoroacetate salt (Intermediate 27; 240 mg, 0.5 mmol) in tetrahydrofuran (1 mL). Diisopropylethylamine (0.5 mL, 2.8 mL) was added slowly and the mixture was stirred for 10 min and then evaporated to dryness and chromatographed using a 30 mm×3" column of silica gel, eluting with 75% ethyl acetate/hexanes, to give 4-[4-(4-methanesulfonyl-phenoxy)-pyrazolo[3,4-d]pyrimidin-1-yl]-piperidine-1-carboxylic acid 2,2,2-trifluoro-1-trifluoromethyl-ethyl ester (70 mg, 28%) as an off-white powder.

Example 113

4-[4-(4-Methanesulfonyl-phenoxy)-pyrazolo[3,4-d]pyrimidin-1-yl]-piperidine-1-carboxylic acid 2,2,2-trifluoro-ethyl ester

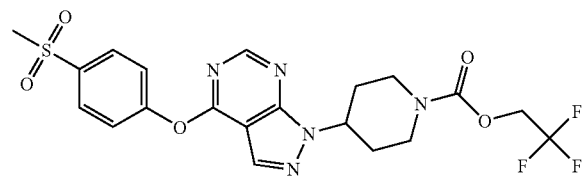

Triphosgene (1.6 g, 5.5 mmol) was added to a solution of 2,2,2-trifluoroethanol (Aldrich Chemical Company, Inc., Milwaukee, Wis., USA; 500 mg, 5 mmol) in pyridine (6 mmol) and carbon tetrachloride (25 mL). The mixture was heated to 60° C. for 6 h, then cooled and washed with 1 M aqueous hydrochloric acid. The organic layer was dried (magnesium sulfate), filtered, and evaporated carefully using a cold rotary evaporator bath. The resulting material was suspended in dichloromethane (10 mL) and 4-(4-methanesulfonyl-phenoxy)-1-piperidin-4-yl-1H-pyrazolo[3,4-d]pyrimidine trifluoroacetate salt (Intermediate 27; 200 mg, 0.41 mmol) and diisopropylethylamine (350 μL, 2 mmol) were added. The mixture was stirred for 15 min and then purified by column chromatography, eluting with 50% ethyl acetate/hexanes, to give 4-[4-(4-Methanesulfonyl-phenoxy)-pyrazolo[3,4-d]pyrimidin-1-yl]-piperidine-1-carboxylic acid 2,2,2-trifluoro-ethyl ester (71 mg, 35%) as a yellow powder.

Example 114

4-[4-(4-Methanesulfonyl-phenoxy)-pyrazolo[3,4-d]pyrimidin-1-yl]-piperidine-1-carboxylic acid 2,2,2-trichloro-1,1-dimethyl-ethyl ester

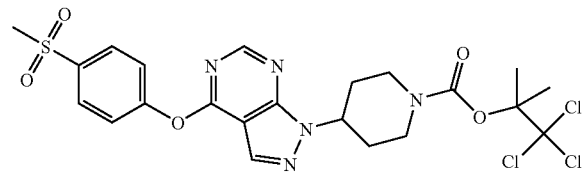

4-[4-(4-Methanesulfonyl-phenoxy)-pyrazolo[3,4-d]pyrimidin-1-yl]-piperidine-1-carboxylic acid 2,2,2-trichloro-1,1-dimethyl-ethyl ester was prepared according to General Procedure E by the reaction of 4-(4-methanesulfonyl-phenoxy)-1-piperidin-4-yl-1H-pyrazolo[3,4-d]pyrimidine trifluoroacetate salt (Intermediate 27) with 2,2,2-trichloro-1,1-dimethylethyl chloroformate (available from Aldrich Chemical Company, Inc., Milwaukee, Wis., USA). $^1$H NMR (400 MHz, DMSO-$d_6$) δ 1.87-1.89 (m, 6H), 2.02-2.08 (m, 4H), 3.00-3.10 (m, 2H), 3.30 (methyl sulfonyl and water peak), 4.10-4.16 (m, 2H), 5.05-5.09 (m, 1H), 7.62-7.65 (m, 2H), 8.05-8.07 (m, 2H), 8.40 (s, 1H), 8.57 (s, 1H). Mass spectrum MH+=576.

Example 115

4-[4-(4-Methanesulfonyl-phenoxy)-pyrazolo[3,4-d]pyrimidin-1-yl]-piperidine-1-carboxylic acid 2,2,2-trichloro-ethyl ester

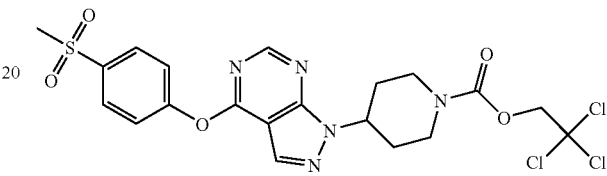

4-[4-(4-Methanesulfonyl-phenoxy)-pyrazolo[3,4-d]pyrimidin-1-yl]-piperidine-1-carboxylic acid 2,2,2-trichloroethyl ester was prepared according to General Procedure E by the reaction of 4-(4-methanesulfonyl-phenoxy)-1-piperidin-4-yl-1H-pyrazolo[3,4-d]pyrimidine trifluoro-acetate salt (Intermediate 27) with 2,2,2-trichloroethyl chloroformate (available from Aldrich Chemical Company, Inc., Milwaukee, Wis., USA). $^1$H NMR (400 MHz, DMSO-$d_6$) δ 1.96-2.08 (m, 4H), 3.30 (methyl sulfonyl and water peak), 4.11-4.20 (m, 2H), 4.86-4.89 (m, 2H), 5.05-5.10 (m, 1H), 7.59-7.62 (m, 2H), 8.03-8.05 (m, 2H), 8.36 (s, 1H), 8.54 (s, 1H). Mass spectrum MH+=548.

Example 116

4-[4-(2-Methyl-pyridin-3-yloxy)-pyrazolo[3,4-d]pyrimidin-1-yl]-piperidine-1-carboxylic acid cyclobutyl ester

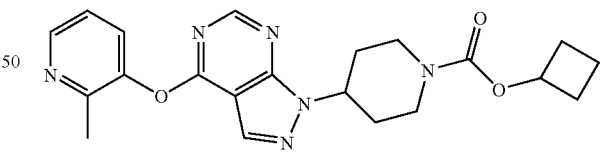

Sodium hydride (60% dispersion in oil; 10 mg, 0.25 mmol) was added to a solution of 4-[4-(2-methyl-pyridin-3-yloxy)-pyrazolo[3,4-d]pyrimidin-1-yl]-piperidine-1-carboxylic acid 4-nitro-phenyl ester (Example 123; 60 mg, 0.13 mmol) in anhydrous tetrahydrofuran (1 mL) under argon. The mixture was stirred for 5 min and then cyclobutanol (11 μL, 0.14 mmol) was added and the mixture was stirred at room temperature for 7 h. Water was added and the mixture was extracted with ethyl acetate. The organic layer was washed with brine, dried (sodium sulfate), filtered, evaporated, and purified on a Silicycle 4 g column, eluting with 0-4% methanol/dichloromethane to give 4-[4-(2-methyl-pyridin-3- yloxy)-pyrazolo[3,4-d]pyrimidin-1-yl]-piperidine-1-carboxylic acid cyclobutyl ester (7 mg, 14%).

Example 117

4-[4-(4-Ethoxy-2-fluoro-phenoxy)-pyrazolo[3,4-d]pyrimidin-1-yl]-piperidine-1-carboxylic acid cyclopentyl ester

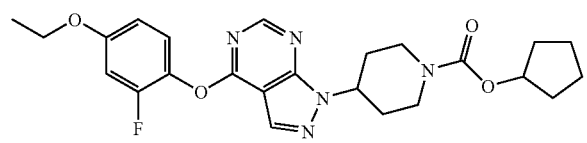

Cyclopentyl chloroformate (12 mg, 0.078 mmol) was added to a mixture of 4-(4-ethoxy-2-fluoro-phenoxy)-1-piperidin-4-yl-1H-pyrazolo[3,4-d]pyrimidine trifluoroacetate salt (Intermediate 29; 28 mg, 0.078 mmol), diisopropylethylamine (30 mg, 0.235 mmol) in dichloromethane (2 mL). The reaction was stirred at room temperature overnight. Water was added to quench the reaction and the aqueous layer was extracted three times with dichloromethane. The combined organic layers were dried (sodium sulfate), filtered, evaporated and purified by flash chromatography on silica gel, eluting with 4% methanol/dichloromethane to give 4-[4-(4-ethoxy-2-fluorophenoxy)-pyrazolo[3,4-d]pyrimidin-1-yl]-piperidine-1-carboxylic acid cyclopentyl ester (36 mg, 99%) as a white solid. Mass spectrum MH+=470.

Example 118

4-[4-(2-Cyano-phenoxy)-pyrazolo[3,4-d]pyrimidin-1-yl]-piperidine-1-carboxylic acid cyclopentyl ester

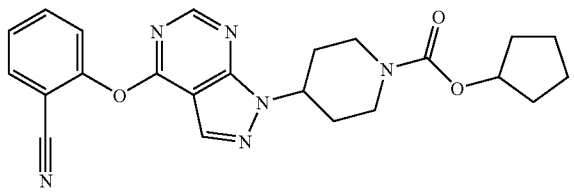

Cyclopentyl chloroformate (51 mg, 0.344 mmol) was added to a mixture of 2-(1-piperidin-4-yl-1H-pyrazolo[3,4-d]pyrimidine-4-yloxy)-benzonitrile trifluoroacetate salt (which was prepared from 4-[4-(2-cyano-phenoxy)-pyrazolo[3,4-d]pyrimidin-1-yl]-piperidine-1-carboxylic acid tert-butyl ester [Example 45] following the procedure described for the preparation of Intermediate 29; 150 mg, 0.344 mmol), diisopropylethylamine (133 mg, 1.03 mmol) in dichloromethane (6 mL). The reaction was stirred at room temperature overnight. Water was added to quench the reaction and the aqueous layer was extracted three times with dichloromethane. The combined organic layers were dried (sodium sulfate), filtered, evaporated and purified by flash chromatography on silica gel, eluting with 4% methanol/dichloromethane to give 4-[4-(2-cyano-phenoxy)-pyrazolo[3,4-d]pyrimidin-1-yl]-piperidine-1-carboxylic acid cyclopentyl ester (107 mg, 72%) as a white solid. Mass spectrum MH+=433.

Example 119

4-[4-(6-Cyano-2,3-difluoro-phenoxy)-pyrazolo[3,4-d]pyrimidin-1-yl]-piperidine-1-carboxylic acid cyclopentyl ester

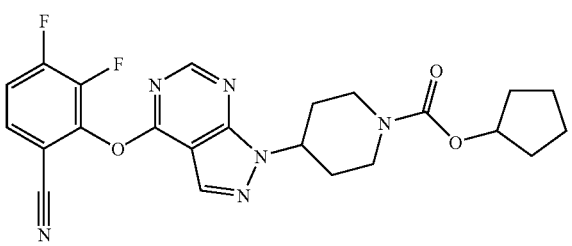

Cyclopentyl chloroformate (3B Scientific Corporation, Libertyville, Ill., USA; 46 mg, 0.31 mmol) was added to a mixture of 3,4-difluoro-2-(1-piperidin-4-yl-1H-pyrazolo[3,4-d]pyrimidine-4-yloxy)-benzonitrile trifluoroacetate salt (which was prepared from 4-[4-(6-cyano-2,3-difluoro-phenoxy)-pyrazolo[3,4-d]pyrimidin-1-yl]-piperidine-1-carboxylic acid tert-butyl ester [Example 49] following the procedure described for the preparation of Intermediate 29; 145 mg, 0.31 mmol), diisopropylethylamine (120 mg, 0.93 mmol) in dichloromethane (10 mL). The reaction was stirred at room temperature overnight. Water was added to quench the reaction and the aqueous layer was extracted three times with dichloromethane. The combined organic layers were dried (sodium sulfate), filtered, evaporated and purified by flash chromatography on silica gel, eluting with 4% methanol/dichloromethane to give 4-[4-(6-cyano-2,3-difluoro-phenoxy)-pyrazolo[3,4-d]pyrimidin-1-yl]-piperidine-1-carboxylic acid cyclopentyl ester (130 mg, 90%) as a white solid. Mass spectrum MH+=469.

Example 120

4-[4-(2-Fluoro-4-methanesulfonyl-phenoxy)-pyrazolo[3,4-d]pyrimidin-1-yl]-piperidine-1-carboxylic acid cyclopentyl ester

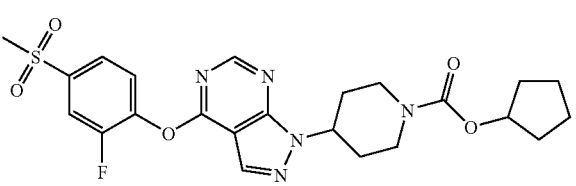

A mixture of 4-[4-(2-fluoro-4-methanesulfonyl-phenoxy)-pyrazolo[3,4-d]pyrimidin-1-yl]-piperidine-1-carboxylic acid tert-butyl ester (Example 60; 520 mg, 1.06 mmol) and 20% trifluoroacetic acid/dichloromethane (12 mL) was stirred at room temperature until tlc (6% methanol/dichloromethane) indicated that the starting material had completely reacted. The solvent was evaporated, ether (5 mL) was added, and the mixture was evaporated to give a white semi-solid which was held under vacuum, then triturated with ether, and held under high vacuum to give 4-[4-(2-fluoro-4-methanesulfonyl-phenoxy)-pyrazolo[3,4-d]pyrimidin-1-yl]-piperidine-1-carboxylic acid (479 mg, 90%) as a white powder. A mixture of 40 mg of this powder (0.08 mmol) and diisopropylethylamine (42 µL) in anhydrous dichloromethane (1 mL) was cooled to 0° C. and a solution of cyclopentyl chloroformate (Waterstone Technology, LLC, Carmel, Ind., USA; 18 mg, 0.12 mmol) in dichloromethane (250 µL) was added dropwise. The mixture was stirred at room temperature for 30 min. Water (3 mL) was added. The layers were separated and the organic layer was washed with brine, dried (sodium sulfate), filtered, evaporated, co-evaporated with ether and purified on a Silicycle 4 g column eluting with 0-10% methanol/dichloromethane to give 4-[4-(2-fluoro-4-methanesulfonyl-phenoxy)pyrazolo[3,4-d]pyrimidin-1-yl]-piperidine-1-carboxylic acid cyclopentyl ester (27 mg, 68%) as a white solid.

Example 121

4-[4-(2-Methyl-pyridin-3-yloxy)-pyrazolo[3,4-d]pyrimidin-1-yl]-piperidine-1-carboxylic acid cyclopentyl ester

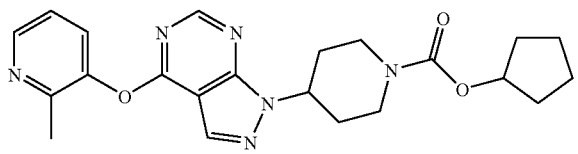

Sodium hydride (60% dispersion in oil; 6 mg, 0.15 mmol) was added to a solution of 4-[4-(2-methyl-pyridin-3-yloxy)-pyrazolo[3,4-d]pyrimidin-1-yl]-piperidine-1-carboxylic acid 4-nitro-phenyl ester (Example 123; 37 mg, 0.078 mmol) in anhydrous tetrahydrofuran (750 µL) under argon. Cyclopentanol (70 µL, 0.77 mmol) was added and the mixture was stirred at room temperature overnight. Water was added and the mixture was extracted with ethyl acetate. The organic layer was dried (sodium sulfate), filtered, evaporated, and purified on an Isco 4 g column, eluting with 0-4% methanol/dichloromethane to give 4-[4-(2-methyl-pyridin-3-yloxy)-pyrazolo[3,4-d]pyrimidin-1-yl]-piperidine-1-carboxylic acid cyclopentyl ester (6 mg, 18%). Mass spectrum (ES) MH+=423.

Example 122

4-[4-(2-Methyl-pyridin-3-yloxy)-pyrazolo[3,4-d]pyrimidin-1-yl]-piperidine-1-carboxylic acid phenyl ester

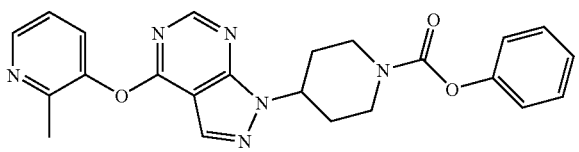

Trifluoroacetic acid (0.5 mL) was added to a solution of 4-[4-(2-methyl-pyridin-3-yloxy)pyrazolo[3,4-d]pyrimidin-1-yl]-piperidine-1-carboxylic acid tert-butyl ester (Example 92; 50 mg, 0.12 mmol) in dichloromethane (2 mL). The solution was stirred at room temperature for 30 min and then the solvents were evaporated, first using house vacuum and then high vacuum. Dichloromethane (4 mL) was added to the residue, and then phenyl chloroformate (23 µL, 0.18 mmol) was added, followed by triethylamine (110 µL, 0.8 mmol). The mixture was stirred overnight at room temperature and then water was added. The layers were separated and the aqueous layer was extracted twice with dichloromethane. The combined organic layers were evaporated, and purified by preparative C18 HPLC, eluting with 10-100% acetonitrile/water to give 4-[4-(2-methyl-pyridin-3-yloxy)-pyrazolo[3,4-d]pyrimidin-1-yl]-piperidine-1-carboxylic acid phenyl ester (8 mg, 15%) as an oil that changed to a waxy solid on standing. $^1$H NMR (300 MHz, CDCl$_3$) δ 2.08-2.17 (m, 2H), 2.34-2.52 (m, 5H), 3.06-3.34 (m, 2H), 4.42-4.58 (m, 2H), 5.02-5.10 (m, 1H), 7.14 (d, 2H, J=7.9 Hz), 7.22-7.25 (m, 1H), 7.28-7.31 (m, 1H), 7.38 (t, 2H, J=7.7 Hz), 7.52 (d, 1H, J=8.1 Hz), 8.10 (s, 1H), 8.48-8.53 (m, 2H). Mass spectrum MH+=431. HRMS Calcd. For $C_{23}H_{23}N_6O_3$ (MH+): 431.1826. Found: 431.1825.

Example 123

4-[4-(2-Methyl-pyridin-3-yloxy)-pyrazolo[3,4-d]pyrimidin-1-yl]-piperidine-1-carboxylic acid 4-nitrophenyl ester

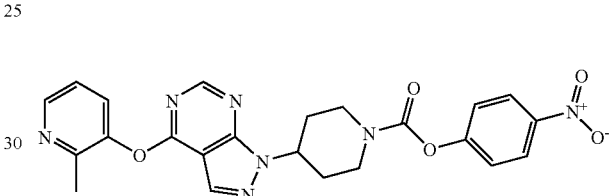

4-Nitrophenyl chloroformate (Aldrich Chemical Company, Inc., Milwaukee, Wis., USA 268 mg, 1.33 mmol) was added in three portions to a cooled (~0° C.) solution of 4-(2-methyl-pyridin-3-yloxy)-1-piperidin-4-yl-1H-pyrazolo[3,4-d]pyrimidine (Intermediate 28; 275 mg, 0.89 mmol), and diisopropylethylamine (390 µL, 2.2 mmol) in anhydrous dichloromethane (10 mL). The mixture was warmed to room temperature and stirred for 1 h. Water (10 mL) was added, the layers were separated and the organic layer was washed with brine, dried (sodium sulfate), filtered, evaporated, and purified on a 23 g Supelco column, eluting with 0-7% methanol/dichloromethane to give 4-[4-(2-methyl-pyridin-3-yloxy)-pyrazolo[3,4-d]pyrimidin-1-yl]-piperidine-1-carboxylic acid 4-nitro-phenyl ester (180 mg, 43%) as a white foam.

Example 124

4-[4-(2-Methyl-pyridin-3-yloxy)-pyrazolo[3,4-d]pyrimidin-1-yl]-piperidine-1-carboxylic acid benzyl ester

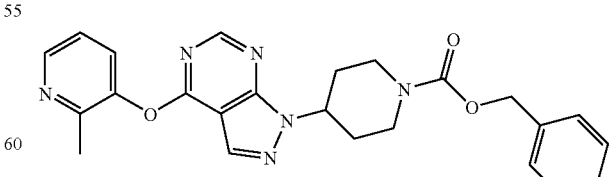

A solution of 4-[4-(2-methyl-pyridin-3-yloxy)-pyrazolo[3,4-d]pyrimidin-1-yl]-piperidine-1-carboxylic acid tert-butyl ester (Example 92; 50 mg, 0.12 mmol) in a mixture of trifluoroacetic acid (0.5 mL) and dichloromethane (2 mL)

was stirred at room temperature for 30 min, then the solvents were evaporated and the residue held under high vacuum. Dichloromethane (4 mL) was added, followed successively by benzyl chloroformate (26 µL, 0.18 mmol) and triethylamine (110 µL, 0.8 mmol). The mixture was stirred overnight at room temperature. Water was added and the mixture was extracted with three times with dichloromethane. The combined dichloromethane layers were evaporated and the residue was purified by C18 reversed phase HPLC using a gradient of 10-100% acetonitrile/water to give 4-[4-(2-methyl-pyridin-3-yloxy)-pyrazolo[3,4-d]pyrimidin-1-yl]-piperidine-1-carboxylic acid benzyl ester (16 mg, 29%) as a white powder. HRMS Calcd. For $C_{24}H_{25}N_6O_3$ (MH+): 445.1983. Found: 445.1981.

Example 125

4-[4-(2-Methyl-pyridin-3-yloxy)-pyrazolo[3,4-d]pyrimidin-1-yl]-piperidine-1-carboxylic acid cyclohexyl ester

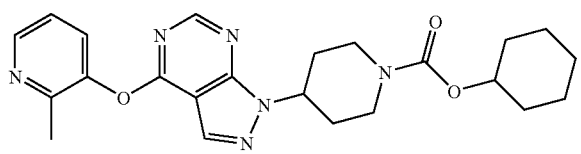

A solution of cyclohexyl chloroformate (Waterstone Technology, LLC, Carmel, Ind., USA; 42 mg, 0.26 mmol) in dichloromethane (150 µL) was added to a cooled (~0° C.) solution of 4-(2-methyl-pyridin-3-yloxy)-1-piperidin-4-yl-1H-pyrazolo[3,4-d]pyrimidine (Intermediate 28; 52 mg, 0.17 mmol), diisopropylethylamine (77 µL, 0.80 mmol) and 4-dimethylaminopyridine (1 mg) in anhydrous dichloromethane (2 mL) over 30 sec. The mixture was stirred at 0° C. for 5 min, then warmed to room temperature and stirred for 1 h. Water (5 mL) was added. The layers were separated and the organic layer was washed with brine, dried (sodium sulfate), filtered, evaporated, and purified on an Isco 4 g column eluting with 0-4% methanol/dichloromethane. Fractions containing the product were pooled, concentrated and lyophilized to give 4-[4-(2-methyl-pyridin-3-yloxy)-pyrazolo[3,4-d]pyrimidin-1-yl]-piperidine-1-carboxylic acid cyclohexyl ester (9.6 mg, 13%). Mass spectrum (ES) MH+=437.

Example 126

1-[1-(3-Isopropyl-[1,2,4]oxadiazol-5-yl)-piperidin-4-yl]-4-(4-methanesulfonyl-phenoxy)-1H-pyrazolo[3,4-d]pyrimidine

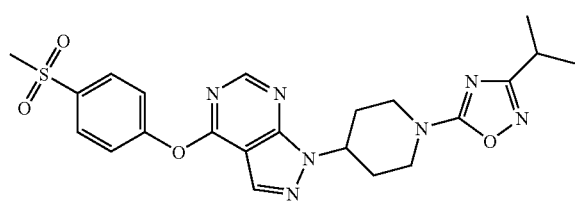

A mixture of 4-methanesulfonyl-phenol (available from Acros Organics, Geel, Belgium; 24 mg, 0.14 mmol), 4-chloro-1-[1-(3-isopropyl-[1,2,4]oxadiazol-5-yl)-piperidin-4-yl]-1H-pyrazolo[3,4-d]pyrimidine (Intermediate 22; 40 mg, 0.11 mmol) and potassium carbonate (19 mg, 0.14 mmol) in anhydrous DMF (2 mL) was heated in a Biotage Optimizer microwave at 180° C. for 10 min. The mixture was cooled and filtered through Celite, concentrated and held under vacuum. The residue was purified by flash column chromatography eluting with 0-3% methanol/dichloromethane to give 4-(4-methanesulfonyl-phenoxy-1-[1-(3-isopropyl-[1,2,4]oxadiazol-5-yl)-piperidin-4-yl]-1H-pyrazolo[3,4-d]pyrimidine (40 mg, 72%). Mass spectrum (ES) MH+=483.5.

Example 127

4-(2-Fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine

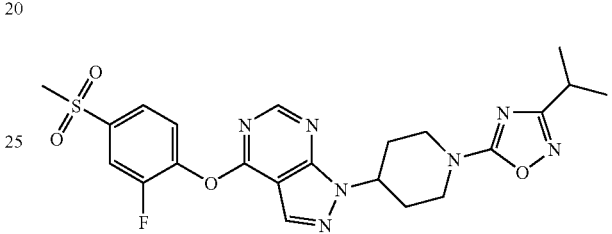

A mixture of 2-fluoro-4-methanesulfonyl-phenol (Intermediate 1; 20 mg, 0.1 mmol), 4-chloro-1-[1-(3-isopropyl-[1,2,4]oxadiazol-5-yl)-piperidin-4-yl]-1H-pyrazolo[3,4-d]pyrimidine (Intermediate 22; 31 mg, 0.09 mmol) and potassium carbonate (14 mg, 0.1 mmol) in DMF (2 mL) was heated in a Biotage Optimizer microwave at 180° C. for 10 min. The mixture was cooled and filtered through Celite, concentrated and held under vacuum. The residue was purified on a silica column (ISCO 4 g) eluting with 0-3% methanol/dichloromethane to give 4-(2-fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine (6 mg, 14%). Mass spectrum (ES) MH+=502.

Example 128

4-(3-Fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine

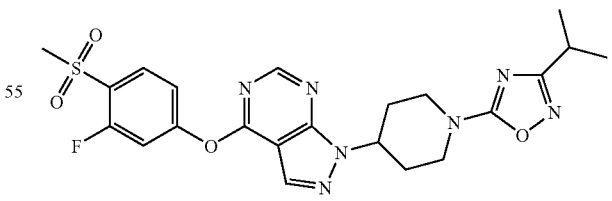

4-(3-Fluoro-4-methanesulfonyl-phenoxy-1-[1-(3-isopropyl-[1,2,4]oxadiazol-5-yl)-piperidin-4-yl]-1H-pyrazolo[3,4-d]pyrimidine was prepared using the procedure described for the preparation of 4-(2-fluoro-4-methanesulfonyl-phenoxy)-1-[4-(3-isopropyl-[1,2,4]oxadiazol-5-yl)-cyclohexyl]-1H-pyrazolo[3,4-d]pyrimidine (Example 131) by the reaction of 4-(4-chloro-pyrazolo[3,4-d]pyrimidin-1-yl)-piperidine-1- carboxylic acid tert-butyl ester (Intermediate 19) with 3-fluoro-4-methanesulfonyl-phenol (Intermediate 2) in dimethylformamide. The product was purified by flash chromatography, eluting with 5% methanol/dichloromethane to give 4-(3-fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine (12 mg, 22%) as a white solid. Mass spectrum: Observed 501.9.

Example 129

1-[1-(3-Isopropyl-[1,2,4]oxadiazol-5-yl)-piperidin-4-yl]-4-(2-methyl-pyridin-3-yloxy)-1H-pyrazolo[3,4-d]pyrimidine

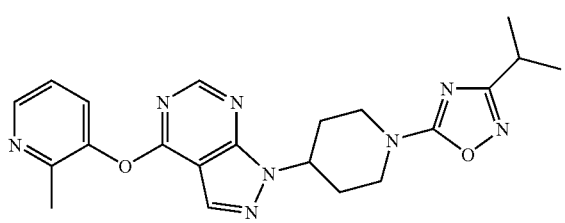

A mixture of 3-hydroxy-2-methylpyridine (Aldrich Chemical Company, Inc., Milwaukee, Wis., USA; 1.25 mg, 0.011 mmol), 4-chloro-1-[1-(3-isopropyl-[1,2,4]oxadiazol-5-yl)-piperidin-4-yl]-1H-pyrazolo[3,4-d]pyrimidine (Intermediate 22; 4 mg, 0.012 mmol) and potassium carbonate (3 mg, 0.022 mmol) in DMF (0.5 mL) was heated in a microwave at 160° C. for 10 min, but TLC showed no reaction. Potassium carbonate (3 mg, 0.022 mmol) and DMF (0.1 mL) were added and the reaction mixture was heated in a microwave at 180° C. for 15 min. The solvent was evaporated and water was added. The mixture was extracted with ethyl acetate and the extracts were dried, held under high vacuum, and purified by HPLC to give 1-[1-(3-Isopropyl-[1,2,4]oxadiazol-5-yl)-piperidin-4-yl]-4-(2-methyl-pyridin-3-yloxy)-1H-pyrazolo[3,4-d]pyrimidine (1.8 mg, 39%).

Example 130

1-[1-(6-Chloro-pyridazin-3-yl)-piperidin-4-yl]-4-(4-methanesulfonyl-phenoxy)-1H-pyrazolo[3,4-d]pyrimidine

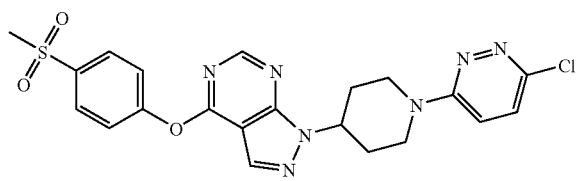

3,6-Dichloropyridazine (0.2 mmol) was added to a mixture of 4-(4-methanesulfonyl-phenoxy)-1-piperidin-4-yl-1H-pyrazolo[3,4-d]pyrimidine trifluoroacetate salt (Intermediate 27; 75 mg, 0.15 mmol) and potassium carbonate (69 mg, 0.5 mmol) in dimethylformamide (1 mL). The mixture was heated to 60° C. overnight and then poured into saturated aqueous ammonium chloride solution. This mixture was extracted three times with ethyl acetate. The combined organic phases were washed twice with water and once with brine, dried (magnesium sulfate), filtered, evaporated, and purified on a silica gel column, eluting with ethyl acetate, to give 1-[1-(6-Chloro-pyridazin-3-yl)-piperidin-4-yl]-4-(4-methanesulfonyl-phenoxy)-1H-pyrazolo[3,4-d]pyrimidine (0.5 mg, 0.7%) as a white powder.

Example 131

4-(2-Fluoro-4-methanesulfonyl-phenoxy)-1-[4-(3-isopropyl-[1,2,4]oxadiazol-5-yl)-cyclohexyl]-1H-pyrazolo[3,4-d]pyrimidine

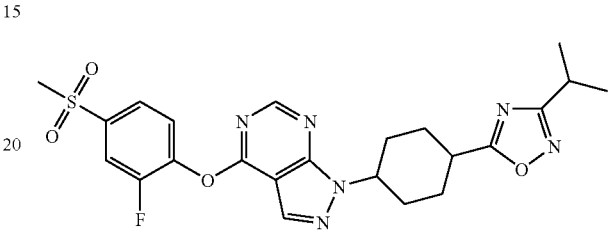

A mixture of 2-fluoro-4-methanesulfonyl-phenol (Intermediate 1; 66 mg, 0.35 mmol), 4-chloro-1-[4-(3-isopropyl-[1,2,4]oxadiazol-5-yl)-cyclohexyl]-1H-pyrazolo[3,4-d]pyrimidine (Intermediate 23; 60 mg, 0.17 mmol) and potassium carbonate (105 mg, 0.76 mmol) in DMF (1.5 mL) was heated in the microwave at 160° C. for 10 min. Saturated aqueous sodium carbonate solution was added to the cooled reaction mixture. The precipitate was filtered, and the filtrate was extracted with ethyl acetate. The extracts were dried (sodium sulfate), filtered, evaporated, and purified by flash chromatography, eluting with 5% methanol/dichloromethane, to give 4-(2-fluoro-4-methanesulfonyl-phenoxy)-1-[4-(3-isopropyl-[1,2,4]oxadiazol-5-yl)-cyclohexyl]-1H-pyrazolo[3,4-d]pyrimidine (16 mg, 19%) as a white solid. Mass spectrum M+=500.9.

Example 132

4-(2-Fluoro-4-methanesulfonyl-phenoxy)-1-[4-(3-isopropyl-[1,2,4]oxadiazol-5-yl)-trans-cyclohexyl]-1H-pyrazolo[3,4-d]pyrimidine

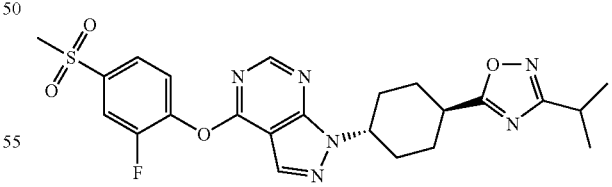

A mixture of 2-fluoro-4-methanesulfonyl-phenol (Intermediate 1; 93 mg, 0.49 mmol), 4-chloro-1-[4-(3-isopropyl-[1,2,4]oxadiazol-5-yl)-trans-cyclohexyl]-1H-pyrazolo[3,4-d]pyrimidine (Intermediate 26; 170 mg, 0.49 mmol) and potassium carbonate (81 mg, 0.59 mmol) in anhydrous DMF (5 mL) was heated in a microwave at 180° C. for 10 min. The mixture was filtered. The filtrate was concentrated and purified using a Supelco 23 g column, eluting with 0-3% methanol/dichloromethane to give 4-(2-fluoro-4-methanesulfonylphenoxy)-1-[4-(3-isopropyl-[1,2,4]oxadiazol-5-yl)-trans-cyclohexyl]-1H-pyrazolo[3,4-d]pyrimidine (153 mg, 62%).

Example 133

1-[4-(3-Isopropyl-[1,2,4]oxadiazol-5-yl)-trans-cyclohexyl]-4-[4-(5-methyl-tetrazol-1-yl)phenoxy]-1H-pyrazolo[3,4-d]pyrimidine

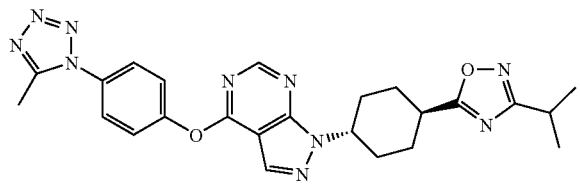

A mixture of 4-(5-methyl-tetrazol-1-yl)-phenol (Chembridge Corporation, San Diego, Calif., USA; 76 mg, 0.43 mmol), 4-chloro-1-[4-(3-isopropyl-[1,2,4]oxadiazol-5-yl)-trans-cyclo-hexyl]-1H-pyrazolo[3,4-d]pyrimidine (Intermediate 26; 150 mg, 0.43 mmol), and potassium carbonate (72 mg, 0.52 mmol) in dimethylformamide (5 mL) was heated in a microwave at 180° C. for 10 min. The mixture was filtered. The filtrate was concentrated and purified using a Supelco 23 g column, eluting with 0-3% methanol/dichloromethane to give 1-[4-(3-isopropyl-[1,2,4]oxadiazol-5-yl)-trans-cyclohexyl]-4-[4-(5-methyl-tetrazol-1-yl)-phenoxy]-1H-pyrazolo[3,4-d]pyrimidine (86 mg, 41%).

Example 134

4-(2-Fluoro-4-methanesulfonyl-phenoxy)-1-[4-(3-isopropyl-[1,2,4]oxadiazol-5-yl)-cis-cyclohexyl]-1H-pyrazolo[3,4-d]pyrimidine

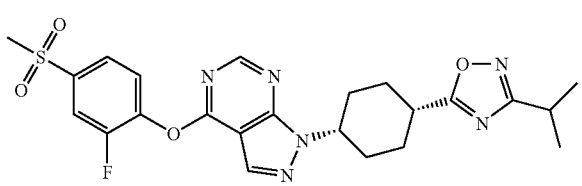

A mixture of 2-fluoro-4-methanesulfonyl-phenol (Intermediate 1; 101 mg, 0.53 mmol), 4-chloro-1-[4-(3-isopropyl-[1,2,4]oxadiazol-5-yl)-cis-cyclohexyl]-1H-pyrazolo[3,4-d]pyrimidine (Intermediate 25; 185 mg, 0.53 mmol) and potassium carbonate (48 mg, 0.53 mmol) in anhydrous DMF (5 mL) was heated in a microwave at 180° C. for 10 min. The mixture was filtered. The filtrate was concentrated and purified using a Supelco 23 g column, eluting with 0-3% methanol/dichloromethane to give 4-(2-fluoro-4-methanesulfonyl-phenoxy)-1-[4-(3-isopropyl-[1,2,4]oxadiazol-5-yl)-cis-cyclohexyl]-1H-pyrazolo[3,4-d]pyrimidine (148 mg, 56%).

Example 135

1-[4-(3-Isopropyl-[1,2,4]oxadiazol-5-yl)-cyclohexyl]-4-(2-methyl-pyridin-3-yloxy)-1H-pyrazolo[3,4-d]pyrimidine

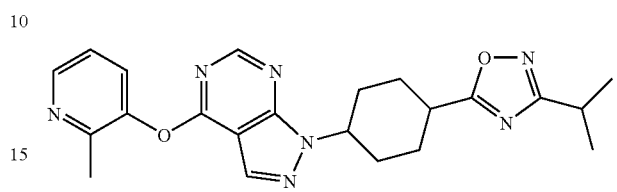

1-[4-(3-Isopropyl-[1,2,4]oxadiazol-5-yl)-cyclohexyl]-4-(2-methyl-pyridin-3-yloxy)-1H-pyrazolo[3,4-d]pyrimidine (60 mg, 76%) was prepared using the procedure described for the preparation of Example 41 by the reaction of 4-chloro-1-[4-(3-isopropyl-[1,2,4]oxadiazol-5-yl)-cyclohexyl]-1H-pyrazolo[3,4-d]pyrimidine (Intermediate 23; 130 mg, 0.375 mmol) with 3-hydroxy-2-methylpyridine (Aldrich Chemical Company, Inc., Milwaukee, Wis., USA; 42 mg, 0.385 mmol) in the presence of potassium carbonate (114 mg, 0.825 mmol). The compound was purified by column chromatography, eluting with 5% methanol/dichloromethane. Mass spectrum MH+=420.

Example 136

1-{4-[4-(4-Methanesulfonyl-phenoxy)-pyrazolo[3,4-d]pyrimidin-1-yl]-piperidin-1-yl}-2-methyl-propan-1-one

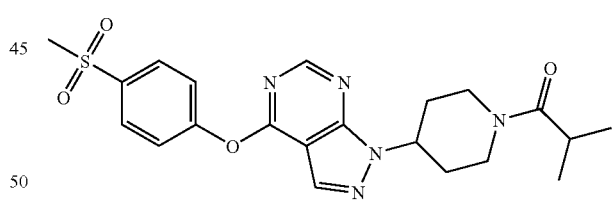

1-{4-[4-(4-Methanesulfonyl-phenoxy)-pyrazolo[3,4-d]pyrimidin-1-yl]-piperidin-1-yl}-2-methyl-propan-1-one was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with isobutyryl chloride (available from Aldrich Chemical Company, Inc., Milwaukee, Wis., USA). $^1$H NMR (400 MHz, DMSO-$d_6$) δ 1.05 (d, 6H, J=6.9 Hz), 1.95-2.06 (m, 4H), 2.80-2.86 (m, 1H), 2.92-2.99 (m, 1H), 3.30 (methyl sulfonyl and water peak), 4.10-4.14 (m, 1H), 4.54-4.57 (m, 1H), 5.08-5.12 (m, 1H), 7.63-7.65 (m, 2H), 8.05-8.07 (m, 2H), 8.38 (s, 1H), 8.57 (s, 1H). Mass spectrum MH+=444.

Example 137

2,2-Dimethyl-1-{4-[4-(2,4,5-trifluoro-phenoxy)-pyrazolo[3,4-d]pyrimidin-1-yl]-piperidin-1-yl}-propan-1-one

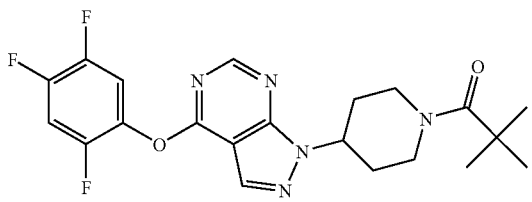

2,2-Dimethyl-1-{4-[4-(2,4,5-trifluoro-phenoxy)-pyrazolo[3,4-d]pyrimidin-1-yl]-piperidin-1-yl}-propan-1-one was prepared according to General Procedure J by the reaction of 4-[4-(2,4,5-trifluoro-phenylamino)-pyrazolo[3,4-d]pyrimidin-1-yl]-piperidine-1-carboxylic acid tert-butyl ester (Example 35) with trifluoroacetic acid in dichloromethane followed by reaction with pivaloyl chloride (available from Aldrich Chemical Company, Inc., Milwaukee, Wis., USA). $^1$H NMR (400 MHz, DMSO-d$_6$) δ 1.24 (s, 9H), 2.00-2.05 (m, 4H), 3.09-3.17 (m, 2H), 3.30 (methyl sulfonyl and water peak), 4.42-4.45 (m, 2H), 5.09-5.13 (m, 1H), 7.88-7.92 (m, 2H), 8.46 (s, 1H), 8.59 (s, 1H). Mass spectrum MH+=434.

Example 138

1-{4-[4-(4-Methanesulfonyl-phenoxy)-pyrazolo[3,4-d]pyrimidin-1-yl]-piperidin-1-yl}-2,2-dimethyl-propan-1-one

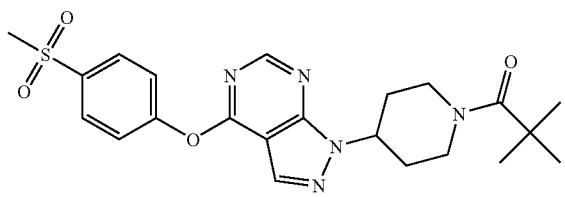

1-{4-[4-(4-Methanesulfonyl-phenoxy)-pyrazolo[3,4-d]pyrimidin-1-yl]-piperidin-1-yl}-2,2-dimethyl-propan-1-one was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with pivaloyl chloride (available from Aldrich Chemical Company, Inc., Milwaukee, Wis., USA). $^1$H NMR (400 MHz, DMSO-d$_6$) δ 1.24 (s, 9H), 1.98-2.03 (m, 4H), 3.06-3.14 (m, 2H), 3.30 (methyl sulfonyl and water peak), 4.40-4.46 (m, 2H), 5.09-5.15 (m, 1H), 7.63-7.65 (m, 2H), 8.05-8.07 (m, 2H), 8.39 (s, 1H), 8.57 (s, 1H). Mass spectrum MH+=458.

Example 139

1-{4-[4-(2-Fluoro-4-methanesulfonyl-phenylamino)-pyrazolo[3,4-d]pyrimidin-1-yl]-piperidin-1-yl}-2,2-dimethyl-propan-1-one

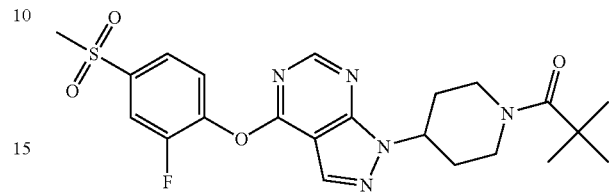

1-{4-[4-(2-Fluoro-4-methanesulfonyl-phenylamino)-pyrazolo[3,4-d]pyrimidin-1-yl]-piperidin-1-yl}-2,2-dimethyl-propan-1-one was prepared according to General Procedure J by the reaction of 4-[4-(2-fluoro-4-methanesulfonyl-phenylamino)-pyrazolo[3,4-d]pyrimidin-1-yl]-piperidine-1-carboxylic acid tert-butyl ester (Example 1) with trifluoroacetic acid in dichloromethane followed by reaction with pivaloyl chloride (available from Aldrich Chemical Company, Inc., Milwaukee, Wis., USA). $^1$H NMR (400 MHz, DMSO-d$_6$) δ 1.23 (s, 9H), 1.98-2.03 (m, 4H), 3.06-3.12 (m, 2H), 3.30 (methyl sulfonyl and water peak), 4.40-4.46 (m, 2H), 4.99-5.03 (m, 1H), 7.79-7.81 (m, 1H), 7.88-7.92 (m, 1H), 8.21-8.25 (m, 1H), 8.30-8.43 (m, 2H), 10.38 (s, 1H). Mass spectrum MH+=475.

Example 140

Cyclobutyl-{4-[4-(4-methanesulfonyl-phenoxy)-pyrazolo[3,4-d]pyrimidin-1-yl]-piperidin-1-yl}-methanone

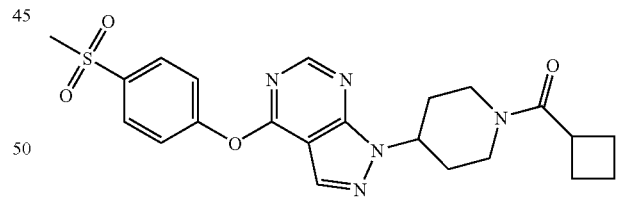

Cyclobutyl-{4-[4-(4-methanesulfonyl-phenoxy)-pyrazolo[3,4-d]pyrimidin-1-yl]-piperidin-1-yl}-methanone was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with cyclobutanecarbonyl chloride (available from Aldrich Chemical Company, Inc., Milwaukee, Wis., USA). $^1$H NMR (400 MHz, DMSO-d$_6$) δ 1.74-2.21 (m, 10H), 2.82-2.87 (m, 1H), 3.30 (methyl sulfonyl and water peak), 3.84-3.87 (m, 1H), 4.49-4.52 (m, 1H), 5.06-5.08 (m, 1H), 7.62-7.65 (m, 2H), 8.05-8.07 (m, 2H), 8.38 (s, 1H), 8.57 (s, 1H). Mass spectrum MH+=456, M+Na=478.

Example 141

Cyclopentyl-{4-[4-(4-methanesulfonyl-phenoxy)-pyrazolo[3,4-d]pyrimidin-1-yl]-piperidin-1-yl}-methanone

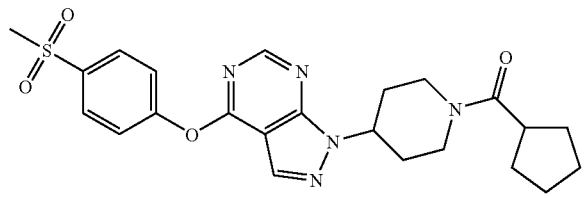

Cyclopentyl-{4-[4-(4-methanesulfonyl-phenoxy)-pyrazolo[3,4-d]pyrimidin-1-yl]-piperidin-1-yl}-methanone was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with cyclopentanecarbonyl chloride (available from Aldrich Chemical Company, Inc., Milwaukee, Wis., USA). $^1$H NMR (400 MHz, DMSO-$d_6$) δ 1.54-1.79 (m, 8H), 1.93-2.10 (m, 4H), 2.82-2.87 (m, 1H), 3.02-3.08 (m, 1H), 3.30 (methyl sulfonyl and water peak), 4.14-4.17 (m, 1H), 4.53-4.56 (m, 1H), 5.07-5.12 (m, 1H), 7.63-7.65 (m, 2H), 8.05-8.07 (m, 2H), 8.38 (s, 1H), 8.57 (s, 1H). Mass spectrum MH+=470.

Example 142

1-{4-[4-(4-Methanesulfonyl-phenoxy)-pyrazolo[3,4-d]pyrimidin-1-yl]-piperidin-1-yl}-3-methyl-butan-1-one

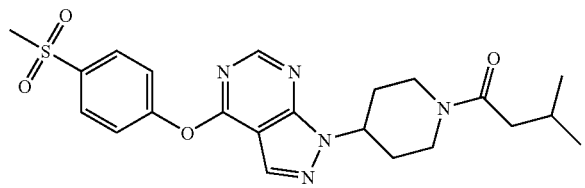

1-{4-[4-(4-Methanesulfonyl-phenoxy)-pyrazolo[3,4-d]pyrimidin-1-yl]-piperidin-1-yl}-3-methyl-butan-1-one was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with isovaleryl chloride (available from Aldrich Chemical Company, Inc., Milwaukee, Wis., USA). $^1$H NMR (400 MHz, DMSO-$d_6$) δ 0.93 (d, 6H, J=6.2 Hz), 1.93-2.06 (m, 4H), 2.25-2.28 (m, 2H), 2.80-2.85 (m, 1H), 3.30 (methyl sulfonyl and water peak), 4.04-4.08 (m, 1H), 4.54-4.58 (m, 1H), 5.06-5.10 (m, 1H), 7.63-7.65 (m, 2H), 8.05-8.07 (m, 2H), 8.38 (s, 1H), 8.57 (s, 1H). Mass spectrum MH+=458.

Example 143

1-{4-[4-(4-Methanesulfonyl-phenoxy)-pyrazolo[3,4-d]pyrimidin-1-yl]-piperidin-1-yl}-4-methylpentan-1-one

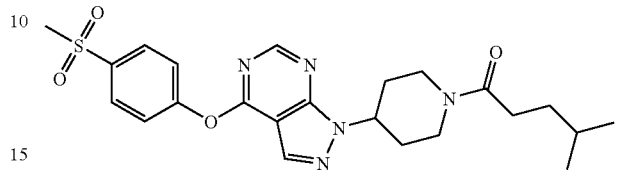

To a stirred mixture of 4-(4-methanesulfonyl-phenoxy)-1-piperidin-4-yl-1H-pyrazolo[3,4-d]pyrimidine trifluoroacetate salt (Intermediate 27; 60 mg, 0.123 mmol) and N,N-diisopropylethylamine (0.11 mL, 0.615 mmol) in dichloromethane (1.0 mL) at room temperature was added 4-methylvaleroyl chloride (Pfaltz & Bauer, Inc., Waterbury, Conn., USA; 20 mg; 0.15 mmol). After 1 h, the mixture was washed with 1 N HCl followed by water. The organic layer was dried (sodium sulfate), filtered and concentrated in vacuo. The crude product was triturated with diethyl ether, filtered, washed with diethyl ether and allowed to air dry to provide 1-{4-[4-(4-Methanesulfonyl-phenoxy)-pyrazolo[3,4-d]pyrimidin-1-yl]-piperidin-1-yl}-4-methyl-pentan-1-one (32 mg, 55%) as an off-white solid. $^1$H NMR (300 MHz, DMSO-$d_6$) δ 0.87 (d, 6H, J=6.6 Hz), 1.36-1.44 (m, 2H), 1.50-1.59 (m, 1H), 1.94-2.10 (m, 4H), 2.33-2.38 (m, 2H), 2.74-2.86 (m, 1H), 3.30 (water peak and SO$_2$CH$_3$), 3.98-4.08 (m, 1H), 4.46-4.57 (m, 1H), 5.00-5.14 (m, 1H), 7.62 (d, 2H, J=8.5 Hz), 8.04 (d, 2H, J=8.7 Hz), 8.38 (s, 1H), 8.55 (s, 1H). Mass spectrum MH+=472.

Example 144

1-{4-[4-(4-Methanesulfonyl-phenoxy)-pyrazolo[3,4-d]pyrimidin-1-yl]-piperidin-1-yl}-3,3-dimethyl-butan-1-one

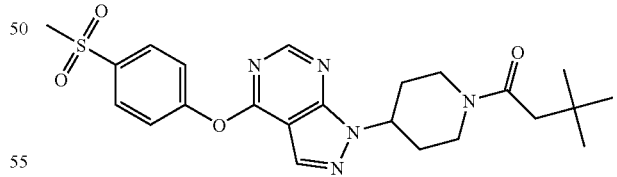

1-{4-[4-(4-Methanesulfonyl-phenoxy)-pyrazolo[3,4-d]pyrimidin-1-yl]-piperidin-1-yl}-3,3-dimethyl-butan-1-one was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with tert-butylacetyl chloride (available from Aldrich Chemical Company, Inc., Milwaukee, Wis., USA). $^1$H NMR (400 MHz, DMSO-$d_6$) δ 1.02 (s, 9H), 1.93-2.06 (m, 4H), 2.30-2.35 (m, 2H), 2.79-2.84 (m, 1H), 3.30 (methyl sulfonyl and water peak), 4.14-4.17 (m, 1H), 4.59-4.62 (m, 1H), 5.05-5.11 (m, 1H), 7.63-7.65 (m, 2H), 8.05-8.07 (m, 2H), 8.38 (s, 1H), 8.57 (s, 1H). Mass spectrum MH+=472, M+Na=493.9.

Example 145

2-Cyclohexyl-1-{4-[4-(4-methanesulfonyl-phenoxy)-pyrazolo[3,4-d]pyrimidin-1-yl]-piperidin-1-yl}-ethanone

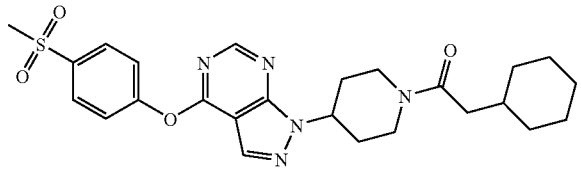

2-Cyclohexyl-1-{4-[4-(4-methanesulfonyl-phenoxy)-pyrazolo[3,4-d]pyrimidin-1-yl]-piperidin-1-yl}-ethanone was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with cyclohexyl-acetyl chloride (available from Aldrich Chemical Company, Inc., Milwaukee, Wis., USA). $^1$H NMR (400 MHz, DMSO-$d_6$) δ 0.90-0.98 (m, 2H), 1.05-1.19 (m, 4H), 1.65-1.78 (m, 7H), 1.95-2.09 (m, 5H), 2.25-2.27 (m, 2H), 2.79-2.85 (m, 1H), 3.30 (methyl sulfonyl and water peak), 4.04-4.08 (m, 1H), 4.54-4.58 (m, 1H), 5.06-5.11 (m, 1H), 7.63-7.65 (m, 2H), 8.05-8.07 (m, 2H), 8.40 (s, 1H), 8.57 (s, 1H). Mass spectrum MH+=498.5.

Example 146

1-{4-[4-(4-Methanesulfonyl-phenoxy)-pyrazolo[3,4-d]pyrimidin-1-yl]-piperidin-1-yl}-3-phenyl-propan-1-one

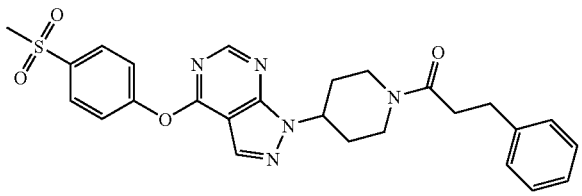

1-{4-[4-(4-Methanesulfonyl-phenoxy)-pyrazolo[3,4-d]pyrimidin-1-yl]-piperidin-1-yl}-3-phenyl-propan-1-one was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 27) with cyclopentanecarbonyl chloride (available from Aldrich Chemical Company, Inc., Milwaukee, Wis., USA). $^1$H NMR (400 MHz, DMSO-$d_6$) δ 1.98-2.06 (m, 4H), 2.67-2.73 (m, 1H), 2.83-2.87 (m, 3H), 3.30 (methyl sulfonyl and water peak), 4.02-4.06 (m, 1H), 4.53-4.57 (m, 1H), 5.04-5.08 (m, 1H), 7.18-7.28 (m, 5H), 7.62-7.65 (m, 2H), 8.05-8.07 (m, 2H), 8.39 (s, 1H), 8.57 (s, 1H). Mass spectrum MH+=506, M+Na=527, M+K=544.

Example 147

Cyclopentyl-{4-[4-(4-ethoxy-2-fluoro-phenoxy)-pyrazolo[3,4-d]pyrimidin-1-yl]-piperidin-1-yl}-methanone

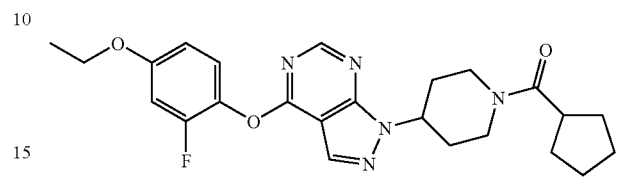

Cyclopentanecarbonyl chloride (10 mg, 0.078 mmol) was added to a mixture of 4-(4-ethoxy-2-fluoro-phenoxy)-1-piperidin-4-yl-1H-pyrazolo[3,4-d]pyrimidine trifluoroacetate salt (Intermediate 29; 28 mg, 0.078 mmol), and diisopropylethylamine (30 mg, 0.235 mmol) in dichloromethane (2 mL). The reaction mixture was stirred at room temperature overnight. Water was added to quench the reaction and the aqueous layer was extracted three times with dichloromethane. The combined organic layers were dried (sodium sulfate), filtered, evaporated and purified by flash chromatography on silica gel, eluting with 4% methanol/dichloromethane to give cyclopentyl-{4-[4-(4-ethoxy-2-fluoro-phenoxy)-pyrazolo[3,4-d]pyrimidin-1-yl]-piperidin-1-yl}-methanone (31 mg, 87%) as a white solid. Mass spectrum MH+=454.

Example 148

2,2,2-Trifluoro-1-{4-[4-(4-methanesulfonyl-phenoxy)-pyrazolo[3,4-d]pyrimidin-1-yl]-piperidin-1-yl}-ethanone

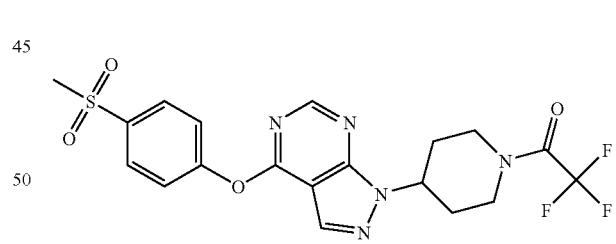

2,2,2-Trifluoro-1-{4-[4-(4-methanesulfonyl-phenoxy)-pyrazolo[3,4-d]pyrimidin-1-yl]-piperidin-1-yl}-ethanone was prepared according to General Procedure J by the reaction of 4-[4-(4-methanesulfonyl-phenoxy)-pyrazolo[3,4-d]pyrimidin-1-yl]-piperidine-1-carboxylic acid tert-butyl ester (Example 59) with trifluoroacetic acid, followed by reaction of the resulting amine with trifluoroacetic anhydride (available from Alfa Aesar, Ward Hill, Mass., USA). $^1$H NMR (400 MHz, DMSO-$d_6$) δ 2.10-2.16 (m, 4H), 3.55-3.65 (m, 1H), 4.00-4.04 (m, 1H), 4.41-4.44 (m, 1H), 5.18-5.24 (m, 1H), 7.63-7.65 (m, 2H), 8.05-8.07 (m, 2H), 8.41 (s, 1H), 8.58 (s, 1H). Mass spectrum MH+=470.

Example 149

{4-[4-(4-Methanesulfonyl-phenoxy)-pyrazolo[3,4-d]pyrimidin-1-yl]-piperidin-1-yl}-phenylmethanone

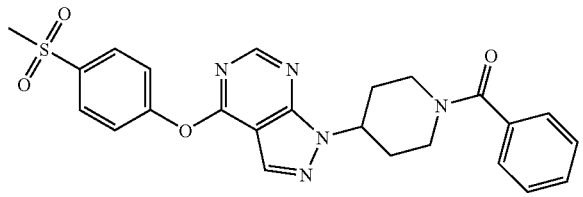

{4-[4-(4-Methanesulfonyl-phenoxy)-pyrazolo[3,4-d]pyrimidin-1-yl]-piperidin-1-yl}-phenylmethanone was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate F1) with benzoyl chloride (available from Aldrich Chemical Company, Inc., Milwaukee, Wis., USA). $^1$H NMR (400 MHz, DMSO-$d_6$) δ 1.98-2.10 (m, 4H), 3.30 (methyl sulfonyl and water peak), 3.70-3.75 (m, 1H), 4.58-4.63 (m, 1H), 5.14-5.17 (m, 1H), 7.42-7.52 (m, 5H), 7.63-7.65 (m, 2H), 8.05-8.07 (m, 2H), 8.41 (s, 1H), 8.58 (s, 1H). Mass spectrum MH+=478.

Example 150

(3,5-Dichloro-phenyl)-{4-[4-(4-methanesulfonyl-phenoxy)-pyrazolo[3,4-d]pyrimidin-1-yl]-piperidin-1-yl}-methanone

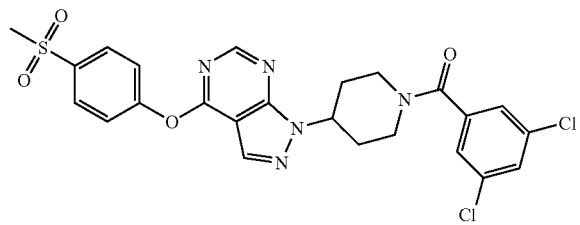

(3,5-Dichloro-phenyl)-{4-[4-(4-methanesulfonyl-phenoxy)-pyrazolo[3,4-d]pyrimidin-1-yl]-piperidin-1-yl}-methanone was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with 3,5-dichlorobenzoyl chloride (available from Aldrich Chemical Company, Inc., Milwaukee, Wis., USA). $^1$H NMR (400 MHz, DMSO-$d_6$) δ 2.02-2.10 (m, 4H), 3.12-3.18 (m, 1H), 3.30 (methyl sulfonyl and water peak), 3.62-3.68 (m, 1H), 4.54-4.60 (m, 1H), 5.10-5.16 (m, 1H), 7.54-7.55 (m, 2H), 7.63-7.65 (m, 2H), 7.72-7.73 (m, 1H), 8.05-8.07 (m, 2H), 8.41 (s, 1H), 8.58 (s, 1H). Mass spectrum MH+=546, M+Na=478.

Example 151

{4-[4-(4-Methanesulfonyl-phenoxy)-pyrazolo[3,4-d]pyrimidin-1-yl]-piperidin-1-yl}-(4-methoxyphenyl)-methanone

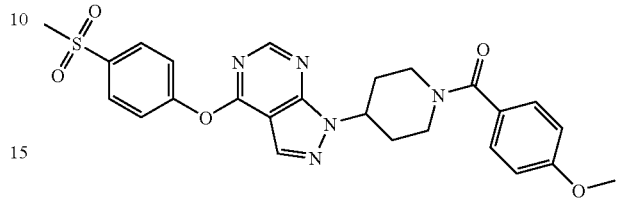

{4-[4-(4-Methanesulfonyl-phenoxy)-pyrazolo[3,4-d]pyrimidin-1-yl]-piperidin-1-yl}-(4-methoxy-phenyl)-methanone was prepared according to General Procedure I by the reaction of 4-(4-methanesulfonyl-phenoxy)-1-piperidin-4-yl-1H-pyrazolo[3,4-d]pyrimidine trifluoroacetate salt (Intermediate 25) with p-anisoyl chloride (available from Aldrich Chemical Company, Inc., Milwaukee, Wis., USA). $^1$H NMR (400 MHz, DMSO-$d_6$) δ 2.04-2.13 (m, 4H), 3.30 (methyl sulfonyl and water peak), 3.80 (m, 3H), 5.10-5.15 (m, 1H), 7.00-7.02 (m, 2H), 7.41-7.43 (m, 2H), 7.62-7.65 (m, 2H), 8.05-8.07 (m, 2H), 8.41 (s, 1H), 8.57 (s, 1H). Mass spectrum MH+=508.

Example 152

(1,5-Dimethyl-1H-pyrazol-3-yl)-{4-[4-(4-methanesulfonyl-phenoxy)-pyrazolo[3,4-d]pyrimidin-1-yl]-piperidin-1-yl}-methanone

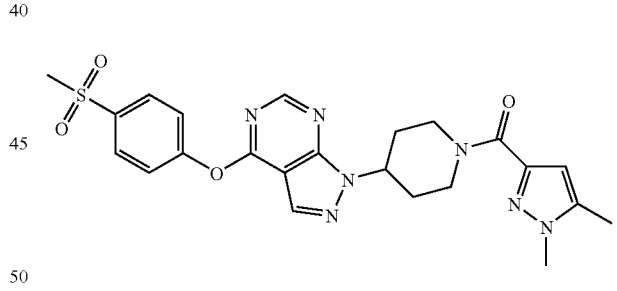

A mixture of 4-(4-methanesulfonyl-phenoxy)-1-piperidin-4-yl-1H-pyrazolo[3,4-d]pyrimidine trifluoroacetate salt (Intermediate 27; 63 mg, 0.13 mmol), TSTU (O—(N-succinimidyl)-1,1,3,3-tetramethyluronium tetrafluoroborate; 78 mg, 0.26 mmol), and diisopropylethylamine (0.14 mL, 0.8 mmol) in dichloromethane (4 mL) was shaken at room temperature for 3 h. 1,5-Dimethyl-1H-pyrazole-3-carbonyl chloride (available from Maybridge, Tintagel, Cornwall, UK; 23 mg, 0.16 mmol) was added and the mixture was shaken at room temperature overnight. The solution was diluted with dichloromethane (~6 mL) and washed with water (2×5 mL), 1 M aqueous hydrochloric acid (5 mL), water (5 mL), saturated aqueous sodium bicarbonate (5 mL) and brine (5 mL). The organic layer was evaporated and the crude product was purified by HPLC to give (1,5-dimethyl-1H-pyrazol-3-yl)-{4-[4-(4-methanesulfonyl-phenoxy)-pyrazolo[3,4-d]pyrimidin-1- yl]-piperidin-1-yl}-methanone (28 mg, 43%) as a white solid. Mass spectrum (ES) MH+=496.

Example 153

{4-[4-(4-Methanesulfonyl-phenoxy)-pyrazolo[3,4-d]pyrimidin-1-yl]-piperidin-1-yl}-(5-methyl-isoxazol-3-yl)-methanone

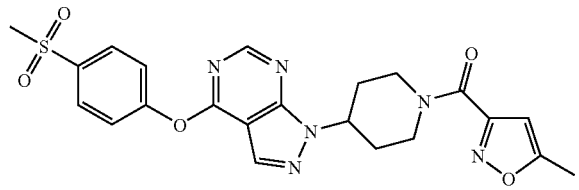

{4-[4-(4-Methanesulfonyl-phenoxy)-pyrazolo[3,4-d]pyrimidin-1-yl]-piperidin-1-yl}-(5-methyl-isoxazol-3-yl)-methanone (14 mg, 22%) was prepared as a white solid using the conditions described in Example 152, by the reaction of 4-(4-methanesulfonyl-phenoxy)-1-piperidin-4-yl-1H-pyrazolo[3,4-d]pyrimidine trifluoroacetate salt (Intermediate 27; 63 mg, 0.13 mmol) with 5-methylisoxazole-3-carboxylic acid (available from Alfa Aesar, Ward Hill, Mass., USA; 20 mg, 0.16 mmol) in the presence of TSTU (O—(N-succinimidyl)-1,1,3,3-tetramethyluronium tetrafluoroborate; 78 mg, 0.26 mmol) and diisopropylethylamine (0.14 mL, 0.8 mmol).

Example 154

(5-Isobutyl-isoxazol-3-yl)-{4-[4-(4-methanesulfonyl-phenoxy)-pyrazolo[3,4-d]pyrimidin-1-yl]-piperidin-1-yl}-methanone

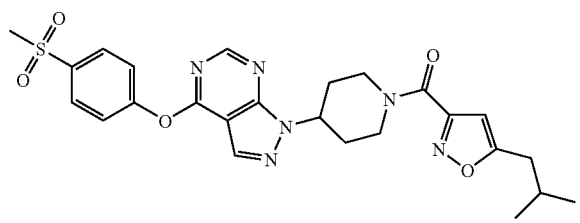

(5-Isobutyl-isoxazol-3-yl)-{4-[4-(4-methanesulfonyl-phenoxy)-pyrazolo[3,4-d]pyrimidin-1-yl]-piperidin-1-yl}-methanone (8 mg, 12%) was prepared as a white solid using the conditions described in Example 152, by the reaction of 4-(4-methanesulfonyl-phenoxy)-1-piperidin-4-yl-1H-pyrazolo[3,4-d]pyrimidine trifluoroacetate salt (Intermediate 27; 63 mg, 0.13 mmol) with 5-isobutyl-isoxazole-3-carboxylic acid (Matrix Scientific, Columbia, S.C., USA; 26 mg, 0.15 mmol) in the presence of TSTU (O—(N-succinimidyl)-1,1,3,3-tetramethyluronium tetrafluoroborate; 78 mg, 0.26 mmol) and diisopropylethylamine (0.14 mL, 0.8 mmol).

Example 155

{4-[4-(4-Methanesulfonyl-phenoxy)-pyrazolo[3,4-d]pyrimidin-1-yl]-piperidin-1-yl}-thiophen-2-yl-methanone

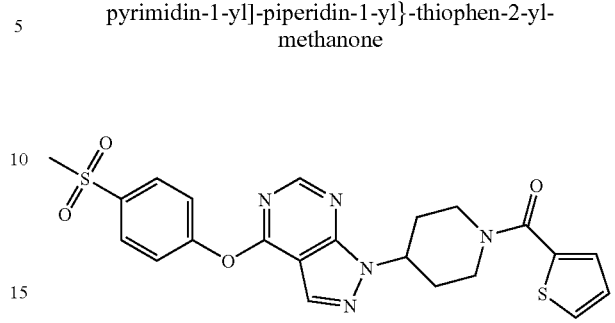

A mixture of 4-(4-methanesulfonyl-phenoxy)-1-piperidin-4-yl-1H-pyrazolo[3,4-d]pyrimidine trifluoroacetate salt (Intermediate 27; 63 mg, 0.13 mmol), thiophene-2-carbonyl chloride (available from Aldrich Chemical Company, Inc., Milwaukee, Wis., USA; 25 mg, 0.17 mmol), and diisopropylethylamine (0.14 mL, 0.8 mmol) in dry dichloromethane (4 mL) was stirred at room temperature over the weekend. The solution was diluted with dichloromethane (~6 mL) and washed with 1 M aqueous hydrochloric acid (5 mL), water (5 mL), saturated aqueous sodium bicarbonate (5 mL) and brine (5 mL). The organic layer was evaporated and the crude product was purified by HPLC to give {4-[4-(4-methanesulfonyl-phenoxy)-pyrazolo[3,4-d]pyrimidin-1-yl]-piperidin-1-yl}-thiophen-2-yl-methanone (52 mg, 83%) as a white solid.

Example 156

Benzothiazol-2-yl-{4-[4-(4-methanesulfonyl-phenoxy)-pyrazolo[3,4-d]pyrimidin-1-yl]-piperidin-1-yl}-methanone

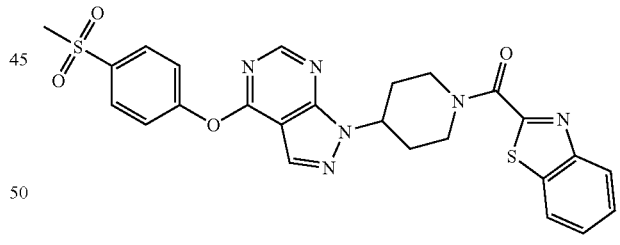

A mixture of 4-(4-methanesulfonyl-phenoxy)-1-piperidin-4-yl-1H-pyrazolo[3,4-d]pyrimidine trifluoroacetate salt (Intermediate 27; 63 mg, 0.13 mmol), benzothiazole-2-carbonyl chloride (available from Alfa Aesar, Ward Hill, Mass., USA; 33 mg, 0.17 mmol), and diisopropylethylamine (0.14 mL, 0.8 mmol) in dry dichloromethane (4 mL) was stirred at room temperature over the weekend. The solution was diluted with dichloromethane (6 mL) and washed with 1 M aqueous hydrochloric acid (5 mL), water (5 mL), saturated aqueous sodium bicarbonate (5 mL) and brine (5 mL). The organic layer was evaporated and the crude product was purified by HPLC to give benzothiazol-2-yl-{4-[4-(4-methanesulfonyl-phenoxy)-pyrazolo[3,4-d]pyrimidin-1-yl]-piperidin-1-yl}-methanone (43 mg, 62%) as a light yellow solid.

Example 157

1-(1-Benzyl-piperidin-4-yl)-4-(4-methanesulfonyl-phenoxy)-1H-pyrazolo[3,4-d]pyrimidine

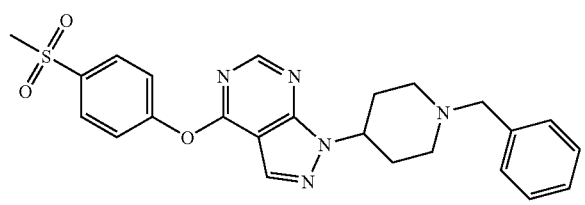

1-(1-Benzyl-piperidin-4-yl)-4-(4-methanesulfonyl-phenoxy)-1H-pyrazolo[3,4-d]pyrimidine was prepared according to General Procedure F by the reaction of 4-[4-(4-methanesulfonyl-phenoxy)pyrazolo[3,4-d]pyrimidin-1-yl]-piperidine-1-carboxylic acid tert-butyl ester (Example 59) with trifluoroacetic acid in dichloromethane followed by reaction with benzyl bromide (available from Aldrich Chemical Company, Inc., Milwaukee, Wis., USA). $^1$H NMR (400 MHz, DMSO-$d_6$) δ 1.93-1.99 (m, 2H), 2.20-2.22 (m, 4H), 2.93-2.99 (m, 2H), 3.30 (methyl sulfonyl and water peak), 3.55 (s, 2H), 4.75-4.81 (m, 1H), 7.26-7.35 (m, 5H), 7.62-7.64 (m, 2H), 8.04-8.06 (m, 2H), 8.37 (s, 1H), 8.55 (s, 1H). Mass spectrum MH+=464.

Example 158

1-[1-(3-Chloro-benzyl)-piperidin-4-yl]-4-(4-methanesulfonyl-phenoxy)-1H-pyrazolo[3,4-d]pyrimidine

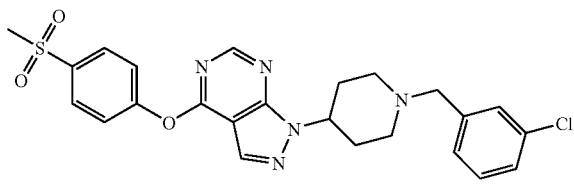

1-[1-(3-Chloro-benzyl)-piperidin-4-yl]-4-(4-methanesulfonyl-phenoxy)-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with 3-chlorobenzaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.89-1.98 (m, 2H), 2.18-2.28 (m, 4H), 2.93-2.99 (m, 2H), 3.30 (methyl sulfonyl and water peak), 3.57 (s, 2H), 4.77-4.83 (m, 1H), 7.32-7.41 (m, 4H), 7.62-7.64 (m, 2H), 8.04-8.07 (m, 2H), 8.37 (s, 1H), 8.55 (s, 1H). Mass spectrum MH+=498.

Example 159

1-[1-(4-Fluoro-benzyl)-piperidin-4-yl]-4-(4-methanesulfonyl-phenoxy)-1H-pyrazolo[3,4-d]pyrimidine

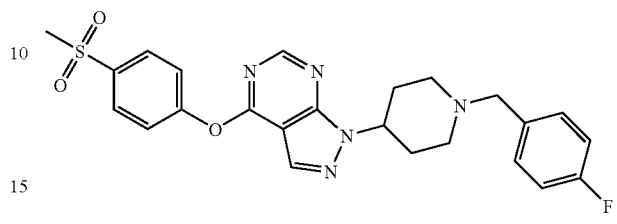

1-[1-(4-Fluoro-benzyl)-piperidin-4-yl]-4-(4-methanesulfonyl-phenoxy)-1H-pyrazolo[3,4-d]-pyrimidine was prepared according to General Procedure H by the reaction 4-(4-methanesulfonyl-phenoxy)-1-piperidin-4-yl-1H-pyrazolo[3,4-d]pyrimidine trifluoroacetate salt (Intermediate 27) with 4-fluorobenzaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.93-1.99 (m, 2H), 2.20-2.30 (m, 4H), 2.93-2.97 (m, 2H), 3.30 (methyl sulfonyl and water peak), 3.53 (s, 2H), 4.75-4.81 (m, 1H), 7.14-7.19 (m, 2H), 7.36-7.40 (m, 2H), 7.62-7.64 (m, 2H), 8.04-8.06 (m, 2H), 8.38 (s, 1H), 8.55 (s, 1H). Mass spectrum MH+=482.

Example 160

1-[1-(4-Chloro-benzyl)-piperidin-4-yl]-4-(4-methanesulfonyl-phenoxy)-1H-pyrazolo[3,4-d]pyrimidine

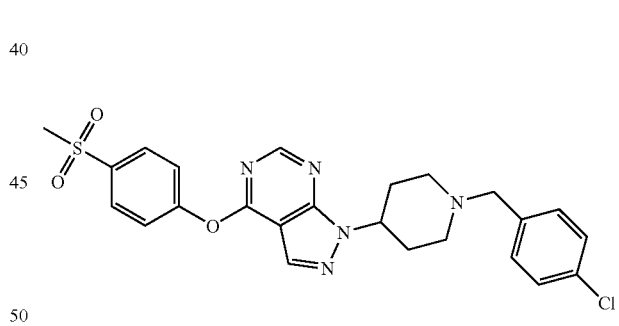

1-[1-(4-Chloro-benzyl)-piperidin-4-yl]-4-(4-methanesulfonyl-phenoxy)-1H-pyrazolo[3,4-d]-pyrimidine was prepared according to General Procedure H by the reaction 4-(4-methanesulfonyl-phenoxy)-1-piperidin-4-yl-1H-pyrazolo[3,4-d]pyrimidine trifluoroacetate salt (Intermediate 27) with 4-chlorobenzaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.90-1.96 (m, 2H), 2.16-2.25 (m, 4H), 2.93-2.97 (m, 2H), 3.30 (methyl sulfonyl and water peak), 3.54 (s, 2H), 4.77-4.82 (m, 1H), 7.36-7.42 (m, 4H), 7.62-7.64 (m, 2H), 8.04-8.06 (m, 2H), 8.37 (s, 1H), 8.55 (s, 1H). Mass spectrum MH+=498.

Example 161

4-(4-Methanesulfonyl-phenoxy)-1-[1-(4-trifluoromethyl-benzyl)-piperidin-4-yl]-1H-pyrazolo[3,4-d]pyrimidine

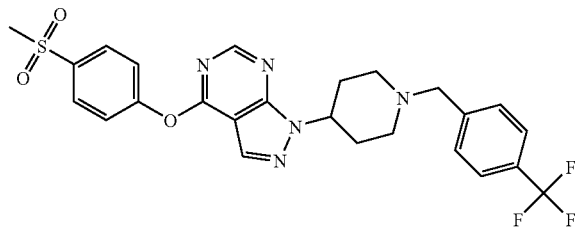

4-(4-Methanesulfonyl-phenoxy)-1-[1-(4-trifluoromethyl-benzyl)-piperidin-4-yl]-1H-pyrazolo[3,4-d]pyrimidine was prepared according to General Procedure H by the reaction 4-(4-methanesulfonyl-phenoxy)-1-piperidin-4-yl-1H-pyrazolo[3,4-d]pyrimidine trifluoroacetate salt (Intermediate 27) with 4-(trifluoromethyl)benzaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.95-1.99 (m, 2H), 2.20-2.33 (m, 4H), 2.93-2.97 (m, 2H), 3.30 (methyl sulfonyl and water peak), 3.66 (s, 2H), 4.77-4.83 (m, 1H), 7.58-7.64 (m, 4H), 7.70-7.72 (m, 2H), 8.04-8.07 (m, 2H), 8.37 (s, 1H), 8.57 (s, 1H). Mass spectrum MH+=532.

Example 162

4-(4-Methanesulfonyl-phenoxy)-1-[1-(3-trifluoromethoxy-benzyl)-piperidin-4-yl]-1H-pyrazolo[3,4-d]pyrimidine

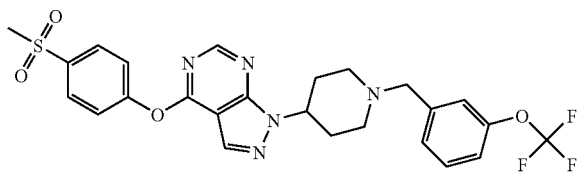

4-(4-Methanesulfonyl-phenoxy)-1-[1-(3-trifluoromethoxy-benzyl)-piperidin-4-yl]-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with 3-(trifluoromethoxy)benzaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.95-1.99 (m, 2H), 2.21-2.28 (m, 4H), 2.92-2.98 (m, 2H), 3.30 (methyl sulfonyl and water peak), 3.62 (s, 2H), 4.77-4.83 (m, 1H), 7.25-7.51 (m, 4H), 7.62-7.64 (m, 2H), 8.04-8.07 (m, 2H), 8.38 (s, 1H), 8.56 (s, 1H). Mass spectrum MH+=548.

Example 163

1-[1-(2,2-Difluoro-benzo[1,3]dioxol-5-ylmethyl)-piperidin-4-yl]-4-(4-methanesulfonyl-phenoxy)-1H-pyrazolo[3,4-d]pyrimidine

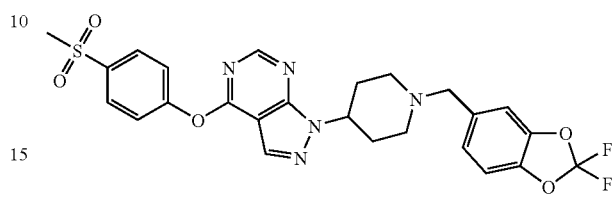

1-[1-(2,2-Difluoro-benzo[1,3]dioxol-5-ylmethyl)-piperidin-4-yl]-4-(4-methanesulfonyl-phenoxy)-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with 2,2-difluoro-5-formylbenzodioxole (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.89-1.98 (m, 2H), 2.15-2.25 (m, 4H), 2.92-2.98 (m, 2H), 3.30 (methyl sulfonyl and water peak), 3.57 (s, 2H), 4.77-4.83 (m, 1H), 7.18-7.20 (m, 1H), 7.35-7.39 (m, 2H), 7.62-7.64 (m, 2H), 8.04-8.07 (m, 2H), 8.37 (s, 1H), 8.55 (s, 1H). Mass spectrum MH+=544.

Example 164

2-{4-[4-(4-Methanesulfonyl-phenoxy)-pyrazolo[3,4-d]pyrimidin-1-yl]-piperidin-1-ylmethyl}-phenol

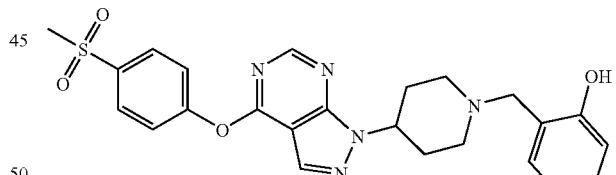

2-{4-[4-(4-Methanesulfonyl-phenoxy)-pyrazolo[3,4-d]pyrimidin-1-yl]-piperidin-1-ylmethyl}-phenol was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with salicylaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.95-2.03 (m, 2H), 2.19-2.28 (m, 4H), 2.32-2.38 (m, 2H), 2.98-3.06 (m, 2H), 3.30 (methyl sulfonyl and water peak), 3.71 (s, 2H), 4.84-4.89 (m, 1H), 6.75-6.79 (m, 2H), 7.08-7.14 (m, 2H), 7.63-7.65 (m, 2H), 8.04-8.07 (m, 2H), 8.40 (s, 1H), 8.56 (s, 1H). Mass spectrum MH+=480.

Example 165

4-(4-Methanesulfonyl-phenoxy)-1-[1-(2-methoxy-benzyl)-piperidin-4-yl]-1H-pyrazolo[3,4-d]pyrimidine

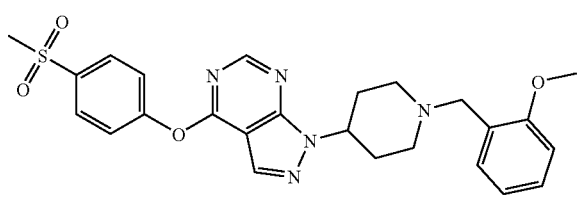

4-(4-Methanesulfonyl-phenoxy)-1-[1-(2-methoxy-benzyl)-piperidin-4-yl]-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 25) with o-anisaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.89-1.98 (m, 2H), 2.19-2.26 (m, 4H), 2.95-3.03 (m, 2H), 3.30 (methyl sulfonyl and water peak), 3.55 (s, 2H), 3.79 (s, 3H), 4.74-4.80 (m, 1H), 6.93-7.00 (m, 2H), 7.22-7.26 (m, 1H), 7.36-7.38 (m, 2H), 7.62-7.64 (m, 2H), 8.04-8.07 (m, 2H), 8.37 (s, 1H), 8.55 (s, 1H). Mass spectrum MH+=494.

Example 166

4-(4-Methanesulfonyl-phenoxy)-1-[1-(4-methoxy-benzyl)-piperidin-4-yl]-1H-pyrazolo[3,4-d]pyrimidine

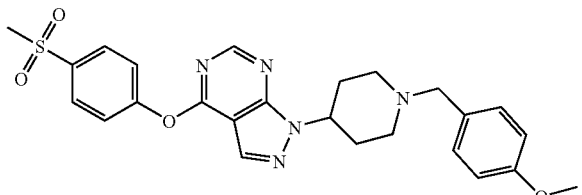

4-(4-Methanesulfonyl-phenoxy)-1-[1-(4-methoxy-benzyl)-piperidin-4-yl]-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with p-anisaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.91-1.94 (m, 2H), 2.13-2.23 (m, 4H), 2.93-2.97 (m, 2H), 3.30 (methyl sulfonyl and water peak), 3.47 (s, 2H), 3.74 (s, 3H), 4.74-4.80 (m, 1H), 6.89-6.91 (m, 2H), 7.24-7.26 (m, 2H), 7.62-7.64 (m, 2H), 8.04-8.06 (m, 2H), 8.36 (s, 1H), 8.55 (s, 1H). Mass spectrum MH+=494.

Example 167

1-[1-(4-Isopropyl-benzyl)-piperidin-4-yl]-4-(4-methanesulfonyl-phenoxy)-1H-pyrazolo[3,4-d]pyrimidine

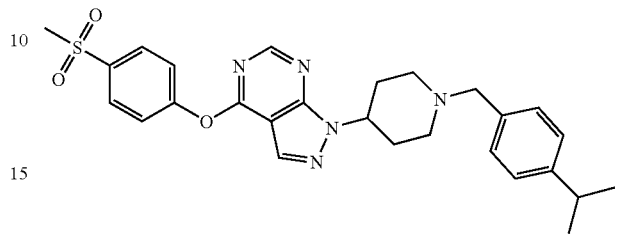

1-[1-(4-Isopropyl-benzyl)-piperidin-4-yl]-4-(4-methanesulfonyl-phenoxy)-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with 4-isopropylbenzaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.18 (d, 6H, J=6.6 Hz), 1.94-1.99 (m, 2H), 2.15-2.24 (m, 4H), 2.85-2.90 (m, 1H), 2.95-2.99 (m, 2H), 3.30 (methyl sulfonyl and water peak), 3.60 (s, 2H), 4.74-4.80 (m, 1H), 7.20-7.27 (m, 4H), 7.62-7.64 (m, 2H), 8.04-8.06 (m, 2H), 8.37 (s, 1H), 8.55 (s, 1H). Mass spectrum MH+=506.

Example 168

3-{4-[4-(4-Methanesulfonyl-phenoxy)-pyrazolo[3,4-d]pyrimidin-1-yl]-piperidin-1-ylmethyl}-benzonitrile

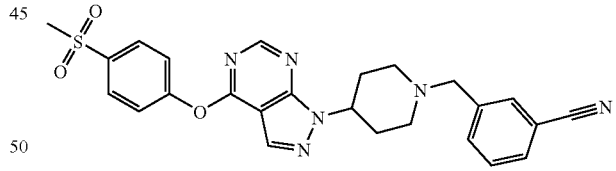

3-{4-[4-(4-Methanesulfonyl-phenoxy)-pyrazolo[3,4-d]pyrimidin-1-yl]-piperidin-1-ylmethyl}-benzonitrile was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 25) with 3-cyanobenzaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.95-1.99 (m, 2H), 2.23-2.29 (m, 4H), 2.94-2.97 (m, 2H), 3.30 (methyl sulfonyl and water peak), 3.62 (s, 2H), 4.78-4.85 (m, 1H), 7.55-7.80 (m, 6H), 8.04-8.07 (m, 2H), 8.38 (s, 1H), 8.56 (s, 1H). Mass spectrum MH+=489.

Example 169

4-(4-Methanesulfonyl-phenoxy)-(1-thiazol-2-ylm-ethyl-piperidin-4-yl)-1H-pyrazolo[3,4-d]pyrimidine

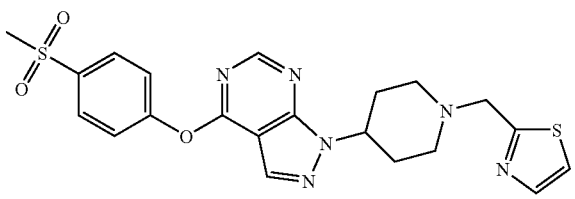

4-(4-Methanesulfonyl-phenoxy)-1-(1-thiazol-2-ylmethyl-piperidin-4-yl)-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 25) with 2-thiazolecarboxaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.95-2.00 (m, 2H), 2.21-2.33 (m, 2H), 2.39-2.45 (m, 3H), 3.04-3.08 (m, 2H), 3.30 (methyl sulfonyl and water peak), 3.92 (s, 2H), 4.79-4.85 (m, 1H), 7.63-7.74 (m, 4H), 8.05-8.07 (m, 2H), 8.39 (s, 1H), 8.56 (s, 1H). Mass spectrum MH+=471.

Example 170

4-(4-Methanesulfonyl-phenoxy)-1-[1-(5-methyl-isoxazol-3-ylmethyl)-piperidin-4-yl]-1H-pyrazolo[3,4-d]pyrimidine

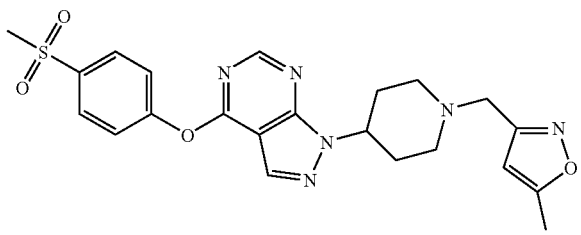

4-(4-Methanesulfonyl-phenoxy)-1-[1-(5-methyl-isoxazol-3-ylmethyl)-piperidin-4-yl]-1H-pyrazolo[3,4-d]pyrimidine was prepared according to General Procedure H by the reaction of 4-(4-methanesulfonyl-phenoxy)-1-piperidin-4-yl-1H-pyrazolo[3,4-d]pyrimidine trifluoroacetate salt (Intermediate 27) with 5-methylisoxazole-3-carboxaldehyde (available from Aldrich Chemical Company, Inc., Milwaukee, Wis., USA), triethylamine, and sodium triacetoxyborohydride in 1,2-dichloroethane. $^1$H NMR (400 MHz, DMSO-$d_6$) δ 1.92-1.95 (m, 2H), 2.17-2.33 (m, 4H), 2.40 (s, 2H), 2.95-2.97 (m, 2H), 3.30 (methyl sulfonyl and water peak), 3.57 (s, 2H), 4.74-4.80 (m, 1H), 6.24 (s, 1H), 7.62-7.64 (m, 2H), 8.04-8.07 (m, 2H), 8.37 (s, 1H), 8.55 (s, 1H). Mass spectrum MH+=469.

Example 171

4-(4-Methanesulfonyl-phenoxy)-1-[1-(2-methyl-propane-1-sulfonyl)-piperidin-4-yl]-1H-pyrazolo[3,4-d]pyrimidine

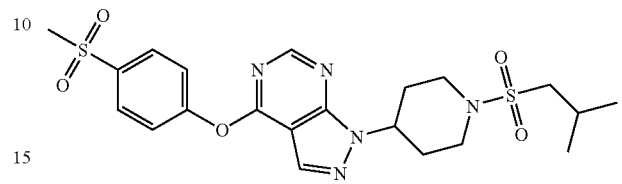

Isobutanesulfonyl chloride (Aldrich Chemical Company, Inc., Milwaukee, Wis., USA; 23 mg, 0.15 mmol) was added dropwise to a stirred solution of 4-(4-methanesulfonyl-phenoxy)-1-piperidin-4-yl-1H-pyrazolo[3,4-d]pyrimidine trifluoroacetate salt (Intermediate 27; 60 mg, 0.12 mmol) and diisopropylethylamine (0.11 mL, 0.62 mmol) in dichloromethane (1 mL) at room temperature. The mixture was stirred at room temperature for 1 h and then washed with water. The organic layers was dried (sodium sulfate), filtered, evaporated, triturated with ether and purified by HPLC to give to give 4-(4-methanesulfonyl-phenoxy)-1-[1-(2-methyl-propane-1-sulfonyl)-piperidin-4-yl]-1H-pyrazolo[3,4-d]pyrimidine (26 mg, 43%) as a white solid.

Example 172

4-[6-Chloro-4-(4-methanesulfonyl-phenoxy)-pyra-zolo[3,4-d]pyrimidin-1-yl]-piperidine-1-carboxylic acid tert-butyl ester

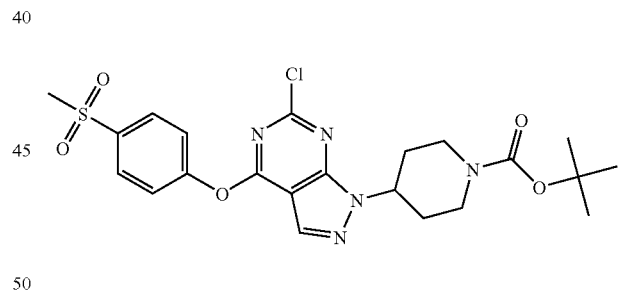

A solution of 4-(methylsulfonyl)phenol (available from Matrix Scientific, Columbia, S.C., USA; 52 mg, 0.3 mmol) in tetrahydrofuran (3 mL) was cooled to 0° C. under argon. Sodium hydride (60% dispersion; 13.2 mg, 0.33 mmol) was added and the mixture was stirred for 10 min. 4-(4,6-Dichloro-pyrazolo[3,4-d]pyrimidin-1-yl)-piperidine-1-carboxylic acid tert-butyl ester (Intermediate 24; 100 mg, 0.27 mmol) was added and the mixture was stirred at room temperature for 4 h and then poured into saturated aqueous ammonium chloride solution. The mixture was extracted three times with ethyl acetate and the combined organic layers were washed with brine, dried (magnesium sulfate), filtered, evaporated and purified by column chromatography, eluting with 25-50% ethyl acetate/hexanes to give 4-[6-chloro-4-(4-methanesulfonyl-phenoxy)-pyrazolo[3,4-d]pyrimidin-1-yl]-piperidine-1-carboxylic acid tert-butyl ester (91 mg, 66%) as a white solid.

Example 173

4-[6-Chloro-4-(4-methanesulfonyl-phenoxy)-pyrazolo[3,4-d]pyrimidin-1-yl]-piperidine-1-carboxylic acid tert-butyl ester

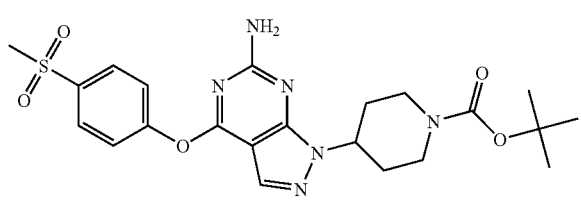

A mixture of: 4-(6-amino-4-chloro-pyrazolo[3,4-d]pyrimidin-1-yl)-piperidine-1-carboxylic acid tert-butyl ester (Intermediate 33; 75 mg, 0.21 mmol), 4-(methylsulfonyl)phenol (available from Matrix Scientific, Columbia, S.C., USA; 52 mg, 0.3 mmol), and potassium carbonate (70 mg, 0.5 mmol) in N,N-dimethylformamide (2 mL) was heated at 70° C., and then cooled. Volatiles were evaporated and the residue was chromatographed (75% ethyl acetate/hexanes) to give 4-[6-chloro-4-(4-methanesulfonyl-phenoxy)-pyrazolo[3,4-d]pyrimidin-1-yl]-piperidine-1-carboxylic acid tert-butyl ester (54 mg, 53%) as a white solid.

Example 174

4-[6-Amino-4-(2-cyano-phenoxy)-pyrazolo[3,4-d]pyrimidin-1-yl]-piperidine-1-carboxylic acid tert-butyl ester

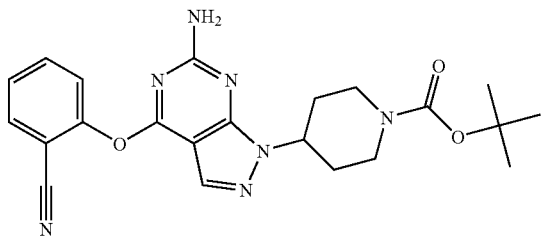

A mixture of: 4-(6-amino-4-chloro-pyrazolo[3,4-d]pyrimidin-1-yl)-piperidine-1-carboxylic acid tert-butyl ester (Intermediate 33; 224 mg, 0.64 mmol), 2-hydroxybenzonitrile (available from Alfa Aesar, Ward Hill, Mass., USA; 95.2 mg, 0.8 mmol), and potassium carbonate (220 mg, 1.6 mmol) in N,N-dimethylformamide (5 mL) was heated at 80° C. for 3 h, and then cooled. Volatiles were evaporated and the residue was chromatographed (50-65% ethyl acetate/hexanes) to give 4-[6-Amino-4-(2-cyano-phenoxy)-pyrazolo[3,4-d]pyrimidin-1-yl]-piperidine-1-carboxylic acid tert-butyl ester (261 mg, 94%) as a white solid.

Example 175

4-[4-(4-Methanesulfonyl-phenoxy)-6-methyl-pyrazolo[3,4-d]pyrimidin-1-yl]-piperidine-1-carboxylic acid tert-butyl ester

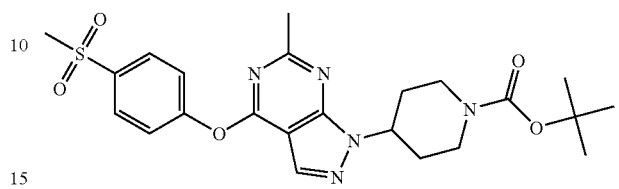

A mixture of 4-[6-chloro-4-(4-methanesulfonyl-phenoxy)-pyrazolo[3,4-d]pyrimidin-1-yl]-piperidine-1-carboxylic acid tert-butyl ester (Example 172; 230 mg, 0.45 mmol), trimethylaluminum (2 M in toluene; 0.5 mL, 1 mmol), and tetrakis(triphenyl-phosphine)palladium(0) (58 mg, 0.05 mmol) in tetrahydrofuran (5 mL) was heated at reflux for 2 h. The solvent was evaporated and the residue was purified by column chromatography to give 4-[4-(4-methanesulfonyl-phenoxy)-6-methyl-pyrazolo[3,4-d]pyrimidin-1-yl]-piperidine-1-carboxylic acid tert-butyl ester (93 mg, 42%) as a white foam/solid.

Example 176

4-[4-(4-Methanesulfonyl-phenoxy)-6-methoxy-pyrazolo[3,4-d]pyrimidin-1-yl]-piperidine-1-carboxylic acid tert-butyl ester

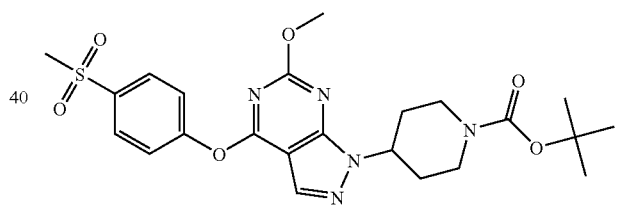

Step 1: 4-(4,6-Dimethoxy-pyrazolo[3,4-d]pyrimidin-1-yl)-piperidine-1-carboxylic acid tert-butyl ester Sodium methoxide (4 mmol) is added to a mixture of 4-(4,6-dichloro-pyrazolo[3,4-d]pyrimidin-1-yl)-piperidine-1-carboxylic acid tert-butyl ester (Intermediate 24; 1 mmol) in methanol. The resulting mixture is heated at reflux for 8 h and then cooled. The solvent is evaporated, and ethyl acetate and water are added. The organic layer is washed with water and brine, dried (magnesium sulfate), filtered, evaporated, and purified by flash chromatography on silica gel to give 4-(4,6-dimethoxy-pyrazolo[3,4-d]pyrimidin-1-yl)-piperidine-1-carboxylic acid tert-butyl ester.

Step 2: 4-(6-Methoxy-4-oxo-4,5-dihydro-pyrazolo[3,4-d]pyrimidin-1-yl)-piperidine-1-carboxylic acid tert-butyl ester A mixture of 4-(4,6-dimethoxy-pyrazolo[3,4-d]pyrimidin-1-yl)-piperidine-1-carboxylic acid tert-butyl ester (1 mmol), 2 M aqueous sodium hydroxide (1 mL) and dioxane (10 mL)

is heated at 40° C. for 5 h. The mixture is allowed to cool, and is then neutralized to approximately pH 7 by the addition of 1 M aqueous hydrochloric acid. Ethyl acetate and water are added. The organic layer is washed with water and brine, dried (magnesium sulfate), filtered, evaporated, and purified by flash chromatography on silica gel to give 4-(6-methoxy-4-oxo-4,5-dihydro-pyrazolo[3,4-d]pyrimidin-1-yl)-piperidine-1-carboxylic acid tert-butyl ester.

Step 3: 4-(4-Chloro-6-methoxy-pyrazolo[3,4-d]pyrimidin-1-yl)-piperidine-1-carboxylic acid tert-butyl ester A mixture of 4-(6-methoxy-4-oxo-4,5-dihydro-pyrazolo[3,4-d]pyrimidin-1-yl)-piperidine-1-carboxylic acid tert-butyl ester (1 mmol), phosphorus oxychloride (2 mmol) and dimethylformamide (5 drops) is heated at 80° C. for 6 h. The mixture is allowed to cool, the solvent is evaporated and the residue is poured into ice-water. The mixture is extracted three times with ethyl acetate. The combined ethyl acetate extracts are washed with brine, dried (magnesium sulfate), filtered, and evaporated to give crude 4-(4-chloro-6-methoxy-pyrazolo[3,4-d]pyrimidin-1-yl)-piperidine-1-carboxylic acid tert-butyl ester.

Step 4: 4-[4-(4-Methanesulfonyl-phenoxy)-6-methoxy-pyrazolo[3,4-d]pyrimidin-1-yl]-piperidine-1-carboxylic acid tert-butyl ester Sodium hydride (60% dispersion in mineral oil; 2 mmol) is added to a solution of 4-(methylsulfonyl)phenol (1.6 mmol) in dimethylformamide (9 mL) and the mixture is stirred at room temperature for 20 min. A solution of crude 4-(4-chloro-6-methoxy-pyrazolo[3,4-d]pyrimidin-1-yl)piperidine-1-carboxylic acid tert-butyl ester (1 mmol) in dimethylformamide (5 mL) is added. The reaction mixture is heated at 50° C. for 8 h. Saturated aqueous ammonium chloride solution is added and the mixture is extracted three times with ethyl acetate. The organic layer is washed with water and brine, dried (magnesium sulfate), filtered, evaporated and purified by flash chromatography on silica gel to give 4-[4-(4-methanesulfonyl-phenoxy)-6-methoxy-pyrazolo[3,4-d]pyrimidin-1-yl]-piperidine-1-carboxylic acid tert-butyl ester.

Example 177

Testing of Compounds of the Invention In Vitro
(cAMP Assay)

The functional agonist activities of compounds of the invention were characterized using a cAMP assay in HIT-T15 hamster pancreatic islet cells (American Type Culture Collection, Manassas, Va., USA) which endogenously express the GPR119 receptor. The cells were cultured in Kaighn's modification of Ham's F12 medium (Invitrogen Corporation, Carlsbad, Calif., USA) containing 10% horse serum, 2.5% FBS, and 1% Pen/Strep and grown in 225 cm² tissue culture flasks until they reached 75-85% confluence.

The cells were harvested 24 h prior to assay with 5 ml Versene®, washed with Kaighn/F12 medium and then plated into white 384-well plates (9000 cells/well) containing Kaighn/F12 medium. Prior to assay, the culture medium was replaced with a Kaighn/F12 medium without phenol red (50 µL/well) containing 0.5 mM 3-isobutyl-1-methylxanthine, 0.5 mg/ml BSA. The cells were incubated in the dark for 30 min at 25° C. in the absence or presence of varying concentrations of agonist (1 µL, 100% DMSO). The incubation media was discarded and replaced with the assay lysis buffer (50 µL/well) provided in the Tropix cAMP-Screen® kit (Applied Biosystems, Foster City, Calif., USA) and the plates incubated for 45 min at 37° C. The intracellular levels of cAMP generated in the HIT-T 15 cells were measured using the Tropix kit. In brief, 20 µL of the lysate was transferred into pre-coated antibody plates (384-well; Tropix kit) along with 10 µL of alkaline phosphatase conjugate and 20 µL of anti-cAMP antibody and the plates were incubated for 1 h at room temperature while shaking. The plates were then washed 5 times with wash buffer (70 µL) and tapped dry. CSPD®/Sapphire-II™ RTU substrate/enhancer solution (Applied Biosystems, Foster City, Calif., USA; 30 µL) was added and the plates were incubated for 45 min at room temperature while shaking. The signal generated was measured using a Wallac Victor V Luminometer (PerkinElmer Life And Analytical Sciences, Inc., Waltham, Mass., USA; 1 sec/well). $EC_{50}$ values were calculated using the XLFit program (ID Business Solutions Ltd., Guildford, Surrey, UK).

The results of the in vitro testing of the activity of representative compounds of the present invention as GPR119 agonists are shown in the following Table:

| Example | HAMSTER EC50 (µM) (cAMP Assay) | Name |
|---|---|---|
| 1 | 0.83 | 4-[4-(2-Fluoro-4-methanesulfonyl-phenylamino)-pyrazolo[3,4-d]pyrimidin-1-yl]-piperidine-1-carboxylic acid isopropyl ester |
| 2 | 3.1 | 4-[4-(2,4,5-Trifluoro-phenylamino)-pyrazolo[3,4-d]pyrimidin-1-yl]-piperidine-1-carboxylic acid isopropyl ester |
| 4 | 0.53 | 4-[4-(2,4,5-Trifluoro-phenylamino)-pyrazolo[3,4-d]pyrimidin-1-yl]-piperidine-1-carboxylic acid tert-butyl ester |
| 5 | 1.5 | 4-[4-(4-Methanesulfonyl-phenylamino)-pyrazolo[3,4-d]pyrimidin-1-yl]-piperidine-1-carboxylic acid tert-butyl ester |
| 6 | 0.24 | 4-[4-(2-Fluoro-4-methanesulfonyl-phenylamino)-pyrazolo[3,4-d]pyrimidin-1-yl]-piperidine-1-carboxylic acid tert-butyl ester |
| 7 | 2.2 | 4-[4-(2-Methyl-pyridin-3-ylamino)-pyrazolo[3,4-d]pyrimidin-1-yl]-piperidine-1-carboxylic acid tert-butyl ester |
| 8 | 0.76 | 4-[4-(6-Methanesulfonyl-2-methyl-pyridin-3-ylamino)-pyrazolo[3,4-d]pyrimidin-1-yl]-piperidine-1-carboxylic acid tert-butyl ester |
| 9 | 2.4 | 4-[4-(2-Methyl-6-[1,2,4]triazol-1-yl-pyridin-3-ylamino)-pyrazolo[3,4-d]pyrimidin-1-yl]-piperidine-1-carboxylic acid tert-butyl ester |
| 10 | 0.46 | 4-[4-(5-Methanesulfonyl-2,3-dihydro-indol-1-yl)-pyrazolo[3,4-d]pyrimidin-1-yl]-piperidine-1-carboxylic acid tert-butyl ester |
| 11 | 2.5 | [1-(1-Benzyl-piperidin-4-yl)-1H-pyrazolo[3,4-d]pyrimidin-4-yl]-(2-fluoro-4-methanesulfonyl-phenyl)-amine |
| 13 | 0.65 | 4-[4-(4-Methanesulfonyl-phenoxy)-pyrazolo[3,4-d]pyrimidin-1-yl]-piperidine-1-carboxylic acid ethyl ester |
| 14 | 0.14 | 4-[4-(2-Fluoro-4-methanesulfonyl-phenoxy)-pyrazolo[3,4-d]pyrimidin-1-yl]-piperidine-1-carboxylic acid ethyl ester |
| 15 | 2 | 4-(4-Phenoxy-pyrazolo[3,4-d]pyrimidin-1-yl)-piperidine-1-carboxylic acid isopropyl ester |
| 16 | 0.21 | 4-[4-(2,4,5-Trifluoro-phenoxy)-pyrazolo[3,4-d]pyrimidin-1-yl]-piperidine-1-carboxylic acid isopropyl ester |
| 17 | 0.7 | 4-[3-Methyl-4-(2,4,5-trifluoro-phenoxy)-pyrazolo[3,4-d]pyrimidin-1-yl]-piperidine-1-carboxylic acid isopropyl ester |
| 18 | 0.38 | 4-[4-(4-Ethoxy-2-fluoro-phenoxy)-pyrazolo[3,4-d]pyrimidin-1-yl]-piperidine-1-carboxylic acid isopropyl ester |

| Example | HAMSTER EC50 (μM) (cAMP Assay) | Name |
|---|---|---|
| 19 | 0.71 | 4-[4-(2-Cyano-phenoxy)-pyrazolo[3,4-d]pyrimidin-1-yl]-piperidine-1-carboxylic acid isopropyl ester |
| 20 | 0.57 | 4-[4-(6-Cyano-2,3-difluoro-phenoxy)-pyrazolo[3,4-d]pyrimidin-1-yl]-piperidine-1-carboxylic acid isopropyl ester |
| 21 | 0.26 | 4-[4-(4-Methanesulfonyl-phenoxy)-pyrazolo[3,4-d]pyrimidin-1-yl]-piperidine-1-carboxylic acid isopropyl ester |
| 22 | 0.21 | 4-[4-(4-Methanesulfonyl-phenoxy)-3-methyl-pyrazolo[3,4-d]pyrimidin-1-yl]-piperidine-1-carboxylic acid isopropyl ester |
| 23 | 0.11 | 4-[4-(2-Fluoro-4-methanesulfonyl-phenoxy)-pyrazolo[3,4-d]pyrimidin-1-yl]-piperidine-1-carboxylic acid isopropyl ester |
| 24 | 0.098 | 4-[4-(3-Fluoro-4-methanesulfonyl-phenoxy)-pyrazolo[3,4-d]pyrimidin-1-yl]-piperidine-1-carboxylic acid isopropyl ester |
| 25 | 0.46 | 4-[4-(4-Acetylamino-phenoxy)-pyrazolo[3,4-d]pyrimidin-1-yl]-piperidine-1-carboxylic acid isopropyl ester |
| 26 | 0.95 | 4-{4-[4-(5-Methyl-tetrazol-1-yl)-phenoxy]-pyrazolo[3,4-d]pyrimidin-1-yl}-piperidine-1-carboxylic acid isopropyl ester |
| 27 | 0.85 | 4-[4-(2-Methyl-pyridin-3-yloxy)-pyrazolo[3,4-d]pyrimidin-1-yl]-piperidine-1-carboxylic acid isopropyl ester |
| 28 | 0.82 | 4-[4-(2-Methyl-pyridin-3-yloxy)-pyrazolo[3,4-d]pyrimidin-1-yl]-piperidine-1-carboxylic acid isopropyl ester hydrochloride salt |
| 29 | 0.14 | 4-[4-(6-Methanesulfonyl-2-methyl-pyridin-3-yloxy)-pyrazolo[3,4-d]pyrimidin-1-yl]-piperidine-1-carboxylic acid isopropyl ester |
| 30 | 0.86 | 4-[4-(2-Methyl-6-[1,2,4]triazol-1-yl-pyridin-3-yloxy)-pyrazolo[3,4-d]pyrimidin-1-yl]-piperidine-1-carboxylic acid isopropyl ester |
| 31 | 3.5 | 4-[4-(1-Methyl-6-oxo-1,6-dihydro-pyridazin-3-yloxy)-pyrazolo[3,4-d]pyrimidin-1-yl]-piperidine-1-carboxylic acid isopropyl ester |
| 32 | 0.19 | 4-[4-(2-Fluoro-phenoxy)-pyrazolo[3,4-d]pyrimidin-1-yl]-piperidine-1-carboxylic acid tert-butyl ester |
| 33 | 0.6 | 4-[4-(3-Fluoro-phenoxy)-pyrazolo[3,4-d]pyrimidin-1-yl]-piperidine-1-carboxylic acid tert-butyl ester |
| 34 | 0.53 | 4-[4-(4-Fluoro-phenoxy)-pyrazolo[3,4-d]pyrimidin-1-yl]-piperidine-1-carboxylic acid tert-butyl ester |
| 35 | 0.088 | 4-[4-(2,4,5-Trifluoro-phenoxy)-pyrazolo[3,4-d]pyrimidin-1-yl]-piperidine-1-carboxylic acid tert-butyl ester |
| 38 | 0.49 | 4-[4-(2,4-Dichloro-phenoxy)-pyrazolo[3,4-d]pyrimidin-1-yl]-piperidine-1-carboxylic acid tert-butyl ester |
| 39 | 0.72 | 4-[4-(4-Methoxy-phenoxy)-pyrazolo[3,4-d]pyrimidin-1-yl]-piperidine-1-carboxylic acid tert-butyl ester |
| 40 | 0.2 | 4-[4-(4-Ethoxy-phenoxy)-pyrazolo[3,4-d]pyrimidin-1-yl]-piperidine-1-carboxylic acid tert-butyl ester |
| 41 | 0.29 | 4-[4-(Benzo[1,3]dioxol-5-yloxy)-pyrazolo[3,4-d]pyrimidin-1-yl]-piperidine-1-carboxylic acid tert-butyl ester |
| 42 | 1.8 | 4-[4-(4-Trifluoromethoxy-phenoxy)-pyrazolo[3,4-d]pyrimidin-1-yl]-piperidine-1-carboxylic acid tert-butyl ester |
| 43 | 0.018 | 4-[4-(4-Ethoxy-2-fluoro-phenoxy)-pyrazolo[3,4-d]pyrimidin-1-yl]-piperidine-1-carboxylic acid tert-butyl ester |
| 44 | 0.19 | 4-[4-(2-Chloro-4-methoxy-phenoxy)-pyrazolo[3,4-d]pyrimidin-1-yl]-piperidine-1-carboxylic acid tert-butyl ester |
| 45 | 0.061 | 4-[4-(2-Cyano-phenoxy)-pyrazolo[3,4-d]pyrimidin-1-yl]-piperidine-1-carboxylic acid tert-butyl ester |
| 46 | 0.48 | 4-[4-(4-Cyano-phenoxy)-pyrazolo[3,4-d]pyrimidin-1-yl]-piperidine-1-carboxylic acid tert-butyl ester |
| 47 | 0.28 | 4-[4-(4-Cyano-2-fluoro-phenoxy)-pyrazolo[3,4-d]pyrimidin-1-yl]-piperidine-1-carboxylic acid tert-butyl ester |
| 48 | 0.22 | 4-[4-(4-Cyano-3-fluoro-phenoxy)-pyrazolo[3,4-d]pyrimidin-1-yl]-piperidine-1-carboxylic acid tert-butyl ester |
| 49 | 0.048 | 4-[4-(6-Cyano-2,3-difluoro-phenoxy)-pyrazolo[3,4-d]pyrimidin-1-yl]-piperidine-1-carboxylic acid tert-butyl ester |
| 50 | 0.69 | 4-[4-(2-Cyano-4,5-difluoro-phenoxy)-pyrazolo[3,4-d]pyrimidin-1-yl]-piperidine-1-carboxylic acid tert-butyl ester |
| 51 | 0.11 | 4-[4-(4-Chloro-2-cyano-phenoxy)-pyrazolo[3,4-d]pyrimidin-1-yl]-piperidine-1-carboxylic acid tert-butyl ester |
| 52 | 0.75 | 4-[4-(4-Bromo-2-cyano-phenoxy)-pyrazolo[3,4-d]pyrimidin-1-yl]-piperidine-1-carboxylic acid tert-butyl ester |
| 53 | 0.49 | 4-[4-(3-Fluoro-5-trifluoromethyl-phenoxy)-pyrazolo[3,4-d]pyrimidin-1-yl]-piperidine-1-carboxylic acid tert-butyl ester |
| 54 | 0.083 | 4-[4-(2-Chloro-4-trifluoromethyl-phenoxy)-pyrazolo[3,4-d]pyrimidin-1-yl]-piperidine-1-carboxylic acid tert-butyl ester |
| 55 | 0.15 | 4-[4-(4-Chloro-3-trifluoromethyl-phenoxy)-pyrazolo[3,4-d]pyrimidin-1-yl]-piperidine-1-carboxylic acid tert-butyl ester |
| 56 | 0.28 | 4-[4-(4-Sulfamoyl-phenoxy)-pyrazolo[3,4-d]pyrimidin-1-yl]-piperidine-1-carboxylic acid tert-butyl ester |
| 57 | 0.3 | 4-[4-(4-Dimethylsulfamoyl-phenoxy)-pyrazolo[3,4-d]pyrimidin-1-yl]-piperidine-1-carboxylic acid tert-butyl ester |
| 58 | 0.42 | 4-[4-(4-Methanesulfinyl-phenoxy)-pyrazolo[3,4-d]pyrimidin-1-yl]-piperidine-1-carboxylic acid tert-butyl ester |
| 59 | 0.043 | 4-[4-(4-Methanesulfonyl-phenoxy)-pyrazolo[3,4-d]pyrimidin-1-yl]-piperidine-1-carboxylic acid tert-butyl ester |
| 60 | 0.048 | 4-[4-(2-Fluoro-4-methanesulfonyl-phenoxy)-pyrazolo[3,4-d]pyrimidin-1-yl]-piperidine-1-carboxylic acid tert-butyl ester |
| 61 | 0.095 | 4-[4-(3-Fluoro-4-methanesulfonyl-phenoxy)-pyrazolo[3,4-d]pyrimidin-1-yl]-piperidine-1-carboxylic acid tert-butyl ester |
| 62 | 0.65 | 4-[4-(4-Carbamoyl-phenoxy)-pyrazolo[3,4-d]pyrimidin-1-yl]-piperidine-1-carboxylic acid tert-butyl ester |
| 63 | 0.42 | 4-[4-(2-Fluoro-4-methoxycarbonyl-phenoxy)-pyrazolo[3,4-d]pyrimidin-1-yl]-piperidine-1-carboxylic acid tert-butyl ester |
| 64 | 0.15 | 4-[4-(4-Acetyl-phenoxy)-pyrazolo[3,4-d]pyrimidin-1-yl]-piperidine-1-carboxylic acid tert-butyl ester |
| 65 | 0.31 | 4-[4-(4-Acetyl-3-methyl-phenoxy)-pyrazolo[3,4-d]pyrimidin-1-yl]-piperidine-1-carboxylic acid tert-butyl ester |
| 66 | 0.75 | 4-[4-(2-Fluoro-4-nitro-phenoxy)-pyrazolo[3,4-d]pyrimidin-1-yl]-piperidine-1-carboxylic acid tert-butyl ester |
| 67 | 0.85 | 4-{4-[4-(4-Acetyl-piperazin-1-yl)-phenoxy]-pyrazolo[3,4-d]pyrimidin-1-yl}-piperidine-1-carboxylic acid tert-butyl ester |
| 68 | 0.73 | 4-[4-(4-Methanesulfonylamino-3-methyl-phenoxy)-pyrazolo[3,4-d]pyrimidin-1-yl]-piperidine-1-carboxylic acid tert-butyl ester |
| 69 | 0.6 | 4-[4-(3-Acetylamino-phenoxy)-pyrazolo[3,4-d]pyrimidin-1-yl]-piperidine-1-carboxylic acid tert-butyl ester |
| 70 | 0.14 | 4-[4-(4-Acetylamino-phenoxy)-pyrazolo[3,4-d]pyrimidin-1-yl]-piperidine-1-carboxylic acid tert-butyl ester |

| Example | HAMSTER EC50 (μM) (cAMP Assay) | Name |
|---|---|---|
| 71 | 0.75 | 4-[4-(Quinolin-5-yloxy)-pyrazolo[3,4-d]pyrimidin-1-yl]-piperidine-1-carboxylic acid tert-butyl ester |
| 72 | 1.2 | 4-[4-(1H-Pyrrolo[2,3-b]pyridin-5-yloxy)-pyrazolo[3,4-d]pyrimidin-1-yl]-piperidine-1-carboxylic acid tert-butyl ester |
| 74 | 1.9 | 4-[4-(1H-Indol-5-yloxy)-pyrazolo[3,4-d]pyrimidin-1-yl]-piperidine-1-carboxylic acid tert-butyl ester |
| 75 | 1.8 | 4-[4-(2-Oxo-2H-chromen-7-yloxy)-pyrazolo[3,4-d]pyrimidin-1-yl]-piperidine-1-carboxylic acid tert-butyl ester |
| 76 | 3 | 4-[4-(4-Methyl-2-oxo-2H-chromen-7-yloxy)-pyrazolo[3,4-d]pyrimidin-1-yl]-piperidine-1-carboxylic acid tert-butyl ester |
| 77 | 0.99 | 4-[4-(Benzo[b]thiophen-5-yloxy)-pyrazolo[3,4-d]pyrimidin-1-yl]-piperidine-1-carboxylic acid tert-butyl ester |
| 78 | 0.75 | 4-[4-(1,1-Dioxo-1H-1λ6-benzo[b]thiophen-5-yloxy)-pyrazolo[3,4-d]pyrimidin-1-yl]-piperidine-1-carboxylic acid tert-butyl ester |
| 79 | 0.82 | 4-[4-(1,1-Dioxo-2,3-dihydro-1H-1λ6-benzo[b]thiophen-5-yloxy)-pyrazolo[3,4-d]pyrimidin-1-yl]-piperidine-1-carboxylic acid tert-butyl ester |
| 80 | 0.046 | 4-[4-[1,2,4]Triazol-1-yl-phenoxy)-pyrazolo[3,4-d]pyrimidin-1-yl]-piperidine-1-carboxylic acid tert-butyl ester |
| 82 | 1.8 | 4-[4-(4-Tetrazol-2-yl-phenoxy)-pyrazolo[3,4-d]pyrimidin-1-yl]-piperidine-1-carboxylic acid tert-butyl ester |
| 83 | 1.6 | 4-[4-(4-Tetrazol-1-yl-phenoxy)-pyrazolo[3,4-d]pyrimidin-1-yl]-piperidine-1-carboxylic acid tert-butyl ester |
| 84 | 0.24 | 4-{4-[4-(5-Methyl-tetrazol-1-yl)-phenoxy]-pyrazolo[3,4-d]pyrimidin-1-yl}-piperidine-1-carboxylic acid tert-butyl ester |
| 85 | 0.55 | 4-{4-[4-(5-Methyl-[1,2,4]oxadiazol-3-yl)-phenoxy]-pyrazolo[3,4-d]pyrimidin-1-yl}-piperidine-1-carboxylic acid tert-butyl ester |
| 86 | 0.49 | 4-[4-(4-Thiophen-3-yl-phenoxy)-pyrazolo[3,4-d]pyrimidin-1-yl]-piperidine-1-carboxylic acid tert-butyl ester |
| 87 | 0.37 | 3-[4-(4-Methanesulfonyl-phenoxy)-pyrazolo[3,4-d]pyrimidin-1-yl]-piperidine-1-carboxylic acid tert-butyl ester |
| 88 and 89 | 0.045 and 0.21 | (R)-3-[4-(4-Methanesulfonyl-phenoxy)-pyrazolo[3,4-d]pyrimidin-1-yl]-piperidine-1-carboxylic acid tert-butyl ester and (S)-3-[4-(4-Methanesulfonyl-phenoxy)-pyrazolo[3,4-d]pyrimidin-1-yl]-piperidine-1-carboxylic acid tert-butyl ester |
| 90 | 0.12 | 3-[4-(2-Cyano-phenoxy)-pyrazolo[3,4-d]pyrimidin-1-yl]-piperidine-1-carboxylic acid tert-butyl ester |
| 91 | 1.2 | 4-[4-(Pyridin-3-yloxy)-pyrazolo[3,4-d]pyrimidin-1-yl]-piperidine-1-carboxylic acid tert-butyl ester |
| 92 | 0.17 | 4-[4-(2-Methyl-pyridin-3-yloxy)-pyrazolo[3,4-d]pyrimidin-1-yl]-piperidine-1-carboxylic acid tert-butyl ester |
| 95 | 0.89 | 4-[4-(2,6-Dimethoxy-pyridin-3-yloxy)-pyrazolo[3,4-d]pyrimidin-1-yl]-piperidine-1-carboxylic acid tert-butyl ester |
| 96 | 1.5 | 4-[4-(6-Methoxy-pyridin-3-yloxy)-pyrazolo[3,4-d]pyrimidin-1-yl]-piperidine-1-carboxylic acid tert-butyl ester |
| 97 | 0.53 | 4-[4-(6-Chloro-2-methyl-pyridin-3-yloxy)-pyrazolo[3,4-d]pyrimidin-1-yl]-piperidine-1-carboxylic acid tert-butyl ester |
| 98 | 0.096 | 4-[4-(6-Methanesulfonyl-2-methyl-pyridin-3-yloxy)-pyrazolo[3,4-d]pyrimidin-1-yl]-piperidine-1-carboxylic acid tert-butyl ester |
| 99 | 0.2 | 4-[4-(2-Cyano-pyridin-3-yloxy)-pyrazolo[3,4-d]pyrimidin-1-yl]-piperidine-1-carboxylic acid tert-butyl ester |
| 100 | 1.8 | 4-[4-(5-Chloro-pyridin-3-yloxy)-pyrazolo[3,4-d]pyrimidin-1-yl]-piperidine-1-carboxylic acid tert-butyl ester |
| 101 | 0.36 | 4-[4-(2-Methyl-6-[1,2,4]triazol-1-yl-pyridin-3-yloxy)-pyrazolo[3,4-d]pyrimidin-1-yl]-piperidine-1-carboxylic acid tert-butyl ester |
| 102 | 0.47 | 4-[4-(1-Methyl-6-oxo-1,6-dihydro-pyridazin-3-yloxy)-pyrazolo[3,4-d]pyrimidin-1-yl]-piperidine-1-carboxylic acid tert-butyl ester |
| 103 | 3.4 | 4-[4-(6-Ethyl-2-methyl-pyrimidin-4-yloxy)-pyrazolo[3,4-d]pyrimidin-1-yl]-piperidine-1-carboxylic acid tert-butyl ester |
| 104 | 0.85 | 4-[4-(2-Methyl-pyridin-3-yloxy)-pyrazolo[3,4-d]pyrimidin-1-yl]-piperidine-1-carboxylic acid butyl ester |
| 105 | 0.15 | 4-[4-(4-Methanesulfonyl-phenoxy)-pyrazolo[3,4-d]pyrimidin-1-yl]-piperidine-1-carboxylic acid (R)-sec-butyl ester |
| 106 | 0.11 | 4-[4-(4-Methanesulfonyl-phenoxy)-pyrazolo[3,4-d]pyrimidin-1-yl]-piperidine-1-carboxylic acid isobutyl ester |
| 107 | 0.19 | 4-[4-(2-Methyl-pyridin-3-yloxy)-pyrazolo[3,4-d]pyrimidin-1-yl]-piperidine-1-carboxylic acid isobutyl ester |
| 108 | 0.1 | 4-[4-(4-Methanesulfonyl-phenoxy)-pyrazolo[3,4-d]pyrimidin-1-yl]-piperidine-1-carboxylic acid 2,2-dimethyl-propyl ester |
| 109 | 0.68 | 4-[4-(4-Methanesulfonyl-phenoxy)-pyrazolo[3,4-d]pyrimidin-1-yl]-piperidine-1-carboxylic acid 2-fluoro-1-fluoromethyl-ethyl ester |
| 110 | 1 | 4-[4-(4-Methanesulfonyl-phenoxy)-pyrazolo[3,4-d]pyrimidin-1-yl]-piperidine-1-carboxylic acid 2,2,2-trifluoro-1-methyl-ethyl ester |
| 111 | 0.05 | 4-[4-(4-Methanesulfonyl-phenoxy)-pyrazolo[3,4-d]pyrimidin-1-yl]-piperidine-1-carboxylic acid 2,2,2-trifluoro-1,1-dimethyl-ethyl ester |
| 112 | 0.5 | 4-[4-(4-Methanesulfonyl-phenoxy)-pyrazolo[3,4-d]pyrimidin-1-yl]-piperidine-1-carboxylic acid 2,2,2-trifluoro-1-trifluoromethyl-ethyl ester |
| 113 | 0.16 | 4-[4-(4-Methanesulfonyl-phenoxy)-pyrazolo[3,4-d]pyrimidin-1-yl]-piperidine-1-carboxylic acid 2,2,2-trifluoro-ethyl ester |
| 114 | 0.044 | 4-[4-(4-Methanesulfonyl-phenoxy)-pyrazolo[3,4-d]pyrimidin-1-yl]-piperidine-1-carboxylic acid 2,2,2-trichloro-1,1-dimethyl-ethyl ester |
| 115 | 0.018 | 4-[4-(4-Methanesulfonyl-phenoxy)-pyrazolo[3,4-d]pyrimidin-1-yl]-piperidine-1-carboxylic acid 2,2,2-trichloro-ethyl ester |
| 116 | 0.55 | 4-[4-(2-Methyl-pyridin-3-yloxy)-pyrazolo[3,4-d]pyrimidin-1-yl]-piperidine-1-carboxylic acid cyclobutyl ester |
| 117 | 0.17 | 4-[4-(4-Ethoxy-2-fluoro-phenoxy)-pyrazolo[3,4-d]pyrimidin-1-yl]-piperidine-1-carboxylic acid cyclopentyl ester |
| 118 | 0.34 | 4-[4-(2-Cyano-phenoxy)-pyrazolo[3,4-d]pyrimidin-1-yl]-piperidine-1-carboxylic acid cyclopentyl ester |
| 119 | 0.063 | 4-[4-(6-Cyano-2,3-difluoro-phenoxy)-pyrazolo[3,4-d]pyrimidin-1-yl]-piperidine-1-carboxylic acid cyclopentyl ester |
| 120 | 0.031 | 4-[4-(2-Fluoro-4-methanesulfonyl-phenoxy)-pyrazolo[3,4-d]pyrimidin-1-yl]-piperidine-1-carboxylic acid cyclopentyl ester |
| 121 | 0.26 | 4-[4-(2-Methyl-pyridin-3-yloxy)-pyrazolo[3,4-d]pyrimidin-1-yl]-piperidine-1-carboxylic acid cyclopentyl ester |
| 122 | 1.1 | 4-[4-(2-Methyl-pyridin-3-yloxy)-pyrazolo[3,4-d]pyrimidin-1-yl]-piperidine-1-carboxylic acid phenyl ester |
| 123 | 2.7 | 4-[4-(2-Methyl-pyridin-3-yloxy)-pyrazolo[3,4-d]pyrimidin-1-yl]-piperidine-1-carboxylic acid 4-nitro-phenyl ester |

| Example | HAMSTER EC50 (µM) (cAMP Assay) | Name |
|---|---|---|
| 124 | 0.24 | 4-[4-(2-Methyl-pyridin-3-yloxy)-pyrazolo[3,4-d]pyrimidin-1-yl]-piperidine-1-carboxylic acid benzyl ester |
| 125 | 0.57 | 4-[4-(2-Methyl-pyridin-3-yloxy)-pyrazolo[3,4-d]pyrimidin-1-yl]-piperidine-1-carboxylic acid cyclohexyl ester |
| 126 | 0.43 | 1-[1-(3-Isopropyl-[1,2,4]oxadiazol-5-yl)-piperidin-4-yl]-4-(4-methanesulfonyl-phenoxy)-1H-pyrazolo[3,4-d]pyrimidine |
| 127 | 0.068 | 4-(2-Fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine |
| 128 | 0.16 | 4-(3-Fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine |
| 129 | 2.3 | 1-[1-(3-Isopropyl-[1,2,4]oxadiazol-5-yl)-piperidin-4-yl]-4-(2-methyl-pyridin-3-yloxy)-1H-pyrazolo[3,4-d]pyrimidine |
| 130 | 0.71 | 1-[1-(6-Chloro-pyridazin-3-yl)-piperidin-4-yl]-4-(4-methanesulfonyl-phenoxy)-1H-pyrazolo[3,4-d]pyrimidine |
| 131 | 0.39 | 4-(2-Fluoro-4-methanesulfonyl-phenoxy)-1-[4-(3-isopropyl-[1,2,4]oxadiazol-5-yl)-cyclohexyl]-1H-pyrazolo[3,4-d]pyrimidine |
| 132 | 0.35 | 4-(2-Fluoro-4-methanesulfonyl-phenoxy)-1-[4-(3-isopropyl-[1,2,4]oxadiazol-5-yl)-cyclohexyl]-1H-pyrazolo[3,4-d]pyrimidine |
| 133 | 3.34 | 1-[4-(3-Isopropyl-[1,2,4]oxadiazol-5-yl)-cyclohexyl]-4-[4-(5-methyl-tetrazol-1-yl)-phenoxy]-1H-pyrazolo[3,4-d]pyrimidine |
| 135 | 0.92 | 1-[4-(3-Isopropyl-[1,2,4]oxadiazol-5-yl)-cyclohexyl]-4-(2-methyl-pyridin-3-yloxy)-1H-pyrazolo[3,4-d]pyrimidine |
| 136 | 0.99 | 1-{4-[4-(4-Methanesulfonyl-phenoxy)-pyrazolo[3,4-d]pyrimidin-1-yl]-piperidin-1-yl}-2-methyl-propan-1-one |
| 137 | 1.6 | 2,2-Dimethyl-1-{4-[4-(2,4,5-trifluoro-phenoxy)-pyrazolo[3,4-d]pyrimidin-1-yl]-piperidin-1-yl}-propan-1-one |
| 138 | 0.78 | 1-{4-[4-(4-Methanesulfonyl-phenoxy)-pyrazolo[3,4-d]pyrimidin-1-yl]-piperidin-1-yl}-2,2-dimethyl-propan-1-one |
| 140 | 0.75 | Cyclobutyl-{4-[4-(4-methanesulfonyl-phenoxy)-pyrazolo[3,4-d]pyrimidin-1-yl]-piperidin-1-yl}-methanone |
| 141 | 0.42 | Cyclopentyl-{4-[4-(4-methanesulfonyl-phenoxy)-pyrazolo[3,4-d]pyrimidin-1-yl]-piperidin-1-yl}-methanone |
| 142 | 0.33 | 1-{4-[4-(4-Methanesulfonyl-phenoxy)-pyrazolo[3,4-d]pyrimidin-1-yl]-piperidin-1-yl}-3-methyl-butan-1-one |
| 143 | 0.44 | 1-{4-[4-(4-Methanesulfonyl-phenoxy)-pyrazolo[3,4-d]pyrimidin-1-yl]-piperidin-1-yl}-4-methyl-pentan-1-one |
| 144 | 0.27 | 1-{4-[4-(4-Methanesulfonyl-phenoxy)-pyrazolo[3,4-d]pyrimidin-1-yl]-piperidin-1-yl}-3,3-dimethyl-butan-1-one |
| 145 | 0.58 | 2-Cyclohexyl-1-{4-[4-(4-methanesulfonyl-phenoxy)-pyrazolo[3,4-d]pyrimidin-1-yl]-piperidin-1-yl}-ethanone |
| 146 | 1 | 1-{4-[4-(4-Methanesulfonyl-phenoxy)-pyrazolo[3,4-d]pyrimidin-1-yl]-piperidin-1-yl}-3-phenyl-propan-1-one |
| 147 | 0.26 | Cyclopentyl-{4-[4-(4-ethoxy-2-fluoro-phenoxy)-pyrazolo[3,4-d]pyrimidin-1-yl]-piperidin-1-yl}-methanone |
| 148 | 1.7 | 2,2,2-Trifluoro-1-{4-[4-(4-methanesulfonyl-phenoxy)-pyrazolo[3,4-d]pyrimidin-1-yl]-piperidin-1-yl}-ethanone |
| 149 | 1.7 | {4-[4-(4-Methanesulfonyl-phenoxy)-pyrazolo[3,4-d]pyrimidin-1-yl]-piperidin-1-yl}-phenyl-methanone |
| 150 | 2.1 | (3,5-Dichloro-phenyl)-{4-[4-(4-methanesulfonyl-phenoxy)-pyrazolo[3,4-d]pyrimidin-1-yl]-piperidin-1-yl}-methanone |
| 152 | 0.39 | (1,5-Dimethyl-1H-pyrazol-3-yl)-{4-[4-(4-methanesulfonyl-phenoxy)-pyrazolo[3,4-d]pyrimidin-1-yl]-piperidin-1-yl}-methanone |
| 153 | 4.4 | {4-[4-(4-Methanesulfonyl-phenoxy)-pyrazolo[3,4-d]pyrimidin-1-yl]-piperidin-1-yl}-(5-methyl-isoxazol-3-yl)-methanone |
| 154 | 0.36 | (5-Isobutyl-isoxazol-3-yl)-{4-[4-(4-methanesulfonyl-phenoxy)-pyrazolo[3,4-d]pyrimidin-1-yl]-piperidin-1-yl}-methanone |
| 155 | 1.6 | {4-[4-(4-Methanesulfonyl-phenoxy)-pyrazolo[3,4-d]pyrimidin-1-yl]-piperidin-1-yl}-thiophen-2-yl-methanone |
| 156 | 0.16 | Benzothiazol-2-yl-{4-[4-(4-methanesulfonyl-phenoxy)-pyrazolo[3,4-d]pyrimidin-1-yl]-piperidin-1-yl}-methanone |
| 157 | 0.58 | 1-(1-Benzyl-piperidin-4-yl)-4-(4-methanesulfonyl-phenoxy)-1H-pyrazolo[3,4-d]pyrimidine |
| 158 | 0.28 | 1-[1-(3-Chloro-benzyl)-piperidin-4-yl]-4-(4-methanesulfonyl-phenoxy)-1H-pyrazolo[3,4-d]pyrimidine |
| 159 | 0.2 | 1-[1-(4-Fluoro-benzyl)-piperidin-4-yl]-4-(4-methanesulfonyl-phenoxy)-1H-pyrazolo[3,4-d]pyrimidine |
| 160 | 0.57 | 1-[1-(4-Chloro-benzyl)-piperidin-4-yl]-4-(4-methanesulfonyl-phenoxy)-1H-pyrazolo[3,4-d]pyrimidine |
| 161 | 0.036 | 4-(4-Methanesulfonyl-phenoxy)-1-[1-(4-trifluoromethyl-benzyl)-piperidin-4-yl]-1H-pyrazolo[3,4-d]pyrimidine |
| 162 | 0.12 | 4-(4-Methanesulfonyl-phenoxy)-1-[1-(3-trifluoromethoxy-benzyl)-piperidin-4-yl]-1H-pyrazolo[3,4-d]pyrimidine |
| 163 | 0.14 | 1-[1-(2,2-Difluoro-benzo[1,3]dioxol-5-ylmethyl)-piperidin-4-yl]-4-(4-methanesulfonyl-phenoxy)-1H-pyrazolo[3,4-d]pyrimidine |
| 164 | 0.36 | 2-{4-[4-(4-Methanesulfonyl-phenoxy)-pyrazolo[3,4-d]pyrimidin-1-yl]-piperidin-1-ylmethyl}-phenol |
| 165 | 1.4 | 4-(4-Methanesulfonyl-phenoxy)-1-[1-(2-methoxy-benzyl)-piperidin-4-yl]-1H-pyrazolo[3,4-d]pyrimidine |
| 168 | 1.5 | 3-{4-[4-(4-Methanesulfonyl-phenoxy)-pyrazolo[3,4-d]pyrimidin-1-yl]-piperidin-1-ylmethyl}-benzonitrile |
| 169 | 3.6 | 4-(4-Methanesulfonyl-phenoxy)-1-(1-thiazol-2-ylmethyl-piperidin-4-yl)-1H-pyrazolo[3,4-d]pyrimidine |
| 171 | 0.4 | 4-(4-Methanesulfonyl-phenoxy)-1-[1-(2-methyl-propane-1-sulfonyl)-piperidin-4-yl]-1H-pyrazolo[3,4-d]pyrimidine |
| 172 | 0.024 | 4-[6-Chloro-4-(methanesulfonyl-phenoxy)-pyrazolo[3,4-d]pyrimidin-1-yl]-piperidine-1-carboxylic acid tert-butyl ester |
| 173 | 1.7 | 4-[6-Chloro-4-(methanesulfonyl-phenoxy)-pyrazolo[3,4-d]pyrimidin-1-yl]-piperidine-1-carboxylic acid tert-butyl ester |
| 174 | 3.4 | 4-[6-Amino-4-(2-cyano-phenoxy)-pyrazolo[3,4-d]pyrimidin-1-yl]-piperidine-1-carboxylic acid tert-butyl ester |
| 175 | 0.028 | 4-[4-(4-Methanesulfonyl-phenoxy)-6-methyl-pyrazolo[3,4-d]pyrimidin-1-yl]-piperidine-1-carboxylic acid tert-butyl ester |

Example 179

Testing of Compounds of the Invention In Vivo

The in vivo activity of selected compounds of the invention was characterized using an oral glucose tolerance test in C57B1/6J mice.

C57B1/6J mice were obtained from Jackson Laboratory (Bar Harbor, Me.) and were maintained in a light-dark cycle with lights on from 0600-1800 hr. The mice were received at age nine weeks and given ad libitum access to diet (LabDiet 5001 chow, PMI Nutrition, Brentwood, Mo.), and were at age 10 weeks at the time of study The experiments were conducted during the light phase of the light-dark cycle. Mice (n=10) were weighed and fasted for a four hour period prior to treatment with GPR119 agonists or formulation vehicle via oral gavage. GPR119 agonists were formulated in Klucel vehicle (2% Klucel LF with 0.1% Tween 80, in water) at a concentration of 4.0 mg/mL and the mice were dosed with a 7.5 mL/kg volume to equal a 30 mg/kg dose. Two hours following dosing, the animals were given an oral glucose tolerance test (OGTT). For the OGTT, the animals were given a 2 g/kg glucose bolus via oral gavage. Blood glucose readings were made immediately prior to the glucose challenge, and 30, 60 and 120 minutes following. The blood glucose measurements were made by snipping off a small portion of the animal's tail (~1 mm) and collecting 15 µL blood into a heparinized capillary tube for analysis with a YSI Model 2700 Biochemistry Analyzer (Yellow Springs Industries, St Louis, Mo.). Area under the curve (AUC) for plots of blood glucose vs. time for the individual mice was calculated by the trapezoidal method. Results were interpreted by comparing the mean AUC values of ten vehicle treated mice with ten GPR119 agonist treated mice. Preferred compounds were considered to be those that exhibited a statistically significant ($p \leq 0.05$) decrease in AUC.

[4-(4-Methanesulfonyl-phenoxy)-pyrazolo[3,4-d]pyrimidin-1-yl]-piperidine-1-carboxylic acid isopropyl ester (Example 21) exhibited a 44% decrease in mean baseline-subtracted AUC in this assay when dosed at 30 mg/kg.

It is to be understood that the invention is not limited to the particular embodiments of the invention described above, as variations of the particular embodiments may be made and still fall within the scope of the appended claims.

What is claimed is:
1. A compound, wherein said compound is:
4-[4-(2-Fluoro-4-methanesulfonyl-phenylamino)-pyrazolo[3,4-d]pyrimidin-1-yl]-piperidine-1-carboxylic acid tert-butyl ester;
4-[4-(2,4,5-Trifluoro-phenylamino)-pyrazolo[3,4-d]pyrimidin-1-yl]-piperidine-1-carboxylic acid isopropyl ester;
4-[4-(4-Methanesulfonyl-phenylamino)-pyrazolo[3,4-d]pyrimidin-1-yl]-piperidine-1-carboxylic acid isopropyl ester;
4-[4-(2,4,5-Trifluoro-phenylamino)-pyrazolo[3,4-d]pyrimidin-1-yl]-piperidine-1-carboxylic acid tert-butyl ester;
4-[4-(4-Methanesulfonyl-phenylamino)-pyrazolo[3,4-d]pyrimidin-1-yl]-piperidine-1-carboxylic acid tert-butyl ester;
4-[4-(2-Fluoro-4-methanesulfonyl-phenylamino)-pyrazolo[3,4-d]pyrimidin-1-yl]-piperidine-1-carboxylic acid isopropyl ester;
4-[4-(2-Methyl-pyridin-3-ylamino)-pyrazolo[3,4-d]pyrimidin-1-yl]-piperidine-1-carboxylic acid tert-butyl ester;
4-[4-(6-Methanesulfonyl-2-methyl-pyridin-3-ylamino)-pyrazolo[3,4-d]pyrimidin-1-yl]-piperidine-1-carboxylic acid tert-butyl ester;
4-[4-(2-Methyl-6-[1,2,4]triazol-1-yl-pyridin-3-ylamino)-pyrazolo[3,4-d]pyrimidin-1-yl]-piperidine-1-carboxylic acid tert-butyl ester;
4-[4-(5-Methanesulfonyl-2,3-dihydro-indol-1-yl)-pyrazolo[3,4-d]pyrimidin-1-yl]-piperidine-1-carboxylic acid tert-butyl ester;
[1-(1-Benzyl-piperidin-4-yl)-1H-pyrazolo[3,4-d]pyrimidin-4-yl]-(2-fluoro-4-methanesulfonyl-phenyl)-amine;
4-[4-(4-Methanesulfonyl-phenoxy)-pyrazolo[3,4-d]pyrimidin-1-yl]-piperidine-1-carboxylic acid methyl ester;
4-[4-(4-Methanesulfonyl-phenoxy)-pyrazolo[3,4-d]pyrimidin-1-yl]-piperidine-1-carboxylic acid ethyl ester;
4-[4-(2-Fluoro-4-methanesulfonyl-phenoxy)-pyrazolo[3,4-d]pyrimidin-1-yl]-piperidine-1-carboxylic acid ethyl ester;
4-(4-Phenoxy-pyrazolo[3,4-d]pyrimidin-1-yl)-piperidine-1-carboxylic acid isopropyl ester;
4-[4-(2,4,5-Trifluoro-phenoxy)-pyrazolo[3,4-d]pyrimidin-1-yl]-piperidine-1-carboxylic acid isopropyl ester;
4-[3-Methyl-4-(2,4,5-trifluoro-phenoxy)-pyrazolo[3,4-d]pyrimidin-1-yl]-piperidine-1-carboxylic acid isopropyl ester;
4-[4-(4-Ethoxy-2-fluoro-phenoxy)-pyrazolo[3,4-d]pyrimidin-1-yl]-piperidine-1-carboxylic acid isopropyl ester;
4-[4-(2-Cyano-phenoxy)-pyrazolo[3,4-d]pyrimidin-1-yl]-piperidine-1-carboxylic acid isopropyl ester;
4-[4-(6-Cyano-2,3-difluoro-phenoxy)-pyrazolo[3,4-d]pyrimidin-1-yl]-piperidine-1-carboxylic acid isopropyl ester;
4-[4-(4-Methanesulfonyl-phenoxy)-pyrazolo[3,4-d]pyrimidin-1-yl]-piperidine-1-carboxylic acid isopropyl ester;
4-[4-(4-Methanesulfonyl-phenoxy)-3-methyl-pyrazolo[3,4-d]pyrimidin-1-yl]-piperidine-1-carboxylic acid isopropyl ester;
4-[4-(2-Fluoro-4-methanesulfonyl-phenoxy)-pyrazolo[3,4-d]pyrimidin-1-yl]-piperidine-1-carboxylic acid isopropyl ester;
4-[4-(3-Fluoro-4-methanesulfonyl-phenoxy)-pyrazolo[3,4-d]pyrimidin-1-yl]-piperidine-1-carboxylic acid isopropyl ester;
4-[4-(4-Acetylamino-phenoxy)-pyrazolo[3,4-d]pyrimidin-1-yl]-piperidine-1-carboxylic acid isopropyl ester;
4-{4-[4-(5-Methyl-tetrazol-1-yl)-phenoxy]-pyrazolo[3,4-d]pyrimidin-1-yl}-piperidine-1-carboxylic acid isopropyl ester;
4-[4-(2-Methyl-pyridin-3-yloxy)-pyrazolo[3,4-d]pyrimidin-1-yl]-piperidine-1-carboxylic acid isopropyl ester;
4-[4-(2-Methyl-pyridin-3-yloxy)-pyrazolo[3,4-d]pyrimidin-1-yl]-piperidine-1-carboxylic acid isopropyl ester hydrochloride salt;
4-[4-(6-Methanesulfonyl-2-methyl-pyridin-3-yloxy)-pyrazolo[3,4-d]pyrimidin-1-yl]-piperidine-1-carboxylic acid isopropyl ester;
4-[4-(2-Methyl-6-[1,2,4]triazol-1-yl-pyridin-3-yloxy)-pyrazolo[3,4-d]pyrimidin-1-yl]-piperidine-1-carboxylic acid isopropyl ester;
4-[4-(1-Methyl-6-oxo-1,6-dihydro-pyridazin-3-yloxy)-pyrazolo[3,4-d]pyrimidin-1-yl]-piperidine-1-carboxylic acid isopropyl ester;
4-[4-(2-Fluoro-phenoxy)-pyrazolo[3,4-d]pyrimidin-1-yl]-piperidine-1-carboxylic acid tert-butyl ester;
4-[4-(3-Fluoro-phenoxy)-pyrazolo[3,4-d]pyrimidin-1-yl]-piperidine-1-carboxylic acid tert-butyl ester;
4-[4-(4-Fluoro-phenoxy)-pyrazolo[3,4-d]pyrimidin-1-yl]-piperidine-1-carboxylic acid tert-butyl ester;
4-[4-(2,4,5-Trifluoro-phenoxy)-pyrazolo[3,4-d]pyrimidin-1-yl]-piperidine-1-carboxylic acid tert-butyl ester;

4-[4-(2,4,6-Trifluoro-phenoxy)-pyrazolo[3,4-d]pyrimidin-1-yl]-piperidine-1-carboxylic acid tert-butyl ester;
4-[4-(2,3,5-Trifluoro-phenoxy)-pyrazolo[3,4-d]pyrimidin-1-yl]-piperidine-1-carboxylic acid tert-butyl ester;
4-[4-(2,4-Dichloro-phenoxy)-pyrazolo[3,4-d]pyrimidin-1-yl]-piperidine-1-carboxylic acid tert-butyl ester;
4-[4-(4-Methoxy-phenoxy)-pyrazolo[3,4-d]pyrimidin-1-yl]-piperidine-1-carboxylic acid tert-butyl ester;
4-[4-(4-Ethoxy-phenoxy)-pyrazolo[3,4-d]pyrimidin-1-yl]-piperidine-1-carboxylic acid tert-butyl ester;
4-[4-(Benzo[1,3]dioxol-5-yloxy)-pyrazolo[3,4-d]pyrimidin-1-yl]-piperidine-1-carboxylic acid tert-butyl ester;
4-[4-(4-Trifluoromethoxy-phenoxy)-pyrazolo[3,4-d]pyrimidin-1-yl]-piperidine-1-carboxylic acid tert-butyl ester;
4-[4-(4-Ethoxy-2-fluoro-phenoxy)-pyrazolo[3,4-d]pyrimidin-1-yl]-piperidine-1-carboxylic acid tert-butyl ester;
4-[4-(2-Chloro-4-methoxy-phenoxy)-pyrazolo[3,4-d]pyrimidin-1-yl]-piperidine-1-carboxylic acid tert-butyl ester;
4-[4-(2-Cyano-phenoxy)-pyrazolo[3,4-d]pyrimidin-1-yl]-piperidine-1-carboxylic acid tert-butyl ester;
4-[4-(4-Cyano-phenoxy)-pyrazolo[3,4-d]pyrimidin-1-yl]-piperidine-1-carboxylic acid tert-butyl ester;
4-[4-(4-Cyano-2-fluoro-phenoxy)-pyrazolo[3,4-d]pyrimidin-1-yl]-piperidine-1-carboxylic acid tert-butyl ester;
4-[4-(4-Cyano-3-fluoro-phenoxy)-pyrazolo[3,4-d]pyrimidin-1-yl]-piperidine-1-carboxylic acid tert-butyl ester;
4-[4-(6-Cyano-2,3-difluoro-phenoxy)-pyrazolo[3,4-d]pyrimidin-1-yl]-piperidine-1-carboxylic acid tert-butyl ester;
4-[4-(2-Cyano-4,5-difluoro-phenoxy)-pyrazolo[3,4-d]pyrimidin-1-yl]-piperidine-1-carboxylic acid tert-butyl ester;
4-[4-(4-Chloro-2-cyano-phenoxy)-pyrazolo[3,4-d]pyrimidin-1-yl]-piperidine-1-carboxylic acid tert-butyl ester;
4-[4-(4-Bromo-2-cyano-phenoxy)-pyrazolo[3,4-d]pyrimidin-1-yl]-piperidine-1-carboxylic acid tert-butyl ester;
4-[4-(3-Fluoro-5-trifluoromethyl-phenoxy)-pyrazolo[3,4-d]pyrimidin-1-yl]-piperidine-1-carboxylic acid tert-butyl ester;
4-[4-(2-Chloro-4-trifluoromethyl-phenoxy)-pyrazolo[3,4-d]pyrimidin-1-yl]-piperidine-1-carboxylic acid tert-butyl ester;
4-[4-(4-Chloro-3-trifluoromethyl-phenoxy)-pyrazolo[3,4-d]pyrimidin-1-yl]-piperidine-1-carboxylic acid tert-butyl ester;
4-[4-(4-Sulfamoyl-phenoxy)-pyrazolo[3,4-d]pyrimidin-1-yl]-piperidine-1-carboxylic acid tert-butyl ester;
4-[4-(4-Dimethylsulfamoyl-phenoxy)-pyrazolo[3,4-d]pyrimidin-1-yl]-piperidine-1-carboxylic acid tert-butyl ester;
4-[4-(4-Methanesulfinyl-phenoxy)-pyrazolo[3,4-d]pyrimidin-1-yl]-piperidine-1-carboxylic acid tert-butyl ester;
4-[4-(4-Methanesulfonyl-phenoxy)-pyrazolo[3,4-d]pyrimidin-1-yl]-piperidine-1-carboxylic acid tert-butyl ester;
4-[4-(2-Fluoro-4-methanesulfonyl-phenoxy)-pyrazolo[3,4-d]pyrimidin-1-yl]-piperidine-1-carboxylic acid tert-butyl ester;
4-[4-(3-Fluoro-4-methanesulfonyl-phenoxy)-pyrazolo[3,4-d]pyrimidin-1-yl]-piperidine-1-carboxylic acid tert-butyl ester;
4-[4-(4-Carbamoyl-phenoxy)-pyrazolo[3,4-d]pyrimidin-1-yl]-piperidine-1-carboxylic acid tert-butyl ester;
4-[4-(2-Fluoro-4-methoxycarbonyl-phenoxy)-pyrazolo[3,4-d]pyrimidin-1-yl]-piperidine-1-carboxylic acid tert-butyl ester;
4-[4-(4-Acetyl-phenoxy)-pyrazolo[3,4-d]pyrimidin-1-yl]-piperidine-1-carboxylic acid tert-butyl ester;
4-[4-(4-Acetyl-3-methyl-phenoxy)-pyrazolo[3,4-d]pyrimidin-1-yl]-piperidine-1-carboxylic acid tert-butyl ester;
4-[4-(2-Fluoro-4-nitro-phenoxy)-pyrazolo[3,4-d]pyrimidin-1-yl]-piperidine-1-carboxylic acid tert-butyl ester;
4-{4-[4-(4-Acetyl-piperazin-1-yl)-phenoxy]-pyrazolo[3,4-d]pyrimidin-1-yl}-piperidine-1-carboxylic acid tert-butyl ester;
4-[4-(4-Methanesulfonylamino-3-methyl-phenoxy)-pyrazolo[3,4-d]pyrimidin-1-yl]-piperidine-1-carboxylic acid tert-butyl ester;
4-[4-(3-Acetylamino-phenoxy)-pyrazolo[3,4-d]pyrimidin-1-yl]-piperidine-1-carboxylic acid tert-butyl ester;
4-[4-(4-Acetylamino-phenoxy)-pyrazolo[3,4-d]pyrimidin-1-yl]-piperidine-1-carboxylic acid tert-butyl ester;
4-[4-(Quinolin-5-yloxy)-pyrazolo[3,4-d]pyrimidin-1-yl]-piperidine-1-carb oxylic acid tert-butyl ester;
4-[4-(1H-Pyrrolo[2,3-b]pyridin-5-yloxy)-pyrazolo[3,4-d]pyrimidin-1-yl]-piperidine-1-carboxylic acid tert-butyl ester;
4-[4-(1H-Indol-4-yloxy)-pyrazolo[3,4-d]pyrimidin-1-yl]-piperidine-1-carboxylic acid tert-butyl ester;
4-[4-(1H-Indol-5-yloxy)-pyrazolo[3,4-d]pyrimidin-1-yl]-piperidine-1-carboxylic acid tert-butyl ester;
4-[4-(2-oxo-2H-chromen-7-yloxy)-pyrazolo[3,4-d]pyrimidin-1-yl]-piperidine-1-carboxylic acid tert-butyl ester;
4-[4-(1,1-Dioxo-1H-1λ6-benzo [b]thiophen-5-yloxy)-pyrazolo[3,4-d]pyrimidin-1-yl]-piperidine-1-carboxylic acid tert-butyl ester;
4-[4-(1,1-Dioxo-1H-1λ6-benzo [b]thiophen-5-yloxy)-pyrazolo[3,4-d]pyrimidin-1-yl]-piperidine-1-carboxylic acid tert-butyl ester;
4-[4-(1,1-Dioxo-2,3-dihydro-1H-1λ6-benzo[b]thiophen-5-yloxy)-pyrazolo[3,4-d]pyrimidin-1-yl]-piperidine-1-carboxylic acid tert-butyl ester;
4-[4-(4-[1,2,4]Triazol-1-yl-phenoxy)-pyrazolo[3,4-d]pyrimidin-1-yl]-piperidine-1-carboxylic acid tert-butyl ester;
4-{4-[4-(1H-Tetrazol-5-yl)-phenoxy]-pyrazolo[3,4-d]pyrimidin-1-yl}-piperidine-1-carboxylic acid tert-butyl ester;
4-[4-(4-Tetrazol-2-yl-phenoxy)-pyrazolo[3,4-d]pyrimidin-1-yl]-piperidine-1-carboxylic acid tert-butyl ester;
4-[4-(4-Tetrazol-1-yl-phenoxy)-pyrazolo[3,4-d]pyrimidin-1-yl]-piperidine-1-carboxylic acid tert-butyl ester;
4-{4-[4-(5-Methyl-tetrazol-1-yl)-phenoxy]-pyrazolo[3,4-d]pyrimidin-1-yl}-piperidine-1-carboxylic acid tert-butyl ester;
4-{4-[4-(5-Methyl-[1,2,4]oxadiazol-3-yl)-phenoxy]-pyrazolo[3,4-d]pyrimidin-1-yl}-piperidine-1-carboxylic acid tert-butyl ester;
4-[4-(4-Thiophen-3-yl-phenoxy)-pyrazolo[3,4-d]pyrimidin-1-yl]-piperidine-1-carboxylic acid tert-butyl ester;
3-[4-(4-Methanesulfonyl-phenoxy)-pyrazolo[3,4-d]pyrimidin-1-yl]-piperidine-1-carboxylic acid tert-butyl ester;

(R)-3-[4-(4-Methanesulfonyl-phenoxy)-pyrazolo[3,4-d]pyrimidin-1-yl]-piperidine-1-carboxylic acid tert-butyl ester;
(S)-3-[4-(4-Methanesulfonyl-phenoxy)-pyrazolo[3,4-d]pyrimidin-1-yl]-piperidine-1-carboxylic acid tert-butyl ester;
3-[4-(2-Cyano-phenoxy)-pyrazolo[3,4-d]pyrimidin-1-yl]-piperidine-1-carboxylic acid tert-butyl ester;
4-[4-(Pyridin-3-yloxy)-pyrazolo[3,4-d]pyrimidin-1-yl]-piperidine-1-carboxylic acid tert-butyl ester;
4-[4-(2-Methyl-pyridin-3-yloxy)-pyrazolo[3,4-d]pyrimidin-1-yl]-piperidine-1-carboxylic acid tert-butyl ester;
4-[4-(2,6-Dimethyl-pyridin-3-yloxy)-pyrazolo[3,4-d]pyrimidin-1-yl]-piperidine-1-carboxylic acid tert-butyl ester;
4-[4-(6-Trifluoromethyl-pyridin-3-yloxy)-pyrazolo[3,4-d]pyrimidin-1-yl]-piperidine-1-carboxylic acid tert-butyl ester;
4-[4-(2,6-Dimethoxy-pyridin-3-yloxy)-pyrazolo[3,4-d]pyrimidin-1-yl]-piperidine-1-carboxylic acid tert-butyl ester;
4-[4-(6-Methoxy-pyridin-3-yloxy)-pyrazolo[3,4-d]pyrimidin-1-yl]-piperidine-1-carboxylic acid tert-butyl ester;
4-[4-(6-Chloro-2-methyl-pyridin-3-yloxy)-pyrazolo[3,4-d]pyrimidin-1-yl]-piperidine-1-carboxylic acid tert-butyl ester;
4-[4-(6-Methanesulfonyl-2-methyl-pyridin-3-yloxy)-pyrazolo[3,4-d]pyrimidin-1-yl]-piperidine-1-carboxylic acid tert-butyl ester;
4-[4-(2-Cyano-pyridin-3-yloxy)-pyrazolo[3,4-d]pyrimidin-1-yl]-piperidine-1-carboxylic acid tert-butyl ester;
4-[4-(5-Chloro-pyridin-3-yloxy)-pyrazolo[3,4-d]pyrimidin-1-yl]-piperidine-1-carboxylic acid tert-butyl ester;
4-[4-(2-Methyl-6-[1,2,4]triazol-1-yl-pyridin-3-yloxy)-pyrazolo[3,4-d]pyrimidin-1-yl]-piperidine-1-carboxylic acid tert-butyl ester;
4-[4-(1-Methyl-6-oxo-1,6-dihydro-pyridazin-3-yloxy)-pyrazolo[3,4-d]pyrimidin-1-yl]-piperidine-1-carboxylic acid tert-butyl ester;
4-[4-(6-Ethyl-2-methyl-pyrimidin-4-yloxy)-pyrazolo[3,4-d]pyrimidin-1-yl]-piperidine-1-carboxylic acid tert-butyl ester;
4-[4-(2-Methyl-pyridin-3-yloxy)-pyrazolo[3,4-d]pyrimidin-1-yl]-piperidine-1-carboxylic acid butyl ester;
4-[4-(4-Methanesulfonyl-phenoxy)-pyrazolo[3,4-d]pyrimidin-1-yl]-piperidine-1-carboxylic acid (R)-sec-butyl ester;
4-[4-(4-Methanesulfonyl-phenoxy)-pyrazolo[3,4-d]pyrimidin-1-yl]-piperidine-1-carboxylic acid isobutyl ester;
4-[4-(2-Methyl-pyridin-3-yloxy)-pyrazolo[3,4-d]pyrimidin-1-yl]-piperidine-1-carboxylic acid isobutyl ester;
4-[4-(4-Methanesulfonyl-phenoxy)-pyrazolo[3,4-d]pyrimidin-1-yl]-piperidine-1-carboxylic acid 2,2-dimethyl-propyl ester;
4-[4-(4-Methanesulfonyl-phenoxy)-pyrazolo[3,4-d]pyrimidin-1-yl]-piperidine-1-carboxylic acid 2-fluoro-1-fluoromethyl-ethyl ester;
4-[4-(4-Methanesulfonyl-phenoxy)-pyrazolo[3,4-d]pyrimidin-1-yl]-piperidine-1-carboxylic acid 2,2,2-trifluoro-1-methyl-ethyl ester;
4-[4-(4-Methanesulfonyl-phenoxy)-pyrazolo[3,4-d]pyrimidin-1-yl]-piperidine-1-carboxylic acid 2,2,2-trifluoro-1,1-dimethyl-ethyl ester;
4-[4-(4-Methanesulfonyl-phenoxy)-pyrazolo[3,4-d]pyrimidin-1-yl]-piperidine-1-carboxylic acid 2,2,2-trifluoro-1-trifluoromethyl-ethyl ester;
4-[4-(4-Methanesulfonyl-phenoxy)-pyrazolo[3,4-d]pyrimidin-1-yl]-piperidine-1-carboxylic acid 2,2,2-trifluoro-ethyl ester;
4-[4-(4-Methanesulfonyl-phenoxy)-pyrazolo[3,4-d]pyrimidin-1-yl]-piperidine-1-carboxylic acid 2,2,2-trichloro-1,1-dimethyl-ethyl ester;
4-[4-(4-Methanesulfonyl-phenoxy)-pyrazolo[3,4-d]pyrimidin-1-yl]-piperidine-1-carboxylic acid 2,2,2-trichloro-ethyl ester;
4-[4-(2-Methyl-pyridin-3-yloxy)-pyrazolo[3,4-d]pyrimidin-1-yl]-piperidine-1-carboxylic acid cyclobutyl ester;
4-[4-(4-Ethoxy-2-fluoro-phenoxy)-pyrazolo[3,4-d]pyrimidin-1-yl]-piperidine-1-carboxylic acid cyclopentyl ester;
4-[4-(2-Cyano-phenoxy)-pyrazolo[3,4-d]pyrimidin-1-yl]-piperidine-1-carboxylic acid cyclopentyl ester;
4-[4-(6-Cyano-2,3-difluoro-phenoxy)-pyrazolo[3,4-d]pyrimidin-1-yl]-piperidine-1-carboxylic acid cyclopentyl ester;
4-[4-(2-Fluoro-4-methanesulfonyl-phenoxy)-pyrazolo[3,4-d]pyrimidin-1-yl]-piperidine-1-carboxylic acid cyclopentyl ester;
4-[4-(2-Methyl-pyridin-3-yloxy)-pyrazolo[3,4-d]pyrimidin-1-yl]-piperidine-1-carboxylic acid cyclopentyl ester;
4-[4-(2-Methyl-pyridin-3-yloxy)-pyrazolo[3,4-d]pyrimidin-1-yl]-piperidine-1-carboxylic acid phenyl ester;
4-[4-(2-Methyl-pyridin-3-yloxy)-pyrazolo[3,4-d]pyrimidin-1-yl]-piperidine-1-carboxylic acid 4-nitro-phenyl ester;
4-[4-(2-Methyl-pyridin-3-yloxy)-pyrazolo[3,4-d]pyrimidin-1-yl]-piperidine-1-carboxylic acid benzyl ester;
4-[4-(2-Methyl-pyridin-3-yloxy)-pyrazolo[3,4-d]pyrimidin-1-yl]-piperidine-1-carboxylic acid cyclohexyl ester;
1-[1-(3-Isopropyl-[1,2,4]oxadiazol-5-yl)-piperidin-4-yl]-4-(4-methanesulfonyl-phenoxy)-1H-pyrazolo[3,4-d]pyrimidine;
4-(2-Fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine;
4-(3-Fluoro-4-methanesulfonyl-phenoxy)-1-[1-(3-isopropyl-[1,2,4]oxadiazol-5-yl)-piperidin-4-yl]-1H-pyrazolo[3,4-d]pyrimidine;
1-[1-(3-Isopropyl-[1,2,4]oxadiazol-5-yl)-piperidin-4-yl]-4-(2-methyl-pyridin-3-yloxy)-1H-pyrazolo[3,4-d]pyrimidine;
1-[1-(6-Chloro-pyridazin-3-yl)-piperidin-4-yl]-4-(4-methanesulfonyl-phenoxy)-1H-pyrazolo[3,4-d]pyrimidine;
4-(2-Fluoro-4-methanesulfonyl-phenoxy)-1-[4-(3-isopropyl-[1,2,4]oxadiazol-5-yl)-cyclohexyl]-1H-pyrazolo[3,4-d]pyrimidine;
4-(2-Fluoro-4-methanesulfonyl-phenoxy)-1-[4-(3-isopropyl-[1,2,4]oxadiazol-5-yl)-trans-cyclohexyl]-1H-pyrazolo[3,4-d]pyrimidine;
1-[4-(3-Isopropyl-[1,2,4]oxadiazol-5-yl)-trans-cyclohexyl]-4-[4-(5-methyl-tetrazol-1-yl)-phenoxy]-1H-pyrazolo[3,4-d]pyrimidine;
4-(2-Fluoro-4-methanesulfonyl-phenoxy)-1-[4-(3-isopropyl-[1,2,4]oxadiazol-5-yl)-cis-cyclohexyl]-1H-pyrazolo[3,4-d]pyrimidine;
1-[4-(3-Isopropyl-[1,2,4]oxadiazol-5-yl)-cyclohexyl]-4-(2-methyl-pyridin-3-yloxy)-1H-pyrazolo[3,4-d]pyrimidine;
1-{4-[4-(4-Methanesulfonyl-phenoxy)-pyrazolo[3,4-d]pyrimidin-1-yl]-piperidin-1-yl}-2-methyl-propan-1-one;

2,2-Dimethyl-1-{4-[4-(2,4,5-trifluoro-phenoxy)-pyrazolo[3,4-d]pyrimidin-1-yl]-piperidin-1-yl}-propan-1-one;

1-{4-[4-(4-Methanesulfonyl-phenoxy)-pyrazolo[3,4-d]pyrimidin-1-yl]-piperidin-1-yl}-2,2-dimethyl-propan-1-one;

1-{4-[4-(2-Fluoro-4-methanesulfonyl-phenylamino)-pyrazolo[3,4-d]pyrimidin-1-yl]-piperidin-1-yl}-2,2-dimethyl-propan-1-one;

Cyclobutyl-{4-[4-(4-methanesulfonyl-phenoxy)-pyrazolo[3,4-d]pyrimidin-1-yl]-piperidin-1-yl}-methanone;

Cyclopentyl-{4-[4-(4-methanesulfonyl-phenoxy)-pyrazolo[3,4-d]pyrimidin-1-yl]-piperidin-1-yl}-methanone;

1-{4-[4-(4-Methanesulfonyl-phenoxy)-pyrazolo[3,4-d]pyrimidin-1-yl]-piperidin-1-yl}-3-methyl-butan-1-one;

1-{4-[4-(4-Methanesulfonyl-phenoxy)-pyrazolo[3,4-d]pyrimidin-1-yl]-piperidin-1-yl}-4-methyl-pentan-1-one;

1-{4-[4-(4-Methanesulfonyl-phenoxy)-pyrazolo[3,4-d]pyrimidin-1-yl]-piperidin-1-yl}-3,3-dimethyl-butan-1-one;

2-Cyclohexyl-1-{4-[4-(4-methanesulfonyl-phenoxy)-pyrazolo[3,4-d]pyrimidin-1-yl]-piperidin-1-yl}-ethanone;

1-{4-[4-(4-Methanesulfonyl-phenoxy)-pyrazolo[3,4-d]pyrimidin-1-yl]-piperidin-1-yl}-3-phenyl-propan-1-one;

Cyclopentyl-{4-[4-(4-ethoxy-2-fluoro-phenoxy)-pyrazolo[3,4-d]pyrimidin-1-yl]-piperidin-1-yl}-methanone;

2,2,2-Trifluoro-1-{4-[4-(4-methanesulfonyl-phenoxy)-pyrazolo[3,4-d]pyrimidin-1-yl]-piperidin-1-yl}-ethanone;

{4-[4-(4-Methanesulfonyl-phenoxy)-pyrazolo[3,4-d]pyrimidin-1-yl]-piperidin-1-yl}-phenyl-methanone;

(3,5-Dichloro-phenyl)-{4-[4-(4-methanesulfonyl-phenoxy)-pyrazolo[3,4-d]pyrimidin-1-yl]-piperidin-1-yl}-methanone;

{4-[4-(4-Methanesulfonyl-phenoxy)-pyrazolo[3,4-d]pyrimidin-1-yl]-piperidin-1-yl}-(4-methoxy-phenyl)-methanone;

(1,5-Dimethyl-1H-pyrazol-3-yl)-{4-[4-(4-methanesulfonyl-phenoxy)-pyrazolo[3,4-d]pyrimidin-1-yl]-piperidin-1-yl}-methanone;

{4-[4-(4-Methanesulfonyl-phenoxy)-pyrazolo[3,4-d]pyrimidin-1-yl]-piperidin-1-yl}-(5-methyl-isoxazol-3-yl)-methanone;

(5-Isobutyl-isoxazol-3-yl)-{4-[4-(4-methanesulfonyl-phenoxy)-pyrazolo[3,4-d]pyrimidin-1-yl]-piperidin-1-yl}-methanone;

{4-[4-(4-Methanesulfonyl-phenoxy)-pyrazolo[3,4-d]pyrimidin-1-yl]-piperidin-1-yl}-thiophen-2-yl-methanone;

Benzothiazol-2-yl-{4-[4-(4-methanesulfonyl-phenoxy)-pyrazolo[3,4-d]pyrimidin-1-yl]-piperidin-1-yl}-methanone;

1-(1-Benzyl-piperidin-4-yl)-4-(4-methanesulfonyl-phenoxy)-1H-pyrazolo[3,4-d]pyrimidine;

1-[1-(3-Chloro-benzyl)-piperidin-4-yl]-4-(4-methanesulfonyl-phenoxy)-1H-pyrazolo[3,4-d]pyrimidine;

1-[1-(4-Fluoro-benzyl)-piperidin-4-yl]-4-(4-methanesulfonyl-phenoxy)-1H-pyrazolo[3,4-d]pyrimidine;

1-[1-(4-Chloro-benzyl)-piperidin-4-yl]-4-(4-methanesulfonyl-phenoxy)-1H-pyrazolo[3,4-d]pyrimidine;

4-(4-Methanesulfonyl-phenoxy)-1-[1-(4-trifluoromethyl-benzyl)-piperidin-4-yl]-1H-pyrazolo[3,4-d]pyrimidine;

4-(4-Methanesulfonyl-phenoxy)-1-[1-(3-trifluoromethoxy-benzyl)-piperidin-4-yl]-1H-pyrazolo[3,4-d]pyrimidine;

1-[1-(2,2-Difluoro-benzo[1,3]dioxol-5-ylmethyl)-piperidin-4-yl]-4-(4-methanesulfonyl-phenoxy)-1H-pyrazolo[3,4-d]pyrimidine;

2-{4-[4-(4-Methanesulfonyl-phenoxy)-pyrazolo[3,4-d]pyrimidin-1-yl]-piperidin-1-ylmethyl}-phenol;

4-(4-Methanesulfonyl-phenoxy)-1-[1-(2-methoxy-benzyl)-piperidin-4-yl]-1H-pyrazolo[3,4-d]pyrimidine;

4-(4-Methanesulfonyl-phenoxy)-1-[1-(4-methoxy-benzyl)-piperidin-4-yl]-1H-pyrazolo[3,4-d]pyrimidine;

1-[1-(4-Isopropyl-benzyl)-piperidin-4-yl]-4-(4-methanesulfonyl-phenoxy)-1H-pyrazolo[3,4-d]pyrimidine;

3-{4-[4-(4-Methanesulfonyl-phenoxy)-pyrazolo[3,4-d]pyrimidin-1-yl]-piperidin-1-ylmethyl}-benzonitrile;

4-(4-Methanesulfonyl-phenoxy)-1-(1-thiazol-2-ylmethyl-piperidin-4-yl)-1H-pyrazolo[3,4-d]pyrimidine;

4-(4-Methanesulfonyl-phenoxy)-1-[1-(5-methyl-isoxazol-3-ylmethyl)-piperidin-4-yl]-1H-pyrazolo[3,4-d]pyrimidine;

4-(4-Methanesulfonyl-phenoxy)-1-[1-(2-methyl-propane-1-sulfonyl)-piperidin-4-yl]-1H-pyrazolo[3,4-d]pyrimidine;

4-[6-Chloro-4-(4-methanesulfonyl-phenoxy)-pyrazolo[3,4-d]pyrimidin-1-yl]-piperidine-1-carboxylic acid tert-butyl ester;

4-[6-Chloro-4-(4-methanesulfonyl-phenoxy)-pyrazolo[3,4-d]pyrimidin-1-yl]-piperidine-1-carboxylic acid tert-butyl ester;

4-[6-Amino-4-(2-cyano-phenoxy)-pyrazolo[3,4-d]pyrimidin-1-yl]-piperidine-1-carboxylic acid tert-butyl ester;

4-[4-(4-Methanesulfonyl-phenoxy)-6-methyl-pyrazolo[3,4-d]pyrimidin-1-yl]-piperidine-1-carboxylic acid tert-butyl ester; or 4-[4-(4-Methanesulfonyl-phenoxy)-6-methoxy-pyrazolo[3,4-d]pyrimidin-1-yl]-piperidine-1-carboxylic acid tert-butyl ester.

2. A pharmaceutical composition, comprising a therapeutically effective amount of a compound according to claim 1 or a pharmaceutically acceptable salt thereof and a pharmaceutically acceptable carrier.

\* \* \* \* \*